(12) United States Patent
Looper et al.

(10) Patent No.: US 10,493,061 B2
(45) Date of Patent: Dec. 3, 2019

(54) COMPOSITIONS AND METHODS COMPRISING 2-(ACYLAMINO)IMIDAZOLES

(71) Applicants: Curza Global, LLC, Provo, UT (US); University of Utah Research Foundation, Salt Lake City, UT (US)

(72) Inventors: Ryan E. Looper, Salt Lake City, UT (US); Rachel M. Vaden, Salt Lake City, UT (US); Joseph B. Gibbons, Salt Lake City, UT (US); Justin M. Salvant, Salt Lake City, UT (US); Anne V. Edwards, Salt Lake City, UT (US); Matthew S. Sigman, Salt Lake City, UT (US); Bryan E. Welm, Edmond, OK (US)

(73) Assignees: Curza Global, LLC, Provo, UT (US); University of Utag Research Foundation, Salt Lake City, UT (US)

( * ) Notice: Subject to any disclaimer, the term of this patent is extended or adjusted under 35 U.S.C. 154(b) by 0 days.

(21) Appl. No.: 15/268,410

(22) Filed: Sep. 16, 2016

(65) Prior Publication Data

US 2017/0100375 A1    Apr. 13, 2017

Related U.S. Application Data

(63) Continuation of application No. PCT/US2015/021602, filed on Mar. 19, 2015.

(60) Provisional application No. 61/955,761, filed on Mar. 19, 2014, provisional application No. 62/051,863, filed on Sep. 17, 2014.

(51) Int. Cl.
| | | |
|---|---|---|
| *A61K 31/4168* | (2006.01) | |
| *A61K 31/4178* | (2006.01) | |
| *A61K 31/427* | (2006.01) | |
| *A61K 31/5377* | (2006.01) | |

(52) U.S. Cl.
CPC ...... *A61K 31/4168* (2013.01); *A61K 31/4178* (2013.01); *A61K 31/427* (2013.01); *A61K 31/5377* (2013.01)

(58) Field of Classification Search
None
See application file for complete search history.

(56) References Cited

U.S. PATENT DOCUMENTS

| | | |
|---|---|---|
| 5,574,057 A | 11/1996 | Ireland et al. |
| 2005/0070588 A1 | 3/2005 | Weinstein et al. |

FOREIGN PATENT DOCUMENTS

| | | |
|---|---|---|
| WO | 2005012263 | 2/2005 |
| WO | 2011080132 | 7/2011 |
| WO | 2012161965 | 11/2012 |
| WO | 2015143240 | 9/2015 |

OTHER PUBLICATIONS

PubChem Open Chemistry Database, Compound ID Nos. MLS003874856 (60157525); MLS003874857 (60157526); MLS003874858 (60157527); MLS003874862 (60157531); MLS003874863 (60157532); MLS003874864 (60157533); MLS003874867 (60157536); MLS003874872 (60157538), entered Sep. 15, 2012.*
Ito, Nobuyuki. Cancer Science 94(1), (2003) 3-8.*
Bain et al., "The selectivity of protein kinase inhibitors: a further update." Biochem. J. 2007, 408, pp. 297-315.
Chiaverini et al., "Protective effect of metallothionein on oxidative stress-induced DNA damage." Free Radical Research, Jun. 2010, vol. 44, No. 6, pp. 605-613.
Copp et al., "Naamidine A is an antagonist of the epidermal growth factor receptor and an in vivo active antitumor agent", J. Med. Chem., vol. 41, No. 20, Sep. 1, 1998, pp. 3909-3911.
Dairkee et al., "A molecular 'signature' of primary breast cancer cultures; patterns resembling tumor tissue," BMC Genomics, 2004, vol. 5, No. 1, 10 pages.
Dalby et al., "Targeting the prodeath and prosurvival functions of autophagy as novel therapeutic strategies in cancer," Autophagy, 2010, vol. 6, No. 3, pp. 322-329.
Database CA (online), PubChem Substance, "Chemical Abstracts Service, Columbus, Ohio, US; Hirabayashi, Shigeto et al: "Silver halide color photographic material pyrazoloazole coupler, retrieved from STN Database accession No. 1997:276858; & JP H93 4067 A (Konishiroku Photo Ind., Japan; Konica Minolta Holdings Inc.), 37 pages.
Database PubChem Substance, "PubChem Open Chemistry database", Jan. 9, 2014, 6 pages.
Deacon et al., "An isoform selective, small molecule inhibitor targets the autoregulatory mechanism of p21-Activated Kinase." Chem. Biol. 2008, vol. 15, Issue 4, pp. 322-331.
Degterev et al., "Chemical inhibitor of nonapoptotic cell death with therapeutic potential for ischemic brain injury," Nat Chem Biol., 2005; vol. 1, No. 2, pp. 112-119.
Ermolat'ev et al., "Concise and Diversity-Oriented Route toward Polysubstituted 2-Aminoimidazole Alkaloids and Their Analogues," Angew. Chem., 2010, vol. 122, pp. 9655-9658.

(Continued)

*Primary Examiner* — Samantha L Shterengarts
(74) *Attorney, Agent, or Firm* — Kilpatrick Townsend & Stockton LLP

(57) ABSTRACT

The present invention presents 2-(acylamino)imidazoles with therapeutic activity, including selective activity against cancer cells, and compositions comprising them. Methods of using and preparing the 2-(acylamino)imidazoles are also presented.

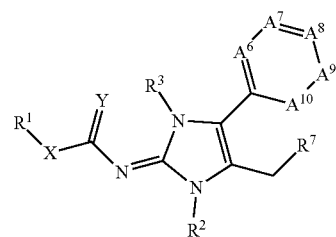

48 Claims, 21 Drawing Sheets
Specification includes a Sequence Listing.

(56) References Cited

OTHER PUBLICATIONS

Han et al., "Shikonin circumvents cancer drug resistance by induction of a necroptotic death," Mol Cancer Ther, May 2007, vol. 6, No. 5, pp. 1641-1649.
Ho et al., "Low intracellular zinc induces oxidative DNA damage, disrupts p53, NFκB, and AP1 DNA binding, and affects DNA repair in a rat glioma cell line," Proc Natl Acad Sci, Dec. 24, 2002, vol. 99, No. 26, pp. 16770-16775.
Huang et al., "Characterization of voltage-gated sodium-channel blockers by electrical stimulation and fluorescence detection of membrane potential," Nature Biotech., 2006, vol. 24, No. 4, pp. 439-446.
Jänicke et al., "Caspase-3 is Required for DNA Fragmentation and Morphological Changes Associated with Apoptosis," J Biol Chem, 1998, vol. 273, No. 16, pp. 9357-9360.
Kilari et al., "Zinc inhibits oxidative stress-induced iron signaling and apoptosis in Caco-2 cells," Free Radic Biol Med, 2010, vol. 48, pp. 961-968.
Kimura et al., "Chloroquine in Cancer Therapy: A Double-Edged Sword of Autophagy," Cancer Res, Jan. 1, 2013, vol. 73, No. 1, 7 pages.
Liu et al., "Rational design of inhibitors that bind to inactive kinase conformations," Nature Chem. Bio., Jul. 2006, vol. 2, No. 7, pp. 358-364.
Margalioth et al., "Copper and Zinc levels in normal and malignant tissues," Cancer, 1983, vol. 52, No. 5, pp. 868-872.
May et al., "Allosteric Modulation of G Protein-Coupled Receptors," Annu. Rev. Pharmacol. Toxicol., 2007, vol. 47, pp. 1-51.
Palmiter et al., "ZnT-2, a mammalian protein that confers resistance to zinc by facilitating vesicular sequestration," The EMBO Journal, 1996; vol. 15, No. 8, pp. 1784-1791.

PCT/US2015/021602, "International Preliminary Report on Patentability", dated Sep. 29, 2016, 12 pages.
PCT/US2015/021602, "International Search Report and Written Opinion", dated Sep. 22, 2015, 19 pages.
Pumiglia et al., "Cell cycle arrest mediated by the MEK/mitogen-activated protein kinase pathway," Proc. Natl. Acad. Sci. USA, Jan. 1997, vol. 94, pp. 448-452.
Qin et al., "Silencing of ZnT1 reduces $Zn^{2+}$ efflux in cultured cortical neurons," Neurosci. Lett., 2009, vol. 450, No. 2, pp. 206-210.
Religa et al., "Elevated cortical zinc in Alzheimer disease," Neurology, 2006, vol. 67, pp. 69-75.
Sewing et al., "High-intensity Raf Signal Causes a Cell Cycle Arrest Mediated by $p21^{Cip1}$," Mol. Cell. Biol., 1997, vol. 17, No. 9, pp. 5588-5597.
Thirumoorthy et al., "A Review of Metallothionein Isoforms and their Role in Pathophysiology," World J Surg Oncol, 2011, vol. 9, 7 pages.
Zhang et al., "4,5-Di-substituted benzyl-imidazol-2-substituted amines as the structure template for the design and synthesis of reversal agents against P-gp-mediated multidrug resistance breast cancer cells.", European Journal of Medicinal Chemistry, vol. 83, Jun. 10, 2014, pp. 74-83.
Zhang et al., "Cooccupancy of the Outer Vestibule of Voltage-Gated Sodium Channels by µ-Conotoxin KIIIA and Saxitoxin or Tetrodotoxin," J Neurophysiol, 2010, vol. 104, No. 1, pp. 88-97.
Zhou et al., "Zinc Supplementation Prevents Alcoholic Liver Injury in Mice through Attenuation of Oxidative Stress," American Journal of Pathology, Jun. 2005, vol. 166, No. 6, pp. 1681-1690.
Japanese Application No. 2016-558138, Office Action dated Dec. 4, 2018, 13 pages.

\* cited by examiner

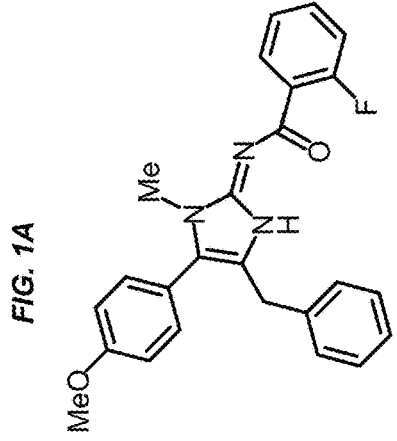

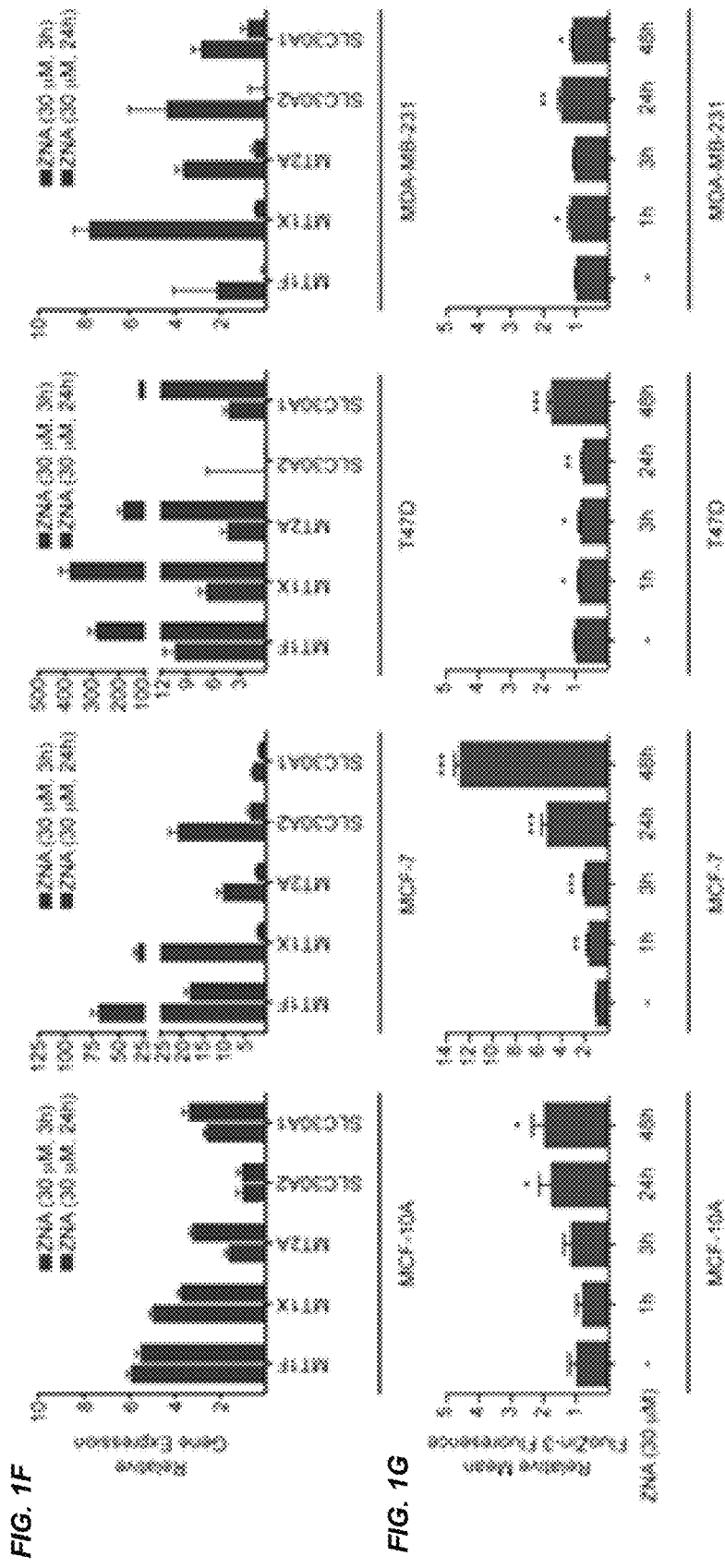

Total zinc concentration (ng Zn per mg total protein) determined by inductively coupled plasma atomic emission spectroscopy

| | MCF-10A | MCF-7 | T47D | MDA-MB-231 |
|---|---|---|---|---|
| Control | ND | ND | ND | ND |
| ZNA (30 μM) | ND | ND | ND | ND |
| ZnSO$_4$ (30 μM) | ND | 0.47 +/- 0.26* | 0.31 +/- 0.07 | ND |
| ZNA + ZnSO$_4$ | ND | 1.35 +/- 0.06 | 0.52 +/- 0.06 | 0.82 +/- 0.08 |

*Values represent mean three independent replicates.*
*ND=not detected/level below instrument threshold; \*average of only two replicates*

FIG. 8

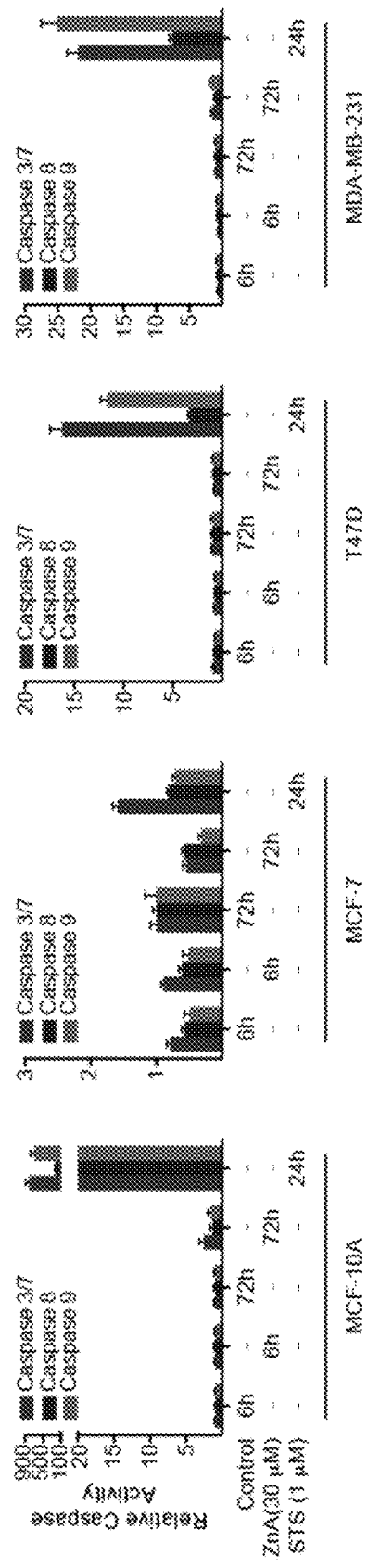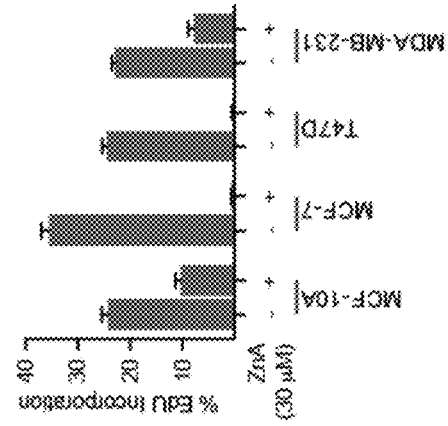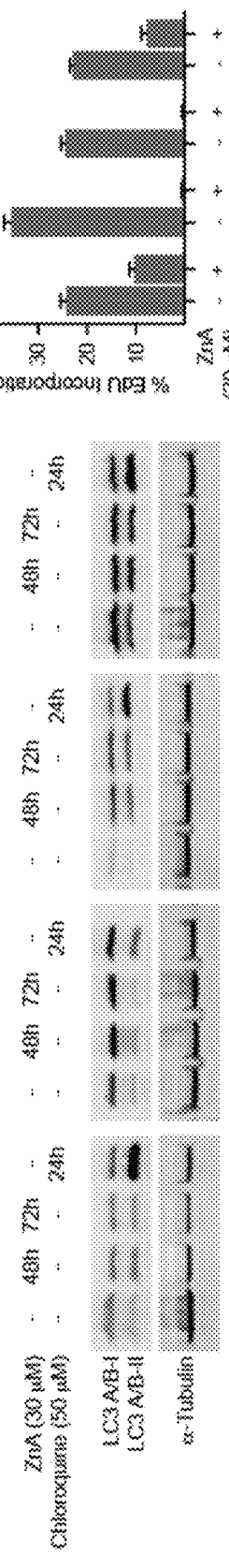
FIG. 10A
FIG. 10B
FIG. 10C

FIG. 11A
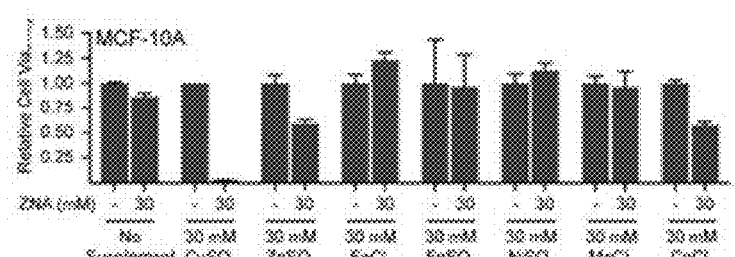
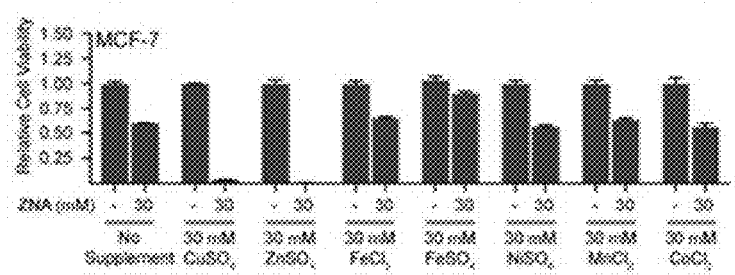
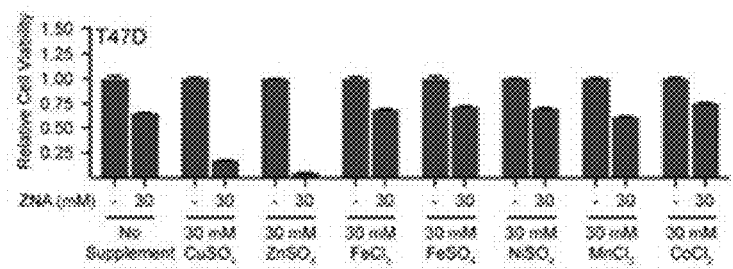
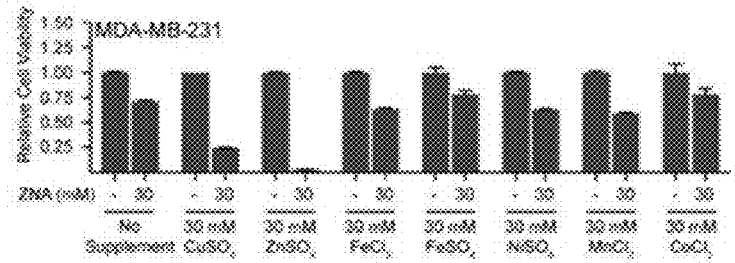
FIG. 11B
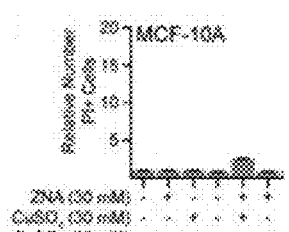
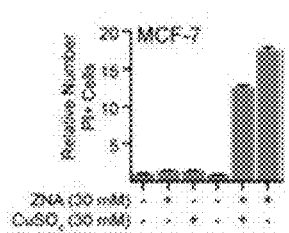
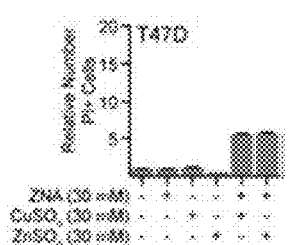
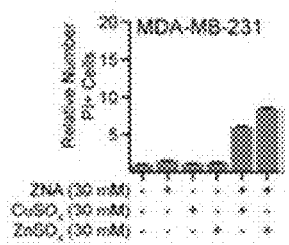

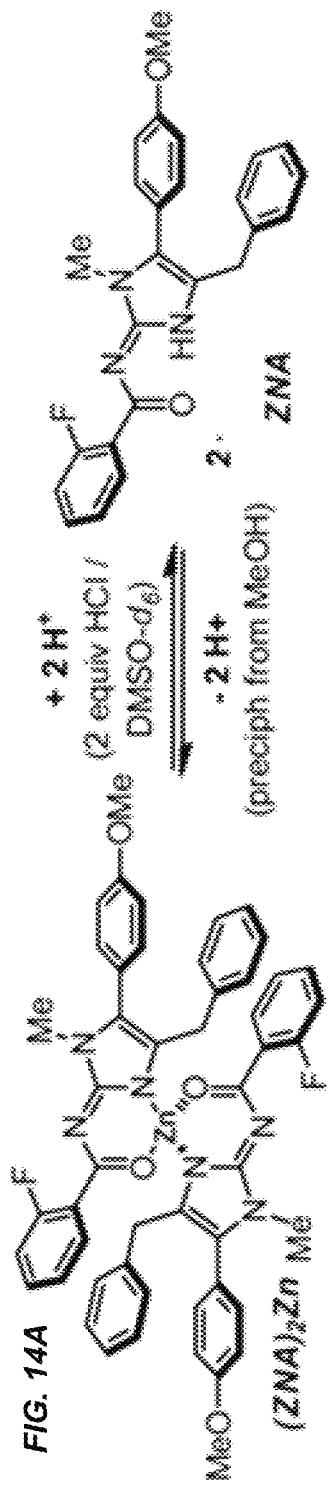
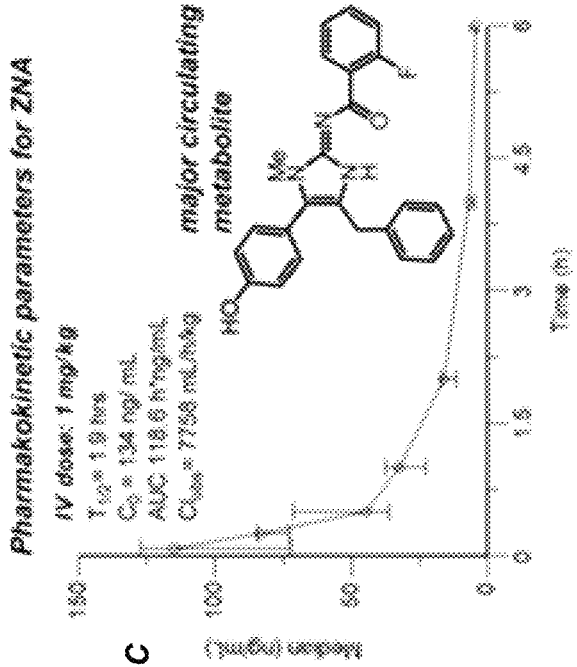
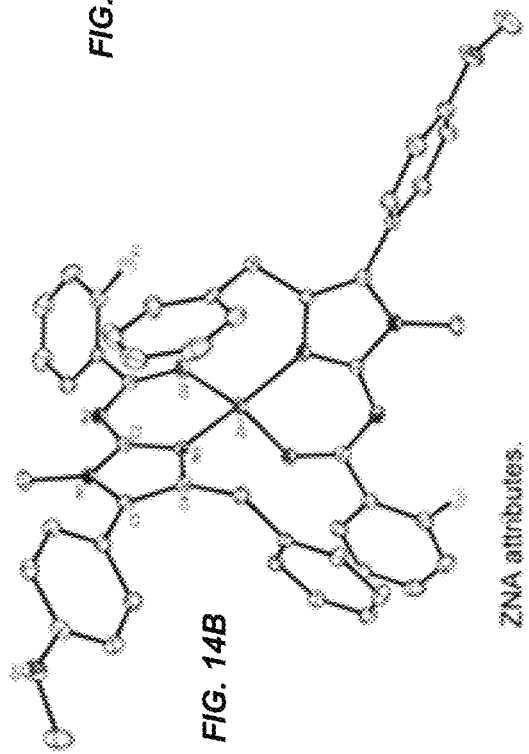
FIG. 14A
FIG. 14B
FIG. 14C

Naamidine A (anti-TB activity)
FIG. 17A
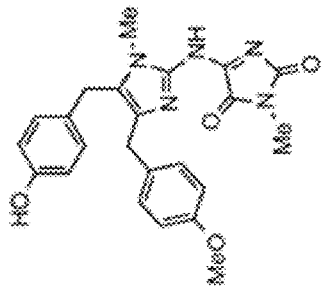
FIG. 17B
$IC_{50}$ = 0.9405 µM, $R^2$ = 0.9800
| Conc'n | % Inhibition | stdv |
|---|---|---|
| 100 µM | 96.38 | 0.42 |
| 50 µM | 95.61 | 0.62 |
| 25 µM | 96.37 | 0.17 |
| 12.5 µM | 93.40 | 0.61 |
| 6.25 µM | 89.83 | 0.66 |
| 3.125 µM | 86.26 | 0.82 |
| 1.5625 µM | 67.47 | 1.86 |
| 0.78125 µM | 44.68 | 2.89 |
| 0.390625 µM | 28.85 | 4.87 |
| 0.195313 µM | 18.78 | 3.68 |
| 0.097656 µM | 22.79 | 4.42 |
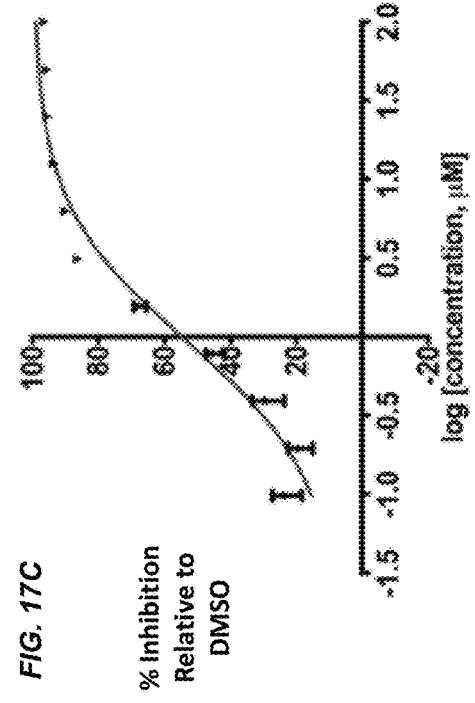
FIG. 17C
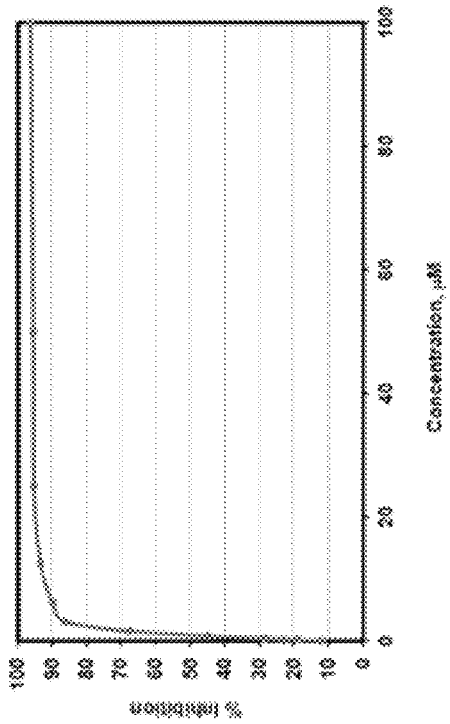
FIG. 17D

```
SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: MT1F Primer, Synthetic

<400> SEQUENCE: 1
agtctctcct cggcttgc                                                 18

<210> SEQ ID NO 2
<211> LENGTH: 21
<212> TYPE: DNA
<213> ORGANISM: Artificial Sequence
<220> FEATURE:
<223> OTHER INFORMATION: MT1F Primer, Synthetic

<400> SEQUENCE: 2
acatctggga gaaaggttgt c                                             21
```

```
<210> SEQ ID NO 3
<211> LENGTH: 21
<212> TYPE: DNA
<213> ORGANISM: Artificial Sequence
<220> FEATURE:
<223> OTHER INFORMATION: MT1X Primer, Synthetic

<400> SEQUENCE: 3
tctccttgcc tcgaaatgga c                                              21

<210> SEQ ID NO 4
<211> LENGTH: 18
<212> TYPE: DNA
<213> ORGANISM: Artificial Sequence
<220> FEATURE:
<223> OTHER INFORMATION: MT1X Primer, Synthetic

<400> SEQUENCE: 4
gggcacactt ggcacagc                                                  18

<210> SEQ ID NO 5
<211> LENGTH: 19
<212> TYPE: DNA
<213> ORGANISM: Artificial Sequence
<220> FEATURE:
<223> OTHER INFORMATION: MT2A Primer, Synthetic

<400> SEQUENCE: 5
ccgactctag ccgcctctt                                                 19

<210> SEQ ID NO 6
<211> LENGTH: 21
<212> TYPE: DNA
<213> ORGANISM: Artificial Sequence
<220> FEATURE:
<223> OTHER INFORMATION: MT2A Primer, Synthetic

<400> SEQUENCE: 6
gtggaagtcg cgttctttac a                                              21

<210> SEQ ID NO 7
<211> LENGTH: 20
<212> TYPE: DNA
<213> ORGANISM: Artificial Sequence
<220> FEATURE:
<223> OTHER INFORMATION: SLC30A2 Primer, Synthetic

<400> SEQUENCE: 7
acagcagcag atcacgaaca                                                20

<210> SEQ ID NO 8
<211> LENGTH: 20
<212> TYPE: DNA
<213> ORGANISM: Artificial Sequence
<220> FEATURE:
<223> OTHER INFORMATION: SLC30A2 Primer, Synthetic

<400> SEQUENCE: 8
ggacaacctt gaccatcctg                                                20

<210> SEQ ID NO 9
<211> LENGTH: 20
<212> TYPE: DNA
<213> ORGANISM: Artificial Sequence
<220> FEATURE:
<223> OTHER INFORMATION: SLC30A1 Primer, Synthetic
```

```
<400> SEQUENCE: 9
tcaccacttc tggggttttc                                          20

<210> SEQ ID NO 10
<211> LENGTH: 20
<212> TYPE: DNA
<213> ORGANISM: Artificial Sequence
<220> FEATURE:
<223> OTHER INFORMATION: SLC30A1 Primer, Synthetic

<400> SEQUENCE: 10
accaggagga gaccaacacc                                          20

<210> SEQ ID NO 11
<211> LENGTH: 18
<212> TYPE: DNA
<213> ORGANISM: Artificial Sequence
<220> FEATURE:
<223> OTHER INFORMATION: GAPDH Reference Gene, Synthetic

<400> SEQUENCE: 11
aaattccatg gcaccgtc                                            18

<210> SEQ ID NO 12
<211> LENGTH: 19
<212> TYPE: DNA
<213> ORGANISM: Artificial Sequence
<220> FEATURE:
<223> OTHER INFORMATION: GAPDH Reference Gene, Synthetic

<400> SEQUENCE: 12
gatggtgatg ggatttcca                                           19
```

COMPOSITIONS AND METHODS COMPRISING 2-(ACYLAMINO)IMIDAZOLES

CROSS-REFERENCES TO RELATED APPLICATION

This application is a continuation of International Application No. PCT/US2015/021602, filed Mar. 19, 2015, which claims the benefit of U.S. Provisional Application Nos. 61/955,761 (filed Mar. 19, 2014) and 62/051,863 (filed Sep. 17, 2014), the entire contents of which are hereby incorporated by reference for all purposes.

STATEMENT AS TO RIGHTS TO INVENTIONS MADE UNDER FEDERALLY SPONSORED RESEARCH AND DEVELOPMENT

Part of the work leading to this invention was carried out with U.S. Government support provided by the National Institute of Health (NIH Grant Nos. R01-RGM090082, P41 GM089158-01, R01-RGM090082-01S1, and R01 CA140296). The U.S. Government therefore has certain rights in this invention.

REFERENCE TO A "SEQUENCE LISTING" SUBMITTED AS AN ASCII FILE

The Sequence Listing written in file 096175-1021509_SEQLIST.TXT, created on Sep. 14, 2016, 2,783 bytes, machine format IBM-PC, MS-Windows operating system, is hereby incorporated by reference in its entirety and for all purposes.

FIELD OF THE INVENTION

In some embodiments, the present invention is directed to compositions and methods comprising 2-(acylamino)imidazoles, including their regioselective preparation and medical uses.

BACKGROUND OF THE INVENTION

Tuberculosis is a world-wide health threat. Agents that can effectively kill this bacterium while maintaining moderate cytotoxicity hold promise to treat this disease in humans. Given the advent of both multi-drug resistant (MDR) and completely drug resistant (XDR) strains of this pathogen, development of a "next-generation" series of small molecules to treat this disease could provide great benefits.

Naamidine A, a natural product isolated from the marine sponge Lucetta chagosensis, displays anti-proliferative activity against both *Mycobacterium tuberculosis* ($IC_{50}$=0.94 µM or 0.41 µg/mL) and *Candida albicans* ($MIC_{100}$=0.78 M). The related natural products kealiinines B and C also display anti-tubercular activity ($IC_{50}$=8.9 µM and 42 µM respectively). Naamidine A has been shown to be relatively well tolerated in vivo for mouse models, with a maximum tolerated dose of 25 mg/Kg (see Ireland et al., *J. Med. Chem.* 1998, 41, 3909). Further, in CEM-TART cells, the $IC_{50}$=34.8 µM, which indicates a selectivity ratio of 37.

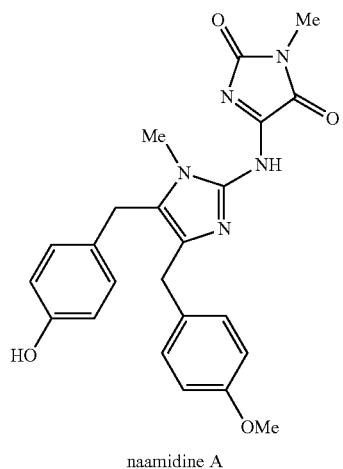 [SMILES: COc1ccc(Cc2nc(NC3=NC(=O)N(C)C3=O)n(C)c2Cc2ccc(O)cc2)cc1]

naamidine A

Naamidine A also displays selective anti-cancer activity of therapeutic interest. See, e.g., U.S. Pat. No. 5,574,057. Many cancer drugs are nearly indiscriminate in their cytotoxicity and affect healthy and tumor cells comparably. The resulting narrow therapeutic treatment windows limit both the amount of drug that can be administered to patients and the duration of treatment, reducing the overall efficacy of the therapy. Additionally, the adverse side effects arising from low therapeutic indices can necessitate additional palliative care efforts and further burden patient recovery. In contrast, naamidine A selectively inhibits proliferation of cancerous cells, thereby providing a potential advantage over less selective agents.

Naamidine A's activity may partially arise from its ability to coordinate zinc. Zinc is an essential trace metal; it is estimated that 10% of the proteome may bind zinc, with 40% of these proteins functioning as transcription factors and the remaining 60% operating in an enzymatic or an ion transport capacity. Andreini et al. J Proteome Res 2005; 5(1): 196-201. Perturbations in zinc homeostasis are correlated with various disease states, and in the case of breast cancer, increased zinc levels have been observed in malignant breast tissue compared to nonmalignant tissue. Margalioth et al. Cancer 1983; 52(5):868-72; Geraki et al. Phys Med Biol 2004; 49(1):99. As such, exploiting differences in zinc homeostasis between healthy and diseased tissue may provide new avenues for the development of anti-cancer therapeutics.

Despite naamidine A's promise as a therapeutic agent, its 1H-imidazole-2,5-dione substituent complicates its preparation and evaluation as a possible drug. Simpler, easier-to-make analogs of naamidine A possessing therapeutically interesting activity, especially anti-tubercular or anti-cancer activity, would present advantages over naamidine A itself, especially if the analogs were available by an efficient synthetic route.

The present invention's 2-aminoimidazole compositions and methods present embodiments with these and other advantages.

BRIEF SUMMARY OF THE INVENTION

In a first embodiment, the invention presents a 2-(acylamino)imidazole compound selected from the group including:

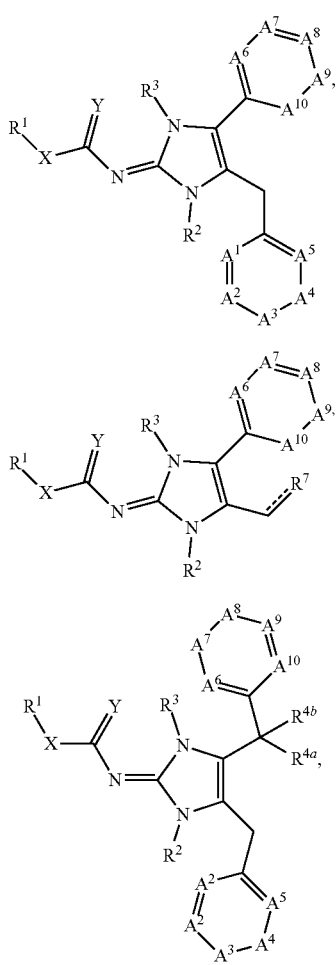

and salts thereof;
wherein:

R¹ is a member selected from the group including alkyl, alkenyl, alkynyl, aryl, arylalkyl, heteroaryl, and heteroarylalkyl;

X is a member selected from the group including a bond, O, and $NR^{5a}$;

Y is a member selected from the group including O, S, or $NR^{5b}$; wherein when X is O or a bond, Y is O;

R² is a member independently selected from the group including hydrogen, alkyl, fluoroalkyl, alkenyl, arylalkyl, acyl, and carbamoyl;

R³ is a member independently selected from the group including hydrogen, alkyl, fluoroalkyl, and arylalkyl;

$R^{4a}$ and $R^{4b}$ are each a member independently selected from the group including hydrogen, alkyl, fluoro, fluoroalkyl, alkenyl, aryl, and heteroaryl; or, alternatively, the two R⁴ join to form a spirocycloalkyl ring;

$R^{5a}$ and $R^{5b}$ are each a member independently selected from the group including hydrogen, alkyl, fluoroalkyl, alkenyl, alkynyl, cycloalkyl, cycloalkylalkyl, arylalkyl, and heteroarylalkyl;

each $A^n$ of the $A^n$ members is independently selected from the group including N and $CR^{6n}$;

each of the $R^{6n}$ members is independently selected from the group including hydrogen, alkyl, hydroxy, alkoxy, aminoalkoxy, alkylamino, alkylaminoalkoxy, alkenyl, alkynyl, aryl, aryloxy, arylamino, cycloalkyl, cycloalkylalkyl, cycloalkoxy, cycloalkylalkoxy, cycloalkylamino, cycloalkylalkylamino, heterocyclyl, heterocyloxy, heterocyclamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, and heteroarylalkylamino; or, alternatively, a pair of adjacent $R^{6n}$ members join to form an additional fused ring that is selected from the group including cycloalkyl, aryl, heterocyclyl, and heterocycloaryl; and R⁷ is a member independently selected from the group including alkyl, aminoalkyl, alkenyl, arylalkyl, and heteroarylalkyl. In a preferred aspect of the first embodiment, the 2-(acylamido)imidazole compound is not a natural product.

In some embodiments, the invention presents a composition for therapeutic use, the composition including a 2-(acylamino)imidazole of one of the aspects herein. In some aspects, the composition further includes a pharmaceutically acceptable excipient.

In a second embodiment, the invention presents a method of killing bacteria in vitro, the method including treating the bacteria with a composition set forth in the first embodiment or one of its aspects.

In a third embodiment, the invention presents a method of killing bacteria in vivo, the method including administering a composition set forth in the first embodiment or one of its aspects to a patient.

In a fourth embodiment, the invention presents a method of treating cancer, the method including administering a composition set forth in the first embodiment or one of its aspects to a patient with cancer, thereby treating the patient.

In a fifth embodiment, the invention presents a method of selectively preparing a 2-acylamino imidazole, the method including the steps:
cyclizing an N-monoprotected α-guanidinyl alkyne reactant to form an 3-N-protected imidazolidin-2-imine product with a 4-exocyclic olefin; and
selectively acylating at the 2-amino position to form a 2-acylamino product;
wherein the 2-acylamino product is substantially free from 1-acyl and 3-acyl regioisomers. In some aspects, the cycling step comprises a π Lewis acid catalyst. In some aspects, the 2-acylamino product is substantially free from $N^2,N^2$-diacyl products.

In a sixth embodiment, the invention presents a method of selectively preparing a 2-acylamino imidazole, the method comprising the steps:
cyclizing an N-acylated α-guanidinyl alkyne reactant to form a 2-acylamino imidazole product. In some aspects, the method comprises a strong Brønsted base catalyst. In some aspects, the 2-acylamino product is substantially free from $N^2,N^2$-diacyl products.

In a seventh embodiment, the invention presents a method of inducing metal ion dyshomeostasis, the method including the steps of:
causing the composition of the first embodiment or one of its aspects to contact a metal ion, thereby forming a chelated complex, wherein the chelated complex forms outside a lysosome;
allowing the chelated complex to enter the lysosome;
allowing the chelated complex to dissociate within the lysosome, thereby increasing the internal concentration of the metal ion. In some aspects, the metal ion is $Zn^{2+}$. In some aspects, the dyshomeostasis causes cell death.

Additional embodiments of the present invention are apparent from the Detailed Description, Examples, and claims.

BRIEF DESCRIPTION OF THE DRAWINGS

FIGS. 1A-1G. FIG. 1A shows the structure of the novel small molecule zinaamidole (ZNA). FIG. 1B shows the dose response measurements following zinaamidole (ZNA) treatment (5 days) in a normal mammary epithelial cell line (MCF-10A) and three breast cancer cell lines (MCF-7, T47D, and MDA-MB-231); additional dose response measurements following ZNA treatment (4 days) in immortalized primary human mammary epithelial cells (hTERT-HMEC) and primary metastatic chemoresistant breast cancer cells (PE1005339). FIG. 1C shows the dose response and cell viability assays for three breast cancer cell lines (MCF-7, T47D, and MDA-MB-231) and an untransformed mammary epithelial cell line (MCF-10A). FIG. 1D shows the effects of 24-hour ZNA exposure on growth after three weeks. FIG. 1E shows the analysis of the most differentially expressed genes as measured by RNA-seq in MCF-7 cells following treatment with ZNA (30 μM, 3 and 12 hours, in triplicate). FIG. 1F shows real-time PCR (RT-PCR) measurements of metal trafficking gene induction following either 3 or 34 hours of treatment with ZNA (30 μM, in quadruplicate). FIG. 1G shows the quantification of intracellular zinc using the fluorescent indicator FluoZin-3; values represent the mean and SEM of three replicates.

FIG. 2A shows the effect on cell viability of ZNA treatment in combination with exogenously added transition metals. Cell viability was quantified by measuring cellular ATP content following 48 hours of treatment. Each value represents the mean and SEM of three replicates normalized to respective controls. FIG. 2B shows the measurement of cell viability following treatment with ZNA in combination with either $ZnSO_4$ or $CuSO_4$. Cells were treated for 24 hours, stained with propidium iodide, and subsequently analyzed by flow cytometry. The values plotted represent the mean and SEM of three replicates.

FIG. 3A shows the quantification of intracellular zinc following treatment with ZNA and $ZnSO_4$ (3 hours) in standard culture media; the fluorescent indicator FluoZin-3 was used to measure intracellular zinc and values represent the mean and SEM of three replicates. FIG. 3B shows the quantification of intracellular zinc following treatment with ZNA and $ZnSO_4$ (3 hours) in zinc-free media using the fluorescent indicator FluoZin-3; values represent the mean and SEM of three replicates.

FIG. 4A shows the measurement of cellular proliferation following treatment with ZNA and $ZnSO_4$ for either 6 or 24 hours. Values represent the mean percent EdU incorporation and SEM of three experimental replicates. FIG. 4B shows the quantification of caspase activity following treatment with ZNA and $ZnSO_4$ for either 6 or 72 hours. Staurosporine (STS) was used as a positive control. The plotted values represent the mean and SEM of three replicates.

FIG. 5A shows the measurement of cell viability following treatment with ZNA in combination with either $ZnSO_4$ and/or the RIP1 kinase inhibitor necrostatin-1 (Nec-1). Cells were treated for 24 hours, stained with propidium iodide, and subsequently analyzed by flow cytometry. The values plotted represent the mean and SEM of three replicates. FIG. 5B shows an immunoblot analysis of the autophagy-associated protein LC3 following treatment of cells with ZNA and $ZnSO_4$. Chloroquine (CQ) was used as a positive control. FIG. 5C shows an analysis of oxidative stress as measured by 2',7'-dichlorodihydrofluorescein diacetate (H2DCFDA, DCF) oxidation following treatment with ZNA and $ZnSO_4$. The values plotted represent the mean and SEM of three replicates.

FIG. 6A shows the results of RT-PCR used to assess mouse metallothionein expression (MT1 and MT2) in murine renal and hepatic tissue. Non-tumor bearing FVB/NJ mice were treated with ZNA (at 100 mg/kg administered via intraperitoneal injection) or a control for either 3 or 24 hours. FIG. 6B shows a Kaplan-Meier survival analysis. FVB mice bearing transplanted PyMT mammary tumors were treated according to the following conditions for 21 days: Control (intraperitoneal PBS injection once per day), ZNA (100 mg/kg, intraperitoneal injection once per day), $ZnSO_4$ (25 mM administered continuously throughout the study via drinking water), or combinatorial treatment (100 mg/kg ZNA, intraperitoneal injection once per day and 25 mM $ZnSO_4$, administered continuously throughout the study via drinking water). Statistical significance: Control versus ZNA,  (p=0.01); $ZnSO_4$ versus combinatorial treatment,  (p=0.007).

FIG. 7 shows the quantification of intracellular zinc following treatment with ZNA and the transcription inhibitor actinomycin D (ACTD) for 24 hours; the fluorescent indicator FluoZin-3 was used to measure intracellular zinc and values represent the mean and SEM of three replicates.

FIG. 8. FIG. 8 shows the quantification of total cellular zinc by inductively coupled plasma atomic emission spectroscopy. Values represent the mean and standard deviation of three independent replicates normalized to total protein.

FIG. 9 shows the analysis of oxidative stress as measured by 2',7'-dichlorodihydrofluorescein diacetate (H2DCFDA, DCF) oxidation following treatment with ZNA and N-acetylcysteine (NAC) for 48 hours. The values plotted represent the mean and SEM of three replicates.

FIGS. 10A-10D. FIG. 10A shows the relative caspase activity measured by Caspase-Glo in four cell lines following treatment with either ZnA (30 μM) or staurosporine (STS, 1 μM) as a positive control. FIG. 10B shows Western blot analyses of the autophagy marker LC3 in four cell lines following treatment with either ZnA (30 μM) or chloroquine (50 μM) as a positive control. FIG. 10C shows the measurement of cell proliferation following treatment with ZnA (30 μM) for 24 hours. FIG. 10D shows a flow cytometry measurement of intracellular DCF oxidation following treatment with ZnA (30 μM).

FIGS. 11A-11C. FIG. 11A shows a measurement of cell viability in four cell lines following treatment with ZnA (30 or 100 μM) in combination with seven different transition metals. Cell viability was measured using an ATPlite assay after 48 hours of treatment. FIG. 11B shows the quantification of cell death by propidium iodide staining and flow cytometry following treatment with ZnA (30 μM) and $CuSO_4$ or $ZnSO_4$ (30 μM) for 24 hours. FIG. 11C shows the analysis of intracellular zinc content following treatment of four cell lines with ZnA (30 μM) and exogenously added $ZnSO_4$ (30 μM) for 3 hours.

FIG. 12 shows a measurement of cell viability of malignant MCF-7 cells and untransformed MCF-10A upon treatment with naamidine A.

FIG. 13A shows the problematic side reaction pathway that preferentially produces a diacyl imidazole product. FIG. 13B shows the synthetic strategy for selective $N^2$ monoacylation.

FIGS. 14A-14C. FIG. 14A shows the precipitation reaction of $Zn^{2+}$ di(naamidine A) complex. FIG. 14B shows the X-ray structure of $Zn^{2+}$ di(naamidine A) complex. FIG. 14C shows the results of initial pharmacokinetic analysis on ZNA at 1 mg/kg IV, 3 mg/kg PO.

FIG. 15 shows a proposed mechanism for $Zn^{2+}$ dyshomeostasis and resulting cell death.

FIG. 16 shows the cell viability of malignant MCF-7 cells and untransformed MCF-10A upon treatment with ZNA analogs, with and without added $ZnSO_4$.

FIGS. 17A-17D. Measurement of antitubercular and antibacterial properties of naamidine A. FIG. 17A shows the structure of naamidine A (NA). FIG. 17B shows the determination of the IC50 against *Mycobacterium tuberculosis*. FIG. 17C shows NA's % inhibition relative to DMSO. FIG. 17D shows NA's % inhibition at different concentrations.

DETAILED DESCRIPTION OF THE INVENTION

Definitions

Figure 2A:
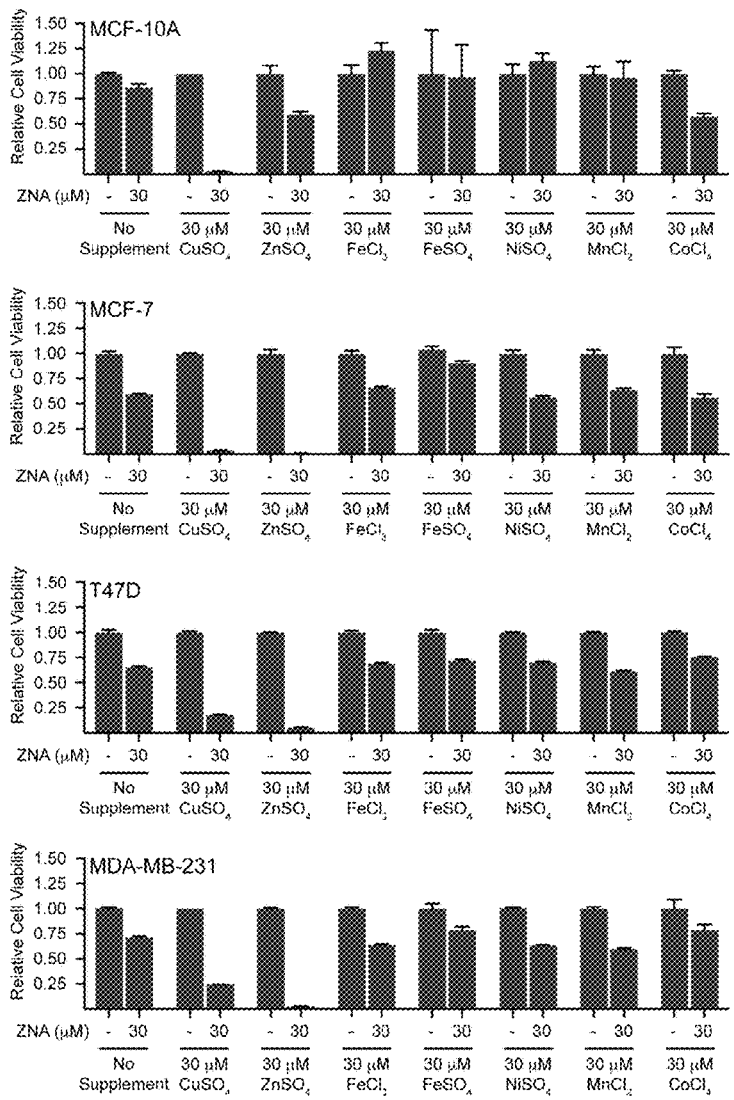
FIGS. 2A-2B.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety, including the U.S. Provisional Application designated by (i.e., U.S. Provisional Appl. No. 62/051,837) and U.S. Pat. Appl. Publ. No. 2013/0197049. In case of conflict, the present specification, including these definitions, will control.

The terms "a," "an," or "the" as used herein not only includes aspects with one member, but also includes aspects with more than one member. For example, an embodiment including "a 2-(acylamino)imidazole and an excipient" should be understood to present certain aspects with at least a second 2-(acylamino)imidazole, at least a second excipient, or both.

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1.

When the term "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%." However, when the modifier "about" is applied to describe only the end of a range or only a later value in a set of values, it applies only to that value or that end of the range. Thus, the range "about 2 to 10" is the same as "about 2 to about 10," but the range "2 to about 10" is not.

The term "acyl" as used herein includes an alkanoyl, aroyl, heterocycloyl, or heteroaroyl group as defined herein. Examples of acyl groups include, but are not limited to, acetyl, benzoyl, and nicotinoyl.

The term "agent" as used herein includes a compound or mixture of compounds that, when added to a composition, tend to produce a particular effect on the composition's properties. For example, a composition comprising a thickening agent is likely to be more viscous than an otherwise identical comparative composition that lacks the thickening agent.

The term "alkanoyl" as used herein includes an alkyl-C(O)— group wherein the alkyl group is as defined herein. Examples of alkanoyl groups include, but are not limited to, acetyl and propanoyl.

The term "alkenyl" as used herein includes a straight or branched chain hydrocarbon containing at least one carbon-carbon double bond. The chain may contain an indicated number of carbon atoms. For example, "$C_1$-$C_{12}$ alkenyl" indicates that the group may have from 1 to 12 (inclusive) carbon atoms and at least one carbon-carbon double bond. When the indicated number of carbon atoms is 1, then the $C_1$ alkenyl is double bonded to a carbon (i.e., a carbon analog to an oxo group). In certain aspects, the chain includes 1 to 12, about 2 to 15, about 2 to 12, about 2 to 8, or about 2 to 6 carbon atoms. Examples of an alkenyl group may include, but are not limited to, ethenyl (i.e., vinyl), allyl, propenyl, butenyl, crotyl, pentenyl, hexenyl, heptenyl, octenyl, nonenyl, decenyl, dodecenyl, cyclopentenyl, cyclohexenyl, 2-isopentenyl, allenyl, butadienyl, pentadienyl, 3-(1,4-pentadienyl), and hexadienyl.

In one aspect, an alkenyl group is unsubstituted. In one aspect, an alkenyl group is optionally substituted. When optionally substituted, one or more hydrogen atoms of the alkenyl group (e.g., from 1 to 4, from 1 to 2, or 1) may be replaced with a moiety independently selected from the group consisting of fluoro, hydroxy, alkoxy, amino, alkylamino, acylamino, thio, and alkylthio, with the proviso that no hydrogen atom substituent on the carbon-carbon double bond is replaced by a hydroxy, amino, or thio group.

As used herein, the term "alkoxy" refers to a straight or branched chain saturated or unsaturated hydrocarbon containing at least one oxygen atom in an ether group (e.g., EtO—). The chain may contain an indicated number of carbon atoms. For example, "$C_1$-$C_{12}$ alkoxy" indicates that the group may have from 1 to 12 (inclusive) carbon atoms and at least one oxygen atom. Examples of $C_1$-$C_{12}$ alkoxy groups include, but are not limited to, methoxy, ethoxy, isopropoxy, butoxy, n-pentoxy, isopentoxy, neopentoxy, and hexoxy.

An alkoxy group can be unsubstituted or optionally substituted. When optionally substituted, one or more hydrogen atoms of the alkoxy group (e.g., from 1 to 4, from 1 to 2, or 1) may be replaced with one or more moieties independently selected from the group including fluoro, hydroxy, alkoxy, amino, alkylamino, acylamino, thio, and alkylthio, with the proviso that any hydrogen atom alpha to the ether oxygen, if replaced, may only be replaced by fluoro or alkoxy.

The term "alkyl" as used herein includes an aliphatic hydrocarbon chain that may be straight chain or branched. The chain may contain an indicated number of carbon atoms: For example, $C_1$-$C_{12}$ indicates that the group may have from 1 to 12 (inclusive) carbon atoms in it. If not otherwise indicated, an alkyl group about 1 to about 20 carbon atoms. In one aspect, alkyl groups have 1 to about 12 carbon atoms in the chain. In another aspect, alkyl groups ("lower alkyl") have 1 to about 6 carbon atoms in the chain. Examples may include, but are not limited to, methyl, ethyl, propyl, isopropyl (iPr), 1-butyl, 2-butyl, isobutyl (iBu), tert-butyl, pentyl, 2-methylbutyl, 1,1-dimethylpropyl, hexyl, heptyl, octyl, nonyl, decyl, docecyl, cyclopentyl, or cyclohexyl. In one aspect, an alkyl group can exclude methyl (e.g., 2 to 6 carbon atoms in the chain).

An alkyl group can be unsubstituted or optionally substituted. When optionally substituted, one or more hydrogen atoms of the alkyl group (e.g., from 1 to 4, from 1 to 2, or 1) may be replaced with a moiety independently selected from the group consisting of fluoro, hydroxy, alkoxy, amino, alkylamino, acylamino, thio, and alkylthio.

The term "alkynyl" as used herein includes a straight, branched, or cyclic hydrocarbon containing at least one carbon-carbon triple bond. Examples may include, but are not limited to, ethynyl, propargyl, propynyl, butynyl, pentynyl, hexynyl, heptynyl, octynyl, nonynyl, decynyl, or decynyl.

An alkynyl group can be unsubstituted or optionally substituted. When optionally substituted, one or more hydrogen atoms of the alkynyl group (e.g., from 1 to 4, from 1 to 2, or 1) may be replaced with a moiety independently selected from the group consisting of fluoro, hydroxy, alkoxy, amino, alkylamino, acylamino, thio, and alkylthio, with the proviso that no sp hydrogen atom substituent is replaced by a hydroxy, amino, or thio group.

As used herein, the term "2-aminoimidazole" refers to a compound having the general ring formula:

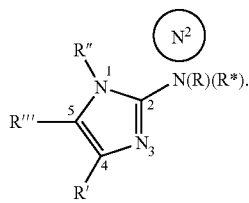

In this formula, "$N^2$" or "N2" references the 2-amino substituent, which is a site for possible reaction (e.g., acylation or diacylation). In some embodiments, a 2-aminoimidazole may be a tautomeric form of general ring formula:

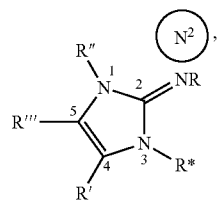

In some aspects of the present application's invention, the ring substituents are as otherwise defined herein (e.g., one of the R groups is acyl; claim 1; and the like).

The term "aroyl" as used herein includes an aryl-CO— group wherein aryl is as defined herein. Examples include, but are not limited to, benzoyl, naphth-1-oyl and naphth-2-oyl.

The term "aryl" as used herein includes cyclic aromatic carbon ring systems containing from 6 to 18 carbons. Examples of an aryl group include, but are not limited to, phenyl, naphthyl, anthracenyl, tetracenyl, biphenyl and phenanthrenyl.

An aryl group can be unsubstituted or optionally substituted. When optionally substituted, one or more hydrogen atoms of the aryl group (e.g., from 1 to 5, from 1 to 2, or 1) may be replaced with a moiety independently selected from the group consisting of alkyl, cyano, acyl, halo, hydroxy, alkoxy, amino, alkylamino, acylamino, thio, and alkylthio.

As used herein, the terms "arylalkyl" and "aralkyl," which are used interchangeably, include an alkyl group as defined herein where at least one hydrogen substituent has been replaced with an aryl group as defined herein. Examples include, but are not limited to, benzyl, 1-phenylethyl, 4-methylbenzyl, and 1,1,-dimethyl-1-phenylmethyl.

As used herein, the term "Brønsted base" refers to a compound capable of accepting a proton (i.e., $H^+$) from a Brønsted acid. Typically, strong Brønsted bases are characterized by $pK_b$ values around or below about 5. Examples of strong Brønsted bases include but are not limited to, sodium hydroxide, lithium hydroxide, potassium carbonate, Huenig's base (i.e., N,N-diisopropylethylamine), lutidines including 2,6-lutidine (i.e., 2,6-dimethylpyridine), and triethylamine.

As used herein, the term "catalyst" refers to a substance that participates in a chemical reaction so as to increase the rate of the reaction, but that is itself not consumed in the reaction. Examples of catalysts include, but are not limited to, metals, metal oxides, metal complexes, acids, and bases.

A group can be unsubstituted or optionally substituted as per its component parts. For example, but without limitation, the aryl group of an arylalkyl group can be substituted, such as in the arylalkyl group 4-methylbenzyl. In some preferred embodiments, a group includes at most three independently selected optional substituents, and these substituents do no include further optional substituents. In some embodiments, a group includes at most three independently selected optional substituents, but these substituents include further optional substituents.

The linking term "comprising" or "comprise" as used herein is not closed. For example, "a composition comprising A" must include at least the component A, but it may also include one or more other components (e.g., B; B and C; B, C, and D; and the like).

The term "cycloalkyl" as used herein includes a cyclic hydrocarbon group that may contain an indicated number of carbon atoms: For example, $C_3$-$C_{12}$ indicates that the group may have from 3 to 12 (inclusive) carbon atoms in it. If not otherwise indicated, a cycloalkyl group includes about 3 to about 20 carbon atoms. In one aspect, cyclo alkyl groups have 3 to about 12 carbon atoms in the group. In another aspect, cycloalkyl groups have 3 to about 7 carbon atoms in the group. Examples may include, but are not limited to, cyclopropyl, cyclobutyl, cyclopentyl, cyclohexyl, 4,4-dimethylcyclohexyl, and cycloheptyl.

A cycloalkyl group can be unsubstituted or optionally substituted. When optionally substituted, one or more hydrogen atoms of the cycloalkyl group (e.g., from 1 to 4, from 1 to 2, or 1) may be replaced with a moiety independently selected from the group consisting of fluoro, hydroxy, alkoxy, amino, alkylamino, acylamino, thio, and alkylthio. In one aspect, a substituted cycloalkyl group can incorporate an exo- or endocyclic alkene (e.g., cyclohex-2-en-1-yl).

The terms "disorder," "disease," and "condition" are used herein interchangeably for a condition in a subject. A disorder is a disturbance or derangement that affects the normal function of the body of a subject. A disease is a pathological condition of an organ, a body part, or a system resulting from various causes, such as infection, genetic defect, or environmental stress that is characterized by an identifiable group of symptoms.

The term "effective amount" or "effective dose" as used herein includes an amount sufficient to achieve the desired result and accordingly will depend on the ingredient and its desired result. Nonetheless, once the desired effect is identified, determining the effective amount is within the skill of a person skilled in the art.

As used herein, "fluoroalkyl" includes an alkyl group wherein the alkyl group includes one or more fluoro-substituents. Examples include, but are not limited to, trifluoromethyl.

As used herein, "geminal" substitution includes two or more substituents that are directly attached to the same atom. An example is 3,3-dimethyl substitution on a cyclohexyl or spirocyclohexyl ring.

As used herein, "halo" or "halogen" includes fluoro, chloro, bromo, or iodo. In one aspect, "halo" includes fluoro or chloro.

The term "heteroaryl" includes mono and bicyclic aromatic groups of about 4 to about 14 ring atoms (e.g., 4 to 10 or 5 to 10 atoms) containing at least one heteroatom. Heteroatom as used in the term heteroaryl refers to oxygen, sulfur and nitrogen. A nitrogen atom of a heteroaryl is optionally oxidized to the corresponding N-oxide. Examples include, but are not limited to, pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl.

A heteroaryl group can be unsubstituted or optionally substituted. When optionally substituted, one or more hydrogen atoms of the heteroaryl group (e.g., from 1 to 5, from 1 to 2, or 1) may be replaced with a moiety independently selected from the group consisting of alkyl, cyano, acyl, halo, hydroxy, alkoxy, amino, alkylamino, acylamino, thio, and alkylthio.

The term "heteroaroyl" as used herein includes a heteroaryl-C(O)— group wherein heteroaryl is as defined herein. Heteroaroyl groups include, but are not limited to, thiophenoyl, nicotinoyl, pyrrol-2-ylcarbonyl, and pyridinoyl.

The term "heterocycloyl" as used herein includes a heterocyclyl-C(O)— group wherein heterocyclyl is as defined herein. Examples include, but are not limited to, N-methyl prolinoyl and tetrahydrofuranoyl.

As used herein, "heterocyclyl" includes a non-aromatic saturated monocyclic or multicyclic ring system of about 4 to about 10 ring atoms (e.g., 5 to about 8 ring atoms, or 5 to about 6 ring atoms), in which one or more of the atoms in the ring system is an element or elements other than carbon, e.g., nitrogen, oxygen or sulfur. A heterocyclyl group optionally comprises at least one $sp^2$-hybridized atom (e.g., a ring incorporating an carbonyl, endocyclic olefin, or exocyclic olefin). In some embodiments, a nitrogen or sulfur atom of the heterocyclyl is optionally oxidized to the corresponding N-oxide, S-oxide or S,S-dioxide. Examples of monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

A heterocycyl group can be unsubstituted or optionally substituted. When optionally substituted, one or more hydrogen atoms of the group (e.g., from 1 to 4, from 1 to 2, or 1) may be replaced with a moiety independently selected from the group consisting of fluoro, hydroxy, alkoxy, amino, alkylamino, acylamino, thio, and alkylthio. In one aspect, a substituted heterocycyl group can incorporate an exo- or endocyclic alkene.

The term "hydrophobic moiety" or "hydrophobic group" as used herein includes a moiety or a functional group that repels water. Examples may include, but are not limited to, a non-polar moiety, such as an unsubstituted alkyl group having more than five carbons, phenyl group and an anthracenyl group.

As used herein, the terms "hydrophilic moiety" or "hydrophilic group" includes a moiety or a functional group that has a strong affinity to water. Examples may include, but are not limited to, a charged moiety, such as cationic moiety and anionic moiety, or a polar uncharged moiety, such as an alkoxy group and amine group.

As used herein, the term "hydroxyalkyl" includes an alkyl group where at least one hydrogen substituent has been replaced with an alcohol (—OH) group. In certain aspects, the hydroxyalkyl group has one alcohol group. In certain aspects, the hydroxyalkyl group has one or two alcohol groups, each on a different carbon atom. In certain aspects, the hydroxyalkyl group has 1, 2, 3, 4, 5, or 6 alcohol groups. Examples may include, but are not limited to, hydroxymethyl, 2-hydroxyethyl, and 1-hydroxyethyl.

When any two substituent groups or any two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different).

As used herein, the term "π Lewis acid" refers to a compound of atomic number 19 or higher that is capable of accepting electrons from an electron-donating Lewis base and forming a Lewis adduct by sharing the electrons donated by the Lewis base. Examples of π Lewis acids include, but are not limited to titanium(IV) chloride ($TiCl_4$), iron(III) chloride ($FeCl_3$), iron(III) bromide ($FeBr_3$), tin(IV) chloride ($SnCl_4$), and the like.

As used herein, "or" should in general be construed non-exclusionarily. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

As used herein, the term "salt" refers to acid or base salts of a compound, e.g., ZNA or another 2-(acylamino)imidazole. Illustrative examples of pharmaceutically acceptable salts are cationic salts such as alkali and alkaline earth metal (such as sodium, lithium, potassium, calcium, and magnesium) salts, ammonium (ammonium, trimethyl ammonium, diethylammonium, and tris-(hydroxymethyl)-methyl-ammonium) salts, mineral acid (hydrochloric acid, hydrobromic acid, phosphoric acid, and the like) salts, organic carboxylic acid (acetic acid, propionic acid, glutamic acid, citric acid, and the like) salts, organic sulfonic acid (methanesulfonic acid) salts, and quaternary ammonium (methyl iodide, ethyl iodide, and the like) salts. Additional information on suitable pharmaceutically acceptable salts can be found in Remington's, Pharmaceutical Sciences (current edition), Mack Publishing Co., Easton, Pa., which is incorporated herein by reference.

The terms "a salt thereof," "salt thereof," or "salts thereof" can be applied to any preceding member of an associated Markush group. For example, a group consisting of A, B, C, and salts thereof would include within its scope embodiments that were a salt of A, embodiments that were a salt of B, and embodiments that were a salt of C.

As used herein, "spirocycloalkyl" as used herein includes a cycloalkyl in which geminal substituents on a carbon atom are replaced to join in forming a 1,1-substituted ring. For example, but without limitation, for a —C(R$^1$)(R$^2$)— group that was part of a longer carbon chain, if R$^1$ and R$^2$ joined to form a cyclopropyl ring incorporating the carbon to which R$^1$ and R$^2$ were bonded, this would be a spirocycloalkyl group (i.e., spirocyclopropyl).

As used herein, "spiroheterocyclyl" as used herein includes a heterocycloalkyl in which geminal substituents on a carbon atom are replaced to join in forming a 1,1-substituted ring. For example, but without limitation, for a —C(R$^1$)(R$^2$)— group that was part of a longer carbon chain, if R$^1$ and R$^2$ joined to form a pyrrolidine ring incorporating the carbon to which R$^1$ and R$^2$ were bonded, this would be a spiroheterocyclyl group.

As used herein, the term "treat," "treating," or "treatment" includes administering or applying a composition (e.g., a composition described herein) in an amount, manner (e.g., schedule of administration), and mode (e.g., route of administration) that is effective to improve a disorder or a symptom thereof, or to prevent, to retard, or to slow the progression of a disorder or a symptom thereof. Such improvements can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable.

"Treating" and "treatment" as used herein also include prophylactic treatment. In certain embodiments, treatment methods comprise administering to a subject a therapeutically effective amount of an active agent. The administering step may consist of a single administration or may comprise a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In one aspect, chronic administration may be required. For example, the compositions are administered to the subject in an amount, and for a duration, sufficient to treat the patient.

In the Summary of the Invention above, Detailed Description, and the claims below, reference is made to particular features and aspects of the invention, including method steps. The disclosure of the invention in this specification includes all possible combinations of such particular features within the embodiments of the invention disclosed, at least to the extent that such combinations are non-contradictory. For example, if the Detailed Description presents aspects A, B, and C of an embodiment, it is understood that this also discloses particular embodiments including both aspects A and B, both aspects B and C, and both aspects A and C, as well as an embodiment with aspects A, B, and C.

Compositions

In a first embodiment, the invention presents a 2-(acylamino)imidazole compound selected from the group including:

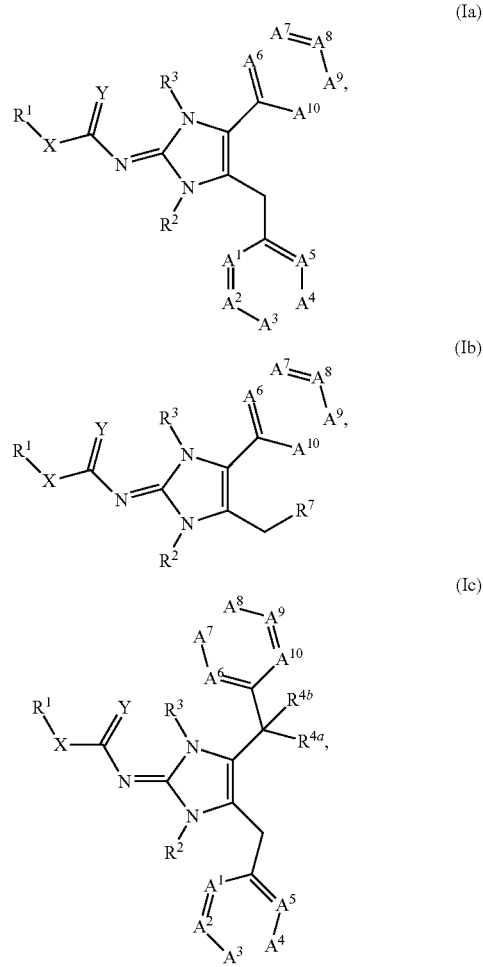

and salts thereof;
wherein:
R$^1$ is a member selected from the group including alkyl, alkenyl, alkynyl, aryl, arylalkyl, heteroaryl, and heteroarylalkyl;
X is a member selected from the group including a bond, O, and NR$^{5a}$;
Y is a member selected from the group including O, S, or NR$^{5b}$; wherein when X is O or a bond, Y is O;
R$^2$ is a member independently selected from the group including hydrogen, alkyl, fluoroalkyl, alkenyl, arylalkyl, acyl, and carbamoyl;
R$^3$ is a member independently selected from the group including hydrogen, alkyl, fluoroalkyl, and arylalkyl;

$R^{4a}$ and $R^{4b}$ are each a member independently selected from the group including hydrogen, alkyl, fluoro, fluoroalkyl, alkenyl, aryl, and heteroaryl; or, alternatively, the two $R^4$ join to form a spirocycloalkyl ring;

$R^{5a}$ and $R^{5b}$ are each a member independently selected from the group including hydrogen, alkyl, fluoroalkyl, alkenyl, alkynyl, cycloalkyl, cycloalkylalkyl, arylalkyl, and heteroarylalkyl;

each $A^n$ of the $A^n$ members is independently selected from the group including N and $CR^{6n}$;

each of the $R^{6n}$ members is independently selected from the group including hydrogen, alkyl, hydroxy, alkoxy, aminoalkoxy, alkylamino, alkylaminoalkoxy, alkenyl, alkynyl, aryl, aryloxy, arylamino, cycloalkyl, cycloalkylalkyl, cycloalkoxy, cycloalkylalkoxy, cycloalkylamino, cycloalkylalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, and heteroarylalkylamino; or, alternatively, a pair of adjacent $R^{6n}$ members join to form an additional fused ring that is selected from the group including cycloalkyl, aryl, heterocyclyl, and heterocycloaryl; and $R^7$ is a member independently selected from the group including alkyl, alkenyl, arylalkyl, and heteroarylalkyl;

wherein the 2-aminoimidazole compound is not a natural product.

In one aspect, the invention sets forth the composition described above, wherein the 2-(acylamino)imidazole compound is

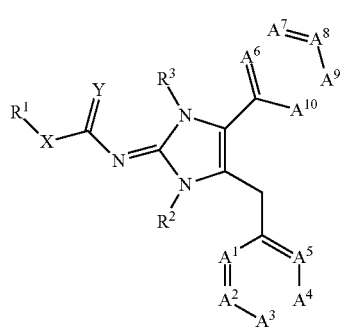

(Ia)

or a salt thereof.

Preferably, the 2-(acylamino)imidazole compound of Formula Ia is substantially free from a regioisomeric compound:

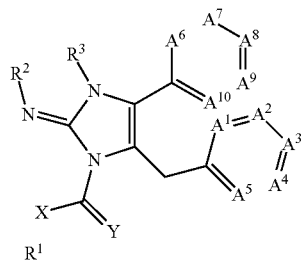

(IIa)

or a salt thereof.

In one aspect, the invention sets forth the composition described above, wherein the 2-(acylamino)imidazole compound is

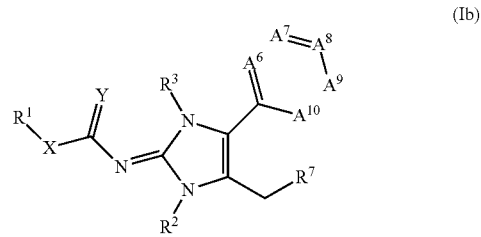

(Ib)

or a salt thereof.

In a preferred aspect, the 2-(acylamino)imidazole compound of Formula Ib is substantially free from a regioisomeric compound

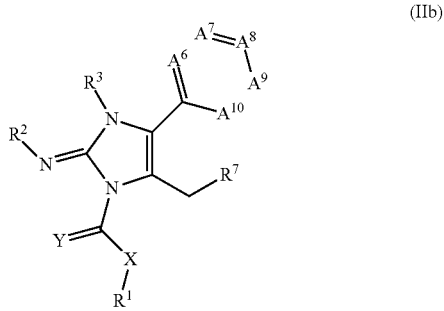

(IIb)

or a salt thereof.

In one aspect, the invention sets forth the composition described above, wherein the 2-aminoimidazole compound is

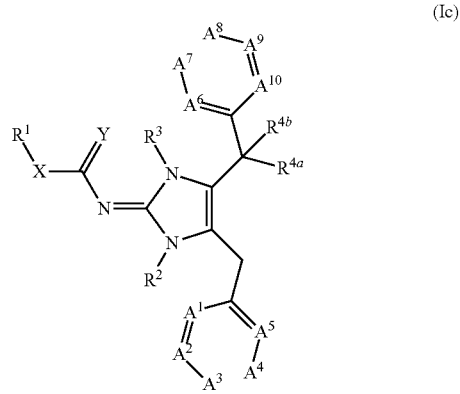

(Ic)

or a salt thereof.

In a preferred aspect, the 2-(acylamino)imidazole compound of Formula Ic is substantially free from a regioisomeric compound (IIc)

or a salt thereof.

In a preferred aspect, the 2-(acylamino)imidazole compound of Formula Ia, Ib, or Ic is substantially free from a $N^2,N^2$-diacyl compound or a salt thereof;
wherein $R^4$ is $R^2$ or $R^3$.

In one aspect, $R^1$ is a member selected from the group including alkyl, aryl, arylalkyl, and heteroaryl. In a more specific aspect, $R^1$ is a member selected from the group including isopropyl, sec-butyl, phenyl, 2-fluorophenyl, 2,4-dichlorophenyl, and 2-thiazolyl. In an alternative more specific aspect, $R^1$ is a member selected from the group including phenyl, 2-fluorophenyl, 3-trifluoromethylphenyl, 4-chlorophenyl, 4-methoxyphenyl, and cyclopropyl.

In one aspect, $R^1$ is alkyl. In a more specific aspect, $R^1$ is methyl, ethyl, isopropyl, sec-butyl, or tert-butyl. In a more specific aspect, $R^1$ is isopropyl or sec-butyl. In a more specific aspect, $R^1$ is tert-butyl.

In one aspect, $R^1$ is alkenyl. In a more specific aspect, $R^1$ is allyl or methallyl.

In one aspect, $R^1$ is alkynyl. In a more specific aspect, $R^1$ is propargyl.

In one aspect, $R^1$ is aryl. In a more specific aspect, $R^1$ is phenyl. In an alternative aspect, $R^1$ is halophenyl. In a more specific aspect, $R^1$ is 2-fluorophenyl or 2,4-dichlorophenyl.

In one aspect, $R^1$ is arylalkyl. In a more specific aspect, $R^1$ is benzyl.

In one aspect, $R^1$ is heteroaryl. In a more specific aspect, $R^1$ is 4-, 3-, or 2-pyridyl.

In one aspect, $R^1$ is heteroarylalkyl. In a more specific aspect, $R^1$ is 4-, 3-, or 2-pyridylmethyl.

In one aspect, X is a bond. In an alternative aspect, X is O. In an alternative aspect, X is $NR^{5a}$.

In one aspect, Y is O. In an alternative aspect, Y is $NR^{5b}$.

In one aspect, $R^2$ is a member independently selected from the group including hydrogen, alkyl, acyl, and carbamoyl. In a more specific aspect, $R^2$ is a member independently selected from the group including hydrogen and carbamoyl.

In a still more specific aspect, $R^2$ is a member independently selected from the group including hydrogen, tert-butyloxycarbonyl (Boc), and benzyloxycarbonyl (Cbz).

In one aspect, $R^3$ is alkyl. In a more specific aspect, $R^3$ is methyl. In one aspect, $R^3$ is allyl.

In one aspect, $R^{4a}$ and $R^{4b}$ are each a member independently selected from the group including hydrogen, alkyl, fluoro, and fluoroalkyl. In a more specific aspect, $R^{4a}$ and $R^{4b}$ are hydrogen.

In one aspect, $R^{5a}$ and $R^{5b}$ are each a member independently selected from the group including hydrogen, alkyl, fluoroalkyl, alkenyl, alkynyl, cycloalkyl, cycloalkylalkyl, arylalkyl, and heteroarylalkyl.

In one aspect, each $A^n$ of the $A^n$ members is an independently selected $CR^{6n}$. In an alternative aspect, only one of the $A^n$ members is N. In an alternative aspect, only two of the $A^n$ members are N. In an alternative aspect, only three of the $A^n$ members are N.

In one aspect, each of the $R^{6n}$ members is independently selected from the group including hydrogen, alkyl, hydroxy, alkoxy, aryl, aryloxy, cycloalkyl, cycloalkoxy, cycloalkylalkoxy, heterocyclyl, heterocycyloxy, halo, fluoroalkyl, fluoroalkyloxy, heteroaryl, heteroaryloxy, arylalkyl, arylalkyloxy, arylalkylamino, and heteroarylalkyloxy. In a more specific aspect, each of the $R^{6n}$ members is independently selected from the group including hydrogen, alkyl, hydroxy, alkoxy, cycloalkylalkoxy, halo, fluoroalkyl, fluoroalkyloxy, and arylalkyloxy. In a still more specific aspect, each of the $R^{6n}$ members is independently selected from the group including hydrogen, alkyl, hydroxy, and alkoxy.

In one aspect, $A^3$ is C(OH) or C(OMe). In an alternative aspect, $A^3$ is CH, CCl, C(OMe), or In one aspect, $A^8$ is C(OH) or C(OMe). In an alternative aspect, $A^8$ is CH, CCl, C(OMe), or In one aspect, at least four of the $R^{6n}$ members are hydrogen. In a more specific aspect, at least six of the $R^{6n}$ members are hydrogen. In a still more specific aspect, at least eight of the $R^{6n}$ members are hydrogen.

In one aspect, $R^7$ is alkyl or heteroarylalkyl.

In one aspect, $R^7$ is aminoalkyl or alkylaminoalkyl. In a more specific aspect, $R^7$ is morpholinylmethyl.

In one aspect, $R^7$ is cycloalkyl. In a more specific aspect, $R^7$ is cyclopropyl.

In a more specific aspect, the invention sets forth the composition comprising a 2-(acylamino)imidazole compound

19

(IIIa)

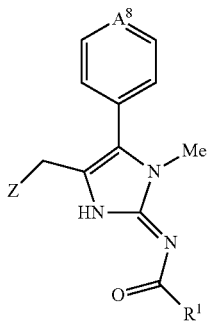

and a salt thereof;

wherein $R^1$ and Z are each selected from the group including phenyl, 2-fluorophenyl, 3-trifluoromethylphenyl, 4-chlorophenyl, 4-methoxyphenyl, and cyclopropyl; and wherein $A^3$ is selected from the group including CH, CCl, C(OMe), and

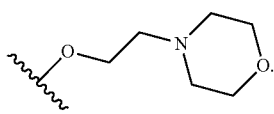 [SMILES: *OCCN1CCOCC1]

In a more specific aspect, the invention sets forth the composition comprising a 2-(acylamino)imidazole compound (IIIa)

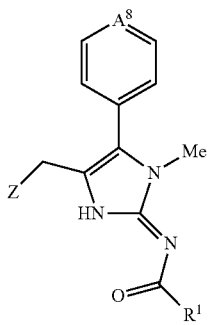

and a salt thereof, wherein $R^1$ and Z are each selected from the group including phenyl, 2-fluorophenyl, 2,4-dichlorophenyl, 2-thiazolyl, isopropyl, and sec-butyl; and wherein $A^3$ is selected from the group including CH and C(OMe).

In one aspect,

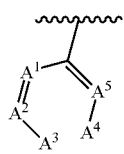

20 is a phenol. In a more specific aspect,

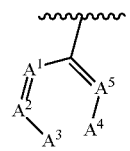

is a p-phenol (e.g., 4-hydroxyphenyl).

In one aspect,

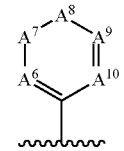

is a phenol. In a more specific aspect,

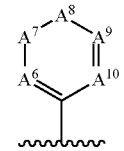

is a p-phenol (e.g., 4-hydroxyphenyl).

In a more specific aspect, the invention sets forth the composition comprising a 2-(acylamino)imidazole compound (IIIb)

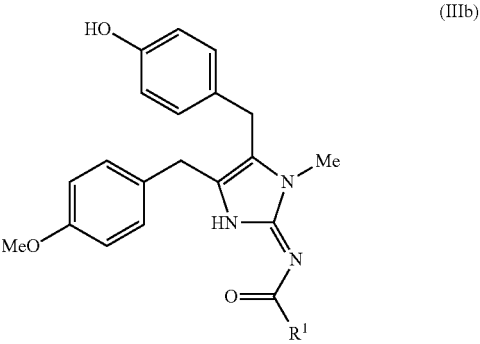

and a salt thereof;

wherein $R^1$ is selected from the group including phenyl, 2-fluorophenyl, 2,4-dichlorophenyl, 2-thiazolyl, isopropyl, and sec-butyl.

In a more specific aspect, the invention sets forth the composition comprising a 2-(acylamino)imidazole compound selected from the group including:

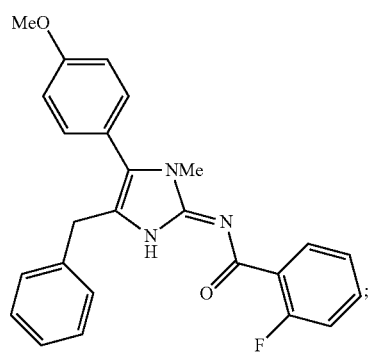
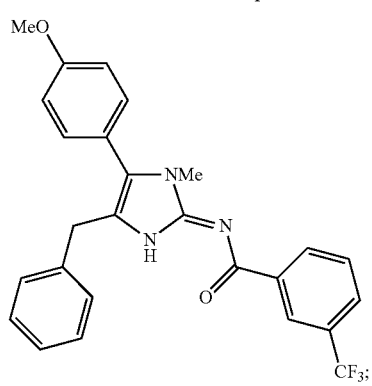
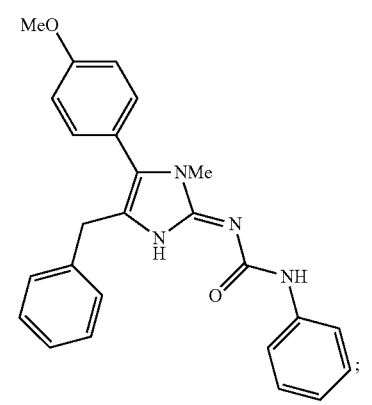
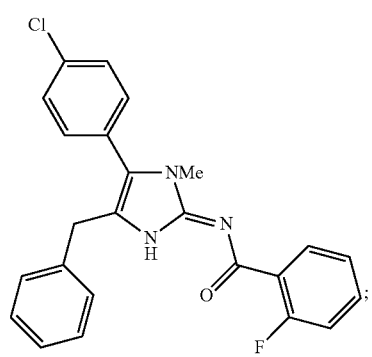
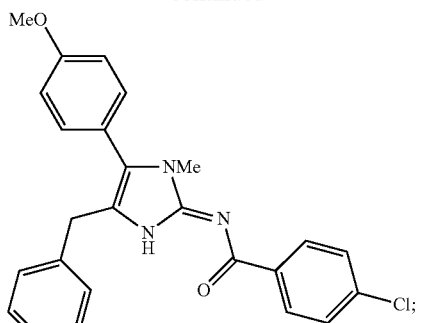
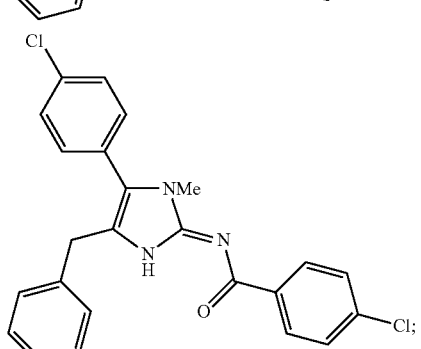
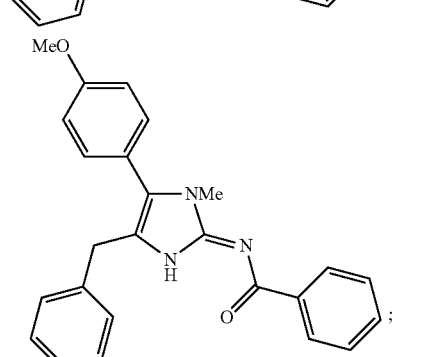
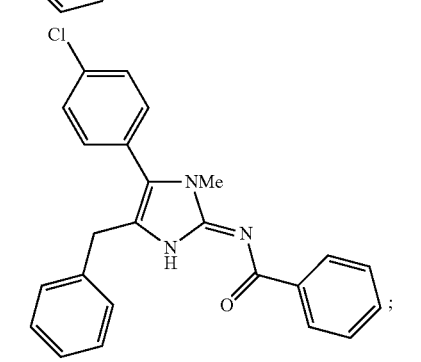
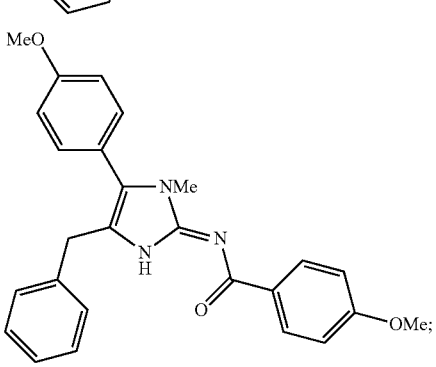

-continued

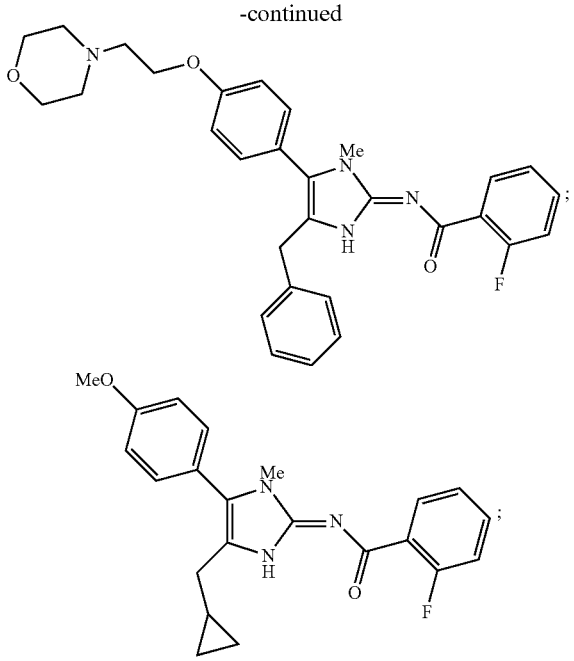

and salts thereof.

In one aspect, the invention sets forth a compound selected from those in Table I and salts thereof:

From a structural standpoint, the N-Me-hydantoin derived headgroup of naamidine A or a similar compound might well serve as a canonical 2-point kinase binder (analogous to a 2-aminopyridine). See Yoon et al. *Invest. Ophthalmol. Vis. Sci.* 2010; Enzenmuller et al. *Anticancer drugs* 2013, 24 (1), 14-9; Xue et al. PLoS One 2014, 9 (10), e109180/1-e109180/6, 6 pp. The hydantoin headgroup might also serve as a highly promiscuous binder (similar to the rhodanines and other hydantoins) contributing to significant "off-target" effects. See Ding et al. *Cancer Res.* 2005, 65 (8), 3389-3395; Lind et al. *Transl. Res.* 2009, 154 (3), 153-159; Yu et al. *Biochem. J.* 2009, 417 (1), 133-139; Takeda et al. PLoS One 2011, 6 (12), e28615; Jiang et al. *Cancer Lett.* 2011, 312 (1), 11-9; Park et al. *Neurobiol. Dis.* 2011, 42 (3), 242-51; Cao et al. *Sci Rep* 2014, 4. Advantageously, these effects should be minimized or avoided in the structurally simpler series of $N^2$-acyl-2-aminoimidazoles of the claimed invention.

Methods of Treatment

In a second embodiment, the invention presents a method of killing bacteria in vitro, the method comprising treating the bacteria with a composition set forth in the first embodiment or one of its aspects. In some alternative aspects of those presented, the invention presents a compound or composition for use in such a method.

In a third embodiment, the invention presents a method of killing bacteria in vivo, the method comprising administering a composition set forth in the first embodiment or one of its aspects to a patient. In some alternative aspects of those presented, the invention presents a compound or composition for use in such a method.

In a fourth embodiment, the invention presents a method of treating cancer, the method comprising administering a composition set forth in the first embodiment or one of its aspects to a patient with cancer, thereby treating the patient. In some alternative aspects of those presented, the invention presents a compound or composition for use in such a method.

Without intending to be bound by theory, the method of action for the inventive compounds and compositions may include modulation of zinc metabolism. Zinc is an essential trace metal. Bioinformatic studies have estimated that 10% of the proteome may bind zinc, 40% of these proteins functioning as transcription factors and the remaining 60% functioning in an enzymatic or an ion transport capacity (15). Considering the ubiquitous nature of the ion and the necessity of zinc for proper cellular function, it is not surprising then that perturbations in zinc homeostasis are correlated with varying disease states: Zinc accumulation has been found to occur in conjunction with the formation of Alzheimer's disease-associated extracellular plaques and increased zinc levels have been observed in malignant breast tissue compared to nonmalignant tissue (16-18). Exploiting the differences in zinc homeostasis between healthy and diseased tissue could provide a beneficial treatment window for therapeutics.

In one aspect, the methods of treating cancer comprise the compound ZNA. As the Examples show, ZNA synergizes strongly with $Zn^{2+}$ to induce cancer-selective cell death via a caspase-independent mechanism. ZNA was found to be effective against primary metastatic cells derived from breast cancer patients treated with multiple frontline chemotherapeutics, and the small molecule's in vivo efficacy was established using a mouse mammary tumor model. Taken together, the Examples suggest that destabilizing $Zn^{2+}$ trafficking pathways and inducing intracellular $Zn^{2+}$ dyshomeostasis are viable mechanisms by which to selectively target breast cancer. Furthermore, ZNA's activity against chemoresistant patient-derived tumor cells, which model the molecular and genomic characteristics of breast cancer following patient treatment initiation, suggests that the affected pathways are clinically relevant in vivo.

In some embodiments, the invention presents a composition for therapeutic use, the composition including a 2-(acylamino)imidazole of one of the aspects herein. In some aspects, the composition further includes a pharmaceutically acceptable excipient.

In instances where the 2-(acylamino)imidazole compound is to be administered to a subject, the compounds can be incorporated into pharmaceutical compositions. The 2-(acylamino)imidazole compound can be incorporated into pharmaceutical compositions as pharmaceutically acceptable salts or derivatives. Some pharmaceutically acceptable derivatives of the 2-(acylamino)imidazole compounds of the present invention may include a chemical group that increases aqueous solubility. As used herein, a "pharmaceutically acceptable carrier" means a substance that can be administered to a subject together with a 2-(acylamino)imidazole compound or salt thereof (i.e., as a carrier), or a combination of a 2-(acylamino)imidazole compound (or salt thereof) with another compound, and that does not destroy the pharmacological activity thereof. Pharmaceutically acceptable carriers include, for example, solvents, binders, dispersion media, coatings, preservatives, colorants, isotonic and absorption delaying agents, and the like that are compatible with pharmaceutical administration. Supplementary active compounds can also be incorporated into the compositions.

Non-limiting examples of pharmaceutically acceptable carriers that can be used include poly(ethylene-co-vinyl acetate), PVA, partially hydrolyzed poly(ethylene-co-vinyl acetate), poly(ethylene-co-vinyl acetate-co-vinyl alcohol), a cross-linked poly(ethylene-co-vinyl acetate), a cross-linked partially hydrolyzed poly(ethylene-co-vinyl acetate), a cross-linked poly(ethylene-co-vinyl acetate-co-vinyl alcohol), poly-D,L-lactic acid, poly-L-lactic acid, polyglycolic acid, PGA, copolymers of lactic acid and glycolic acid (PLGA), polycaprolactone, polyvalerolactone, poly(anhydrides), copolymers of polycaprolactone with polyethylene glycol, copolymers of polylactic acid with polyethylene glycol, polyethylene glycol; and combinations and blends thereof.

Other carriers include, e.g., an aqueous gelatin, an aqueous protein, a polymeric carrier, a cross-linking agent, or a combination thereof. In other instances, the carrier is a matrix. In yet another instances, the carrier includes water, a pharmaceutically acceptable buffer salt, a pharmaceutically acceptable buffer solution, a pharmaceutically acceptable antioxidant, ascorbic acid, one or more low molecular weight pharmaceutically acceptable polypeptides, a peptide comprising about 2 to about 10 amino acid residues, one or more pharmaceutically acceptable proteins, one or more pharmaceutically acceptable amino acids, an essential-to-human amino acid, one or more pharmaceutically acceptable carbohydrates, one or more pharmaceutically acceptable carbohydrate-derived materials, a non-reducing sugar, glucose, sucrose, sorbitol, trehalose, mannitol, maltodextrin, dextrins, cyclodextrin, a pharmaceutically acceptable chelating agent, EDTA, DTPA, a chelating agent for a divalent metal ion, a chelating agent for a trivalent metal ion, glutathione, pharmaceutically acceptable nonspecific serum albumin, or combinations thereof.

The route of administration of a therapeutic agent (e.g., a therapeutically active 2-(acylamino)imidazole or a salt thereof) can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art. In one aspect, the 2-(acylamino)imidazole therapeutic agent or a salt thereof is administered orally, intravenously, or intraperitoneally.

In one aspect, the 2-(acylamino)imidazole therapeutic agent or a salt thereof is administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

In one aspect, 2-(acylamino)imidazole therapeutic agent or a salt thereof is administered in combination with a second therapeutic agent. In one aspect, the second therapeutic agent is a chemotherapeutic agent. In one aspect, the chemotherapeutic agent is an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel). In one aspect, the chemotherapeutic agent is gemcitabine.

Co-administered therapeutic agents (e.g., a 2-(acylamino)imidazole therapeutic agent or a salt thereof, and a second therapeutic agent as described herein) can be administered together or separately, simultaneously or at different times. When administered, the therapeutic agents independently can be administered once, twice, three, or four times daily, or more or less often, as needed. In one aspect, the administered therapeutic agents are administered once daily. In one aspect, the administered therapeutic agents are administered at the same time or times, for instance as an admixture. In one aspect, one or more of the therapeutic agents is administered in a sustained-release formulation.

In one aspect, an 2-(acylamino)imidazole therapeutic agent or a salt thereof, and a second therapeutic agent are administered concurrently. In one aspect, the 2-(acylamino)imidazole therapeutic agent or salt thereof is administered first, for example for about 1, 2, 3, 4, 5, 6, 7, 8, 9, 10, 15, 20, 25, 30, 40, 50, 60, 70, 80, 90, 100 days or more prior to administering the second therapeutic agent (e.g., chemotherapeutic agent). In one aspect, the second therapeutic agent (e.g., chemotherapeutic agent) is administered first, for example for about 1, 2, 3, 4, 5, 6, 7, 8, 9, 10, 15, 20, 25, 30, 40, 50, 60, 70, 80, 90, 100 days or more prior to administering the 2-(acylamino)imidazole therapeutic agent or salt thereof.

In one aspect, a 2-(acylamino)imidazole therapeutic agent or a salt thereof (and optionally a second therapeutic agent, e.g., a chemotherapeutic agent as described herein) is administered to the subject over an extended period of time, e.g., for at least 30, 40, 50, 60, 70, 80, 90, 100, 150, 200, 250, 300, 350 days or longer.

In another aspect, compositions and kits for use in treating or preventing a cancer in a subject are provided.

In one aspect, compositions and kits for treating a cancer are provided. In some embodiments, the composition or kit comprises:

a composition set forth in the first embodiment or one of its aspects.

In one aspect, pharmaceutical compositions comprising a 2-(acylamino)imidazole therapeutic agent or a salt thereof, for use in administering to a subject having a cancer are provided. In one aspect, the 2-(acylamino)imidazole therapeutic agent or salt thereof is as described above. In one aspect, a 2-(acylamino)imidazole therapeutic agent or a salt thereof, and a second therapeutic agent (e.g., a chemotherapeutic agent as described herein) are formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols.

Guidance for preparing formulations for use in the present invention is found in, for example, in *Remington: The Science and Practice of Pharmacy*, 21$^{st}$ Ed., 2006, supra; *Martindale: The Complete Drug Reference*, Sweetman, 2005, London: Pharmaceutical Press; Niazi, *Handbook of Pharmaceutical Manufacturing Formulations,* 2004, CRC Press; and Gibson, *Pharmaceutical Preformulation and Formulation: A Practical Guide from Candidate Drug Selection to Commercial Dosage Form,* 2001, Interpharm Press, which are hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one aspect, a 2-(acylamino)imidazole therapeutic agent or a salt thereof (and optionally a second therapeutic agent, e.g., a chemotherapeutic agent as described herein) is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

For oral administration, a 2-(acylamino)imidazole therapeutic agent or a salt thereof (and optionally a second therapeutic agent, e.g., a chemotherapeutic agent as described herein) can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

The 2-(acylamino)imidazole therapeutic agent or salt thereof (and optionally a second therapeutic agent, e.g., a chemotherapeutic agent as described herein) can be formulated for parenteral administration by injection, e.g., by bolus injection or continuous infusion. For injection, the compound or compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In one aspect, compounds can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

The 2-(acylamino)imidazole therapeutic agent or salt thereof (and optionally a second therapeutic agent, e.g., a chemotherapeutic agent as described herein) can be administered systemically by transmucosal or transdermal means. For transmucosal or transdermal administration, penetrants appropriate to the barrier to be permeated are used in the formulation. For topical administration, the agents are formulated into ointments, creams, salves, powders and gels. In one aspect, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplary transdermal delivery formulations include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

In one aspect, a pharmaceutical composition comprises an acceptable carrier and/or excipients. A pharmaceutically acceptable carrier includes any solvents, dispersion media, or coatings that are physiologically compatible and that preferably do not interfere with or otherwise inhibit the activity of the therapeutic agent. In one aspect, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, *Remington: The Science and Practice of Pharmacy,* 21st Edition, Philadelphia, Pa. Lippincott Williams & Wilkins, 2005. Various pharmaceutically acceptable excipients are well-known in the art and can be found in, for example, Handbook of Pharmaceutical Excipients (5$^{th}$ ed., Ed. Rowe et al., Pharmaceutical Press, Washington, D.C.).

In one aspect, kits for use in administering to a subject having a cancer are provided. In one aspect, the kit comprises:

a 2-(acylamino)imidazole therapeutic agent or a salt thereof; and a second therapeutic agent.

In one aspect, the 2-(acylamino)imidazole therapeutic agent or salt thereof is as described above. In one aspect, the second therapeutic agent is a chemotherapeutic agent. In one aspect, the chemotherapeutic agent is an alkylating agent, an anthracycline, a cytoskeletal disruptor, a histone deacetylase inhibitor, an inhibitor of topoisomerase, a kinase inhibitor, a nucleoside analog or precursor analog, a peptide antibiotic, a platinum-based agent, or a plant alkaloid. In one aspect, the chemotherapeutic agent is a nucleoside analog.

In one aspect, the kits can further comprise instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

For biological methods, specific immunological binding of an antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously. In one aspect, the amount of signal can be quantified using an automated high-content imaging system. High-content imaging systems are commercially available (e.g., ImageXpress, Molecular Devices Inc., Sunnyvale, Calif.).

Antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Analysis of nucleic acid expression levels or genotype can be achieved using routine techniques such as Southern analysis, reverse-transcriptase polymerase chain reaction (RT-PCR), or any other methods based on hybridization to a nucleic acid sequence that is complementary to a portion of the coding sequence of interest (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid expression levels or genotype can also be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), pyrosequencing (Ronaghi et al., *Science*, 281:363-365 (1998)), and sequencing by hybridization. Chee et al., *Science*, 274:610-614 (1996); Drmanac et al., *Science*, 260:1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. In one aspect, methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE), and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

The analysis can be carried out in a variety of physical formats. For example, the use of microtiter plates or automation could be used to facilitate the processing of large numbers of test samples.

Alternatively, for detecting the level of protein or nucleic acid expression, antibody or nucleic acid probes can be applied to subject samples immobilized on microscope slides. The resulting antibody staining or in situ hybridization pattern can be visualized using any one of a variety of light or fluorescent microscopic methods known in the art.

Analysis of the protein or nucleic acid can also be achieved, for example, by high pressure liquid chromatography (HPLC), alone or in combination with mass spectrometry (e.g., MALDI/MS, MALDI-TOF/MS, tandem MS, etc.).

Methods of Synthesis

In a fifth embodiment, the invention presents a method of selectively preparing a 2-acylamino imidazole, the method comprising the steps:
  cyclizing an N-monoprotected α-guanidinyl alkyne reactant to form an 3-N-protected imidazolidin-2-imine product with a 4-exocyclic olefin; and
  selectively acylating at the 2-amino position to form a 2-acylamino product;
wherein the 2-acylamino product is substantially free from 1-acyl and 3-acyl regioisomers. In some aspects, the cycling step comprises a ic Lewis acid catalyst.

In a sixth embodiment, the invention presents a method of selectively preparing a 2-acylamino imidazole, the method comprising the steps:
  cyclizing an N-acylated α-guanidinyl alkyne reactant to form a 2-acylamino imidazole product. In some aspects, the method comprises a strong Brønsted base catalyst.

In one aspect of the fifth or sixth embodiments, the method further comprises the step of deprotecting the 3-N-protected 2-acyl imidazolidin-2-imine to produce a 2-acyl imidazolidin-2-imine. In a more specific aspect of the fifth embodiment, the method further comprises the step of isomerizing the 2-acyl imidazolidin-2-imine to produce a 2-acylamino imidazole.

In one aspect of the fifth embodiment, the method further comprises the step of isomerizing the 3-N-protected imidazolidin-2-imine to produce a 3-N-protected 2-aminoimidazole.

In one aspect of the fifth or sixth embodiment, the method further comprises the step of deprotecting the 3-N-protected 2-acylamino imidazole to produce a 2-acylamino imidazole.

In one aspect of the fifth or sixth embodiment, the 3-N-protecting group is a carbamate protecting group. In a more specific aspect, the 3-N-protecting group is a Cbz group.

In one aspect of the fifth or sixth embodiment, the 2-acylamino imidazole is a compound of the first embodiment or any of its aspects.

Any suitable π Lewis acid catalyst can be used in the methods of the invention. In some embodiments, the π Lewis acid catalyst is a transition metal salt, wherein the transition metal is selected from the group including silver, platinum, palladium, rhodium, mercury, and gadolinium.

Examples of suitable silver salts include, but are not limited to, silver acetate; silver bis(trifluoromethanesulfonyl)imide; silver bromide; silver carbonate; silver chloride; silver diethyldithiocarbamate; silver hexafluoroantimonate (V); silver hexafluorophosphate; silver methanesulfonate; silver nitrate; silver perchlorate; silver p-toluenesulfonate; silver sulfate; silver tetrafluoroborate; silver trifluoroacetate; silver trifluoromethanesulfonate (silver triflate); silver(I) fluoride; silver(I) oxide; tetrakis(acetonitrile)silver(I) tetrafluoroborate; (1,5-cyclooctadiene)(hexafluoroacetylacetonato)silver(I); 2,6-bis[(di-tert-butylphosphino)methyl]pyridine silver(I) tetrafluoroborate; potassium dicyanoargentate; hydrates thereof, and mixtures thereof.

Examples of suitable rhodium catalysts include, but are not limited to, (1,5-cyclooctadiene)(8-quinolinolato)rhodium(I); (acetylacetonato)(1,5-cyclooctadiene)rhodium(I); (acetylacetonato)(norbornadiene)rhodium(I); (acetylacetonato)dicarbonylrhodium(I); [(bisacetonitrile)(norbornadiene)]rhodium(I) hexafluoroantimonate; acetylacetonatobis (ethylene)rhodium(I); bicyclo[2.2.1]hepta-2,5-diene-rhodium(I) chloride dimer; bis(1,5-cyclooctadiene)rhodium (I) hexafluoroantimonate; bis(1,5-cyclooctadiene)rhodium (I) tetrafluoroborate; bis(1,5-cyclooctadiene)rhodium(I) trifluoromethanesulfonate; bis(norbornadiene)rhodium(I) tetrafluoroborate; bis(triphenylphosphine)rhodium(I) carbonyl chloride; chloro(1,5-cyclooctadiene)rhodium(I) dimer; pentamethylcyclopentadienylrhodium(III) chloride dimer; pentamethylcyclopentadienylrhodium(III) chloride dimer; rhodium(II) acetate; rhodium(II) heptafluorobutyrate dimer; rhodium(II) hexanoate; rhodium(II) octanoate, dimer; rhodium(II) trifluoroacetate dimer; rhodium(II) trimethylacetate, dimer; rhodium(II) triphenylacetate dimer; rhodium (III) acetylacetonate; rhodium(III) chloride; rhodium(III) oxide; tetrarhodium dodecacarbonyl; tris(triphenylphosphine)rhodium(I) carbonyl hydride; tris(triphenylphosphine)rhodium(I) chloride; hydrates thereof; and mixtures thereof.

Examples of suitable platinum catalysts include, but are not limited to, (1,5-cyclooctadiene)dimethylplatinum(II); (2,2'-bipyridine)dichloroplatinum(II); (ethylenediamine)iodoplatinum(II) dimer dinitrate; bis(tri-tert-butylphosphine) platinum(0); cis-bis(acetonitrile)dichloroplatinum(II); cis-dichlorobis(diethyl sulfide)platinum(II); cis-dichlorobis (dimethyl sulfoxide)platinum(II); cis-dichlorobis(pyridine) platinum(II); cis-dichlorobis(triethylphosphine)platinum (II); cis-dichlorobis(triphenylphosphine)platinum(II); dichloro(1,10-phenanthroline)platinum(II); dichloro(1,2-diaminocyclohexane)platinum(II); dichloro(1,5-cyclooctadiene)platinum(II); dichloro(dicyclopentadienyl)platinum(II); dichloro(ethylenediamine)platinum(II); dichloro(norbornadiene)platinum(II); dichlorobis(dimethyl sulfide)platinum (II); ethylenebis(triphenylphosphine)platinum(0); platinum (II) acetylacetonate; platinum(II) bromide; platinum(II) chloride; platinum(II) iodide; platinum(IV) chloride; platinum(IV) oxide; potassium hexachloroplatinate(IV); potassium trichloro(ethylene)platinate(II); sodium hexahydroxyplatinate(IV); tetraammineplatinum(II) chloride; tetraammineplatinum(II) nitrate; tetrabutylammonium hexachloroplatinate(IV); tetrakis(triphenylphosphine)platinum(0); and trans-dichlorobis(triethylphosphine)platinum (II); hydrates thereof; and mixtures thereof.

Examples of suitable palladium catalysts include, but are not limited to, allylpalladium(II) chloride dimer; allylpalladium(II) trifluoroacetate dimer; bis(tricyclohexylphosphine) palladium(0); bis(triphenylphosphine)palladium(II) dichloride; chloro(1,5-cyclooctadiene)methylpalladium(II); dibromo(1,5-cyclooctadiene)palladium(II); dichlorobis (methyldiphenylphosphine)palladium(II); palladium pivalate; palladium(II) acetate; palladium(II) acetylacetonate; palladium(II) bromide; palladium(II) chloride; palladium(II) cyanide; palladium(II) hexafluoroacetylacetonate; palladium(II) iodide; palladium(II) nitrate; palladium(II) oxide; palladium(II) propionate; palladium(II) sulfate; palladium (II) sulfide; palladium(II) trifluoroacetate; tetraamminepalladium(II) acetate; tetrakis(triphenylphosphine) palladium (0); trans-benzyl(chloro)bis(triphenylphosphine)palladium (II); trans-dibromobis (triphenylphosphine)palladium(II); tris(dibenzylideneacetone)dipalladium(0); hydrates thereof; and mixtures thereof.

Examples of suitable mercury catalysts include, but are not limited to, mercury(I) chloride; mercury(I) nitrate; mercury(II) acetate; mercury(II) amidochloride; mercury(II) bromide; mercury(II) chloride; mercury(II) fluoride; mercury(II) iodate; mercury(II) iodide; mercury(II) nitrate; mercury(II) oxide; mercury(II) sulfate; mercury(II) thiocyanate; mercury(II) trifluoroacetate; mercury(II) trifluoromethanesulfonate; hydrates thereof, and mixtures thereof.

Examples of suitable gadolinium catalysts include, but are not limited to, gadolinium(III) acetate; gadolinium(III) acetylacetonate; gadolinium(III) bromide; gadolinium(III) carbonate; gadolinium(III) chloride; gadolinium(III) fluoride; gadolinium(III) hydroxide; gadolinium(III) iodide; gadolinium(III) nitrate; gadolinium(III) oxalate; gadolinium (III) oxide; gadolinium(III) sulfate; gadolinium(III) trifluoromethanesulfonate; gadolinium(III) tris(isopropoxide); tris (cyclopentadienyl)gadolinium(III); tris (tetramethylcyclopentadienyl)gadolinium(III); tris[N,N-bis (trimethylsilyl)amide]gadolinium(III); hydrates thereof; and mixtures thereof.

Suitable catalysts also include titanium tetrachloride; zinc dichloride; antimony pentafluorides; and tin di- and tetrachlorides. Other catalysts can be used in the methods of the invention, including $IrHCl_2(Me_2SO)_3$; $IrHCl_2(CO)(PPh_3)_2$; $IrH_2Cl(PPh_3)_3$; $IrHCl_2(PPh_3)_3$; $IrH_3(PPh_3)_2$; $IrH_5(PPh_3)_3$; $IrCl(CO)(PPh_3)_2$; $IrBr(CO)(PPh_3)_2$; $IrI(CO)(PPh_3)_2$; $IrH(CO)(PPh_3)_3$; $IrH(COMPPh_3)_2$; $IrCl(CsH_{12})PPh_3$; $IrH[P(OPh)_3]_4$; $Os(CF_3CO_2)(CO)(PPh_3)_2$; $OsHCl(PPh_3)_3$; $OsH(CO)Cl(PPh_3)_3$; $FeCl_2(PPh_3)_2$; $CoCl_2(PPh_3)_2$; $NiCl_2(Pn-Bu_3)_2$; $ReCl_5$; and $CoH[P(OPh)_3]_3$; $RuCl_2(PPh_3)_4$; $RuH_2(PPh_3)_4$; $RuH_2(CO)(PPh_3)_3$; $RuH(CO)Cl(PPh_3)_3$; $RuH(CF_3CO_2)(CO)(PPh_3)_2$; $RuCl_2(PPh_3)_4$; $RuCl_3$; and the like.

In some embodiments, the π Lewis acid catalyst is selected from the group including silver chloride, silver nitrate, silver triflate, and silver hexaflurophosphate. In some embodiments, the Lewis acid catalyst is silver nitrate.

Any suitable base can be used in the methods of the invention. Examples of suitable bases include a metal halide (e.g., sodium or potassium hydride). Other bases can also be suitable in the methods of the invention, including sodium hexamethyldisilazide (NaHMDS) or other strong bases (i.e., a base with a conjugate acid that is $pK_a$ 15 or higher, $pK_a$ 18 or higher, $pK_a$ 25 or higher, or $pK_a$ 30 or higher, wherein "higher" indicates a weaker conjugate acid), especially bases that are non-nucleophilic. Combinations of two or more bases can be used.

Any suitable amount of catalyst can be used in the methods of the invention. Typically, a substoichiometric amount of catalyst with respect to the starting materials of Formula II is used in the reaction. That is, the number of moles of catalyst in the reaction mixture is less than the number of moles of starting material in the reaction mixture. The molar ratio of catalyst to starting material is generally less than 1:1, such as 0.9:1, 0.8:1, 0.7:1, 0.6:1, 0.5:1, 0.4:1, 0.35:1, 0.3:1, 0.25:1, 0.2:1, 0.15:1, or 0.1:1. In some embodiments, the molar ratio of catalyst to starting material is less than 0.1:1, such as 0.09:1, 0.08:1, 0.07:1, 0.06:1, 0.05:1, 0.04:1, 0.03:1, 0.02:1, or 0.01:1. In some embodiments, the molar ratio of catalyst to starting material is less than 0.01:1, such as 0.009:1, 0.008:1, 0.007:1, 0.006:1, 0.005:1, 0.004:1, 0.003:1, 0.002:1, or 0.001:1. One of skill in the art will appreciate that the molar ratios set forth herein can also be expressed as mole % values and will know how to derive a mole % value from a molar ratio.

The cyclization reaction in the methods of the invention can be conducted at any suitable temperature. In general, reactions are conducted at temperatures ranging between about 10° C. and about 200° C. A reaction can be conducted, for example, at from about 10° C. to about 100° C., or from about 10° C. to about 40° C., or from about 15° C. to about 150° C., or from about 15° C. to about 35° C., or from about 15° C. to about 25° C. A reaction can be conducted at temperature less than about 20, 25, 30, 35, 40, 45, 50, 55, 60, 65, 70, 75, 80, 85, 90, 95, 100, 105, 110, 115, 120, 125, 130, 135, 140, 145, 150, or 155° C. Other reaction temperatures can be used in the methods of the invention, depending in part on the particular compound used for the cyclization reaction.

Any suitable solvent or combination of solvents can be used in the methods of the invention. Suitable solvents include, but are not limited to, diethyl ether, diisopropyl ether, ethyl acetate, pentane, hexane, heptane, cyclohexane, benzene, toluene, chloroform, dichloromethane, carbon tetrachloride, 1,2-dichloroethane, 1,1-dichloroethane, N,N-dimethylformamide, N,N-dimethylacetamide, dimethylsulfoxide, N-methyl 2-pyrrolidone, acetic acid, trifluoroacetic acid, trichloroacetic acid, methyl ethyl ketone, methyl isobutylketone, acetonitrile, propionitrile, 1,4-dioxane, sulfolane, 1,2-dimethyoxyethane, and combinations thereof. In some embodiments, the reaction mixture comprises acetonitrile.

Any suitable reaction time can be used in the methods of the invention. In general, reactions are allowed to run for a time sufficient for consumption of the starting material and conversion to the desired product, or until conversion of the starting material comes to a stop (e.g., because of decomposition of a reaction catalyst). Reactions are typically allowed to run for any amount of time ranging from a few minutes to several hours. Reactions can be run, for example, for anywhere between 5 minutes and 48 hours. Reactions can be run for about 20 minutes, or about 40 minutes, or about 60 minutes. Reactions can be run for about 1.5, 2, 2.5, 3, 3.5, 4, 4.5, 5, 5.5, 6, 6.5, 7, 7.5, 8, 8.5, 9, 9.5, 10, 11, 12, 14, 16, 18, 20, 22, 24, 30, 36, 42, or 48 hours. In some embodiments, reactions are run for less than 24 hours. In some embodiments, reactions are run for less than 12 hours. In some embodiments, reactions are run for less than 10 hours. Other reaction times can be used in the methods of the invention, depending on the particular catalysts or compounds of Formula II that are used.

While simple in design, it is very difficult to selectively acylate 2-aminoimidazoles. Zhang et al. *Eur J Med Chem* 2014, 83, 74-83. Predominance of the imino-tautomer initiates $N^2$-acylation over the expected $N^3$-acylation, and with a product acidified by the acyl group, the second acylation event is facile leading to the diacylated products. In one aspect of the present invention, a regioselective cyclization of mono-N-acylpropargylguanidines was employed to achieve selectivity. If a mono-Cbz guanidine is used, Ag(I)-mediated cyclization proceeds exclusively through the imino nitrogen to give the $N^3$-acyl-2-aminoimidazole. Acylation and reductive cleavage of the Cbz group provided a N²-acyl-2-aminoimidazole in good yield as the exclusive product.

The compounds in the tables below were made using the methods set forth herein:

TABLE I

Selected 2-(Acylamino)imidazoles

| COMPOUND | CHEMICAL STRUCTURE |
|---|---|
| ZNA (38) | 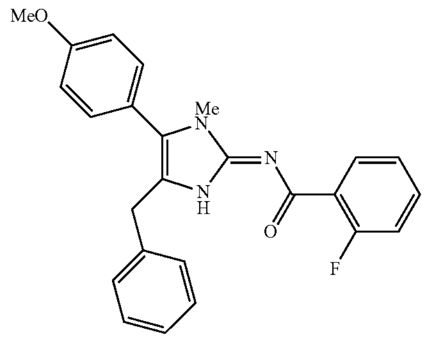 [SMILES: COc1ccc(-c2c(Cc3ccccc3)[nH]/c(=N\C(=O)c3ccccc3F)n2C)cc1] |
| ZNA-1 (91) | 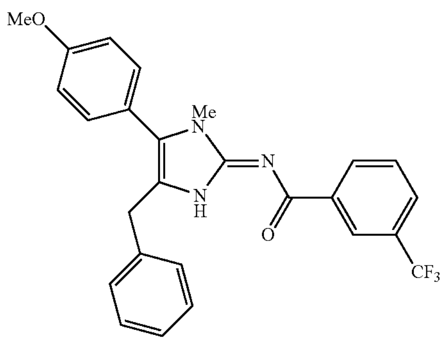 [SMILES: COc1ccc(-c2c(Cc3ccccc3)[nH]/c(=N\C(=O)c3cccc(C(F)(F)F)c3)n2C)cc1] |
| ZNA-2 (88) | 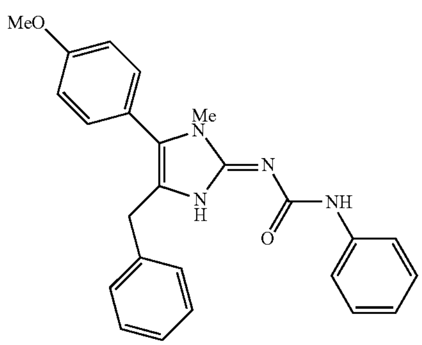 [SMILES: COc1ccc(-c2c(Cc3ccccc3)[nH]/c(=N\C(=O)Nc3ccccc3)n2C)cc1] |
| ZNA-3 (41) | 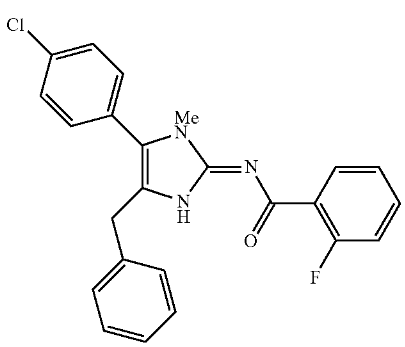 [SMILES: Cn1c(-c2ccc(Cl)cc2)c(Cc2ccccc2)[nH]/c1=N\C(=O)c1ccccc1F] |

TABLE I-continued

Selected 2-(Acylamino)imidazoles

| COMPOUND | CHEMICAL STRUCTURE |
|---|---|
| ZNA-4 (39) | 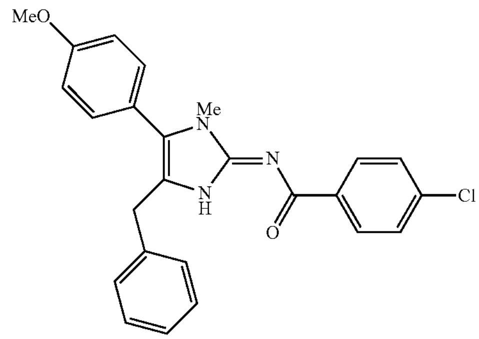 [SMILES: COc1ccc(-c2c(Cc3ccccc3)[nH]/c(=N\C(=O)c3ccc(Cl)cc3)n2C)cc1] |
| ZNA-5 (42) | 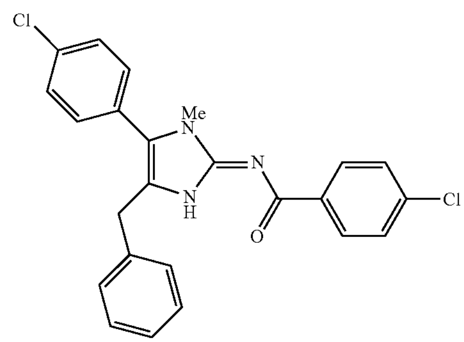 [SMILES: Cn1c(-c2ccc(Cl)cc2)c(Cc2ccccc2)[nH]/c1=N\C(=O)c1ccc(Cl)cc1] |
| ZNA-6 (37) | 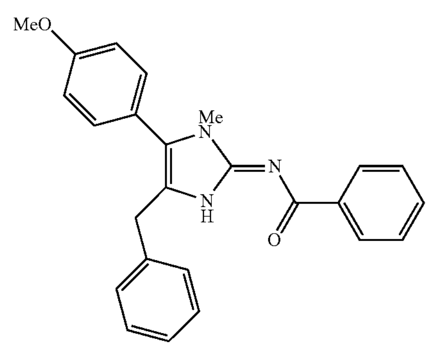 [SMILES: COc1ccc(-c2c(Cc3ccccc3)[nH]/c(=N\C(=O)c3ccccc3)n2C)cc1] |
| ZNA-7 (43) | 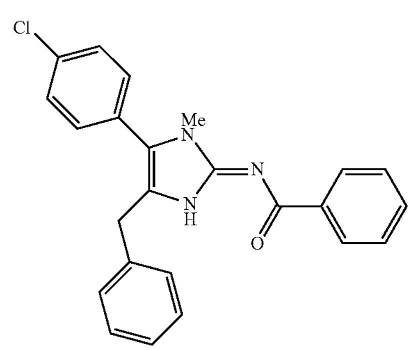 [SMILES: Cn1c(-c2ccc(Cl)cc2)c(Cc2ccccc2)[nH]/c1=N\C(=O)c1ccccc1] |

TABLE I-continued
Selected 2-(Acylamino)imidazoles
| COMPOUND | CHEMICAL STRUCTURE |
|---|---|
| ZNA-8 (40) | 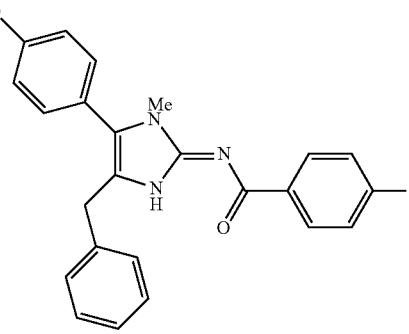 |
| ZNA-9 (45) | 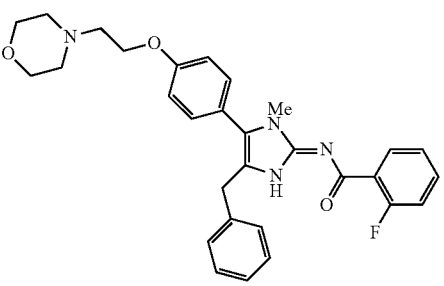 [SMILES: Cn1c(-c2ccc(OCCN3CCOCC3)cc2)c(Cc2ccccc2)[nH]/c1=N\C(=O)c1ccccc1F] |
| ZNA-10 (50) | 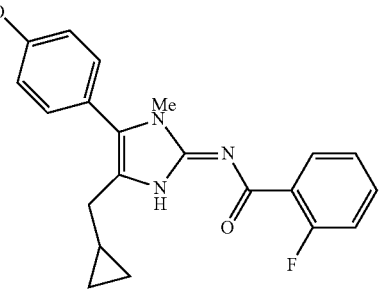 |
| ZNA-11 (46) | 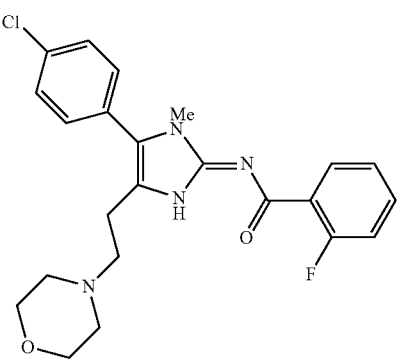 [SMILES: Cn1c(-c2ccc(Cl)cc2)c(CCN2CCOCC2)[nH]/c1=N\C(=O)c1ccccc1F] |
| ZNA-12 (49) | 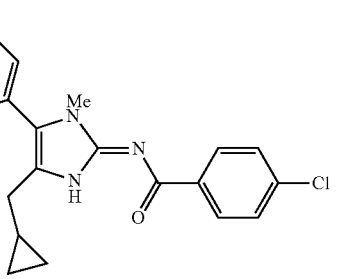 |
| ZNA-13 (47) | 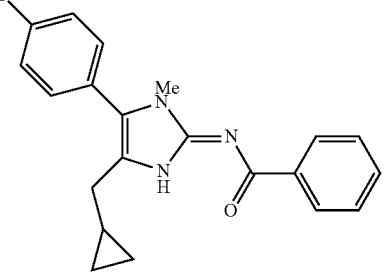 |
| ZNA-14 (48) | 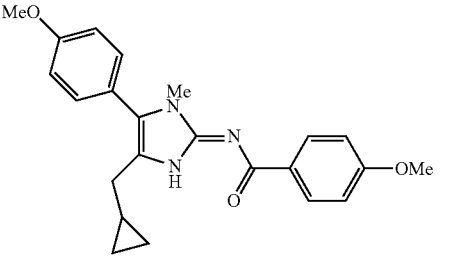 [SMILES: COc1ccc(C(=O)/N=c2\[nH]c(CC3CC3)c(-c3ccc(OC)cc3)n2C)cc1] |
| ZNA-15 (51) | 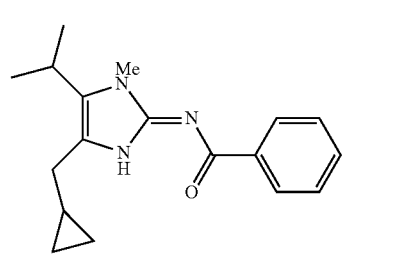 [SMILES: CC(C)c1c(CC2CC2)[nH]/c(=N\C(=O)c2ccccc2)n1C] |

TABLE I-continued

Selected 2-(Acylamino)imidazoles

| COMPOUND | CHEMICAL STRUCTURE |
|---|---|
| ZNA-16 (95) | 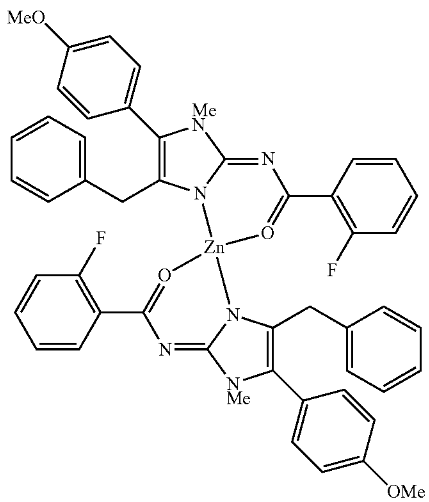 |
| ZNA-17 (94) | 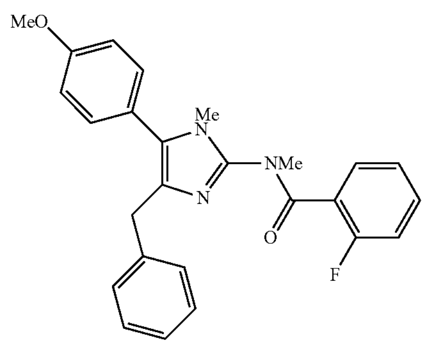 [SMILES: COc1ccc(-c2c(Cc3ccccc3)nc(N(C)C(=O)c3ccccc3F)n2C)cc1] |
| ZNA-18 (101) | 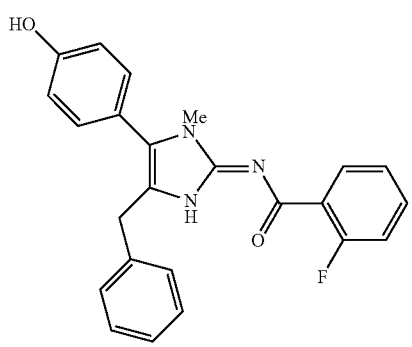 [SMILES: Cn1c(-c2ccc(O)cc2)c(Cc2ccccc2)[nH]/c1=N\C(=O)c1ccccc1F] |
| ZNA-19 (54) | 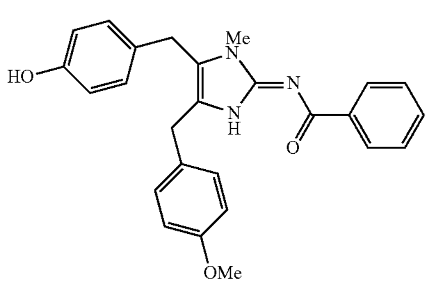 [SMILES: COc1ccc(Cc2[nH]/c(=N\C(=O)c3ccccc3)n(C)c2Cc2ccc(O)cc2)cc1] |
| ZNA-20 (56) | 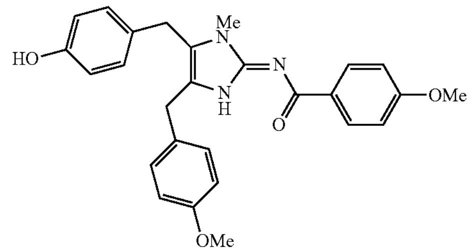 [SMILES: COc1ccc(Cc2[nH]/c(=N\C(=O)c3ccc(OC)cc3)n(C)c2Cc2ccc(O)cc2)cc1] |
| ZNA-21 (57) | 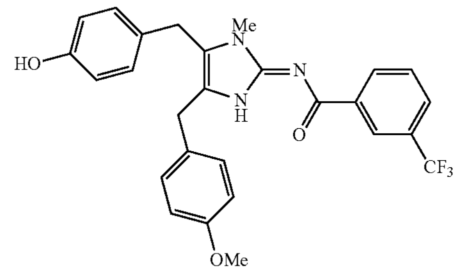 [SMILES: COc1ccc(Cc2[nH]/c(=N\C(=O)c3cccc(C(F)(F)F)c3)n(C)c2Cc2ccc(O)cc2)cc1] |
| ZNA-22 (14) | 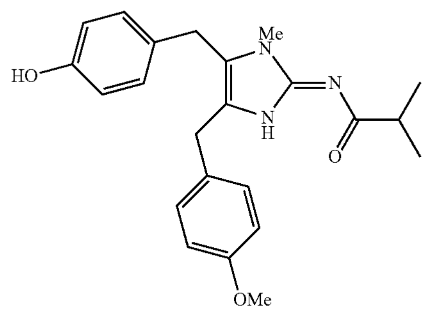 [SMILES: COc1ccc(Cc2[nH]/c(=N\C(=O)C(C)C)n(C)c2Cc2ccc(O)cc2)cc1] |
| ZNA-23 (15) | 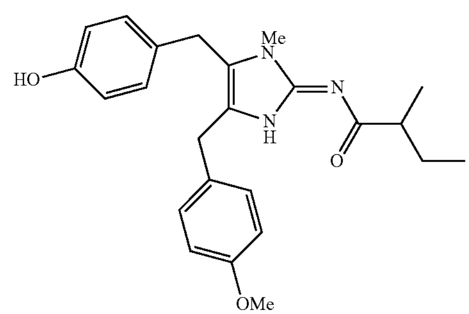 [SMILES: CCC(C)C(=O)/N=c1\[nH]c(Cc2ccc(OC)cc2)c(Cc2ccc(O)cc2)n1C] |
| ZNA-24 (35) | 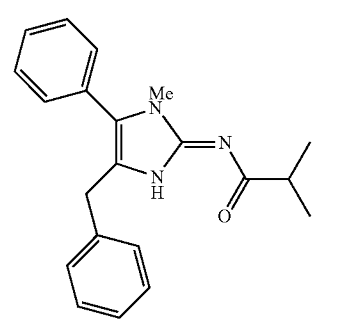 [SMILES: CC(C)C(=O)/N=c1\[nH]c(Cc2ccccc2)c(-c2ccccc2)n1C] |

TABLE I-continued
Selected 2-(Acylamino)imidazoles
| COMPOUND | CHEMICAL STRUCTURE |
|---|---|
| ZNA-25 (36) | 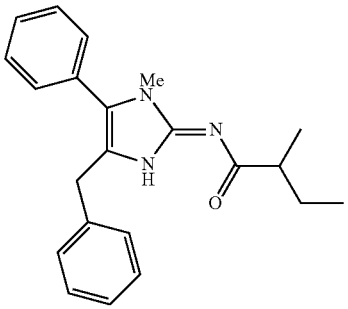 [SMILES: CCC(C)C(=O)/N=c1\[nH]c(Cc2ccccc2)c(-c2ccccc2)n1C] |
| ZNA-26 (89) | 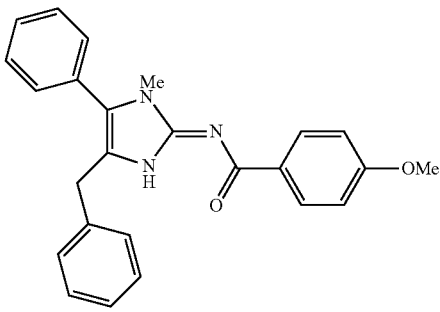 [SMILES: COc1ccc(C(=O)/N=c2\[nH]c(Cc3ccccc3)c(-c3ccccc3)n2C)cc1] |
| ZNA-27 (90) | 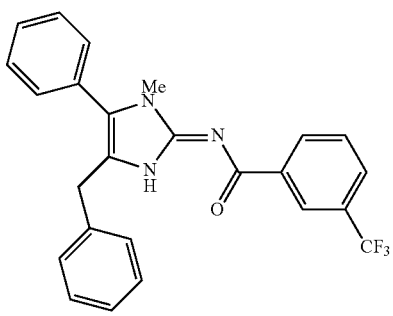 [SMILES: Cn1c(-c2ccccc2)c(Cc2ccccc2)[nH]/c1=N\C(=O)c1cccc(C(F)(F)F)c1] |
| ZNA-28 (33) | 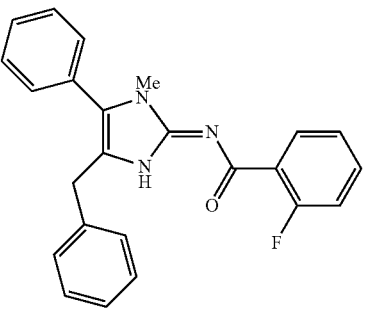 [SMILES: Cn1c(-c2ccccc2)c(Cc2ccccc2)[nH]/c1=N\C(=O)c1ccccc1F] |
| ZNA-29 (102) | 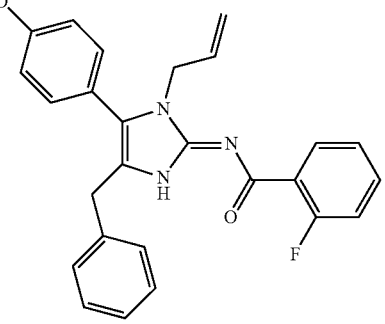 |
TABLE II
Selected Synthetic Intermediates
| COMPOUND NO. | CHEMICAL STRUCTURE |
|---|---|
| 16 | 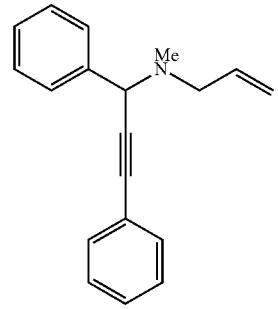 [SMILES: C=CCN(C)C(C#Cc1ccccc1)c1ccccc1] |
| 17 | 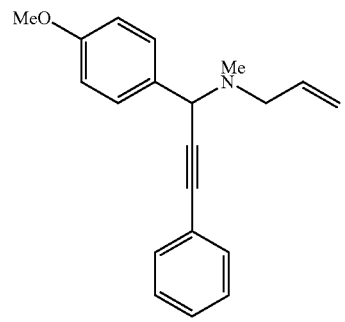 [SMILES: C=CCN(C)C(C#Cc1ccccc1)c1ccc(OC)cc1] |
| 58 | 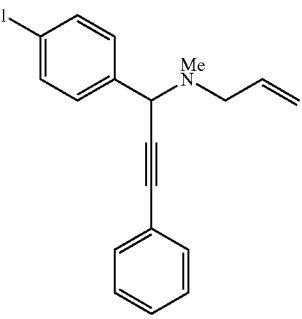 |

TABLE II-continued

Selected Synthetic Intermediates

| COMPOUND NO. | CHEMICAL STRUCTURE |
|---|---|
| 59 | 4-MeO-C6H4-CH(N(Me)(allyl))-C≡C-cyclopropyl |
| A | (iPr)-CH(N(Me)(allyl))-C≡C-cyclopropyl |
| 60 | morpholino-CH2CH2-O-C6H4-CH(N(Me)(allyl))-C≡C-Ph |
| 61 | 4-Cl-C6H4-CH(N(Me)(allyl))-C≡C-CH2-morpholino |
| 62 | 4-MeO-C6H4-CH(N(allyl)2)-C≡C-Ph |
| 18 | Ph-CH(NHMe)-C≡C-Ph |
| 19 | 4-MeO-C6H4-CH(NHMe)-C≡C-Ph |
| 63 | 4-Cl-C6H4-CH(NHMe)-C≡C-Ph |
| 64 | 4-MeO-C6H4-CH(NHMe)-C≡C-cyclopropyl |
| B | (iPr)-CH(NHMe)-C≡C-cyclopropyl |

TABLE II-continued
Selected Synthetic Intermediates
| COMPOUND NO. | CHEMICAL STRUCTURE |
|---|---|
| 65 | 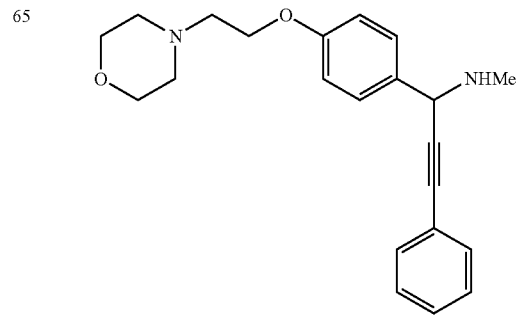 |
| 66 | 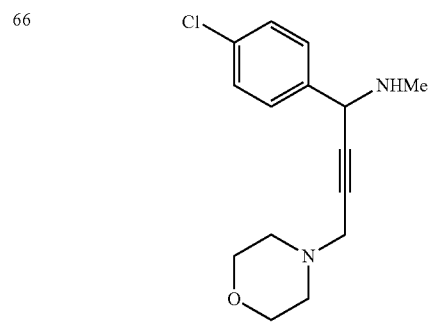 |
| 67 | 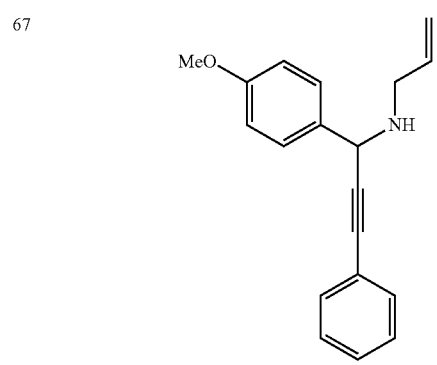 |
| 20 | 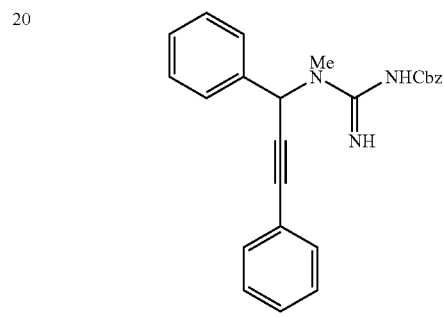 |
TABLE II-continued
Selected Synthetic Intermediates
| COMPOUND NO. | CHEMICAL STRUCTURE |
|---|---|
| 21 | 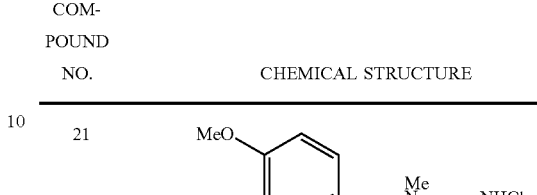 |
| 22 | 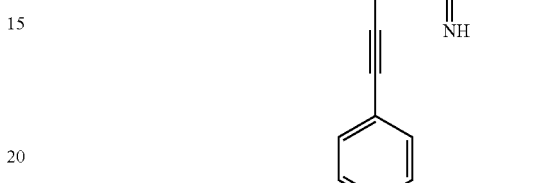 |
| 23 | 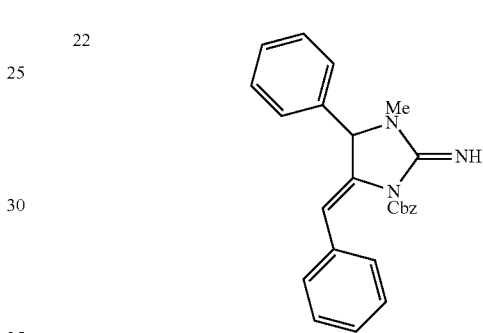 |
| 24 | 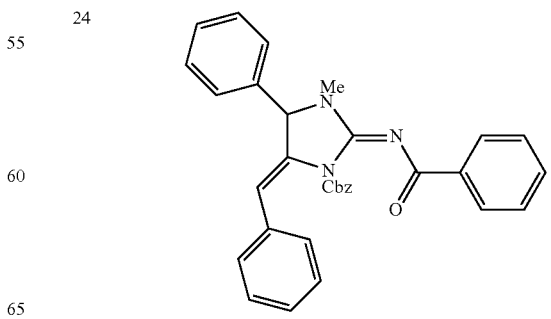 |

TABLE II-continued

Selected Synthetic Intermediates

| COMPOUND NO. | CHEMICAL STRUCTURE |
|---|---|
| 25 | 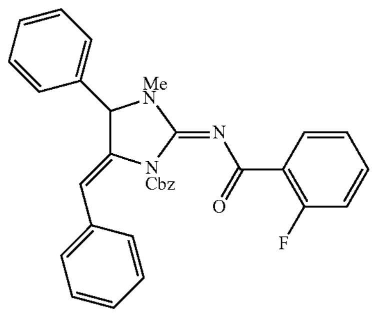 |
| 28 | 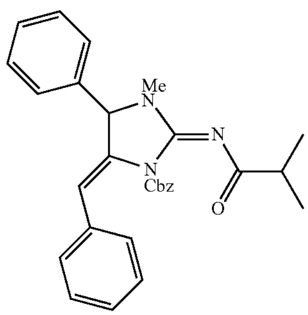 |
| 29 | 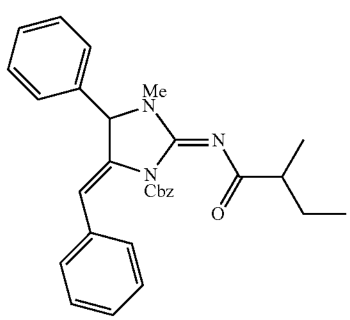 |
| 85 | 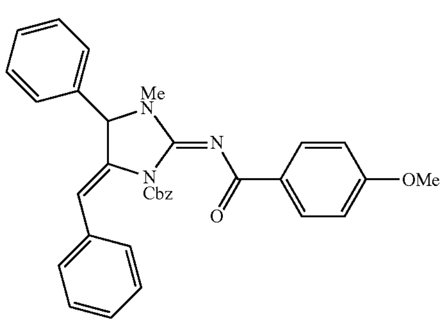 |
| 90 | |
| 86 | |
| 31 | |
| 87 | |

TABLE II-continued

Selected Synthetic Intermediates

| COMPOUND NO. | CHEMICAL STRUCTURE |
|---|---|
| 68 | 4-MeO-C6H4-CH(NMe)-C(=NH)-NH-C(=O)-(2-F-C6H4), with C≡C-Ph substituent |
| 69 | 4-MeO-C6H4-CH(NMe)-C(=NH)-NH-C(=O)-(4-Cl-C6H4), with C≡C-Ph substituent |
| 70 | 4-MeO-C6H4-CH(NMe)-C(=NH)-NH-C(=O)-C6H5, with C≡C-Ph substituent |
| 71 | 4-MeO-C6H4-CH(NMe)-C(=NH)-NH-C(=O)-(4-MeO-C6H4), with C≡C-Ph substituent |
| C | 4-MeO-C6H4-CH(NMe)-C(=NH)-NH-C(=O)-(2,4-Cl2-C6H3), with C≡C-Ph substituent |
| 72 | 4-MeO-C6H4-CH(NMe)-C(=NH)-NH-C(=O)-(4-F-C6H4), with C≡C-Ph substituent |
| 73 | 4-Cl-C6H4-CH(NMe)-C(=NH)-NH-C(=O)-(2-F-C6H4), with C≡C-Ph substituent |
| 74 | 4-Cl-C6H4-CH(NMe)-C(=NH)-NH-C(=O)-(4-Cl-C6H4), with C≡C-Ph substituent |
| 75 | 4-Cl-C6H4-CH(NMe)-C(=NH)-NH-C(=O)-C6H5, with C≡C-Ph substituent |
| 76 | 4-Cl-C6H4-CH(NMe)-C(=NH)-NH-C(=O)-(4-MeO-C6H4), with C≡C-Ph substituent |

TABLE II-continued
Selected Synthetic Intermediates
| COMPOUND NO. | CHEMICAL STRUCTURE |
|---|---|
| 80 | 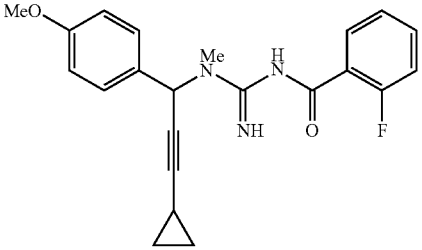 |
| 78 | 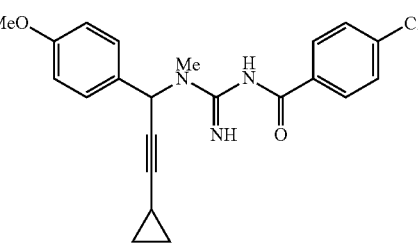 |
| 79 | 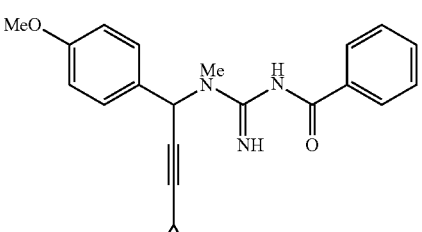 |
| 81 | 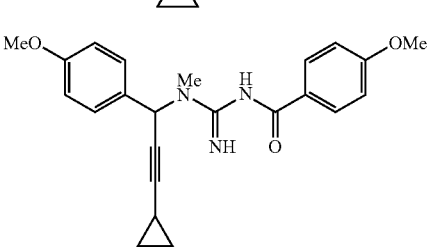 |
| 77 | 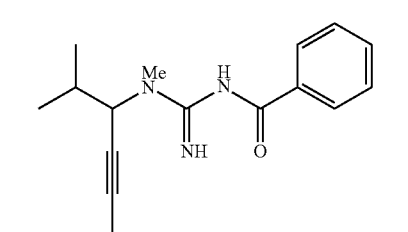 |
| 82 | 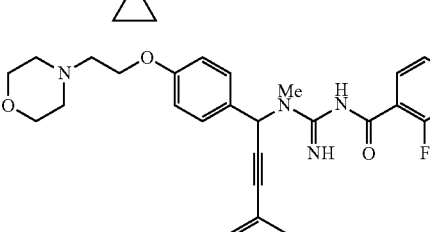 |
| 83 | 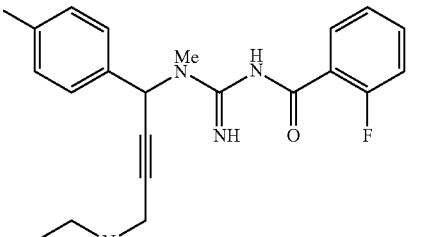 |
| 84 | 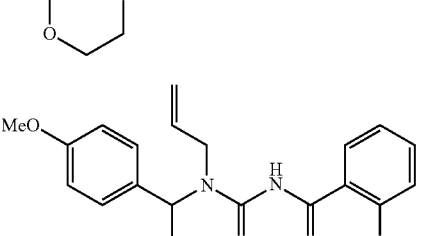 |
| 96 | 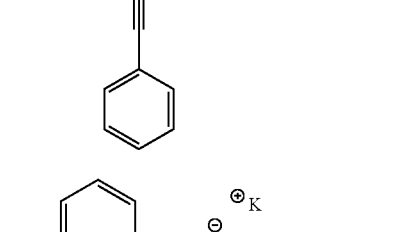 |
| 98 | 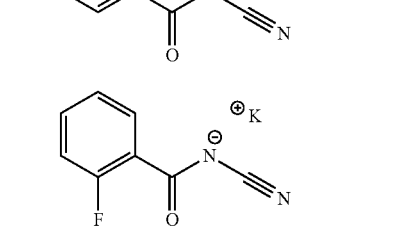 |
| 99 | 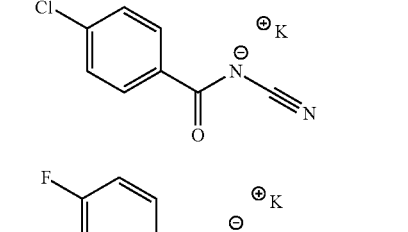 |
| 100 | 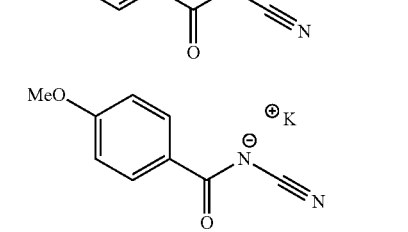 |
| 97 | 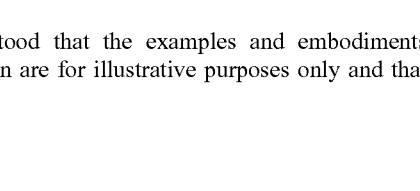 |
It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Preparation of N-Allyl-1-(4-(benzyloxy)phenyl)-4-(4-methoxyphenyl)-N-methylbut-3-yn-2-amine (2)

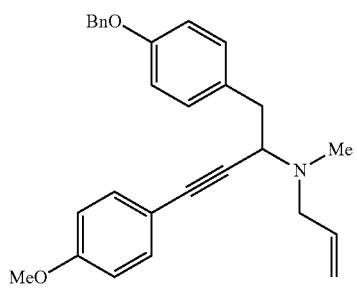

2

To a 500 mL pressure flask equipped with a stir bar was added 4-methoxyphenylacetylene (5.35 mL, 40.5 mmol), N-allylmethylamine (3.46 mL, 36.4 mmol), p-benzyloxyphenylacetaldehyde (9.16 g, 40.5 mmol), CuBr (0.52 g, 3.64 mmol), acetonitrile (140 mL) and 1 g of oven-dried 4 Å molecular sieves. The flask was heated at 80° C. for 24 hours, then allowed to cool to room temperature. The mixture was filtered through Celite diatomaceous earth and rinsed with EtOAc (500 mL). The organic layer was washed with saturated NaHCO$_3$ (500 mL) and brine (500 mL). The organic layer was dried over Na$_2$SO$_4$. After filtration, the organic layer was concentrated and purified via flash chromatography using 4:1 hexanes/EtOAc to give 2 as a dark red oil (10.8 g, 65%). R$_f$=0.35 (4:1 hexanes/EtOAc); $^1$H NMR (CDCl$_3$, 300 MHz): δ 7.37-7.27 (m, 4H), 7.24 (d, J=8.8 Hz, 3H), 7.15 (d, J=8.3 Hz, 2H), 6.84 (d, J=8.8 Hz, 2H), 6.73 (d, J=8.8 Hz, 2H), 5.78 (ddt, J=6.4, 10.7, 17.1 Hz, 1H), 5.14 (dd, J=1.5, 17.1 Hz, 1H), 5.05 (dd, J=2.0, 10.3 Hz, 1H), 4.95 (s, 2H), 3.72 (dd, J=6.3, 8.8 Hz, 1H), 3.70 (s, 3H), 3.15 (dd, J=5.9, 13.7 Hz, 1H), 3.03 (dd, J=7.3, 13.5 Hz, 1H), 2.27 (s, 3H) ppm. $^{13}$C NMR (CDCl$_3$, 75 MHz): δ 159.2, 157.4, 137.2, 136.0, 133.0 131.2, 130.4, 128.5, 127.8, 127.4, 117.6, 115.5, 114.5, 113.8, 88.5, 85.0, 69.9, 65.8, 58.4, 58.2, 55.2, 39.5, 37.7, 15.2 ppm. IR (thin film) 2954, 1606, 1508, 1454, 1420, 1381, 1289, 1243, 1173, 1106, 1026, 921, 831, 807, 791, 732, 696 cm$^{-1}$.

Example 2: Preparation of 1-(4-(Benzyloxy)phenyl)-4-(4-methoxyphenyl)-N-methylbut-3-yn-2-amine (3)

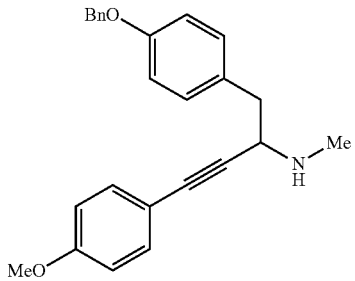

3

To a 500 mL round bottom flask equipped with a stir bar was added 2 (10.7 g, 26.0 mmol), thiosalicylic acid (8.0 g, 52.0 mmol), Pd(PPh$_3$)$_4$ (0.6 g, 0.52 mmol), and CH$_2$Cl$_2$ (260 mL). The reaction was allowed to stir at room temperature under N$_2$ overnight. The reaction mixture was concentrated and re-dissolved in EtOAc (200 mL). The organic layer was washed with saturated NaHCO$_3$ (200 mL) and brine (200 mL). The organic layer was dried over Na$_2$SO$_4$. After filtration, the organic layer was concentrated and purified via flash chromatography using 100% EtOAc (with 0.5% NEt$_3$) to give 3 as an orange oil (6.6 g, 91%). R$_f$=0.35 (100% EtOAc); $^1$H NMR (CDCl$_3$, 500 MHz): δ 7.45 (d, J=7.3, 2H), 7.40 (t, J=6.8 Hz, 2H), 7.34 (d, J=8.8 Hz, 3H), 7.27 (d, J=8.3 Hz, 2H), 6.95 (d, J=8.8 Hz, 2H), 6.83 (d, J=8.8 Hz, 2H), 5.06 (s, 2H), 3.80 (s, 3H), 3.72 (t, J=6.4 Hz, 1H), 2.98 (dd, J=2.4, 9.4 Hz, 2H), 2.55 (s, 3H) ppm. $^{13}$C NMR (CDCl$_3$, 125 MHz): δ 159.4, 157.7, 137.2, 133.0, 130.8, 128.7, 128.0, 127.6, 115.5, 114.7, 88.7, 84.6, 70.1, 55.3, 53.9, 41.3, 34.2 ppm. IR (thin film) 2933, 1606, 1508, 1454, 1441, 1380, 1289, 1244, 1173, 1107, 1027, 831, 737, 697, 668 cm$^{-1}$. Calc. C$_{25}$H$_{26}$NO$_2$ m/z (M+H) 372.1964, Obsd. 372.1966.

Example 3: Preparation of Cbz-Protected Guanidine 4

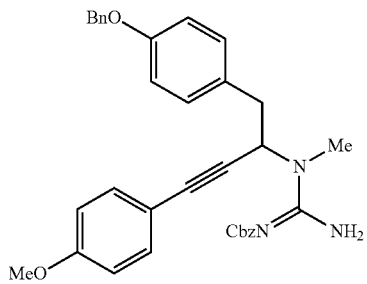

4

To a 250 mL round bottom flask equipped with a stir bar was added TMSCl (1.65 mL, 13.0 mmol), benzyloxycarbonylcyanamide potassium salt (2.58 g, 12.0 mmol) and 50 mL acetonitrile. The reaction mixture was allowed to stir for 10 min under N$_2$. A solution of 3 (4.8 g, 13.0 mmol) in acetonitrile (15 mol) was added to the suspension, and the reaction was allowed to stir for 1 hour. The reaction mixture was concentrated to approximately one-quarter of the original volume, then diluted with EtOAc (100 mL). The organic layer was washed with saturated Na$_2$CO$_3$ (100 mL) and brine (100 mL). The organic layer was dried over Na$_2$SO$_4$. After filtration, the organic layer was concentrated and purified via flash chromatography using 1:1 hexanes/EtOAc to give 4 as a yellow foam (5.91 g, 90%). R$_f$=0.42 (1:1 hexanes/EtOAc); $^1$H NMR (CDCl$_3$, 500 MHz): δ 7.44 (d, J=7.3 Hz, 4H), 7.42-7.27 (m, 8H), 7.20 (d, J=8.8 Hz, 2H), 6.90 (d, J=8.3 Hz, 2H), 6.83 (d, J=8.8 Hz, 2H), 6.02 (bs, 2H), 5.16 (d, J=2.4 Hz, 2H), 5.03 (s, 2H), 3.80 (s, 3H), 3.04 (dd, J=7.3, 13.2 Hz, 1H), 2.95 (dd, J=6.4, 13.2 Hz, 1H), 2.90 (s, 3H) ppm. $^{13}$C NMR (CDCl$_3$, 125 MHz): δ 173.1, 164.0, 160.7, 159.8, 157.9, 137.8, 137.1, 133.2, 130.7, 129.1, 128.7, 128.4, 128.0, 127.9, 127.7, 114.8, 114.0, 86.1, 84.9, 70.1, 66.8, 55.4, 50.2, 39.7 ppm. IR (thin film) 2934, 1642, 1589, 1536, 1508, 1440, 1378, 1280, 1244, 1172, 1152, 1107, 1026, 909, 831, 799, 732, 696 cm$^{-1}$. Calc. C$_{34}$H$_{34}$N$_3$O$_4$ m/z (M+H) 548.2549, Obsd. 548.2556.

Example 4: Preparation of (Z)-Benzyl 4-(4-(benzyloxy)benzyl)-2-imino-5-(4-methoxybenzylidene)-3-methylimidazolidine-1-carboxylate (5)

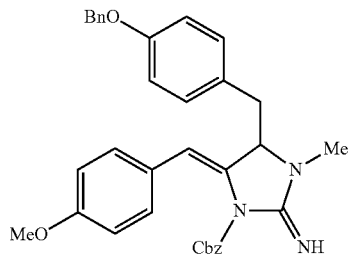

5

To a 25 mL round bottom flask equipped with a stir bar was added 4 (0.51 g, 0.91 mmol), AgNO$_3$ (0.016 g, 0.09 mmol) and dichloromethane (9.1 mL). The flask was wrapped with aluminum foil, and the reaction was allowed to stir at room temperature under N$_2$ overnight. The reaction mixture was concentrated and purified via flash chromatography using 5% MeOH in CH$_2$Cl$_2$ to give 5 as a light yellow foam (0.43 g, 87%). R$_f$=0.28 (5% MeOH in CH$_2$Cl$_2$); $^1$H NMR (CDCl$_3$, 300 MHz): δ 7.46-7.20 (m, 8H), 6.97 (d, J 8.7 Hz, 2H), 6.94-6.87 (m, 4H), 6.74 (d, J=4.3 Hz, 2H), 6.71 (d, J=4.0 Hz, 2H), 5.39 (s, 1H), 4.99 (s, 2H), 4.91 (d, J 11.8 Hz, 1H), 4.29 (d, J=11.8 Hz, 1H), 4.08 (dd, J=3.6, 4.1, 6.6 Hz, 1H), 3.77 (s, 3H), 3.08 (s, 3H), 2.99 (dd, J=4.2, 13.7 Hz, 1H), 2.73 (dd, J=7.3, 13.6 Hz, 1H) ppm. $^{13}$C NMR (CDCl$_3$, 125 MHz): δ 158.7, 157.9, 154.0, 151.2, 137.1, 134.2, 131.1, 129.5, 128.8, 128.7, 128.5, 128.4, 128.3, 128.1, 127.5, 114.8, 113.8, 113.4, 70.0, 68.6, 65.0, 55.4, 37.8 ppm. IR (thin film) 2923, 2851, 1734, 1607, 1510, 1454, 1382, 1299, 1247, 1178, 1033, 830, 738, 698 cm$^{-1}$. Calc. C$_{34}$H$_{34}$N$_3$O$_4$ m/z (M+H) 548.2549, Obsd. 548.2555.

Example 5: Preparation of Naamine A (6)

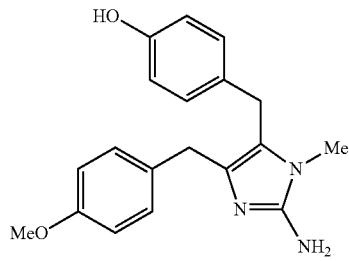

6

To a 10 mL round bottom flask equipped with a stir bar was added 5 (0.25 g, 0.46 mmol), Pd(OH)$_2$ on carbon (20% wt, 0.032 g, 0.046 mmol) and MeOH (4.6 mL). A H$_2$ balloon was attached, and the reaction was allowed to stir overnight. The reaction mixture was filtered through Celite diatomaceous earth and rinsed with dichloromethane. The reaction mixture was concentrated to a pale yellow solid (0.123 g, 84%) to give naamine A (6) and used without further purification. $^1$H NMR (CD$_3$OD, 500 MHz): δ 7.08 (d, J=8.3 Hz, 2H), 6.84 (d, J=8.3 Hz, 2H), 6.76 (d, J=8.3 Hz, 2H), 6.64 (d, J=8.8 Hz, 2H), 3.76 (s, 2H), 3.72 (s, 3H), 3.69 (s, 2H), 3.08 (s, 3H) ppm. $^{13}$C NMR (CD$_3$OD, 125 MHz): δ 168.5, 157.8, 156.2, 148.9, 134.5, 132.4, 130.6, 130.1, 129.5, 120.3, 115.8, 114.0, 55.6, 32.7, 29.4, 28.6 ppm. IR (thin film) 2923, 2852, 1610, 1511, 1457, 1369, 1245, 1175, 1035, 814, 773, 668, 652 cm$^{-1}$. Calc. C$_{19}$H$_{22}$N$_3$O$_2$ m/z (M+H) 324.1712, Obsd. 324.1714.

Example 6: Preparation of Naamidine A (7)

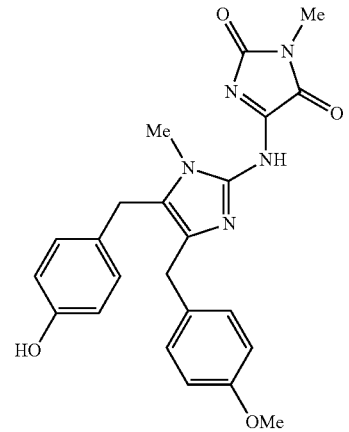

7

Naamidine A (1) was prepared according to the procedure of Ohta et al. *Heterocycles* 2000, 53 (9), 1939-1955. To a 50 mL round bottom, two-neck flask equipped with a stir bar and reflux condenser was added 1-methylparabanic acid (2.04 g, 15.9 mmol) and acetonitrile (14.5 mL). Bis(trimethylsilyl)acetamide (4.9 mL, 19.9 mmol) was added via syringe, and the reaction mixture was allowed to reflux for 2 hours. Without exposing reaction flask to the open atmosphere, the solvent was removed under reduced pressure. The reaction mixture was placed under N$_2$ and diluted with toluene (10.5 mL). The solution was transferred to a 50 mL round bottom, two-neck flask equipped with a stir bar and reflux condenser, containing 6 (1.03 g, 3.2 mmol) under a $N_2$ atmosphere. The reaction mixture was allowed to reflux for 16 hours. The reaction was allowed to cool to room temperature, dilute with EtOAc (10 mL), then transferred to a 100 mL round bottom flash to be concentrated. The mixture was purified via flash chromatography using 85:15 PhMe/MeOH with 1% $NEt_3$ to give 7 as a bright yellow solid (1.05 g, 76%). $R_f$=0.4 (85:15 PhMe/MeOH with 1% $NEt_3$); $^1$H NMR (CDCl$_3$, 500 MHz): δ 7.11 (d, J=8.8 Hz, 2H), 6.83 (d, J=7.8 Hz, 2H), 6.81 (d, J=8.8 Hz, 2H), 6.73 (d, J=8.8 Hz, 2H), 3.87 (s, 4H), 3.77 (s, 3H), 3.40 (s, 3H), 3.17 (s, 3H) ppm. $^{13}$C NMR (CDCl$_3$, 125 MHz): δ 163.3, 158.5, 157.0, 155.2, 146.7, 134.7, 131.3, 129.5, 129.3, 128.7, 127.0, 115.0, 114.3, 55.5, 32.1, 30.0, 28.8, 25.0 ppm. IR (thin film) 3335, 1789, 1736, 1665, 1612, 1569, 1512, 1486, 1445, 1392, 1303, 1247, 1174, 1153, 1035, 821, 776, 727, 606 cm$^{-1}$. Calc. $C_{23}H_{24}N_5O_4$ m/z (M+H) 434.1828, Obsd. 434.1840.

Example 7: Preparation of (2Z,5Z)-Benzyl 2-(benzoylimino)-4-(4-(benzyloxy)benzyl)-5-(4-methoxybenzylidene)-3-methylimidazolidine-1-carboxylate (8)

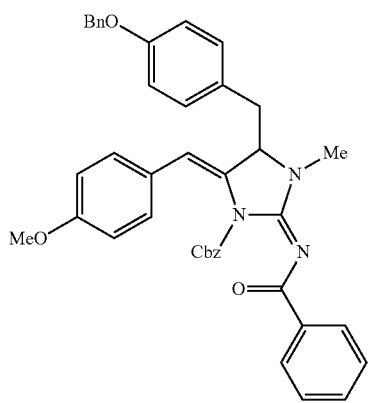

8

To a 25 mL round bottom flask equipped with a stir bar was added 5 (0.5 g, 0.91 mmol), NEt$_3$ (0.25 mL, 1.8 mmol), benzoyl chloride (0.16 mL, 1.4 mmol) and dichloromethane (9.1 mL). The reaction was allowed to stir for 1 hour. The reaction mixture was concentrated and purified via flash chromatography using 1:1 hexanes/EtOAc to give 8 as a light yellow foam (0.54 g, 92%). $R_f$=0.43 (1:1 hexanes/EtOAc); $^1$H NMR (CDCl$_3$, 300 MHz): δ 8.12 (d, J=7.0 Hz, 2H), 7.51-7.11 (m, 13H), 7.08 (d, J=8.8 Hz, 2H), 6.98 (d, J=8.7 Hz, 2H), 6.78 (d, J=8.7 Hz, 2H), 6.75 (d, J=8.9 Hz, 2H), 5.45 (s, 1H), 5.01 (s, 2H), 4.80 (d, J=11.9 Hz, 1H), 4.42 (d, J=11.8 Hz, 1H), 4.08 (dd, J=4.1, 6.6 Hz, 1H), 3.77 (s, 3H), 3.14 (s, 3H), 3.03 (dd, J=4.3, 13.5 Hz, 1H), 2.78 (dd, J=7.6, 13.5 Hz, 1H) ppm. $^{13}$C NMR (CDCl$_3$, 75 MHz): δ 175.6, 158.7, 157.9, 151.9, 149.1, 137.3, 137.0, 134.5, 131.4, 131.1, 129.7, 129.3, 128.7, 128.6, 128.2, 128.1, 128.0, 127.8, 127.5, 127.1, 117.4, 114.8, 113.7, 70.0, 68.7, 64.6, 55.3, 37.9, 31.0 ppm. IR (thin film) 3033, 2933, 1746, 1647, 1607, 1511, 1455, 1379, 1315, 1282, 1248, 1178, 1075, 1037, 1024, 866, 826, 739, 713, 697 cm$^{-1}$. Calc. $C_{41}H_{37}N_3O_5$ m/z (M+Na) 674.2631, Obsd. 674.2632.

Example 8: Preparation of (2Z,5Z)-Benzyl 4-(4-(benzyloxy)benzyl)-2-((2-fluoro-benzoyl)imino)-5-(4-methoxybenzylidene)-3-methylimidazolidine-1-carboxylate (9)

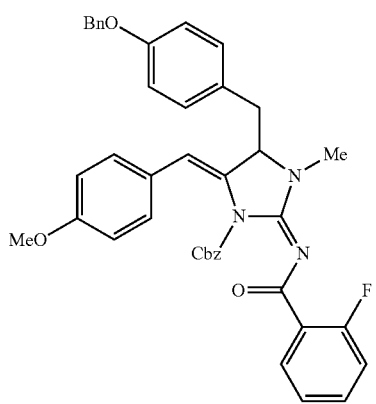

9

To a 25 mL round bottom flask equipped with a stir bar was added 5 (0.64 g, 1.2 mmol), NEt$_3$ (0.33 mL, 2.4 mmol), 2-fluorobenzoyl chloride (0.16 mL, 1.4 mmol) and dichloromethane (12 mL). The reaction was allowed to stir for 1 hour. The reaction mixture was concentrated and purified via flash chromatography using 1:1 hexanes/EtOAc to give 9 as a yellow oil (0.71 g, 89%). $R_f$=0.42 (1:1 hexanes/EtOAc); $^1$H NMR (CDCl$_3$, 300 MHz): δ 7.91 (dt, J=2.0, 7.8 Hz, 1H), 7.44-7.01 (m, 11H), 6.97 (d, J=8.8 Hz, 4H), 6.85 (t, J=8.8 Hz, 2H), 6.77 (d, J=8.8 Hz, 2H), 6.66 (d, J=8.8 Hz, 2H), 5.46 (s, 1H), 5.00 (s, 2H), 4.83 (d, J=11.7 Hz, 1H), 4.46 (d, J=12.3 Hz, 1H), 4.11 (dd, J=3.4, 7.3 Hz, 1H), 3.76 (s, 3H), 3.15 (s, 3H), 3.00 (dd, J=4.4, 13.7 Hz, 1H), 2.78 (dd, J=7.7, 13.7 Hz, 1H) ppm. $^{13}$C NMR (CDCl$_3$, 75 MHz): δ 172.7, 163.0, 159.7, 158.8, 158.0, 151.9, 149.1, 137.0, 134.4, 132.6, 132.4, 132.3, 131.1, 129.5, 128.7, 128.3, 128.2, 127.7, 127.5, 127.0, 123.7, 117.4, 116.6, 116.3, 114.9, 113.7, 70.1, 68.9, 64.6, 55.3, 37.9, 31.0 ppm. IR (thin film) 3033, 2930, 1743, 1598, 1510, 1483, 1452, 1407, 1379, 1314, 1282, 1246, 1177, 1116, 1029, 909, 862, 817, 756, 733, 696 cm$^{-1}$. Calc. $C_{41}H_{36}N_3O_5F$ m/z (M+Na) 692.2537, Obsd. 692.2545.

Example 9: Preparation of (2Z,5Z)-Benzyl 4-(4-(benzyloxy)benzyl)-2-((2,4-dichloro-benzoyl)imino)-5-(4-methoxybenzylidene)-3-methylimidazolidine-1-carboxylate (10)

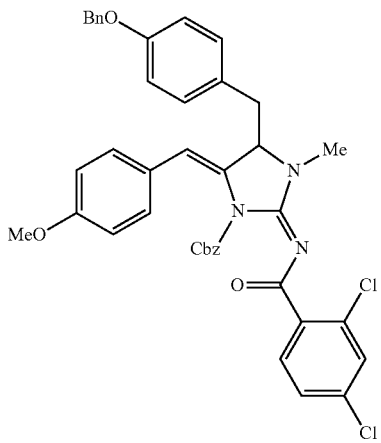

To a 5 mL round bottom flask equipped with a stir bar was added 5 (0.05 g, 0.09 mmol), NEt$_3$ (0.025 mL, 0.18 mmol), 2,4-dichlorobenzoyl chloride (0.017 mL, 0.14 mmol) and dichloromethane (0.9 mL). The reaction was allowed to stir for 1 hour. The reaction mixture was concentrated and purified via flash chromatography using 2:1 hexanes/EtOAc to give 10 as a yellow oil (0.054 g, 86%). R$_f$=0.26 (2:1 hexanes/EtOAc); $^1$H NMR (CDCl$_3$, 300 MHz): δ 7.76 (d, J=8.3 Hz, 1H), 7.44-7.14 (m, 10H), 6.97 (d, J=8.8 Hz, 2H), 6.90 (d, J=8.8 Hz, 2H), 6.83 (d, J=7.1 Hz, 2H), 6.77 (d, J=8.3 Hz, 2H), 6.70 (d, J=8.8 Hz, 2H), 5.54 (s, 1H), 5.00 (s, 2H), 4.70 (d, J=11.7 Hz, 1H), 4.48 (d, J=12.2 Hz, 1H), 4.15 (dd, J=3.9, 6.3 Hz, 1H), 3.38 (s, 3H), 3.16 (s, 3H), 3.00 (dd, J=3.9, 13.7 Hz, 1H), 2.82 (dd, J=6.8, 13.7 Hz, 1H) ppm. $^{13}$C NMR (CDCl$_3$, 75 MHz): δ 173.3, 158.9, 158.0, 152.7, 137.0, 135.9, 135.7, 134.2, 133.4, 133.2, 131.0, 130.1, 129.5, 129.1, 128.8, 128.7, 128.3, 128.2, 128.1, 127.5, 126.7, 126.6, 117.6, 114.9, 113.7, 70.0, 69.0, 64.7, 55.2, 37.8, 31.1 ppm. IR (thin film) 3032, 2931, 1743, 1582, 1510, 1455, 1375, 1284, 1247, 1177, 1100, 1030, 909, 862, 831, 757, 734, 696 cm$^{-1}$. Calc. C$_{41}$H$_{35}$N$_3$O$_5$Cl$_2$ m/z (M+Na) 742.1851, Obsd. 742.1868.

Example 10: Preparation of (2Z,5Z)-Benzyl 4-(4-(benzyloxy)benzyl)-5-(4-methoxybenzylidene)-3-methyl-2-((thiazole-2-carbonyl)imino)imidazolidine-1-carboxylate (11)

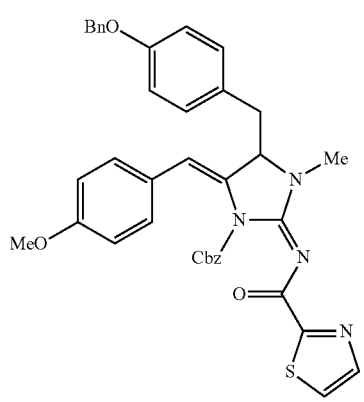

To a 5 mL round bottom flask equipped with a stir bar was added 5 (0.05 g, 0.09 mmol), NEt$_3$ (0.025 mL, 0.18 mmol), 1,3-thiazolebenzoyl chloride (0.02 g, 0.14 mmol) and dichloromethane (0.9 mL). The reaction was allowed to stir for 1 hour. The reaction mixture was concentrated and purified via flash chromatography using 5% MeOH in EtOAc to give 11 as a yellow oil (0.054 g, 92%). R$_f$=0.58 (5% MeOH in EtOAc); $^1$H NMR (CDCl$_3$, 500 MHz): δ 7.91 (d, J=2.9 Hz, 1H), 7.49 (d, J=2.9 Hz, 1H), 7.44-7.29 (m, 5H), 7.21 (t, J=7.3 Hz, 1H), 7.16 (t, J=7.8 Hz, 2H), 7.01 (d, J=8.8 Hz, 2H), 6.96 (d, J=8.8 Hz, 2H), 6.82 (d, J=9.3 Hz, 2H), 6.77 (d, J=8.8 Hz, 2H), 6.71 (d, J=8.8 Hz, 2H), 5.38 (s, 1H), 5.00 (s, 2H), 4.87 (d, J=12.2 Hz, 1H), 4.39 (d, J=11.7 Hz, 1H), 4.12 (dd, J=4.4, 7.8 Hz, 1H), 3.76 (s, 3H), 3.17 (s, 3H), 3.04 (dd, J=4.9, 13.7 Hz, 1H), 2.73 (dd, J=8.8, 13.7 Hz, 1H) ppm. $^{13}$C NMR (CDCl$_3$, 125 MHz): δ 173.1, 167.4, 167.1, 158.8, 158.0, 153.6, 149.0, 144.2, 137.0, 134.2, 131.1, 129.5, 128.9, 128.7, 128.3, 128.2, 128.1, 127.7, 127.5, 126.9, 124.1, 117.6, 114.9, 113.7, 70.0, 69.0, 65.0, 55.3, 37.7, 31.2 ppm. IR (thin film) 3032, 2932, 1741, 1594, 1510, 1489, 1454, 1397, 1380, 1281, 1236, 1176, 1076, 1026, 908, 863, 847, 821, 727, 696, 644, 609 cm$^{-1}$.

Example 11: Preparation of (2Z,5Z)-Benzyl 4-(4-(benzyloxy)benzyl)-2-(isobutyrylimino)-5-(4-methoxybenzylidene)-3-methylimidazolidine-1-carboxylate (12)

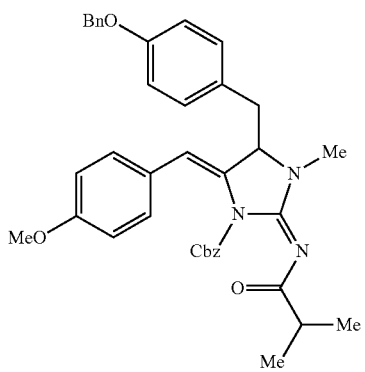

12

To a 5 mL round bottom flask equipped with a stir bar was added 5 (0.05 g, 0.09 mmol), NEt₃ (0.025 mL, 0.18 mmol), isobutyryl chloride (0.014 mL, 0.14 mmol) and dichloromethane (0.9 mL). The reaction was allowed to stir for 1 hour. The reaction mixture was concentrated and purified via flash chromatography using 1:1 hexanes/EtOAc to give 12 as a yellow oil (0.044 g, 87%). $R_f$=0.32 (1:1 hexanes/EtOAc); ¹H NMR (CDCl₃, 500 MHz): δ 7.64-7.37 (m, 10H), 7.28 (d, J=8.8 Hz, 2H), 7.15 (d, J=8.8 Hz, 2H), 7.08 (d, J=7.8 Hz, 2H), 6.96 (d, J=8.8 Hz, 2H), 5.60 (s, 1H), 5.21 (s, 2H), 5.08 (d, J=11.7 Hz, 1H), 4.71 (d, J=11.7 Hz, 1H), 4.20 (dd, J=3.9, 6.8 Hz, 1H), 3.97 (s, 3H), 3.24 (s, 3H), 3.18 (dd, J=4.4, 13.7 Hz, 1H), 2.93 (dd, J=7.3, 13.2 Hz, 1H), 2.84 (sep, J=6.8 Hz, 1H), 1.44 (d, J=6.8 Hz, 3H), 1.39 (d, J=6.8 Hz, 3H) ppm. ¹³C NMR (CDCl₃, 75 MHz): δ 188.0, 158.7, 157.9, 150.3, 149.2, 137.0, 134.6, 131.0, 129.5, 129.4, 128.7, 128.6, 128.2, 128.0, 127.9, 127.4, 127.2, 117.0, 114.8, 113.7, 70.0, 68.6, 64.6, 55.2, 38.6, 37.9, 30.8, 20.1 ppm. IR (thin film) 3033, 2964, 2929, 1745, 1663, 1607, 1455, 1379, 1273, 1249, 1179, 1123, 1077, 1037, 923, 864, 826, 738, 697 cm⁻¹. Calc. C₃₈H₃₉N₃O₅ m/z (M+Na) 640.2787, Obsd. 640.2775.

Example 12: Preparation of (2Z,5Z)-Benzyl 4-(4-(benzyloxy)benzyl)-5-(4-methoxybenzylidene)-3-methyl-2-((2-methylbutanoyl)imino)imidazolidine-1-carboxylate (13)

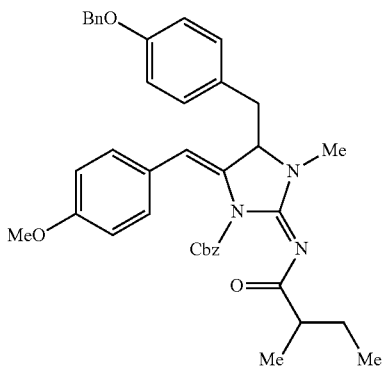

13

To a 5 mL round bottom flask equipped with a stir bar was added 5 (0.05 g, 0.09 mmol), NEt₃ (0.025 mL, 0.18 mmol), 2-methylbutyryl chloride (0.017 mL, 0.14 mmol) and dichloromethane (0.9 mL). The reaction was allowed to stir for 1 hour. The reaction mixture was concentrated and purified via flash chromatography using 1:1 hexanes/EtOAc to give 13 as a yellow oil (0.049 g, 85%). $R_f$=0.44 (1:1 hexanes/EtOAc); ¹H NMR (CDCl₃, 500 MHz): δ 7.44-7.17 (m, 8H), 7.08 (d, J=8.7 Hz, 2H), 6.94 (d, J=8.5 Hz, 2H), 6.86 (d, J=7.3 Hz, 2H), 6.75 (d, J=8.4 Hz, 2H), 5.39 (d, J=5.8 Hz, 1H), 5.00 (s, 2H), 4.87 (dd, J=2.3, 12.0 Hz, 1H), 4.51 (dd, J=3.8, 12.0 Hz, 1H), 3.99 (p, J=3.7, 1H), 3.75 (s, 3H), 3.03 (s, 3H), 2.97 (dd, J=4.4, 13.5 Hz, 1H), 2.72 (m, 1H), 2.46 (ddq, J=6.9, 6.8, 5.6, 7.0 Hz, 1H), 1.83 (m, 1H), 1.51 (m, 1H), 1.18 (dd, J=6.9, 7.0, 3H), 0.97 (dt, J=4.0, 7.4, 7.6 Hz, 3H) ppm. ¹³C NMR (CDCl₃, 75 MHz): δ 187.5, 158.9, 158.0, 151.1, 150.7, 149.4, 137.2, 134.7, 131.2, 129.7, 128.8, 128.7, 128.4, 128.2, 128.0, 127.6, 127.4, 127.3, 117.2, 114.9, 113.8, 70.1, 68.8, 64.8, 55.4, 45.9, 45.5, 38.1, 31.1, 27.7, 27.5, 17.2, 16.4, 12.2, 12.0. IR (thin film) 2963, 2931, 2873, 1746, 1653, 1607, 1511, 1456, 1378, 1249, 1179, 1119, 1077, 1039, 827, 741, 696 cm⁻¹. Calc. C₃₉H₄₁N₃O₅ m/z (M+Na) 654.2944, Obsd. 654.2941.

Example 13: (E)-N-(5-(4-hydroxybenzyl)-4-(4-methoxybenzyl)-1-methyl-1H-imidazol-2(3H)-ylidene)isobutyramide (14)

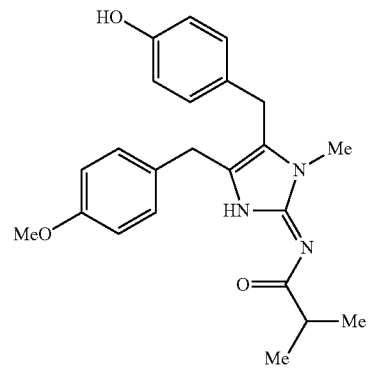

14

To a 5 mL round bottom flask equipped with a stir bar was added 12 (0.05 g, 0.08 mmol), PdCl₂ (0.025 mL, 0.18 mmol) and methanol (0.9 mL). The reaction was allowed to stir overnight under and H2 atmosphere balloon. The reaction mixture was filtered through Celite diatomaceous earth, and rinsed with additional methanol. The solvent was removed and the mixture was taken up in dichloromethane. The organic layer was washed with sat. NaHCO3, then brine. The organic layer was dried over Na₂SO₄, then concentrated. The crude product is purified by trituration with methanol was taken up in methanol, and product was isolated by trituration to give an off white solid. ¹H NMR (MeOD, 300 MHz): δ 7.09 (d, J=8.8 Hz, 2H), 6.82 (d, J=8.3 Hz, 2H), 6.75 (d, J=8.8 Hz, 2H), 6.64 (d, J 8.3 Hz, 2H), 3.86 (s, 2H), 3.80 (s, 2H), 3.72 (s, 3H), 3.16 (s, 3H), 2.63 (sep, J 6.8 Hz, 1H), 1.19 (d, J=6.8 Hz, 6H) ppm; ¹³C NMR (MeOD, 75 MHz): δ 170.5, 157.1, 130.5, 130.1, 116.4, 114.7, 55.7, 36.1, 32.9, 30.6, 29.3, 19.7 ppm. IR (thin film) 3274, 2986, 2472, 1670, 1611, 1510, 1465, 1404, 1301, 1255, 1175, 1102, 1032, 973, 816 cm⁻¹.

Example 14: Preparation of (E)-N-(5-(4-Hydroxybenzyl)-4-(4-methoxybenzyl)-1-methyl-1H-imidazol-2(3H)-ylidene)-2-methylbutanamide (15)

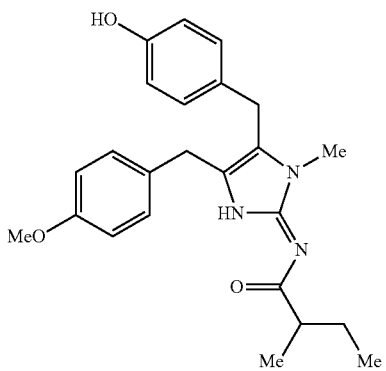

To a 5 mL round bottom flask equipped with a stir bar was added 12 (0.05 g, 0.08 mmol), PdCl$_2$ (0.025 mL, 0.18 mmol) and methanol (0.9 mL). The reaction was allowed to stir overnight under and H2 atmosphere balloon. The reaction mixture was filtered through Celite, and rinsed with additional methanol. The solvent was removed and the mixture was taken up in chloroform. The organic layer was washed with 10% NaCO$_3$, then brine. The organic layer was dried over Na$_2$SO$_4$, then concentrated. The organic layer was dried over Na$_2$SO$_4$, then concentrated to give 15 as a yellow oil. $^1$H NMR (MeOD, 300 MHz): δ 7.09 (d, J=8.8 Hz, 2H), 6.82 (d, J=8.3 Hz, 2H), 6.76 (d, J=8.8 Hz, 2H), 6.64 (d, J 8.3 Hz, 2H), 4.59 (s, 1H), 3.87 (s, 2H), 3.81 (s, 2H), 3.72 (s, 3H), 3.18 (s, 3H), 2.44 (sextet, J=6.8 Hz, 1H), 1.71 (m, J=7.3 Hz, 1H), 1.48 (m, J=6.8 Hz, 1H), 1.19 (d, J=6.8 Hz, 3H), 0.97 (t, J=7.3 Hz, 3H) ppm. $^{13}$C NMR (MeOD, 75 MHz): δ 170.5, 159.5, 157.0, 130.5, 130.1, 116.4, 114.7, 55.7, 43.6, 32.9, 30.8, 29.3, 28.2, 17.9, 12.3 ppm. IR (thin film) 3357, 2965, 2486, 2076, 1670, 1653, 1635, 1612, 1558, 1510, 1458, 1405, 1301, 1245, 1175, 1118, 1033, 971, 816 cm$^{-1}$.

Example 15: General Procedure for the 3-Component Coupling

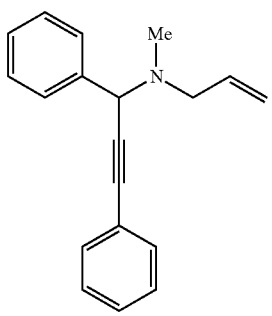

In a 250 mL high pressure flask containing a magnetic stir bar were added benzaldehyde (3.1 g, 28.9 mmol), phenylacetylene (2.95 g, 28.9 mmol), N-allylmethylamine (1.88 g, 26.3 mmol), oven dried molecular sieves (Grade 564, 3 Å, 8-12 mesh) (ca. 2 g) and acetonitrile (200 mL). The flask was sealed and placed in a preheated 80° C. oil bath for 24 h. The reaction flask was removed from the oil bath and allowed to cool to room temperature. CuBr (0.38 g, 2.63 mmol) was then added and the flask was sealed and returned to the preheated 80° C. oil bath for 48 h. The reaction tube was removed from the oil bath an allowed to cool to room temperature. The mixture was filtered through Celite and rinsed with EtOAc (50 mL). The filtrate was concentrated under reduced pressure. The crude product was purified via flash chromatography, eluting with 9:1 hexanes/EtOAc to give N-(1,3-diphenylprop-2-yn-1-yl)-N-methylprop-2-en-1-amine (16) as a dark orange oil (5.32 g, 88%). $^1$H NMR (CDCl$_3$, 300 MHz): δ 7.65 (d, J=6.9 Hz, 2H), δ 7.56-7.53 (m, 2H), δ 7.40-7.26 (m, 6H), δ 5.93 (ddt, J=6.6 Hz, 10.5 Hz, 17.1 Hz, 1H), δ 5.32 (dd, J=17.1 Hz, 1.5 Hz, 1H), δ 5.18 (dd, J=10.3 Hz, 1.2 Hz, 1H), δ 4.99 (s, 1H), δ 3.89 (s, 3H), δ 3.19 (d, J=5.1 Hz, 2H), δ 2.23 (s, 3H). $^{13}$C NMR (CDCl$_3$, 300 MHz): δ 138.9, δ 136.3, δ 131.9, δ 128.5, δ 128.4, δ 128.3, δ 127.7, δ 123.4, δ 117.8, δ 88.5, δ 84.9, δ 59.8, δ 57.9 ppm. IR (thin film): 3061, 3030, 2978, 2945, 2844, 2788, 1598, 1489, 1448, 1324, 1273, 1196, 1155, 1127, 1070, 1023, 994, 963, 917, 754, 726, 689 cm$^{-1}$.

Example 16: Preparation of N-(1-(4-Methoxyphenyl)-3-phenylprop-2-yn-1-yl)-N-methylprop-2-en-1-amine (17)

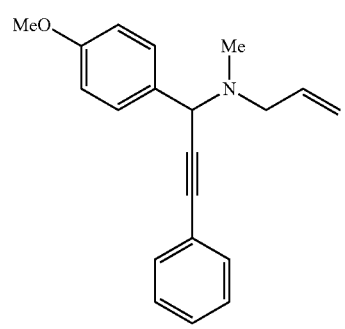

In a 250 mL high pressure flask containing a magnetic stir bar were added p-anisaldehyde (10 g, 73.4 mmol), phenylacetylene (7.5 g, 73.4 mmol), N-allylmethylamine (4.75 g, 66.7 mmol), oven-dried molecular sieves (Grade 564, 3 Å, 8-12 mesh) (ca. 2 g) and acetonitrile (200 mL). The flask was sealed and placed in a preheated 80° C. oil bath for 24 h. The reaction flask was removed from the oil bath and allowed to cool to room temperature. CuBr (0.95 g, 6.67 mmol) was then added and the flask was sealed and returned to the preheated 80° C. oil bath for 48 h. The reaction tube was removed from the oil bath an allowed to cool to room temperature. The mixture was filtered through Celite diatomaceous earth and rinsed with EtOAc (50 mL). The filtrate was concentrated under reduced pressure. The crude product was purified via flash chromatography, eluting with 9:1 hexanes/EtOAc to give N-(1-(4-methoxyphenyl)-3-phenylprop-2-yn-1-yl)-N-methylprop-2-en-1-amine (17) as a dark orange oil. R$_f$=0.78 (2:1 hexanes/EtOAc); $^1$H NMR (CDCl$_3$, 300 MHz): δ 7.59-7.53 (m, 4H), δ 7.37-7.26 (m, 3H), δ 6.49 (d, J=8.7 Hz, 2H), δ 5.92 (ddt, J=6.6 Hz, 10.5 Hz, 17.1 Hz, 1H), δ 5.33 (dd, J=17.7 Hz, 2.1 Hz, 1H), δ 5.19 (dd, J=9.3 Hz, 1.9 Hz, 1H), δ 4.94 (s, 1H), δ 3.83 (s, 3H), δ 3.19 (d, J=6.6 Hz, 2H), δ 2.24 (s, 3H). $^{13}$C NMR (CDCl$_3$, 300 MHz): δ 159.1, δ 136.3, δ 131.9, δ 131.1, δ 129.7, δ 128.4, δ 128.2, δ 123.4, δ 117.7, δ 113.6, δ 88.3, δ 85.3, δ 59.3, δ 57.8, δ 55.4, δ 37.8 ppm. IR (thin film) 2948, 2834, 2786, 1642, 1609, 1583, 1507, 1488, 1441, 1301, 1244, 1169, 1126, 1107, 1033, 994, 962, 916, 850, 807, 778, 754, 689, 583, 524 cm$^{-1}$. Calc. C$_{20}$H$_{21}$NO m/z 291.1623, Obsd. 292.1699 (M+H).

Example 17: General Procedure for the Deallylation of Allylic Amines

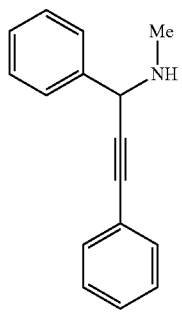

18

In a 250 mL round bottom flask containing a magnetic stir bar were added Pd(PPh$_3$)$_4$ (1.31 g, 1.14 mmol), thiosalicylic acid (7.0 g, 45.4 mmol) and CH$_2$Cl$_2$ (100 mL). A solution of $$$ (5.25 g, 22.7 mmol) in 15 mL in CH$_2$Cl$_2$ was added, and the reaction mixture was allowed to stir at room temperature under N2 for 12 h. The solvent was then removed under reduced pressure and the crude product was re-dissolved in Et$_2$O (10 mL). The organic layer was washed with NaHCO$_3$ (50 mL) and brine (50 mL) and dried and filtered over Na$_2$SO$_4$. The crude product was purified via flash chromatography, eluting with 8:2 hexanes/EtOAc to give N-methyl-1,3-diphenylprop-2-yn-1-amine (18) as a dark orange oil (3.12 g, 73%). $^1$H NMR (CDCl$_3$, 300 MHz): δ 7.61-7.31 (m, 10H), δ 4.76 (s, 1H), δ 2.57 (s, 3H), δ 1.47 (s, 1H) ppm. IR (thin film) 3060, 3029, 2933, 2850, 2793, 1653, 1598, 1559, 1540, 1489, 1473, 1449, 1306, 1214, 1177, 1098, 1071, 1027, 915, 755, 691 cm$^{-1}$.

Example 18: Preparation of 1-(4-Methoxyphenyl)-N-methyl-3-phenylprop-2-yn-1-amine (19)

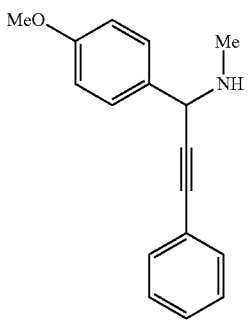

19

In a 250 mL round bottom flask containing a magnetic stir bar were added Pd(PPh$_3$)$_4$ (0.22 g, 0.192 mmol), N,N-dimethylbarbituric acid (9 g, 57.69 mmol) and CH$_2$Cl$_2$ (100 mL). A solution of $$$ (5.6 g, 19.23 mmol) in 25 mL in CH$_2$Cl$_2$ was added, and the reaction mixture was allowed to stir at room temperature under N2 for 12 h. The solvent was then removed under reduced pressure and the crude product was re-dissolved in Et$_2$O (10 mL). The organic layer was washed with NaHCO$_3$ (50 mL) and brine (50 mL) and dried and filtered over Na$_2$SO$_4$. The crude product was purified via flash chromatography, eluting with 8:2 hexanes/EtOAc to give 1-(4-methoxyphenyl)-N-methyl-3-phenylprop-2-yn-1-amine (19) as a dark orange oil (2.13 g, 44%). R$_f$=0.22 (2:1 hexanes/EtOAc); $^1$H NMR (CDCl$_3$, 300 MHz): δ 7.54-7.48 (m, 4H), δ 7.33-7.31 (m, 3H), δ 6.9 (d, J=8.7 Hz, 2H), δ 5.18 (s, 1H), δ 3.81 (s, 3H), δ 2.56 (s, 3H), δ 1.81 (s, 1H) ppm. $^{13}$C NMR (CDCl$_3$, 300 MHz): δ 159.2, δ 132.4, δ 131.7, δ 128.8, 128.3, 128.1, δ 123.1, δ 113.8, δ 89.2, δ 85.5, δ 55.6, δ 55.3, δ 33.7 ppm. IR (thin film) 2953, 2834, 2790, 1609, 1584, 1508, 1488, 1462, 1440, 1301, 1243, 1171, 1095, 1031, 956, 913, 829, 754, 727, 703, 689, 573, 547, 524 cm$^{-1}$. Calc. C$_{17}$H$_{17}$NO m/z (M+H) 251.1310, Obsd. 274.1213 (M+Na).

Example 19: General Procedure for the Guanylation of Propargylamines

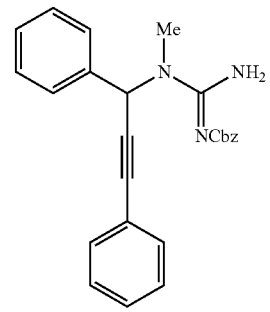

20

In a 100 mL round bottom flask containing a magnetic stir bar were added potassium benzyloxycarbonylcyanamide (0.65 g, 3.0 mmol), TMSCl (0.34 g, 3.1 mmol) and acetonitrile (15 mL). The solution was stirred at room temperature for 10 minutes. A solution of 18 (0.46 g, 2.4 mmol) in acetonitrile (3.5 mL) was then added, and the reaction mixture was allowed to stir at room temperature for 1 h. The solvent was then removed under reduced pressure and the crude product was re-dissolved in EtOAc (150 mL). The organic layer was washed with NaHCO$_3$ (50 mL) and brine (50 mL) and dried and filtered over Na$_2$SO$_4$. The crude product was purified via flash chromatography, eluting with 1:1 hexanes/EtOAc to give 20 as a dark brown oil (0.75 g, 85%). IR (thin film) 3331, 3031, 2939, 1736, 1646, 1596, 1534, 1491, 1450, 1379, 1153, 1050, 1028, 801, 757, 696 cm$^{-1}$.

Example 20: Preparation of Cbz-Protected Guanidine 21

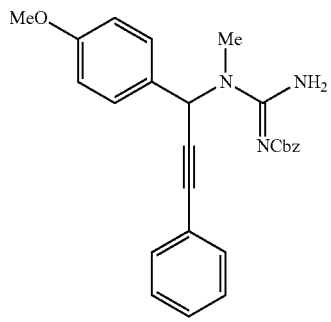

In a 100 mL round bottom flask containing a magnetic stir bar were added potassium benzyloxycarbonylcyanamide (2.176 g, 10.16 mmol), TMSCl (1.15 g, 10.59 mmol) and acetonitrile (45 mL). The solution was stirred at room temperature for 10 minutes. A solution of 19 in acetonitrile (10 mL) was then added, and the reaction mixture was allowed to stir at room temperature for 1 h. The solvent was then removed under reduced pressure and the crude product was re-dissolved in EtOAc (150 mL). The organic layer was washed with NaHCO$_3$ (50 mL) and brine (50 mL) and dried and filtered over Na$_2$SO$_4$. The crude product was purified via flash chromatography, eluting with 1:1 hexanes/EtOAc to give 21 as a dark brown oil (2.97 g, 82%). R$_f$=0.48 (1:1 hexanes/EtOAc); $^1$H NMR (CDCl$_3$, 300 MHz): δ 7.51-7.43 (m, 6H), δ 7.36-7.25 (m, 7H), δ 6.9 (d, J=6.3 Hz, 2H), δ 5.18 (s, 2H), δ 3.80 (s, 3H), δ 2.80 (s, 3H). $^{13}$C NMR (CDCl$_3$, 300 MHz): δ 164.1, δ 160.9, δ 159.4, δ 137.6, δ 131.9, δ 129.0, δ 128.7, δ 128.6, δ 128.4, δ 128.0, δ 127.7, δ 122.2, δ 113.9, δ 86.6, δ 85.2, δ 66.9, δ 55.3, δ 50.6, δ 29.7 ppm. IR (thin film) 3403, 2932, 1646, 1584, 1532, 1508, 1488, 1440, 1376, 1273, 1246, 1121, 1150, 1110, 1027, 908, 845, 799, 775, 755, 729, 690, 647, 586, 552 cm$^{-1}$. Calc. C$_{26}$H$_{25}$N$_3$O$_3$ m/z (M+H) 427.1896, Obsd. 428.1979 (M+H).

Example 21: General Procedure for the Cyclization of Propargyl Guanidines

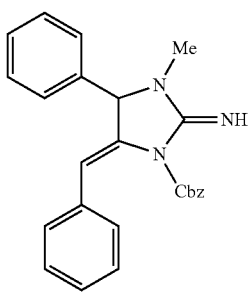

In a 50 mL foil-wrapped round bottom flask containing a magnetic stir bar were added a solution of 20 (0.75, 2.04 mmol), AgNO$_3$ (35 mg, 0.204 mmol), and CH$_2$Cl$_2$ (20 mL). The solution was stirred at room temperature for 6 h. The solvent was then removed under reduced pressure and the crude product was re-dissolved in EtOAc (50 mL). The organic layer was washed with NaHCO$_3$ (15 mL) and brine (15 mL) and dried and filtered over Na$_2$SO$_4$. The crude product was purified via flash chromatography, eluting with 1:1 hexanes/EtOAc to give (Z)-benzyl 5-benzylidene-2-imino-3-methyl-4-phenylimidazolidine-1-carboxylate (22) as a dark brown oil (0.53 g, 71%). R$_f$=0.31 (1:1 hexanes/EtOAc). IR (thin film) 3346, 3031, 1734, 1684, 1652, 1495, 1426, 1386, 1303, 1249, 1197, 1161, 1047, 1026, 957, 797, 696 cm$^{-1}$.

Example 22: Preparation of (Z)-Benzyl 5-benzylidene-2-imino-4-(4-methoxyphenyl)-3-methyl-imidazolidine-1-carboxylate

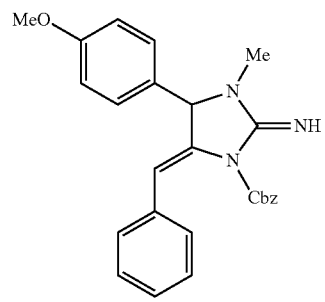

In a 50 mL foil-wrapped round bottom flask containing a magnetic stir bar were added a solution of 21 (1.37 g, 3.27 mmol), AgNO$_3$ (55.5 mg, 0.327 mmol), and CH$_2$Cl$_2$ (25 mL). The solution was stirred at room temperature for 6 h. The solvent was then removed under reduced pressure and the crude product was re-dissolved in EtOAc (50 mL). The organic layer was washed with NaHCO$_3$ (15 mL) and brine (15 mL) and dried and filtered over Na$_2$SO$_4$. The crude product was purified via flash chromatography, eluting with 2:1 hexanes/EtOAc to give (Z)-benzyl 5-benzylidene-2-imino-4-(4-methoxyphenyl)-3-methylimidazolidine-1-carboxylate (23) as a dark brown oil (1.21 g, 87%). R$_f$=0.18 (hexanes/EtOAc); $^1$H NMR (CDCl$_3$, 300 MHz): δ 7.28-7.16 (m, 9H), δ 7.10-7.08 (m, 2H), δ 6.92-6.88 (m, 4H), δ 5.47 (d, J=2.1 Hz, 1H), δ 4.92 (d, J=2.1 Hz, 1H), δδ 4.58 (ABq, 136.2, 11.7 Hz, 2H), δ 3.81 (s, 3H), δ 2.75 (s, 3H) ppm. $^{13}$C NMR (CDCl$_3$, 300 MHz): δ 106.1, δ 153.5, δ 151.4, δ 136.5, δ 135.1, δ 134.4, δ 129.7, δ 129.6, δ 128.7, δ 128.4, δ 127.4, δ 127.0, δ 114.5, δ 113.0, δ 62.2, δ 67.0, δ 55.4, δ 30.1 ppm. IR (thin film) 3404, 2932, 1646, 1548, 1532, 1508, 1488, 1440, 1376, 1273, 1246, 1171, 1150, 1110, 1027, 908, 845, 799, 779, 755, 728, 690, 647, 586, 552 cm$^{-1}$. Calc. C$_{26}$H$_{25}$N$_3$O$_3$ m/z (M+H) 427.1896, Obsd. 428.1979 (M+H).

Example 23: General Procedure for Acylation of Monoprotected Cyclic Guanidines

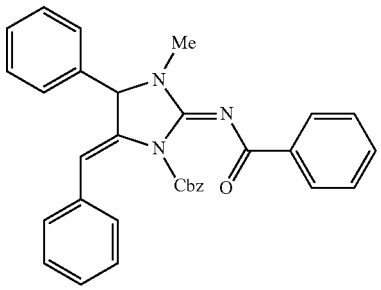

24

In a 10 mL round-bottomed flask containing a magnetic stir bar were added 22 (73.1 mg, 0.18 mmol), benzoyl chloride (0.032 mL, 0.276 mmol), triethylamine (0.051 mL, 0.37 mmol), and dichloromethane (2 mL) under $N_2$. The reaction was stirred at room temperature for 2 hours. The solution was concentrated via rotary evaporation under reduced pressure and the crude material was dissolved in 20 mL EtOAc. The organic layer was washed with $NaHCO_3$ (15 mL) and brine (15 mL). The organics were dried over $Na_2SO_4$, and the resulting material was purified via flash chromatography (6:4 hexanes/EtOAc) to yield (2Z,5Z)-benzyl 2-(benzoylimino)-5-benzylidene-3-methyl-4-phenylimidazolidine-1-carboxylate (24) as a light brown foam (85.7 mg, 92.8%). $^1$H NMR ($CDCl_3$, 300 MHz): δ 8.21-8.18 (m, 2H), δ 7.51-7.32 (m, 8H), δ 7.25-7.11 (m, 8H), δ 6.8-6.78 (m, 2H), δ 5.77 (d, J=2.1 Hz, 1H), δ 5.16 (d, J=1.8 Hz, 1H), δ 4.67 (q, J=9.6 Hz, 2H), δ 2.93 (s, 3H) ppm. $^{13}$C NMR ($CDCl_3$, 300 MHz): δ 178.8, δ 151.8, δ 149.3, δ 137.1, δ 136.8, δ 135.4, δ 134.5, δ 133.9, δ 131.6, δ 129.7, δ 129.4, δ 129.3, δ 127.8, δ 127.5, δ 116.9, δ 68.8, δ 67.0, δ 30.6 ppm. IR (thin film) 3060, 3029, 1744, 1557, 1494, 1448, 1404, 1377, 1315, 1277, 1226, 1173, 1144, 1080, 1036, 1020, 976, 909, 856, 794, 752, 727, 696, 668 cm$^{-1}$. Calc. m/z $C_{32}H_{27}N_3O_3$ (M+H) 501.2052, Obsd. 524.1963 (M+Na).

Example 24: Preparation of (2Z,5Z)-Benzyl 5-benzylidene-2-((2-fluorobenzoyl)imino)-3-methyl-4-phenylimidazolidine-1-carboxylate (25)

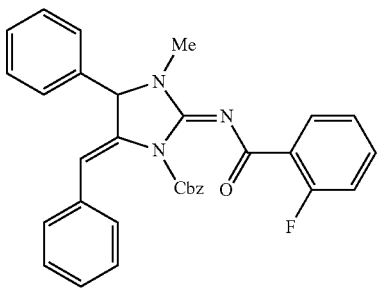

25

Acylation of 22 (95.5 mg, 0.24 mmol) using 2-fluorobenzoyl chloride (0.043 mL, 0.36 mmol), triethylamine (0.067 mL, 0.48 mmol), and dichloromethane (2 mL) provided (2Z,5Z)-benzyl 5-benzylidene-2-((2-fluorobenzoyl)imino)-3-methyl-4-phenylimidazolidine-1-carboxylate (25) as a light brown foam (119.8 mg, 95%). $^1$H NMR ($CDCl_3$, 500 MHz): δ 7.99 (t, J=8 Hz, 1H), δ 7.50-7.34 (m, 4H), δ 7.34-7.29 (m, 2H), δ 7.21-7.07 (m, 8H), δ 6.99 (d, J=8 Hz, 2H), δ 6.84 (d, J=7 Hz) δ 5.71 (d, J=2 Hz, 1H), δ 5.17 (d, J=2 Hz, 1H), δ 4.74 (q, J=12 Hz, 2H), δ 2.93 (s, 3H) ppm. $^{13}$C NMR ($CDCl_3$, 300 MHz): δ 172.3, δ 163.0, δ 159.5, δ 151.4, δ 149.3, δ 136.6, δ 135.2, δ 134.4, δ 133.9, δ 132.6, δ 132.5, δ 134.4, δ 129.4, δ 128.7, δ 128.4, δ 128.3, δ 128.0, δ 127.9, δ 127.5, δ 123.8, δ 123.7, δ 117.2, δ 116.7, δ 116.4, δ 69.0, δ 67.9, δ 30.5 ppm. IR (thin film) 3031, 1745, 1596, 1483, 1404, 1378, 1316, 1280, 1263, 1223, 1179, 1157, 1111, 1081, 1023, 974, 909, 866, 782, 755, 732, 696, 655 cm$^{-1}$. Calc. m/z $C_{32}H_{26}FN_3O_3$(M+H) 519.1958, Obsd. 542.1865 (M+Na).

Example 25: Preparation of (2Z,5Z)-Benzyl-5-benzylidene-2-((2,4-dichlorobenzoyl)imino)-3-methyl-4-phenylimidazolidine-1-carboxylate (26)

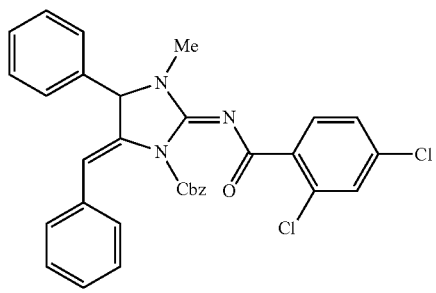

26

Acylation of 22 (42.6 mg, 0.107 mmol) using 2,4-dichlorobenzoyl chloride (0.023 mL, 0.161 mmol), triethylamine (0.030 mL, 0.21 mmol), and dichloromethane (2 mL) provided (2Z,5Z)-benzyl-5-benzylidene-2-((2,4-dichlorobenzoyl)imino)-3-methyl-4-phenylimidazolidine-1-carboxylate (26) as a light brown foam (54.7 mg, 89.6%). $^1$H NMR ($CDCl_3$, 500 MHz): δ 7.86 (d, J=8 Hz, 1H), δ 7.52-7.39 (m, 4H), δ 7.32-7.29 (m, 2H), δ 7.02 (d, J=6.5 Hz, 2H), δ 6.84 (d, J=7 Hz, 2H), δ 5.71 (d, J=2 Hz, 1H), δ 5.17 (d, J=2 Hz, 1H), δ 4.69 (q, J=12 Hz, 2H), δ 2.93 (s, 3H) ppm. $^{13}$C NMR ($CDCl_3$, 500 MHz): δ 173.0, δ 153, δ 149, δ 136.5, δ 136.3, δ 135.9, δ 135.3, δ 134.4, δ 130.4, δ 129.6, δ 128.8, δ 128.5, δ 128.4, δ 128.1, δ 127.9, δ 127.8, δ 126.9, δ 117.5, δ 69.3, δ 67.4, δ 30.9 ppm. IR (thin film) 3063, 3031, 1744, 1580, 1454, 1456, 1404, 1373, 1277, 1222, 1177, 1138, 1099, 1055, 1021, 973, 908, 865, 833, 792, 758, 728, 695 cm$^{-1}$. Calc. m/z $C_{32}H_{25}Cl_2N_3O_3$ (M+H) 569.1273, Obsd. 592.1183 (M+Na).

Example 26: Preparation of (2Z,5Z)-Benzyl-5-benzylidene-3-methyl-4-phenyl-2-((thiazole-2-carbonyl)imino)imidazolidine-1-carboxylate (27)

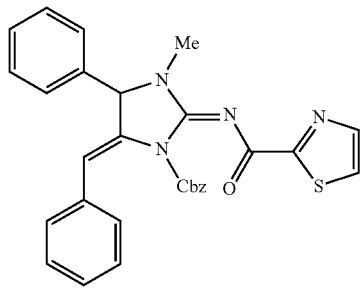

27

Acylation of 22 (35.2 mg, 0.089 mmol) using thiazole-2-carbonyl chloride (20 mg, 0.133 mmol), triethylamine (0.025 mL, 0.177 mmol), and dichloromethane (2 mL) provided (2Z,5Z)-benzyl-5-benzylidene-3-methyl-4-phenyl-2-((thiazole-2-carbonyl)imino)imidazolidine-1-carboxylate (27) as a light brown foam (19.8 mg, 43.9%). $^1$H NMR (CDCl$_3$, 500 MHz): δ 7.94 (d, J=4.5 Hz, 1H), δ 7.52 (d, J=4.5 Hz, 1H), δ 7.40-7.13 (m, 13H), δ 6.82 (d, J=7 Hz, 2H), δ 5.76 (d, J=2 Hz, 1H), δ 5.21 (d, J=2 Hz, 1H), δ 4.69 (q, J=12 Hz, 2H), δ 2.96 (s, 3H) ppm. $^{13}$C NMR (CDCl$_3$, 500 MHz): δ 162.1, δ 153.8, δ 149.1, δ 144.2, δ 136.5, δ 135.4, δ 134.2, δ 133.9, δ 129.7, δ 129.6, δ 128.8, δ 128.6, δ 128.5, δ 128.4, δ 128.2, δ 128.1, δ 127.7, δ 124.4, δ 117.2, δ 69.2, δ 67.4, δ 30.8 ppm. IR (thin film) 3031, 1744, 1595, 1489, 1456, 1396, 1328, 1278, 1228, 1177, 1133, 1080, 1057, 1019, 971, 906, 843, 821, 724, 694, 644, 606 cm$^{-1}$. Calc. m/z C$_{29}$H$_{24}$N$_4$O$_3$S (M+H) 508.1569, Obsd. 531.1462 (M+Na).

Example 27: Preparation of (2Z,5Z)-Benzyl-5-benzylidene-2-(isobutyrylimino)-3-methyl-4-phenylimidazolidine-1-carboxylate (28)

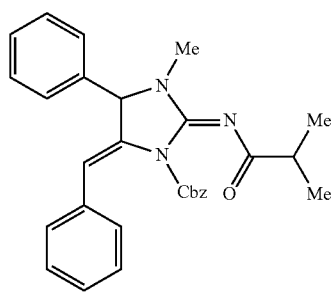

28

Acylation of 22 (35.5 mg, 0.0893 mmol) using isobutryl chloride (0.013 mL, 0.134 mmol), triethylamine (0.025 mL, 0.179 mmol), and dichloromethane (2 mL) provided (2Z,5Z)-benzyl-5-benzylidene-2-(isobutyrylimino)-3-methyl-4-phenylimidazolidine-1-carboxylate (28) as a light brown foam (38.2 mg, 91.5%). $^1$H NMR (CDCl$_3$, 500 MHz): δ 7.42-7.35 (m, 3H), δ 7.29-7.15 (m, 10H), δ 6.86 (d, J=7 Hz, 2H), δ 5.72 (d, J=2 Hz, 1H), δ 5.07 (d, J=2 Hz, 1H), δ 4.71 (q, J=10.5 Hz, 2H), δ 2.81 (s, 3H), δ 2.71 (m, 1H), δ 1.26 (d, J=7 Hz, 6H) ppm. $^{13}$C NMR (CDCl$_3$, 500 MHz): δ 187.6, δ 150.2, δ 149.5, δ 137.1, δ 135.6, δ 134.7, δ 134.1, δ 129.5, δ 128.6, δ 128.4, δ 128.3, δ 127.8, δ 127.6, δ 116.6, δ 68.8, δ 67.1, δ 38.8, δ 30.6, δ 20.0 ppm. IR (thin film) 3030, 2966, 2360, 2340, 1743, 1653, 1598, 1494, 1455, 1403, 1378, 1345, 1261, 1175, 1121, 1080, 1023, 977, 919, 847, 820, 752, 730, 695, 668, 634, 598, 557 cm$^{-1}$. Calc. m/z C$_{29}$H$_{29}$N$_3$O$_3$ (M+H) 467.2209, Obsd. 490.2103 (M+Na).

Example 28: Preparation of (2Z,5Z)-Benzyl-5-benzylidene-3-methyl-2-((2-methylbutanoyl)imino)-4-phenylimidazolidine-1-carboxylate (29)

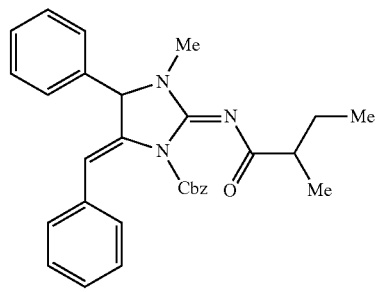

29

Acylation of 22 (56.9 mg, 0.171 mmol) using 2-methylbutyl chloride (0.037 mL, 0.256 mmol), triethylamine (0.048 mL, 0.341 mmol), and dichloromethane (2 mL) provided (2Z,5Z)-benzyl-5-benzylidene-3-methyl-2-((2-methylbutanoyl)imino)-4-phenylimidazolidine-1-carboxylate (29) as a light brown foam (56.9 mg, 69.5%). $^1$H NMR (CDCl$_3$, 500 MHz): δ 7.42-7.12 (m, 13H), δ 6.86 (d, J=7.5 Hz, 2H), δ 5.72 (d, J=2 Hz, 1H), δ 5.08 (d, J=2 Hz, 1H), δ 4.71 (q, J=10.5 Hz, 2H), δ 2.81 (s, 3H), δ 2.53 (m, 1H), δ 1.87 (m, 1H), δ 1.55 (m, 1H), δ 1.23 (d, J=7 Hz, 3H), δ 1.01 (t, J=6.5 Hz, 3H), ppm. $^{13}$C NMR (CDCl$_3$, 500 MHz): δ 186.8, δ 150.6, δ 149.6, δ 137.3, δ 137.1, δ 135.6, δ 134.7, δ 134.3, δ 134.1, δ 129.5, δ 129.4, δ 128.5, δ 128.4, δ 128.3, δ 127.9, δ 127.8, δ 127.5, δ 116.4, δ 68.8, δ 45.8, δ 45.8, δ 30.7, δ 27.6, δ 16.8, δ 12.1 ppm. IR (thin film) 3031, 2963, 2931, 2873, 1744, 1653, 1597, 1494, 1456, 1403, 1375, 1264, 1175, 1113, 1080, 1039, 978, 908, 752, 730, 695, 668, 633, 588 cm$^{-1}$. Calc. m/z C$_{30}$H$_{31}$N$_3$O$_3$ (M+H) 481.2365, Obsd. 504.2275 (M+Na).

Example 29: Preparation of (2Z,5Z)-Benzyl-2-(benzoylimino)-5-benzylidene-4-(4-methoxyphenyl)-3-methylimidazolidine-1-carboxylate (30)

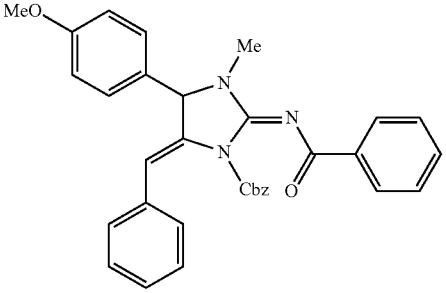

30

Acylation of 23 (97 mg, 0.227 mmol) using benzoyl chloride (0.040 mL, 0.341 mmol), triethylamine (0.063 mL, 0.454 mmol), and dichloromethane (2 mL) provided (2Z, 5Z)-benzyl-2-(benzoylimino)-5-benzylidene-4-(4-methoxyphenyl)-3-methylimidazolidine-1-carboxylate (30) as a light brown foam (96.9 mg, 80.3%). $^1$H NMR (CDCl$_3$, 500 MHz): δ 8.18 (d, J=8 Hz, 2H), δ 7.50-7.21 (m, 14H), δ 6.91 (d, J=8.5 Hz, 2H), δ 6.80 (d, J=7 Hz, 2H), δ 5.74 (d, J=2 Hz, 1H), δ 5.13 (d, J=1.5 Hz, 1H), δ 4.67 (q, J=22.5, 11.5, 2H), δ 3.82 (s, 3H), δ 2.90 (s, 3H) ppm. $^{13}$C NMR (CDCl$_3$, 500 MHz): δ 175.2, δ 160.5, δ 151.9, δ 149.4, δ 137.3, δ 135.6, δ 134.7, δ 134.6, δ 134.4, δ 131.7, δ 129.8, δ 129.4, δ 128.7, δ 128.5, δ 128.4, δ 128.3, δ 128.2, δ 127.6, δ 116.8, δ 114.9, δ 69.0, δ 66.8, δ 55.6, δ 30.71 ppm. IR (thin film) 3030, 2929, 1746, 162, 1607, 1510, 1447, 1378, 1317, 1244, 1173, 1131, 1081, 1021, 972, 908, 832, 727, 694, 6672, 646, 612 cm$^{-1}$. Calc. m/z C$_{33}$H$_{29}$N$_3$O$_4$ (M+H) 531.2158, Obsd. 554.2066 (M+Na).

Example 30: Preparation of (2Z,5Z)-Benzyl-5-benzylidene-2-((2-fluorobenzoyl)imino)-4-(4-methoxyphenyl)-3-methylimidazolidine-1-carboxylate (31)

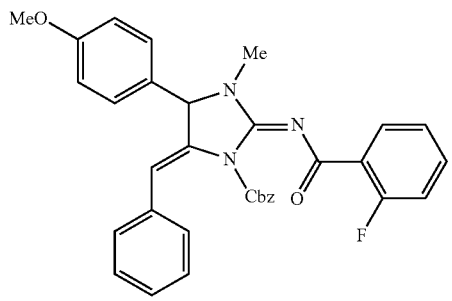

31

Acylation of 23 (0.9156 g, 2.14 mmol) using 2-fluorobenzoyl chloride (0.38 mL, 3.21 mmol), triethylamine (0.6 mL, 4.28 mmol), and dichloromethane (20 mL) provided (2Z, 5Z)-benzyl-5-benzylidene-2-((2-fluorobenzoyl)imino)-4-(4-methoxyphenyl)-3-methylimidazolidine-1-carboxylate (31) as a light brown foam (0.9795 g, 83.0%). $^1$H NMR (CDCl$_3$, 300 MHz): δ 7.99 (t, J=6 Hz, 1H), δ 7.44 (m, 1H), δ 7.24-7.05 (m, 10H), δ 6.99-6.83 (m, 5H) δ 5.69 (d, J=1.5 Hz, 1H), δ 5.15 (d, J=2.1 Hz, 1H), δ 4.71 (q, J=11.7 Hz, 2H), δ 3.82 (s, 3H), δ 2.89 (s, 3H) ppm. $^{13}$C NMR (CDCl$_3$, 300 MHz): δ 164.1, δ 160.5, δ 152.6, δ 149.6, δ 135.3, δ 134.4, δ 134.3, δ 132.7, δ 132.6, δ 129.4, δ 128.8, δ 128.4, δ 128.3, δ 128.0, δ 127.5, δ 123.8, δ 117.1, δ 116.7, δ 116.6, δ 114.8, δ 69.0, δ 66.6, δ 55.4, δ 30.4 ppm. IR (thin film) 2933, 2834, 2790, 109, 1584, 1508, 1488, 1462, 1440, 1301, 1243, 1171, 1095, 1031, 956, 913, 829, 783, 754, 727, 689, 660, 634, 618, 573, 547, 524 cm$^{-1}$. Calc. m/z C$_{33}$H$_{28}$FN$_3$O$_4$(M+H) 549.2064, Obsd. 554.2056 (M+Na).

Example 31: General Procedure for Hydrogenation of Acylated, Protected Cyclic Guanidines

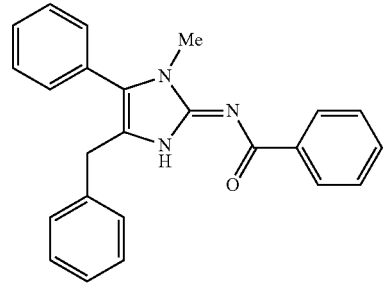

32

In a 5 mL test tube containing a magnetic stir bar were added 24 (84.4 mg, 0.17 mmol), Pd/C (10% w/w, 9 mg), and distilled MeOH (2 mL) under a stream of N$_2$. The reaction tube was then sealed in a pressure vessel and purged with H$_2$ three times. The pressure vessel was then charged with H$_2$, and the reaction was stirred at room temperature for 24 hours. After releasing the H$_2$ from the pressure vessel, the solution was filtered, followed by addition of 5 mL of hot methanol to wash the filter. The filtrate was concentrated via rotary evaporation under reduced pressure, and the resulting material was purified via flash chromatography (6:4 hexanes/EtOAc) to yield (E)-N-(4-benzyl-1-methyl-5-phenyl-1H-imidazol-2(3H)-ylidene)benzamide (32) as a light brown foam (44.4 mg, 72%). $^1$H NMR (CDCl$_3$, 500 MHz): δ 8.28 (d, J=8.5 Hz, 2H), δ 7.51-7.46 (m, 8H), δ 7.36-7.26 (m, 2H), δ 7.18-7.09 (m, 3H), δ 3.80 (s, 2H), δ 3.50 (s, 3H) ppm. $^{13}$C NMR (CDCl$_3$, 500 MHz): δ 170.9, δ 137.9, δ 137.2, δ 132.8, δ 132.6, δ 130.6, δ 130.2, δ 129.7, δ 129.4, δ 129.2, δ 128.9, δ 128.6, δ 128.5, δ 127, δ 34.6, δ 31 ppm. Calc. m/z C$_{24}$H$_{21}$N$_3$O (M+H) 367.1685, Obsd. 368.1768 (M+H).

Example 32: Preparation of (E)-N-(4-Benzyl-1-methyl-5-phenyl-1H-imidazol-2(3H)-ylidene)-2-fluorobenzamide (33)

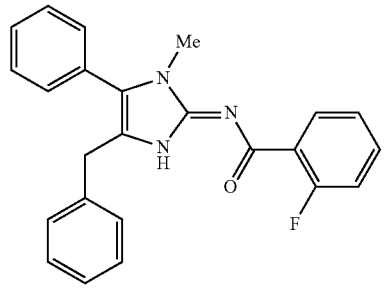

33

Hydrogenation of 25 (10.8 mg, 0.021 mmol) using Pd/C (10% w/w, 2 mg) and distilled MeOH (2 mL) provided (E)-N-(4-benzyl-1-methyl-5-phenyl-1H-imidazol-2(3H)-ylidene)-2-fluorobenzamide (33) as a light brown foam (7.1 mg, 89%). IR (thin film) 3029, 1683, 1560, 1494, 1452, 1350, 1286, 1250, 1222, 1155, 1127, 1075, 1054, 1030, 1014, 967, 817, 755, 725, 696, 643, 558, 539 cm$^{-1}$.

Example 33: Preparation of (E)-N-(4-Benzyl-1-methyl-5-phenyl-1H-imidazol-2(3H)-ylidene)-2,4-dichlorobenzamide (34)

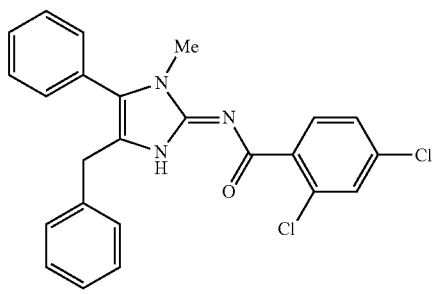

34

Hydrogenation of 26 (34.5 mg, 0.060 mmol) using Pd/C (10% w/w, 4 mg) and distilled MeOH (2 mL) provided (E)-N-(4-benzyl-1-methyl-5-phenyl-1H-imidazol-2(3H)-ylidene)-2,4-dichlorobenzamide (34) as a light brown foam (20.8 mg, 79%). $^1$H NMR (CDCl$_3$, 500 MHz): δ 8.27 (d, J=7 Hz, 2H), δ 7.62-7.51 (m, 4H), δ 7.47 (t, J=7.5 Hz 2H), δ 7.36-7.32 (m, 2H), δ 7.29-7.20 (m, 4H) δ 3.95 (s, 2H), δ 3.62 (s, 3H) ppm. $^{13}$C NMR (CDCl$_3$, 500 MHz): δ 162.1, δ 136.2, δ 135.9, δ 130.8, δ 129.7, δ 129.4, δ 129.3, δ 129.0, δ 128.7, δ 127.6, δ 126.5, δ 125.5, δ 34.6, δ 30.6 ppm. IR (thin film) 2934, 2835, 2359, 2340, 1652, 1609, 1585, 1558, 1540, 1509, 1489, 1472, 1457, 1441, 1302, 1246, 1172, 1097, 1034, 831, 784, 755, 691, 667 cm$^{-1}$.

Example 34: Preparation of (E)-N-(4-Benzyl-1-methyl-5-phenyl-1H-imidazol-2(3H)-ylidene)isobutyramide (35)

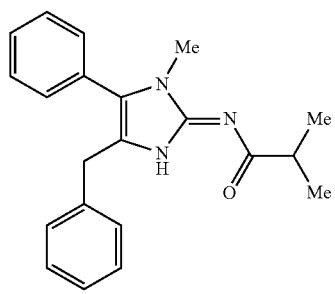

35

Hydrogenation of 28 (45.1 mg, 0.096 mmol) using Pd/C (10% w/w, 5 mg) and distilled MeOH (2 mL) to give (E)-N-(4-benzyl-1-methyl-5-phenyl-1H-imidazol-2(3H)-ylidene)isobutyramide (35) as a light brown foam (23.8 mg, 74%). $^1$H NMR (CDCl$_3$, 500 MHz): δ 7.42-7.39 (m, 3H), δ 7.33 (d, J=8 Hz, 2H), δ 7.24-7.20 (m, 3H), δ 7.13 (d, J=8 Hz 2H), δ 3.83 (s, 2H), δ 3.31 (s, 3H), δ 2.49 (m, 1H), δ 1.13 (d, 7 Hz, 6H) ppm. IR (thin film) 3028, 2968, 2873, 1695, 1653, 1602, 1540, 1506, 1494, 1466, 1456, 1437, 1399, 1383, 1312, 1221, 1190, 1156, 1098, 1014, 950, 910, 867, 725, 697 cm$^{-1}$. Calc. m/z C$_{21}$H$_{23}$N3O (M+H) 333.1841, Obsd. 334.1919 (M+H).

Example 35: Preparation of (E)-N-(4-benzyl-1-methyl-5-phenyl-1H-imidazol-2(3H)-ylidene)-2-methylbutanamide (36)

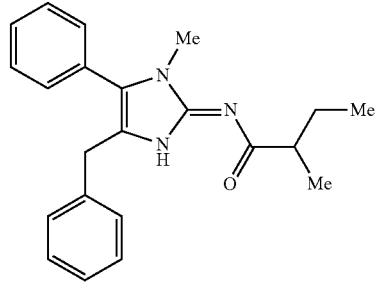

36

Hydrogenation of 29 (56.9 mg, 0.118 mmol) using Pd/C (10% w/w, 6 mg) and distilled MeOH (2 mL) to give (E)-N-(4-benzyl-1-methyl-5-phenyl-1H-imidazol-2(3H)-ylidene)-2-methylbutanamide (36) as a light brown foam (32.8 mg, 80%). $^1$H NMR (CDCl$_3$, 500 MHz): δ 7.42-7.39 (m, 3H), δ 7.29 (d, J=8 Hz, 2H), δ 7.24-7.20 (m, 3H), δ 7.05 (d, J=8 Hz 2H), δ 3.77 (s, 2H), δ 3.30 (s, 3H), δ 2.43 (m, 1H), δ 1.69 (m, 1H), δ 1.41 (m, 1H), δ 1.10 (d, 7 Hz, 3H), δ 0.87 (t, 7 Hz, 3H) ppm. $^{13}$C NMR (CDCl$_3$, 500 MHz): δ 139.9, δ 130.3, δ 129.1, δ 128.8, δ 128.6, δ 128.5, δ 42.8, δ 32.3, δ 27.2, δ 17.7, δ 11.1 ppm. IR (thin film) 2835, 1609, 1583, 1508, 1488, 1442, 1419, 1301, 1244, 1169, 1126, 1107, 1069, 1033, 994, 962, 917, 850, 807, 778, 754, 690, 584 cm$^{-1}$. Calc. m/z C$_{22}$H$_{25}$N$_3$O (M+H) 347.1998, Obsd. 348.2082 (M+H).

Example 36: Preparation of (E)-N-(4-benzyl-5-(4-methoxyphenyl)-1-methyl-1H-imidazol-2(3H)-ylidene)benzamide (37)

37

Hydrogenation of 30 (15.4 mg, 0.029 mmol) using Pd/C (10% w/w, 2 mg) and distilled MeOH (2 mL) to give (E)-N-(4-benzyl-5-(4-methoxyphenyl)-1-methyl-1H-imidazol-2(3H)-ylidene)benzamide (37) as a light brown foam (9.7 mg, 84%). $^1$H NMR (CDCl$_3$, 500 MHz): δ 8.27 (d, J=7 Hz, 2H), δ 7.45-7.40 (m, 3H), δ 7.32-7.27 (m, 4H), δ 7.22 (m, 1H), δ 7.15 (d, J=7.5 Hz, 2H), δ 7.01 (d, J=9 Hz, 2H), δ 3.86 (s, 3H), δ 3.83 (s, 2H), δ 3.49 (s, 3H) ppm. $^{13}$C NMR (CDCl$_3$, 500 MHz): δ 160.5, δ 138.7, δ 131.9, δ 130.8, δ 129.2, δ 128.9, δ 128.4, δ 128.1, δ 127.2, δ 124.5, δ 120.0, δ 114.8, δ 55.7, δ 32.4, δ 31.0 ppm. IR (thin film) 3061, 2933, 1675, 1636, 1566, 1541, 1494, 1464, 1453, 199, 1350, 1288, 1246, 1174, 1108, 1025, 1004, 906, 832, 718, 709, 645, 593 cm$^{-1}$. Calc. m/z $C_{22}H_{25}N_3O$ (M+H) 397.1790, Obsd. 420.1698 (M+Na).

Example 37: Preparation of (E)-N-(4-benzyl-5-(4-methoxyphenyl)-1-methyl-1H-imidazol-2(3H)-ylidene)-2-fluorobenzamide (38) (Zinaamidole, ZNA)

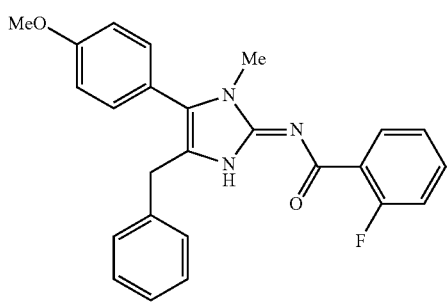

38

Hydrogenation of 31 (20.8 mg, 0.038 mmol) using Pd/C (10% w/w, 3 mg) and distilled MeOH (2 mL) to give (E)-N-(4-benzyl-5-(4-methoxyphenyl)-1-methyl-1H-imidazol-2(3H)-ylidene)-2-fluorobenzamide (38) as a light brown foam (12.7 mg, 81%). $^1$H NMR (CDCl$_3$, 500 MHz): δ 8.07 (t, J=8 Hz, 2H), δ 7.34 (m, 1H), δ 7.32-7.27 (m, 4H), δ 7.21 (t, J=8.5 Hz, 1H), δ 7.19-7.16 (m, 3H), δ 7.08 (t, J=9.5 Hz, 1H), δ 7.00 (d, J=8.5 Hz, 2H), δ 3.86 (s, 3H), δ 3.81 (s, 2H), δ 3.44 (s, 3H) ppm. $^{13}$C NMR (CDCl$_3$, 500 MHz): δ 162.9, δ 160.9, δ 132.0, δ 129.1, δ 128.4, δ 127.1, δ 123.9, δ 120.1, δ 116.6, δ 116.8, δ 114.7, δ 55.7, δ 32.4, δ 30.4 ppm. IR (thin film) 2929, 2360, 2340, 1684, 1569, 1511, 1494, 1455, 1401, 1339, 1290, 1248, 1176, 1032, 834, 815, 757, 731, 696, 667 cm$^{-1}$. Calc. m/z $C_{22}H_{25}N_3O$ (M+H) 347.1998, Obsd. 438.1594 (M+Na).

Example 38: General Procedure for NaH-Mediated Cyclization

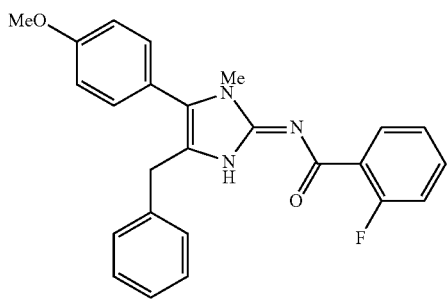

38

In a 25 mL round bottom flask containing a magnetic stir bar were added (E)-N-(amino((1-(4-methoxyphenyl)-3-phenylprop-2-yn-1-yl)(methyl)amino)methylene)-2-fluorobenzamide (44.5 mg, 0.107 mmol), NaH (3 mg, 0.107 mmol) and THF (10 mL) under N$_2$. The solution was stirred at room temperature for 30 minutes, after which the solvent was removed under reduced pressure and the crude product was re-dissolved in EtOAc (25 mL). The organic layer was washed with saturated aqueous NH$_4$Cl (10 mL) and brine (10 mL), dried over Na$_2$SO$_4$, filtered, and concentrated. The resulting yellow solid (E)-N-(4-benzyl-5-(4-methoxyphenyl)-1-methyl-1,3-dihydro-2H-imidazol-2-ylidene)-2-fluorobenzamide (38) required no further purification (33.8 mg, 75.9%).

Example 39: Preparation of (E)-N-(4-Benzyl-5-(4-methoxyphenyl)-1-methyl-1,3-dihydro-2H-imidazol-2-ylidene)-4-chlorobenzamide (39)

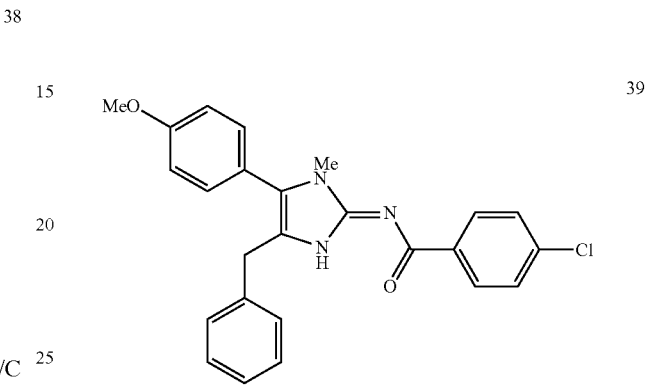

39

(E)-N-(4-Benzyl-5-(4-methoxyphenyl)-1-methyl-1,3-dihydro-2H-imidazol-2-ylidene)-4-chlorobenzamide (39) was obtained via NaH-mediated cyclization of (E)-N-(amino((1-(4-methoxyphenyl)-3-phenylprop-2-yn-1-yl)(methyl)amino)methylene)-4-chlorobenzamide in THF in 81.6% yield as a yellow oil. $^1$H NMR (CDCl$_3$, 500 MHz): δ 8.19 (d, J=8 Hz, 2H), δ 7.34 (d, J=8 Hz, 2H), δ 7.30-7.21 (m, 5H), δ 7.12 (d, J=7.5 Hz, 2H), δ 7.01 (d, J=8 Hz, 2H), δ 3.86 (s, 3H), δ 3.82 (s, 2H), δ 3.47 (s, 3H) ppm.

Example 40: Preparation of (E)-N-(4-Benzyl-5-(4-methoxyphenyl)-1-methyl-1,3-dihydro-2H-imidazol-2-ylidene)benzamide (37)

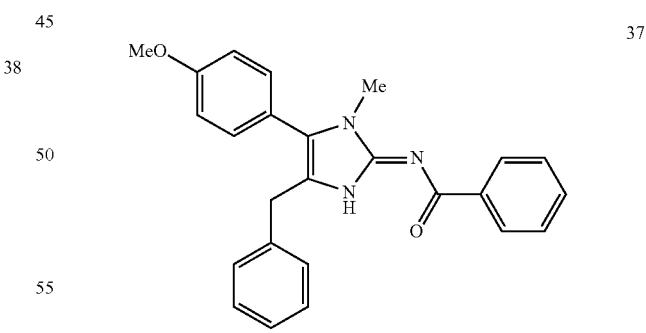

37

(E)-N-(4-Benzyl-5-(4-methoxyphenyl)-1-methyl-1,3-dihydro-2H-imidazol-2-ylidene)benzamide (37) was obtained via NaH-mediated cyclization of (E)-N-(amino((1-(4-methoxyphenyl)-3-phenylprop-2-yn-1-yl)(methyl)amino)methylene)benzamide in THF in 63.2% yield as a white solid. $^1$H NMR (CDCl$_3$, 500 MHz): δ 8.26 (dd, J=0.6 Hz, 6 Hz, 2H), δ 7.44-7.39 (m, 3H), δ 7.29-7.26 (m, 5H), δ 7.14 (d, J=4.8 Hz, 2H), δ 7.00 (d, J=5.1 Hz, 2H), δ 3.86 (s, 3H), δ 3.82 (s, 2H), δ 3.48 (s, 3H) ppm.

Example 41: Preparation of (E)-N-(4-Benzyl-5-(4-methoxyphenyl)-1-methyl-1,3-dihydro-2H-imidazol-2-ylidene)-4-methoxybenzamide (40)

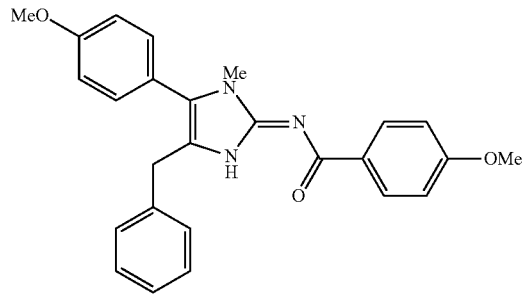

(E)-N-(4-Benzyl-5-(4-methoxyphenyl)-1-methyl-1,3-dihydro-2H-imidazol-2-ylidene)-4-methoxybenzamide (40) was obtained via NaH-mediated cyclization of (E)-N-(amino((1-(4-methoxyphenyl)-3-phenylprop-2-yn-1-yl)(methyl)amino)methylene)-4-methoxybenzamide in THF in 84.1% yield as a yellow oil. $^1$H NMR (CDCl$_3$, 300 MHz): δ 8.08 (d, J=8.7 Hz, 2H), δ 7.30-7.21 (m, 5H), δ 7.14 (d, J=8.7, 2H), δ 7.01 (d, J=9, 2H), δ 6.90 (d, J=8.7 Hz, 2H), δ 3.87 (s, 3H), δ 3.85 (s, 3H), δ 3.82 (s, 2H), δ 3.47 (s, 3H) ppm.

Example 42: Preparation of (E)-N-(4-Benzyl-5-(4-chlorophenyl)-1-methyl-1,3-dihydro-2H-imidazol-2-ylidene)-2-fluorobenzamide (41)

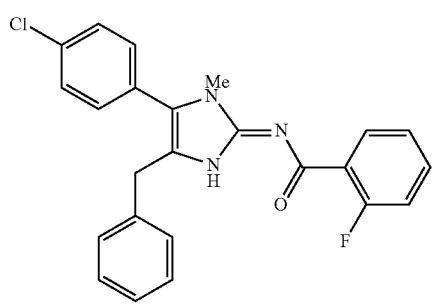

(E)-N-(4-Benzyl-5-(4-chlorophenyl)-1-methyl-1,3-dihydro-2H-imidazol-2-ylidene)-2-fluorobenzamide (41) was obtained via NaH-mediated cyclization of (E)-N-(amino((1-(4-chlorophenyl)-3-phenylprop-2-yn-1-yl)(methyl)amino)methylene)-2-fluorobenzamide in THF in 62% yield as a yellow solid. $^1$H NMR (CDCl$_3$, 500 MHz): δ 8.08 (t, J=2.5 Hz, 1H), δ 7.46 (d, J=8 Hz, 2H), δ 7.40 (m, 1H), δ 7.30-7.25 (m, 4H), δ 7.22-7.10 (m, 5H), δ 3.84 (s, 2H), δ 3.43 (s, 3H) ppm.

Example 43: Preparation of (E)-N-(4-Benzyl-5-(4-chlorophenyl)-1-methyl-1,3-dihydro-2H-imidazol-2-ylidene)-4-chlorobenzamide (42)

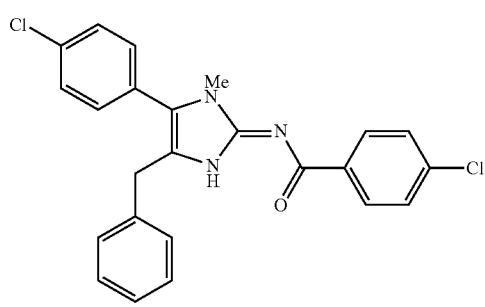

(E)-N-(4-Benzyl-5-(4-chlorophenyl)-1-methyl-1,3-dihydro-2H-imidazol-2-ylidene)-4-chlorobenzamide (42) was obtained via NaH-mediated cyclization of (E)-N-(amino((1-(4-chlorophenyl)-3-phenylprop-2-yn-1-yl)(methyl)amino)methylene)-4-chlorobenzamide in THF in 64% yield as a yellow oil. $^1$H NMR (CDCl$_3$, 500 MHz): δ 8.18 (d, J=8.5 Hz, 2H), δ 7.47 (d, J=8 Hz, 2H), δ 7.35 (d, J=8 Hz, 2H), δ 7.30-7.25 (m, 5H), δ 7.12 (d, J=7 Hz, 2H), δ 3.83 (s, 2H), δ 3.48 (s, 3H) ppm.

Example 44: Preparation of (E)-N-(4-Benzyl-5-(4-chlorophenyl)-1-methyl-1,3-dihydro-2H-imidazol-2-ylidene)benzamide (43)

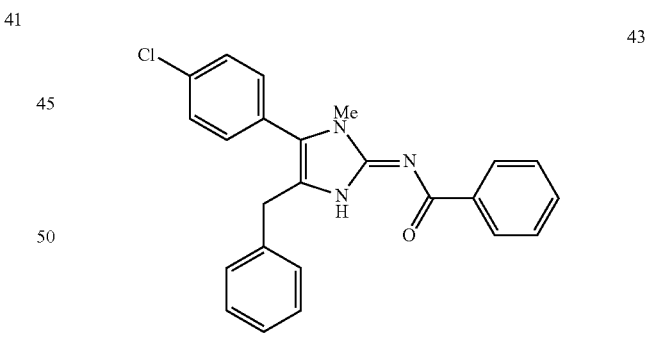

(E)-N-(4-Benzyl-5-(4-chlorophenyl)-1-methyl-1,3-dihydro-2H-imidazol-2-ylidene)benzamide (43) was obtained via NaH-mediated cyclization of (E)-N-(amino((1-(4-chlorophenyl)-3-phenylprop-2-yn-1-yl)(methyl)amino)methylene)benzamide in THF in 77% yield as a white solid. $^1$H NMR (CDCl$_3$, 500 MHz): δ 8.24 (d, J=8 Hz, 2H), δ 7.46 (d, J=8 Hz, 2H), δ 7.45-7.39 (m, 3H), δ 7.30-7.20 (m, 5H), δ 7.12 (d, J=7 Hz, 2H), δ 3.83 (s, 2H), δ 3.48 (s, 3H) ppm.

Example 45: Preparation of (E)-N-(4-Benzyl-5-(4-chlorophenyl)-1-methyl-1,3-dihydro-2H-imidazol-2-ylidene)-4-methoxybenzamide (44)

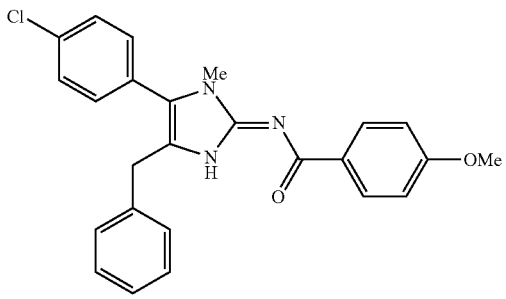

44

(E)-N-(4-Benzyl-5-(4-chlorophenyl)-1-methyl-1,3-dihydro-2H-imidazol-2-ylidene)-4-methoxybenzamide (44) was obtained via cyclization of (E)-N-(amino((1-(4-chlorophenyl)-3-phenylprop-2-yn-1-yl)(methyl)amino)methylene)-4-methoxybenzamide in THF. $^1$H NMR (CDCl$_3$, 300 MHz): δ 8.19 (d, J=8.7 Hz, 2H), δ 7.46 (d, J=8.4 Hz, 2H), δ 7.30-7.23 (m, 5H), δ 7.13 (d, J=8.4 Hz, 2H), δ 6.90 (d, J=9 Hz, 2H), δ 3.84 (s, 2H), δ 3.83 (s, 2H), δ 3.48 (s, 3H) ppm.

Example 46: Preparation of (E)-N-(4-Benzyl-1-methyl-5-(4-(2-morpholinoethoxy)phenyl)-1,3-dihydro-2H-imidazol-2-ylidene)-2-fluorobenzamide (45)

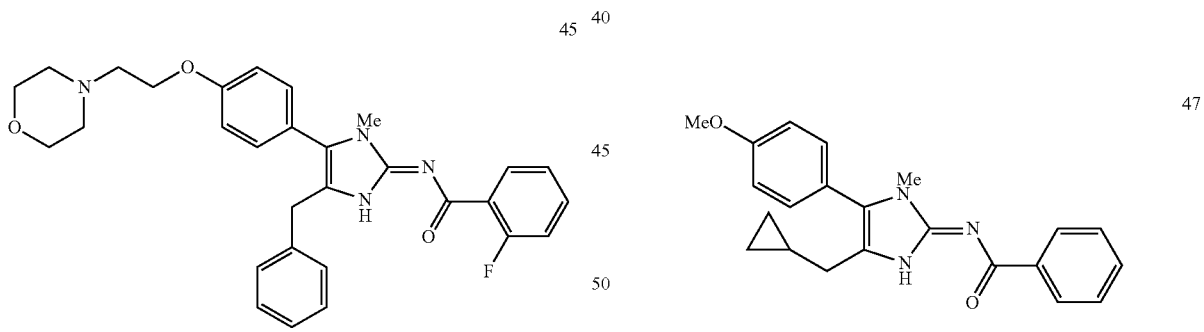

45

(E)-N-(4-Benzyl-1-methyl-5-(4-(2-morpholinoethoxy)phenyl)-1,3-dihydro-2H-imidazol-2-ylidene)-2-fluorobenzamide (45) was obtained via cyclization of (E)-N-(amino((1-(4-chlorophenyl)-3-phenylprop-2-yn-1-yl)(methyl)amino)methylene)-4-methoxybenzamide in THF. $^1$H NMR (CDCl$_3$, 300 MHz): δ 8.19 (d, J=8.7 Hz, 2H), δ 7.46 (d, J=8.4 Hz, 2H), δ 7.30-7.23 (m, 5H), δ 7.13 (d, J=8.4 Hz, 2H), δ 6.90 (d, J=9 Hz, 2H), δ 3.84 (s, 2H), δ 3.83 (s, 2H), δ 3.48 (s, 3H) ppm.

Example 47: Preparation of (E)-N-(5-(4-Chlorophenyl)-1-methyl-4-(2-morpholinoethyl)-1H-imidazol-2(3H)-ylidene)-2-fluorobenzamide (46)

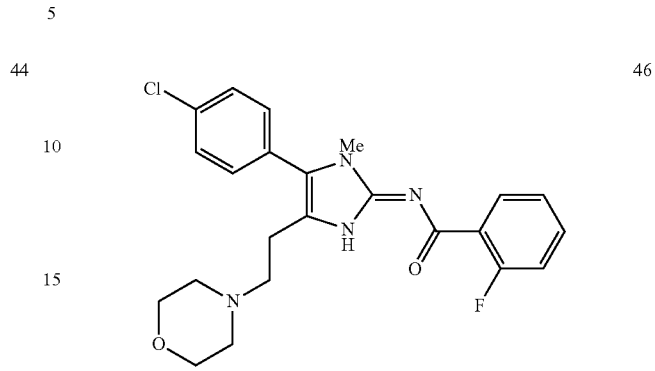

46

(E)-N-(5-(4-Chlorophenyl)-1-methyl-4-(2-morpholinoethyl)-1H-imidazol-2(3H)-ylidene)-2-fluorobenzamide (46) was obtained via NaH-mediated cyclization of (E)-N-(amino((1-(4-chlorophenyl)-4-morpholinobut-2-yn-1-yl)(methyl)amino)methylene)-2-fluorobenzamide in THF in 50% yield as a yellow oil. $^1$H NMR (CDCl$_3$, 500 MHz): δ 8.05 (dt, J=3 Hz, 12.5 Hz, 1H), δ 7.46 (d, J=14 Hz, 2H), δ 7.42-7.34 (m, 1H), δ 7.28-7.24 (m, 2H), δ 7.17 (dt, J=2 Hz, 10.5 Hz, 1H), δ 7.13-7.06 (m, 1H), δ 3.82 (t, J=7.5 Hz, 4H), δ 3.44 (s, 3H), 2.68-2.58 (m, 4H), 2.53-2.46 (m, 4H) ppm. Calc. C$_{23}$H$_{24}$N$_4$O$_2$FNaCl m/z (M+Na) 465.1470, Obsd. 465.1469 (M+Na).

Example 48: Preparation of (E)-N-(4-(Cyclopropylmethyl)-5-(4-methoxyphenyl)-1-methyl-1,3-dihydro-2H-imidazol-2-ylidene)benzamide (47)

47

(E)-N-(4-(Cyclopropylmethyl)-5-(4-methoxyphenyl)-1-methyl-1,3-dihydro-2H-imidazol-2-ylidene)benzamide (47) was obtained via NaH-mediated cyclization cyclization of N—(N-(3-cyclopropyl-1-(4-methoxyphenyl)prop-2-yn-1-yl)-N-methylcarbamimidoyl)benzamide in THF in 91% yield as a yellow oil. $^1$H NMR (CDCl$_3$, 500 MHz): δ 8.31 (d, J=7.3 Hz, 2H), δ 7.47-7.39 (m, 4H), δ 7.24 (d, J=9.0 Hz, 3H), δ 7.01 (d, J=8.7 Hz, 2H), δ 3.87 (s, 3H), δ 3.47 (s, 3H), δ 2.41 (d, J=7.03 Hz, 2H), δ 0.97-0.89 (m, 1H), δ 0.58 (d, J=7.8 Hz, 2H), δ 0.19 (d, J=4.8 Hz, 2H) ppm. $^{13}$C NMR (CDCl$_3$, 500 MHz): δ 174.9, 173.2, 160.2, 138.8, 130.7, 128.9, 128.0, 123.1, 120.2, 114.5, 55.6, 29.9, 29.3, 10.3, 4.7 ppm.

Example 49: Preparation of (E)-N-(4-(Cyclopropylmethyl)-5-(4-methoxyphenyl)-1-methyl-1,3-dihydro-2H-imidazol-2-ylidene)-4-methoxybenzamide (48)

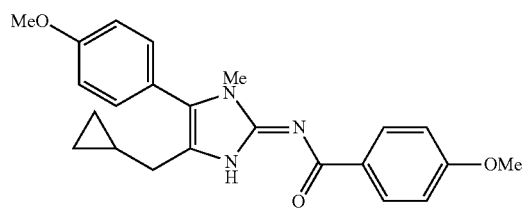

48

(E)-N-(4-(Cyclopropylmethyl)-5-(4-methoxyphenyl)-1-methyl-1,3-dihydro-2H-imidazol-2-ylidene)-4-methoxybenzamide (48) was obtained via NaH-mediated cyclization cyclization of N—(N-(3-cyclopropyl-1-(4-methoxyphenyl)prop-2-yn-1-yl)-N-methylcarbamimidoyl)-4-methoxybenzamide in THF in 84% yield as a yellow oil. $^1$H NMR (CDCl$_3$, 500 MHz): δ 8.27 (d, J=8.1 Hz, 2H), δ 7.24 (d, J=8.4 Hz, 2H), δ 7.00 (d, J=8.7 Hz, 2H), δ 6.92 (d, J=8.2 Hz, 2H), δ 3.86 (s, 3H), δ 3.85 (s, 3H), δ 3.45 (s, 3H), δ 2.39 (d, J=6.8 Hz, 2H), δ 0.97-0.88 (m, 1H), δ 0.57 (d, J=8.1 Hz, 2H), δ 0.17 (d, J=4.7 Hz, 2H) ppm. $^{13}$C NMR (CDCl$_3$, 500 MHz): δ 174.6, 173.1, 161.9, 160.2, 131.8, 130.6, 122.9, 120.9, 114.5, 113.2, 95.1, 55.7, 29.9, 29.3, 10.3, 4.7 ppm.

Example 50: Preparation of (E)-4-Chloro-N-(4-(cyclopropylmethyl)-5-(4-methoxyphenyl)-1-methyl-1,3-dihydro-2H-imidazol-2-ylidene)benzamide (49)

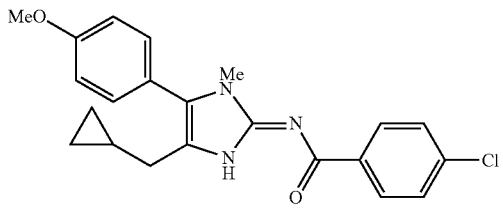

49

(E)-4-Chloro-N-(4-(cyclopropylmethyl)-5-(4-methoxyphenyl)-1-methyl-1,3-dihydro-2H-imidazol-2-ylidene)benzamide (49) was obtained via NaH-mediated cyclization cyclization of 4-chloro-N—(N-(3-cyclopropyl-1-(4-methoxyphenyl)prop-2-yn-1-yl)-N-methylcarbamimidoyl)benzamide in THF in 87% yield as a white solid. $^1$H NMR (CDCl$_3$, 500 MHz): δ 8.24 (d, J=7.8 Hz, 2H), δ 7.37 (d, J=8.5 Hz, 2H), δ 7.23 (d, J=8.2 Hz, 2H), δ 7.00 (d, J=8.4 Hz, 2H), δ 3.86 (s, 3H), δ 3.45 (s, 3H), δ 2.40 (d, J=6.8 Hz, 2H), δ 0.97-0.88 (m, 1H), δ 0.57 (d, J=7.1 Hz, 2H), δ 0.18 (d, J=5.5 Hz, 2H) ppm. $^{13}$C NMR (CDCl$_3$, 500 MHz): δ 173.8, 173.2, 160.3, 150.3, 137.3, 136.7, 131.8, 130.3, 128.1, 123.2, 121.7, 120.0, 114.5, 55.6, 29.9, 29.3, 10.2, 4.7 ppm.

Example 51: Preparation of (E)-N-(4-(Cyclopropylmethyl)-5-(4-methoxyphenyl)-1-methyl-1,3-dihydro-2H-imidazol-2-ylidene)-2-fluorobenzamide (50)

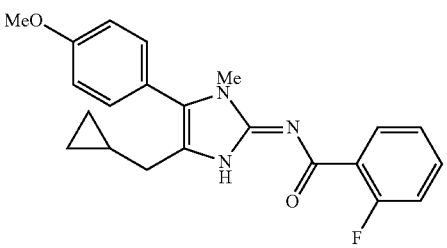

50

(E)-N-(4-(Cyclopropylmethyl)-5-(4-methoxyphenyl)-1-methyl-1,3-dihydro-2H-imidazol-2-ylidene)-2-fluorobenzamide (50) was obtained via NaH-mediated cyclization cyclization of N—(N-(3-cyclopropyl-1-(4-methoxyphenyl)prop-2-yn-1-yl)-N-methylcarbamimidoyl)-2-fluorobenzamide in THF in 86% yield as a yellow oil. $^1$H NMR (CDCl$_3$, 500 MHz): δ 8.09 (dt, J 1.7, 6.1 Hz, 1H), δ 7.40-7.34 (m, 2H), δ 7.23 (d, J=7.3 Hz, 2H), δ 7.16 (t, J=8.4, 1H), δ 7.09 (dd, J=3.0, 8.4 Hz, 1H), δ 6.99 (d, J 9.0 Hz, 2H), δ 3.86 (s, 3H), δ 3.42 (s, 3H), δ 2.40 (d, J=6.7 Hz, 2H), δ 0.97-0.88 (m, 1H), δ 0.56 (d, J 8.3 Hz, 2H), δ 0.17 (d, J=4.8 Hz, 2H) ppm.

Example 52: Preparation of (E)-N-(4-(Cyclopropylmethyl)-5-isopropyl-1-methyl-1,3-dihydro-2H-imidazol-2-ylidene)benzamide (51)

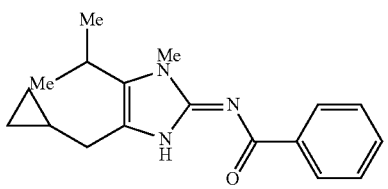

51

(E)-N-(4-(Cyclopropylmethyl)-5-isopropyl-1-methyl-1,3-dihydro-2H-imidazol-2-ylidene)benzamide (51) was obtained via NaH-mediated cyclization cyclization of N—(N-(1-cyclopropyl-4-methylpent-1-yn-3-yl)-N-methylcarbamimidoyl)benzamide in THF in 47% yield as a colorless oil. $^1$H NMR (CDCl$_3$, 500 MHz): δ 8.29 (d, J=6.4 Hz, 2H), δ 7.43-7.38 (m, 3H), δ 3.63 (s, 3H), δ 3.02 (sp, J=7.9 Hz, 1H), δ 2.49 (d, J=6.8 Hz, 2H), δ 1.33 (d, J=6.8 Hz, 6H), δ 0.99-0.90 (m, 1H), δ 0.63 (q, J=4.8 Hz, 2H), δ 0.26 (q, J=4.8 Hz, 2H) ppm. $^{13}$C NMR (CDCl$_3$, 500 MHz): δ 174.7, 173.2, 138.7, 130.5, 128.7, 127.9, 126.4, 118.9, 29.4, 24.5, 21.8, 10.3, 4.7 ppm.

Example 53: General Methods for Biological Experiments

Tissue culture: Human normal mammary epithelial cells collected from consented patients undergoing voluntary reduction mammoplasties were immortalized by lentiviral-induced expression of human telomerase reverse transcriptase (hTERT-HMEC) and cultured in modified M87 media as described previously in Gligorich et al., *Breast*

Cancer Res 2013; 15(4):R58. Primary metastatic tumor tissue originating from pleural effusions of chemoresistant breast cancer patients were characterized and cultured as described previously in Gligorich et al. MCF-10A and MCF-7 cells were cultured in growth media consisting of DMEM/F-12 (Life Technologies, Grand Island, N.Y., USA), 10% fetal bovine serum (FBS, HyClone, Logan, Utah, USA), 5.0 µg/mL insulin-transferrin-selenium-X (Life Technologies), penicillin-streptomycin-glutamine (Life Technologies), and 2.5 nM human recombinant epidermal growth factor (BD Biosciences, San Jose, Calif., USA). T47D and MDA-MB-231 cells were cultured in growth media consisting of RPMI-1640 (Life Technologies), 10% fetal bovine serum (FBS, HyClone, Logan, Utah, USA), 5.0 µg/mL insulin-transferrin-selenium-X (Life Technologies), penicillin-streptomycin-glutamine (Life Technologies), and 2.5 nM human recombinant epidermal growth factor (BD Biosciences, San Jose, Calif., USA). All cells were cultured at 37° C. with 5% $CO_2$ in a humidified incubator. All cell lines were authenticated by the ATCC in conjunction with Promega using short tandem repeat analysis.

Reagents and antibodies: Propidium iodide was obtained from Cell Signaling (Danvers, Mass., USA). The $Zn^{2+}$ indicator FluoZin-3 was obtained from Life Technologies. Actinomycin D was obtained from Sigma (St. Louis, Mo., USA). Antibodies against LC3A/B (Cell Signaling) and α-Tubulin (Sigma) were used at used at a concentration of 1:1000. IR800CW and IR680 secondary antibodies were obtained from LI-COR (Lincoln, Nebr., USA) and used at a concentration of 1:7500.

Dose response assays: hTERT-HMEC and pleural effusion cells were seeded in 96-well plates and allowed to recover overnight. Cells were then treated in triplicate with compound dissolved in DMSO or with a matched DMSO vehicle control; the cells were then cultured for 96 hours in drug before cell viability was measured using a luciferase-based ATP quantification assay (ATPlite, PerkinElmer, Waltham, Mass., USA). Luminescence was measured on a PerkinElmer 2104 EnVision plate reader (PerkinElmer) and raw data were averaged and normalized to the corresponding vehicle controls. MCF-10A cells were seeded at 8,000 cells/well in 96-well plates in standard culture media; MCF-7, T47D, and MDA-MB-231 cells were seeded at 1,500 cells/well in 96-well plates in standard culture media. After allowing the cells to recover overnight, the media was replaced with reduced serum (2% FBS) media containing compound or DMSO as a vehicle control. Following the start of treatment, the media was replaced at 48 and 96 hours with fresh drug-containing media. Cell viability was measured 120 hours after the start of treatment using an ATPlite assay (PerkinElmer); raw data were averaged and normalized to the corresponding vehicle controls. For all dose response assays, normalized values were plotted as an average±standard deviation of three replicates then analyzed using the dose response nonlinear curve fitting function from Prism 6.0 (GraphPad Software, San Diego, Calif., USA) to calculate the $EC_{50}$. Clonogenic cell survival assays were conducted as described in Franken NAP, Rodermond H M, Stap J, Haveman J, van Bree C. Clonogenic assay of cells in vitro. Nat Protocols 2006; 1(5):2315-19

Transcriptome sequencing: In preparation for transcriptome sequencing, MCF-7 cells were seeded in triplicate in 10-cm tissue culture-treated plates such that the plate would be 80% confluent at the time of drug treatment. Cells were treated with 10 mL of low serum media containing either 30 µM ZNA or DMSO as a vehicle control for 3 or 12 hours. Following the completion of treatment, RNA was isolated using an RNeasy RNA isolation and purification kit (Qiagen, Hilden, Germany) per the manufacturer's protocol.

Library construction was performed using the Illumina TruSeq Stranded mRNA Sample Preparation Kit as described herein. Briefly, total RNA (100 ng to 4 µg) was poly-A selected using poly-T oligo-attached magnetic beads. Poly-A RNA eluted from the magnetic beads was fragmented and primed with random hexamers in preparation for cDNA synthesis. First strand reverse transcription was accomplished using Superscript II Reverse Transcriptase (Life Technologies). Second strand cDNA synthesis was accomplished using DNA polymerase I and RNase H under conditions in which dUTP is substituted for dTTP, yielding blunt-ended cDNA fragments. An A-base was added to the blunt ends in preparation for adapter ligation and to prevent concatemer formation. Adapters containing a T-base overhang were ligated to the A-tailed DNA fragments. Ligated fragments were PCR-amplified (12-15 cycles) under conditions that enabled only amplification of the first strand cDNA product. The PCR-amplified library was purified using Agencourt AMPure XP beads (Beckman Coulter Genomics). The concentration of the amplified library was measured with a NanoDrop spectrophotometer and an aliquot of the library was resolved on an Agilent 2200 Tape Station using a D1K or a High Sensitivity D1K assay to define the size distribution of the sequencing library. Libraries were adjusted to a 10 nM concentration, and quantitative PCR (qPCR) was conducted with the Kapa Library Quantification Kit (Kapa Biosystems, Boston, Mass., USA) to calculate the molarity of adapter-ligated library molecules. The concentration was further adjusted following qPCR to prepare the library for sequence analysis on an Illumina HiSeq instrument. Following completion of sequencing, genome alignment was conducted using NCBI build GRch37, and differential expression analysis was performed using the RNAseq application, which wraps the DESeq Bioconductor package (http://useq.sourceforge.net/cmdLnMenus.html#RNASeq); statistical significance was calculated as described by Anders and Huber. Anders S, Huber W. Genome Biol 2010; 11(10):R106. Sequencing data were deposited into Gene Expression Omnibus (accession number GSE59251).

Real-Time PCR (RT-PCR): For experiments designed to measure gene expression, real-time PCR (RT-PCR) was conducted using a LightCycler 480 (Roche, Basel, Switzerland) and KAPA SYBR FAST qPCR Master Mix (Kapa Biosystems, Boston, Mass., USA). Following drug treatment, RNA was isolated using an RNeasy RNA isolation and purification kit (Qiagen) per the manufacturer's protocol. Genomic DNA was removed with a DNase digest and 1 µg of RNA was used to synthesize cDNA using a Superscript III Reverse Transcriptase kit from Invitrogen per the manufacturer's protocol; after an RNase H digestion, RT-PCR was performed in a 5 µL reaction using KAPA SYBR FAST qPCR Master Mix (Kapa Biosystems, Boston, Mass., USA). The following primer sets were used: MT1F 5'-AGTCTCTCCTCGGCTTGC-3' (SEQ ID NO:1) and 5'-ACATCTGGGAGAAAGGTTGTC-3' (SEQ ID NO:2); MT1X 5'-TCTCCTTGCCTCGAAATGGAC-3' (SEQ ID NO:3) and 5'-GGGCACACTTGGCACAGC-3' (SEQ ID NO:4); MT2A 5'-CCGACTCTAGCCGCCTCTT-3' (SEQ ID NO:5) and 5'-GTGGAAGTCGCGTTCTTTACA-3' (SEQ ID NO:6); SLC30A2 5'-ACAGCAGCAGATCAC-GAACA-3' (SEQ ID NO:7) and 5'-GGACAACCTTGAC-CATCCTG-3' (SEQ ID NO:8); SLC30A1 5'-TCACCACT-TCTGGGGTTTTC-3' (SEQ ID NO:9) and 5'-ACCAGGAGGAGACCAACACC-3' (SEQ ID NO:10).

Data were normalized to an internal reference gene (GAPDH 5'-AAATTCCATGGCACCGTC-3' (SEQ ID NO:11) and 5'-GATGGTGATGGGATTTCCA-3' (SEQ ID NO:12)) and relative gene expression was assessed using the comparative CT method set forth in Schmittgen T D, Livak K J. Analyzing real-time PCR data by the comparative CT method. Nat Protocols 2008; 3(6):1101-08. For tissue derived from mouse in vivo experiments, fresh tissue was homogenized using a TissueLyser II for 3 minutes at 30 Hz before isolating RNA.

Measurement of intracellular $Zn^{2+}$ by FluoZin-3 staining: Cells were seeded in 6-well plates at a density such that at the time of analysis, wells would be 70-80% confluent. Following the completion of treatment, the drug-containing media was removed and replaced with Hank's Balanced Salt Solution (HBSS, Life Technologies) containing 2.5 µM FluoZin-3. The cells were incubated with the indicator for 30 minutes at room temperature in the dark. After staining, the cells were trypsinized, resuspended in HBSS containing 2% FBS, and relative mean fluorescence was measured by flow cytometry (FACscan, BD Biosciences, San Jose, Calif., USA).

Measurement of cell death by propidium iodide staining: Cells were cultured to 80% confluence in 6-well plates and the growth media was then replaced with low serum (2% FBS) drug-containing media. Each condition was assessed in triplicate. Following the completion of treatment, the media and floating cells were collected and combined with the trypsinized adherent cells. The cells were washed with 2% FBS/HBSS, and resuspended in a propidium iodide solution (Cell Signaling) for analysis by flow cytometry. The percentage of propidium iodide positive cells for each treatment condition were averaged and normalized to the vehicle-treated control. The normalized data were plotted as the average±standard error of three replicates.

Inductively coupled plasma-atomic emission spectroscopy (ICP-AES) analysis: Cells were cultured to 80% confluence in 10-cm plates and the growth media was then replaced with low serum (2% FBS) drug-containing media. After three hours of treatment, the media was discarded and the cells washed with 1×PBS. To each 10-cm plate, 1 mL of nitric acid (TraceSELECT Ultra for trace analysis, Sigma) was added directly to the plate. The nitric acid mixture was submitted for inductively coupled plasma-atomic emission spectroscopy (ICP-AES) analysis following methods established by the Environmental Protection Agency. Martin T D, Brockhoff C A, Creed J T. Method 200.7 Determination of Metals and Trace Elements in Water and Wastes by Inductively Coupled Plasma-Atomic Emission Spectrometry. Environmental Monitoring Systems Laboratory, US Environmental Protection Agency 1994. The experiment was performed in triplicate for each cell line and a fourth plate of cells was used to measure total protein (BCA assay, Thermo Fisher, Waltham, Mass., USA). The ICP-AES data were then normalized to total protein for each cell line used.

Measurement of caspase activity: Caspase 3/7, 8, and 9 activities were measured using Promega (Madison, Wis., USA) Caspase-Glo assays. Briefly, cells were seeded in 96-well white-bottom, white-wall plates at a density such that at the time of analysis wells would be 80% confluent. Following the completion of treatment, the Caspase-Glo assay was conducted per the manufacturer's protocol and luminescence was measured on a PerkinElmer 2104 EnVision plate reader (PerkinElmer). Raw data were averaged and normalized to the corresponding vehicle controls; normalized values were then plotted as an average±standard deviation.

Western blot analysis: For analysis of protein expression by Western blot analysis, the procedure set forth in Gligorich et al. was used. Gligorich K, Vaden R, Shelton D, Wang G, Matsen C, Looper R, et al. Development of a screen to identify selective small molecules active against patient-derived metastatic and chemoresistant breast cancer cells. Breast Cancer Res 2013; 15(4):R58. The cells were cultured and treated in 10-cm plates. Cells were harvested in cold radioimmunoprecipitation assay (RIPA) buffer (50 mM Tris-HCl, 150 mM NaCl, 0.1% sodium dodecyl sulfate (SDS), 0.5% sodium deoxycholate, and 1% Triton X-100) supplemented with protease and phosphatase inhibitors (Sigma). Protein concentration was measured using a BCA assay (Thermo Scientific) and 50 g of protein was resolved by gel electrophoresis using an SDS polyacrylamide gel. Protein was transferred to an Immobilon-FL PVDF membrane (Millipore, Billerica, Mass., USA) and the membrane was blocked for 1 hour at room temperature with Odyssey blocking buffer (Li—COR). The membrane was incubated with primary antibody diluted in Odyssey blocking buffer overnight at 4° C. then washed with tris-buffered saline. After incubation for 1 hour at room temperature with secondary antibodies diluted in Odyssey blocking buffer, the blot was imaged with the Odyssey Infrared Imaging System (LI-COR).

Measurement of cellular proliferation: Cells were seeded in six-well plates at densities such that wells would be approximately 80% confluent at the end of treatment. Cells were treated with drug diluted in low serum (2% FBS) media for the appropriate length of time then 5-ethynyl-2'-deoxyuridine (EdU, Life Technologies) was added directly to the media to achieve a final concentration of 10 M EdU; the cells were then incubated at 37° C. for 30 minutes. EdU incorporation and propidium iodide staining were assessed by flow cytometry following the manufacturer's protocol (Life Technologies) and analyzed as described in Gligorich et al.

Measurement of oxidative stress: Oxidative stress induced by drug treatment was assessed by measuring the oxidation of 2',7'-dichlorodihydrofluorescein diacetate (H2DCFDA). Briefly, cells were seeded in 6-well plates and treated with drug diluted in low serum (2% FBS) media for the appropriate length of time. The media was then replaced with HBSS containing 30 µM H2DCFDA and the plates incubated at room temperature for 30 minutes. Cells were then trypsinized, washed with 2% FBS/HBSS, and resuspended in 2% FBS/HBSS for analysis by flow cytometry. The relative mean fluorescence for each condition was normalized to the corresponding vehicle-treated control and the values were then plotted as an average±standard error.

In vivo ZNA studies: Mouse studies were conducted with the approval of an institutional animal care and use committee. FVB/NJ mice were obtained from The Jackson Laboratory (Bar Harbor, Me., USA). In preparation for the in vivo study, EF1α-PyMT mouse mammary tumors were generated in donor mice and the tumors resected and prepared as single cells as described previously by Smith et al. (6). These cells were suspended in Matrigel (BD Biosciences) and injected (50,000 cells per 10 µL injection) into the uncleared mammary fat pad of 3-week old female recipient FVB/NJ mice. Twenty-one days following the transplant, the mice were randomized, and drug treatment was initiated; the mice were treated once a day for 21 days, and a tumor diameter ≥2 cm was established as an endpoint. ZNA (100 mg/kg) or the matched vehicle control was administered to each mouse via a 200-µL intraperitoneal injection of ZNA diluted into DMSO, then diluted into phosphate buffered saline to a final DMSO concentration of 5%. ZnSO$_4$ was administered continuously for the 21-day treatment period to the appropriate groups via drinking water (25 mM ZnSO$_4$.7H$_2$O).

Statistics: The student's t-test (unpaired) was used to assess statistical significance and a p≤0.05 was considered statistically significant. Statistical significance between Kaplan-Meier survival curves was measured by the Mantel-Cox test using Prism 6.0 (GraphPad Software). The following P-values were used to annotate statistical significance: p≤0.05=*; p≤0.01=; p≤0.001=*.

Example 54: Selective Cytotoxicity of Zinaamidole (ZNA) Against Cancer Cells

To identify novel small molecules capable of selectively killing patient-derived metastatic cancer cells, a screen was designed using 560 compounds. Gligorich K., Vaden R., Shelton D., Wang G., Matsen C., Looper R., et al. *Breast Cancer Res* 2013; 15(4):R58. Normal human mammary epithelial cells immortalized by lentiviral-induced expression of human telomerase reverse transcriptase (hTERT-HMECs) were used in conjunction with primary metastatic cells obtained from a chemoresistant breast cancer patient pleural effusion (PE1007070) to model compound selectivity. hTERT-HMEC and PE1007070 cells were treated for four days with 20 µM of each compound from the library, and cell viability was subsequently measured using an ATP quantification assay; the data were then normalized to a vehicle-treated control.

From this screen, a small molecule containing a cyclic guanidine core was identified for its ability to kill metastatic tumor cells while sparing normal mammary epithelial cells. Validation of the initial result in a 12-point dose response assay against a second pleural effusion (PE1100025) obtained from a different chemoresistant breast cancer patient revealed that the small molecule, zinaamidole (ZNA), was effective at low micromolar concentrations against tumor cells and maintained a relatively large therapeutic treatment window even at high concentrations (FIGS. 1A and 1B). ZNA selectively killed primary metastatic breast cancer cells while leaving normal mammary epithelial cells largely unaffected.

To further assess the generality of ZNA's breast cancer selectivity and cytotoxicity, dose response assays were performed using three breast cancer cell lines (MCF-7, T47D, and MDA-MB-231) and a normal mammary epithelial cell line (MCF-10A); cell viability was again measured using a luciferase-based ATP assay following five days of treatment with either ZNA or a vehicle control. As with the immortalized human mammary epithelial cells and primary patient-derived cancer cells, treatment with ZNA resulted in decreased cell viability in the malignant cell lines examined, but the normal mammary epithelial cell line was largely unaffected (FIG. 1C).

Further experiments were also conducted to assess the effects of short-term ZNA treatment on long-term cell survival and proliferation. Cells were treated for 24 hours with ZNA then cultured in the absence of the small molecule; following three weeks of growth, colonies were stained with crystal violet and quantified (FIG. 1D). From this assay, it was discovered that short-term exposure, even at normally sub-lethal concentrations, significantly affected long-term proliferative potential in cancer cells; again, as with the dose response assays, the effect on untransformed MCF-10A cells was greatly attenuated compared to the malignant cell types tested.

Upon establishing that ZNA was cytotoxic against aggressive metastatic patient-derived cancer cells in addition to three breast cancer cell lines, a transcriptome sequencing experiment was conducted to study the mechanistic basis for ZNA's efficacy and cancer selectivity. MCF-7 breast cancer cells were treated with 30 µM ZNA or a matched vehicle control for either 3 or 12 hours; RNA was then isolated and the transcriptome profiled by next-generation sequencing. The three most upregulated genes following three hours of treatment with ZNA were metallothionein genes MT1F, MT1X, and MT2A; this increased metallothionein gene expression was sustained following 12 hours of ZNA treatment (FIG. 1E).

Members of the metallothionein family are cysteine-rich redox-active proteins known to directly bind transition metals such as copper and zinc (as reviewed by Thirumoorthy et al.). Thirumoorthy N, Shyam Sunder A, Manisenthil Kumar K T, Senthil kumar M, Ganesh GNK, Chatterjee M. A Review of Metallothionein Isoforms and their Role in Pathophysiology. World J Surg Oncol 2011; 9(1):54. Moreover, metallothioneins are involved in intracellular metal distribution and sequestration and are thought to play a role in maintaining appropriate cellular redox states. Thornalley P J, Vasak M. Possible role for metallothionein in protection against radiation-induced oxidative stress. Kinetics and mechanism of its reaction with superoxide and hydroxyl radicals. Biochim Biophys Acta—Protein Structure and Molecular Enzymology 1985; 827(1):36-44. Chiaverini N, De Ley M. Protective effect of metallothionein on oxidative stress-induced DNA damage. FRA 2010; 44(6):605-13.

Transcriptome profiling also revealed that ZNA treatment resulted in the increased expression of two transcripts encoding zinc transport proteins SLC30A1 and SLC30A2. This effect, however, was only apparent following three hours of treatment, and the increased transcription was not sustained after a 12-hour treatment with ZNA. SLC30A2 and are genes encoding for two members of the ZnT family of Zn$^{2+}$ transporters.

Since MT proteins are known to participate in intracellular metal trafficking and sequestration and ZnT proteins have been shown to function in a Zn$^{2+}$ transport capacity, it is reasonable that the changes in gene expression observed following treatment with ZNA occur in response to ZNA-induced metal dyshomeostasis, specifically Zn$^{2+}$ imbalances. See Palmiter et al. *EMBO J* 1996; 15(8): 1784-91; Qin et al. *Neurosci Lett* 2009; 450(2):206-10.

In order to assess the extent of ZNA's effect on transcription in other cell lines, real-time PCR (RT-PCR) experiments were conducted using primers against the five metal trafficking genes identified from the transcriptome sequencing analysis. Three breast cancer cell lines (MCF-7, T47D, and MDA-MB-231) and a normal mammary epithelial cell line (MCF-10A) were treated for either 3 or 24 hours with 30 µM ZNA or a matched vehicle control and gene expression was measured by RT-PCR (FIG. 1F). Treatment with ZNA stimulated transcriptional increases in metal trafficking genes in the four cell lines examined although these changes varied in both magnitude and temporal induction between the cell lines. Collectively, the transcriptome profiling and RT-PCR results suggest that ZNA treatment affects intracellular metal trafficking, while the transcriptional changes associated with SLC30A1 and SLC30A2 suggest a more specific role for zinc dyshomeostasis. Since MT proteins are known to participate in intracellular metal trafficking and sequestration and ZnT proteins have been shown to function in a Zn$^{2+}$ transport capacity, it was hypothesized that the changes in gene expression were the result of ZNA-induced $Zn^{2+}$ imbalances. See Palmiter et al. EMBO J 1996; 15(8): 1784-91; Qin et al. Neurosci Lett 2009; 450(2):206-10.

In order to determine whether the transcriptional changes in metal trafficking genes were functionally relevant to ZNA's mechanism of action, intracellular $Zn^{2+}$ was quantified using the fluorescent indicator FluoZin-3 followed by flow cytometry analysis (FIG. 1G). Four cell lines were treated with 30 µM ZNA or a matched vehicle control for 1, 3, 24 or 48 hours then stained with the $Zn^{2+}$ indicator, and their fluorescence was measured. With MCF-7 breast cancer cells, ZNA resulted in a 13-fold increase in FluoZin-3 fluorescence after 48 hours of treatment. However, this result with MCF-7 cells surpassed the only modest increases in intracellular zinc in the other three cell lines examined.

Figure 7:
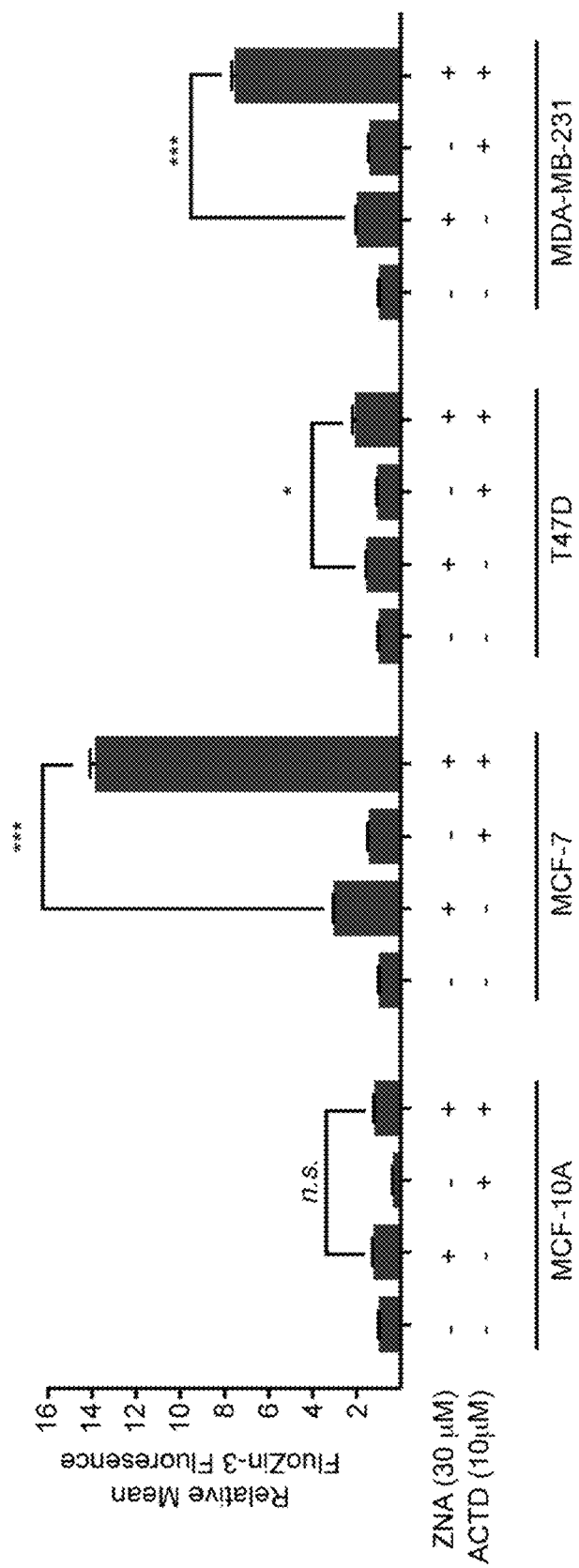
FIG. 7.

Considering that increased metallothionein gene expression might participate in attenuating a rise in intracellular zinc, cells were exposed to ZNA in conjunction with an inhibitor of transcription (Actinomycin D, ACTD) for 24 hours and intracellular zinc was subsequently measured by FluoZin-3 staining (FIG. 7). With the exception of the ZNA-insensitive MCF-10A cells, co-treatment of all cells with ZNA and ACTD resulted in statistically significant increases in intracellular $Zn^{2+}$ compared to ZNA alone, with MCF-7 and MDA-MB-231 cells responding most dramatically. These data suggest that as ZNA stimulates an increase in intracellular $Zn^{2+}$, a simultaneous increase in metal trafficking gene transcription likely plays a role in attenuating intracellular $Zn^{2+}$ accumulation.

Example 55: $Cu^{2+}$ and $Zn^{2+}$ Synergism with ZNA

Considering ZNA's ability to stimulate an increase in intracellular zinc and its effect on the transcription of metal trafficking genes, a study was next initiated to determine the effect of ZNA on cells treated in combination with exogenously added transition metals. Three breast cancer cell lines (MCF-7, T47D, and MDA-MB-231) and a normal mammary epithelial cell line (MCF-10A) were treated with 30 µM ZNA in conjunction with 30 M $CuSO_4$, $ZnSO_4$, $Fe(III)Cl_3$, $Fe(II)SO_4$, $NiSO_4$, $MnCl_2$, or $CoCl_2$ for 48 hours; following the completion of treatment, cell viability was measured using an ATP quantification assay (FIG. 2A). Surprisingly, synergism was discovered between ZNA and $Cu^{2+}$, and a significant reduction in cell viability was observed in every cell line following treatment. A similar striking synergism was also observed between ZNA and $Zn^{2+}$ but in this case, only the breast cancer cell lines experienced a decrease in cell viability as a result of the combination treatment; the normal mammary epithelial cells exhibited only a partial reduction in cell number. In contrast, combination treatments with the remaining five transition metals resulted in no significant change in cell viability compared to treatment with ZNA alone.

Figure 2B:
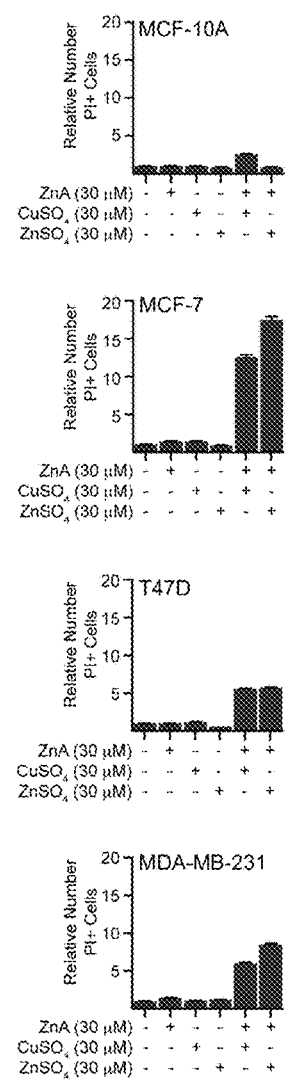

In order to validate the transition metal screen with a second cell viability assay, propidium iodide uptake was measured in four cell lines by flow cytometry following a 24-hour treatment with either 30 µM ZNA alone or in combination with 30 M $CuSO_4$ or 30 µM $ZnSO_4$ (FIG. 2B). Consistent with the measurements obtained at 48 hours using an ATP quantification assay, the propidium iodide staining experiment revealed that ZNA was synergistic with both $Cu^{2+}$ and $Zn^{2+}$ and the combination induced cell death in cancer cells more rapidly than with ZNA alone. Most notably though, the normal mammary epithelial cell line was unaffected by the combination of ZNA and $Zn^{2+}$.

Example 56: ZNA Promotion of Extracellular $Zn^{2+}$ Uptake

To better understand the cancer-selective synergism observed between ZNA and $Zn^{2+}$, an experiment was conducted to measure intracellular $Zn^{2+}$ using the fluorescent $Zn^{2+}$ indicator FluoZin-3. MCF-10A, MCF-7, T47D, and MDA-MB-231 cells were treated for three hours with either 30 µM ZNA alone or 30 µM ZNA in conjunction with 30 µM $ZnSO_4$ and then stained with FluoZin-3 before analysis by flow cytometry (FIG. 3A). The three breast cancer cell lines examined experienced no less than a 34-fold increase in FluoZin-3 fluorescence as a result of the combination treatment of ZNA and $Zn^{2+}$, while only a 9-fold increase in FluoZin-3 fluorescence was observed in the ZNA-insensitive normal mammary epithelial cell line.

Figure 3B:
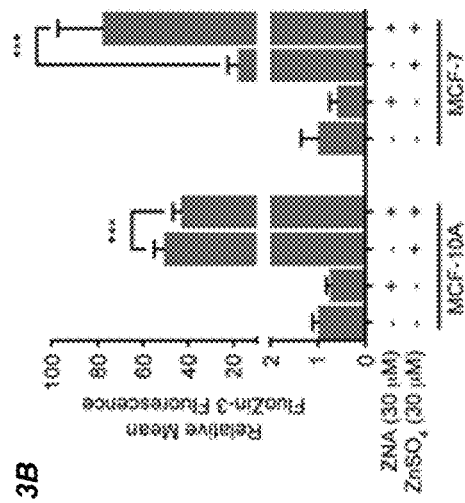
FIGS. 3A-3B.
Figure 3A:
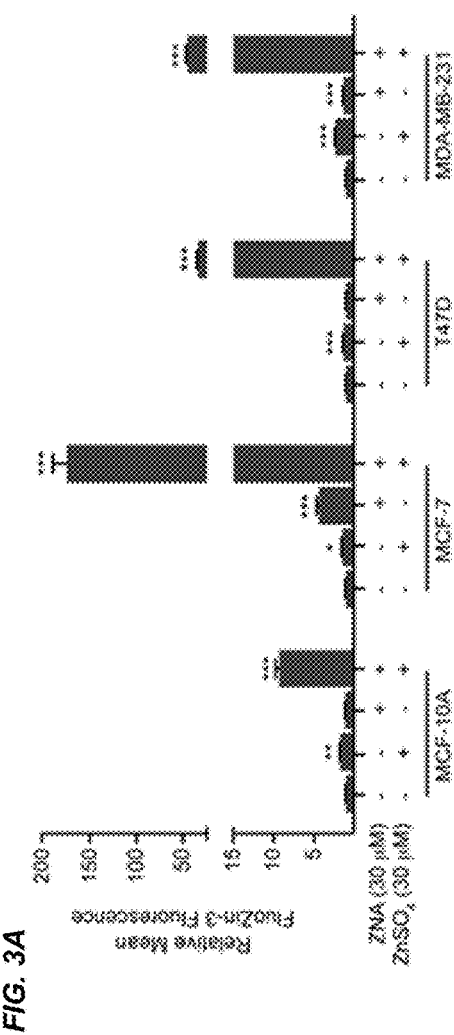

Further probing the ability of ZNA to stimulate increases in intracellular $Zn^{2+}$, MCF-10A and MCF-7 cells were treated for three hours with 30 µM ZNA (both with and without exogenous $ZnSO_4$) in zinc-free media; intracellular zinc was then quantified by FluoZin-3 staining (FIG. 3B). From this experiment, no significant increase in FluoZin-3 fluorescence was observed after treatment with ZNA alone in either cell line. However, combination treatment with ZNA and $ZnSO_4$ resulted in a 4.3 fold increase in fluorescence in MCF-7 cells compared to $ZnSO_4$ alone, while MCF-10A cells experienced a reduction in fluorescence under the same conditions. This result suggests that in MCF-7 cells, ZNA modulates $Zn^{2+}$ transport primarily across the plasma membrane.

To further validate the combinatorial effect of ZNA and $Zn^{2+}$, inductively coupled plasma-atomic emission spectroscopy (ICP-AES) was employed to quantify absolute levels of cellular $Zn^{2+}$ following treatment. Four cell lines were treated with either 30 µM ZNA alone or 30 µM ZNA in conjunction with 30 µM $ZnSO_4$ for three hours before harvesting. The samples were then analyzed by ICP-AES and the resulting data normalized to total protein (FIG. 8). The concentration of $Zn^{2+}$ in MCF-7, T47D, and MDA-MB-231 cells was found to be 1.35, 0.52, and 0.82 ng $Zn^{2+}$ per microgram of protein, respectively, following combinatorial treatment with ZNA and $ZnSO_4$. In contrast, the ion was not detectable by ICP-AES (i.e., levels fell below the detection limit of 1.00 µg/L) in ZNA-insensitive MCF-10A cells following the same treatment, despite the analysis of protein concentrations similar to the other cell types. The values obtained from the ICP-AES experiment correlate with the trends observed following FluoZin-3 measurements of $Zn^{2+}$, confirming the specificity of the fluorophore for $Zn^{2+}$ over other ions. Collectively, the results of these studies demonstrate that ZNA promotes increases in intracellular $Zn^{2+}$ via transport across the plasma membrane. Of particular interest though, ZNA-insensitive MCF-10A cells experience smaller fluctuations in intracellular $Zn^{2+}$ following treatment than the three breast cancer cell lines examined, suggesting a basis for the cancer-selective nature of ZNA.

Figures 4A, 4B:
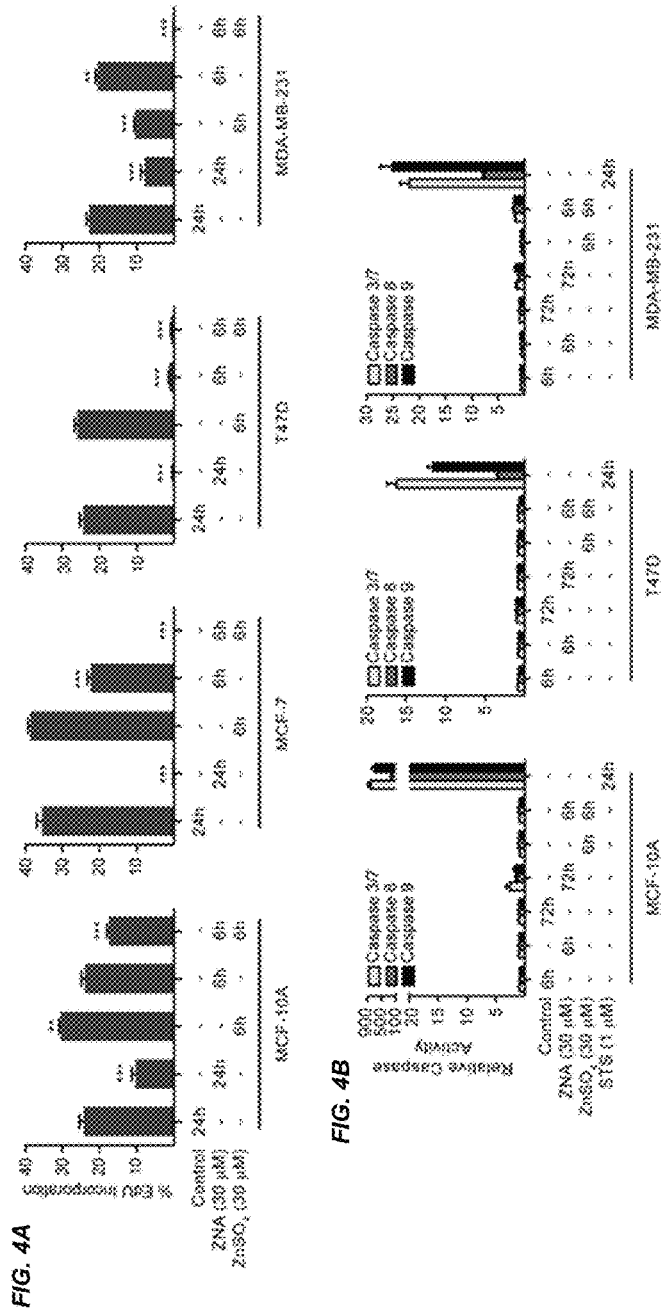
FIGS. 4A-4B.

Example 57: Selective Growth Inhibition and Caspase-Independent Cell Death Induction Upon finding that ZNA synergized strongly with exogenously added $Zn^{2+}$ to promote rapid and cancer-specific cell death, experiments were conducted to determine the effect of treatment on cellular proliferation and to characterize the cell death induced by the combinatorial treatment. First, a 5-ethynyl-2'-deoxyuridine (EdU) incorporation assay was utilized to assess the effects of ZNA and ZNA/ZnSO$_4$ treatment on cellular proliferation. Since combinatorial treatment results in cell death more quickly than ZNA treatment alone, which makes comparisons between single and combination treatments challenging at a single time point, two time points were chosen for the proliferation assay; cells were cultured with the small molecule for 6 hours (for combinatorial treatment) or 24 hours (in the case of ZNA treatment alone) and subsequently incubated with EdU. MCF-10A, MCF-7, T47D, and MDA-MB-231 cells were cultured with the small molecule for 6 hours and subsequently incubated with EdU; EdU incorporation was then measured by flow cytometry (FIG. 4A). Treatment with ZNA alone resulted in a statistically significant decrease in EdU incorporation in MCF-7 and T47D cells, but not in MCF-10A and MDA-MB-231 cells. Most interesting, however, was the combinatorial effect of ZNA/ZnSO$_4$ on proliferation: after only 6 hours of treatment, the three cancer cell lines examined presented with a complete block in proliferation, though the normal mammary epithelial cell line was also somewhat affected. These striking results again support the idea that Zn$^{2+}$ dyshomeostasis contributes directly to the cancer-selective phenotype observed with ZNA treatment.

In order to establish whether ZNA-treated cells undergo apoptosis, caspase 3/7, 8 and 9 activities were measured using a luciferase-based Caspase-Glo assay. MCF-10A, T47D, and MDA-MB-231 cells were treated with 30 μM ZNA, 30 μM ZNA in combination with 30 μM ZnSO$_4$, or the appropriate control for 6 hours; MCF-7 cells were not included in the experiment since these cells lack functional caspase 3. Jänicke R U, Sprengart M L, Wati M R, Porter A G. Caspase-3 Is Required for DNA Fragmentation and Morphological Changes Associated with Apoptosis. J Biol Chem 1998; 273(16):9357-60. Caspase activity was then measured for each condition and normalized to the vehicle-treated control (FIG. 4B). Surprisingly, no caspase 3/7, 8, or 9 activity was observed for any of the treatment conditions in the four cell lines examined with the exception of the positive control (1 μM staurosporine, STS). Furthermore, treatment of the four cell types with 30 μM ZNA for a longer time period (72 hours) also did not activate caspases 3/7, 8 or 9. These data suggest that ZNA alone or ZNA in combination with ZnSO$_4$ does not promote classic caspase-mediated apoptotic cell death.

In an effort to further elucidate the type of cell death induced in cancer cells by ZNA treatment, the next experiment investigated whether ZNA mediated cell death via mechanisms involving receptor interaction protein kinase 1 (RIP1). RIP1 has been shown to directly participate in necroptosis, a form of programmed cell death that presents with the morphological features of necrosis, occurs independently of caspase activation, and can be blocked by RIP1 inhibition. Degterev et al. *Nat Chem Biol* 2005; 1(2): 112-19.

Figures 5A, 5B:
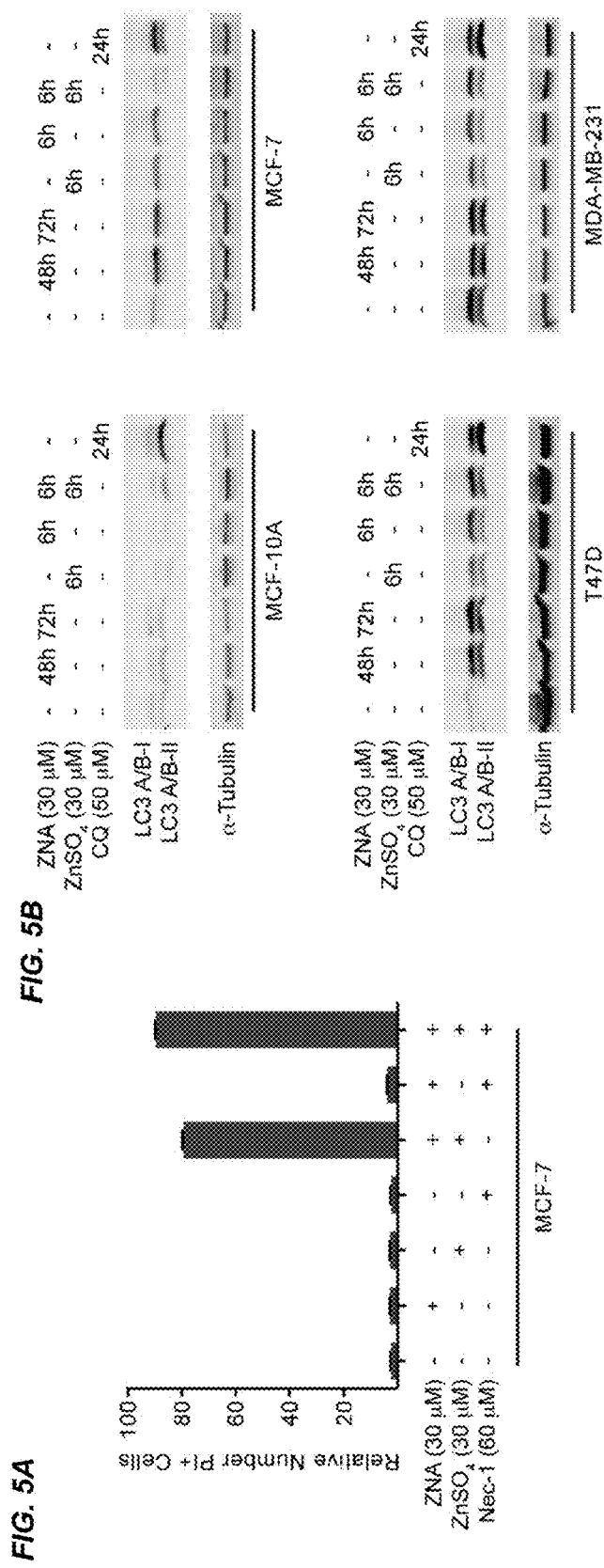
FIGS. 5A-5C.

As such, MCF-7 cells were treated with 30 μM ZNA alone or in combination with ZnSO$_4$ and/or the RIP1 inhibitor Necrostatin-1 for 24 hours; a positive control, the small molecule shikonin, was also included in the assay. Han W et al. Shikonin circumvents cancer drug resistance by induction of a necroptotic death. Mol Cancer Ther 2007; 6(5): 1641-49. Cells were subsequently stained with propidium iodide and fluorescence was measured by flow cytometry to quantify cell death (FIG. 5A). While the synergistic combination of ZNA and ZnSO$_4$ resulted in significantly higher levels of cell death than with ZNA alone, no rescue in cell death was observed with the addition of necrostatin-1. These data suggest that RIP1 does not mediate ZNA-promoted MCF-7 cell death; ZNA's mechanism of action is therefore unlikely to occur via the induction of necroptosis.

Further cell death characterization studies were also conducted to establish the role of autophagy in ZNA-mediated cell death. To assess the level of autophagic induction following treatment with ZNA, levels of the autophagosome-associated protein LC3A/B were measured by western blot analysis. Both increased expression of LC3 and the conversion of the 16 kDa LC3-I isoform to the processed 14 kDa LC3-II isoform have been used as indicators of autophagic processes. Kabeya et al. *EMBO J* 2000; 19(21): 5720-28. MCF-10OA, MCF-7, T47D, and MDA-MB-231 cells were treated with 30 μM ZNA, 30 μM ZNA in combination with 30 μM ZnSO$_4$, or the appropriate control for 6 hours before harvesting cells for analysis by western blot (FIG. 5B). An increase in LC3 was observed following 48- and 72-hour ZNA treatment, but only in the cancer cell lines. Taking into consideration the rapid cell death induced by the combination of ZNA and ZnSO$_4$, an earlier time point (6 hours) was chosen to assess LC3 levels for the combination treatment condition. Combinatorial treatment resulted in an apparent increase in LC3 protein in T47D cells, but significant increases were not observed in the other three cell lines tested.

Figure 5C:
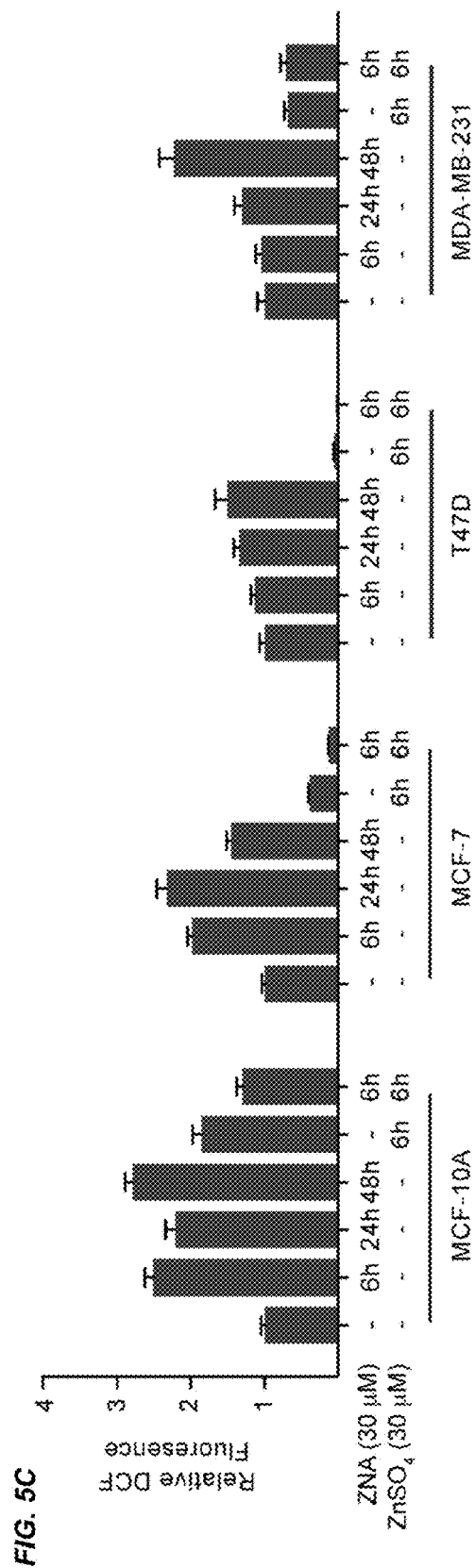

Since autophagy can stimulate both pro-death and pro-survival pathways, experiments were next conducted to assess how autophagic inhibitors impacted ZNA's cell death profile. If autophagy contributes to ZNA-induced cell death, then an inhibitor of autophagic processes would be expected to reduce ZNA-promoted cell death. See Dalby et al., Autophagy 2010; 6(3):322-29. As such, cells were treated with ZNA in combination with chloroquine, an inhibitor of autophagosome function, and cell death was assessed by propidium iodide stain following 72 hours of treatment. Kimura et al. Cancer Res 2013; 73(1):3-7. From these experiments, it was discovered that chloroquine-treatment decreased ZNA-induced cell death in T47D cells, but did not significantly affect cell death in the other three cell types evaluated (FIG. 5C).

Collectively, the results of these experiments suggest that ZNA-treatment alone can stimulate autophagic processes in cancer cells and, at least in the case of T47D cells, these processes contribute to the cell death phenotype. That combinatorial treatment with ZNA and ZnSO$_4$ does not induce the same levels of LC3 as with ZNA alone may reflect the differential cell death kinetics of the two treatment conditions; combinatorial treatment may induce injury more rapidly than the initiation of cellular autophagic responses. ZNA may cause cell death by rupturing lysosomes, thereby releasing cathepsins and other hydrolases, which leads to rapid necrotic cell death.

Figure 9:
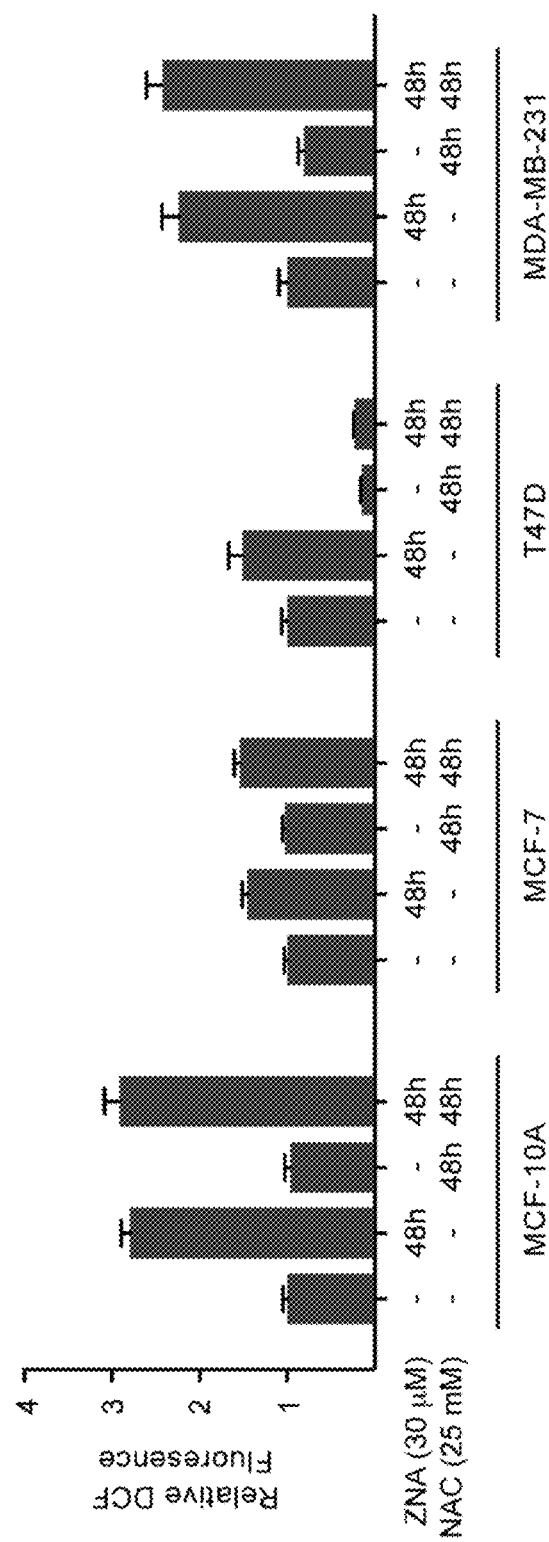
FIG. 9.
Figure 10D:
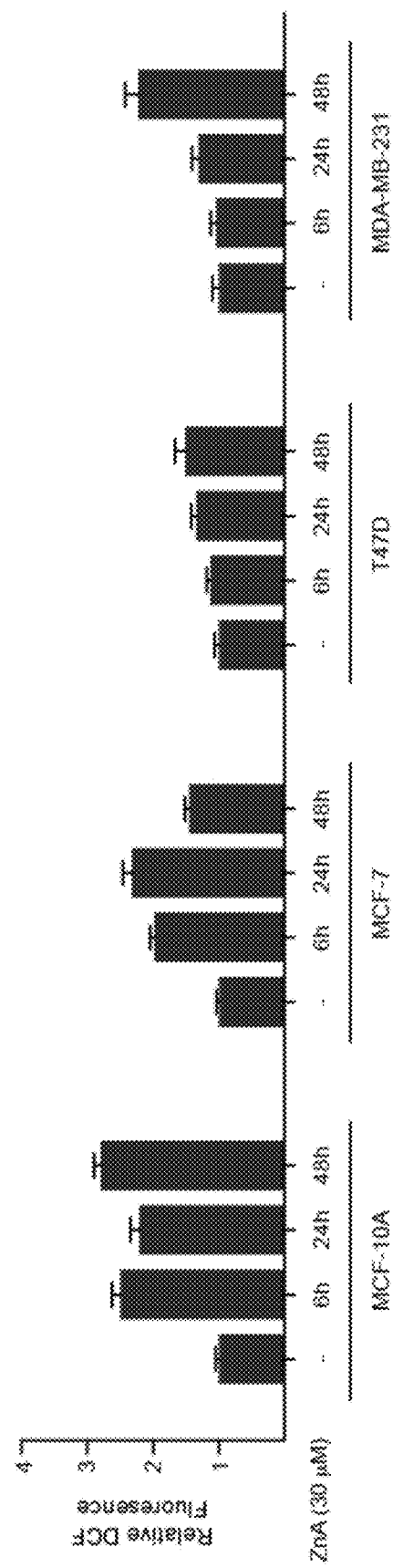
Figure 11C:
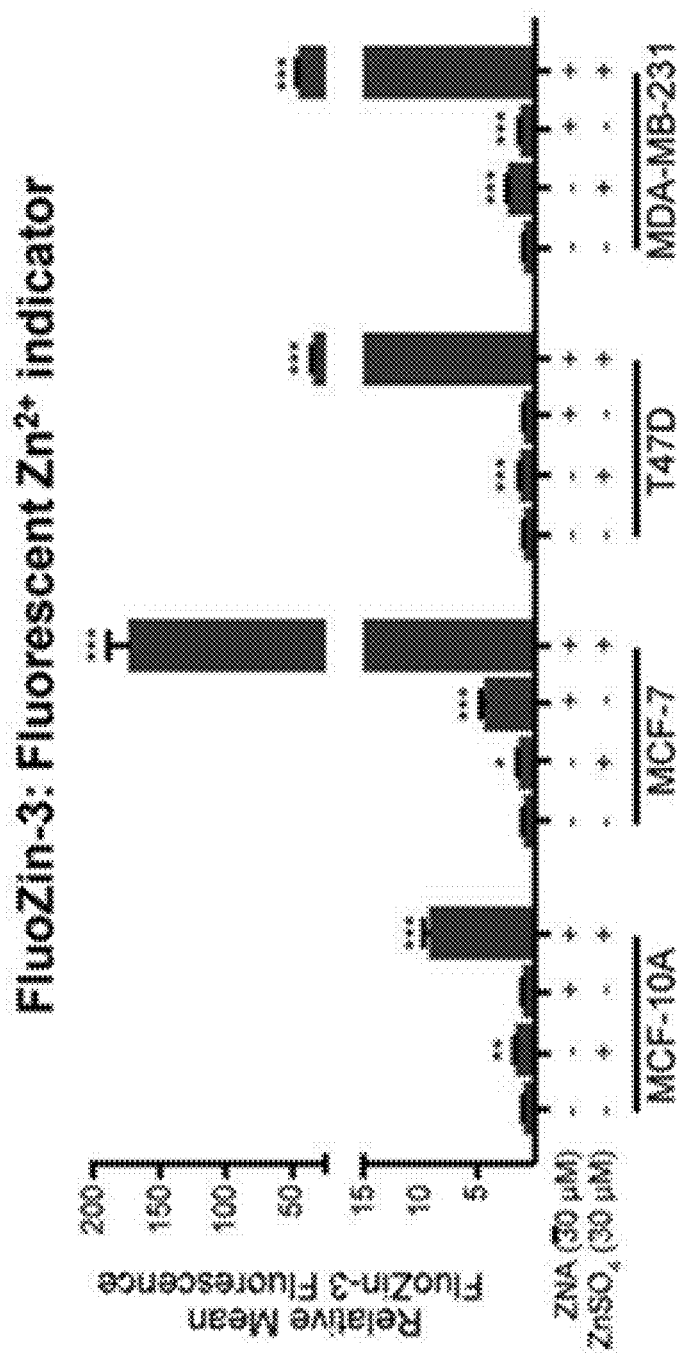
Figure 12:
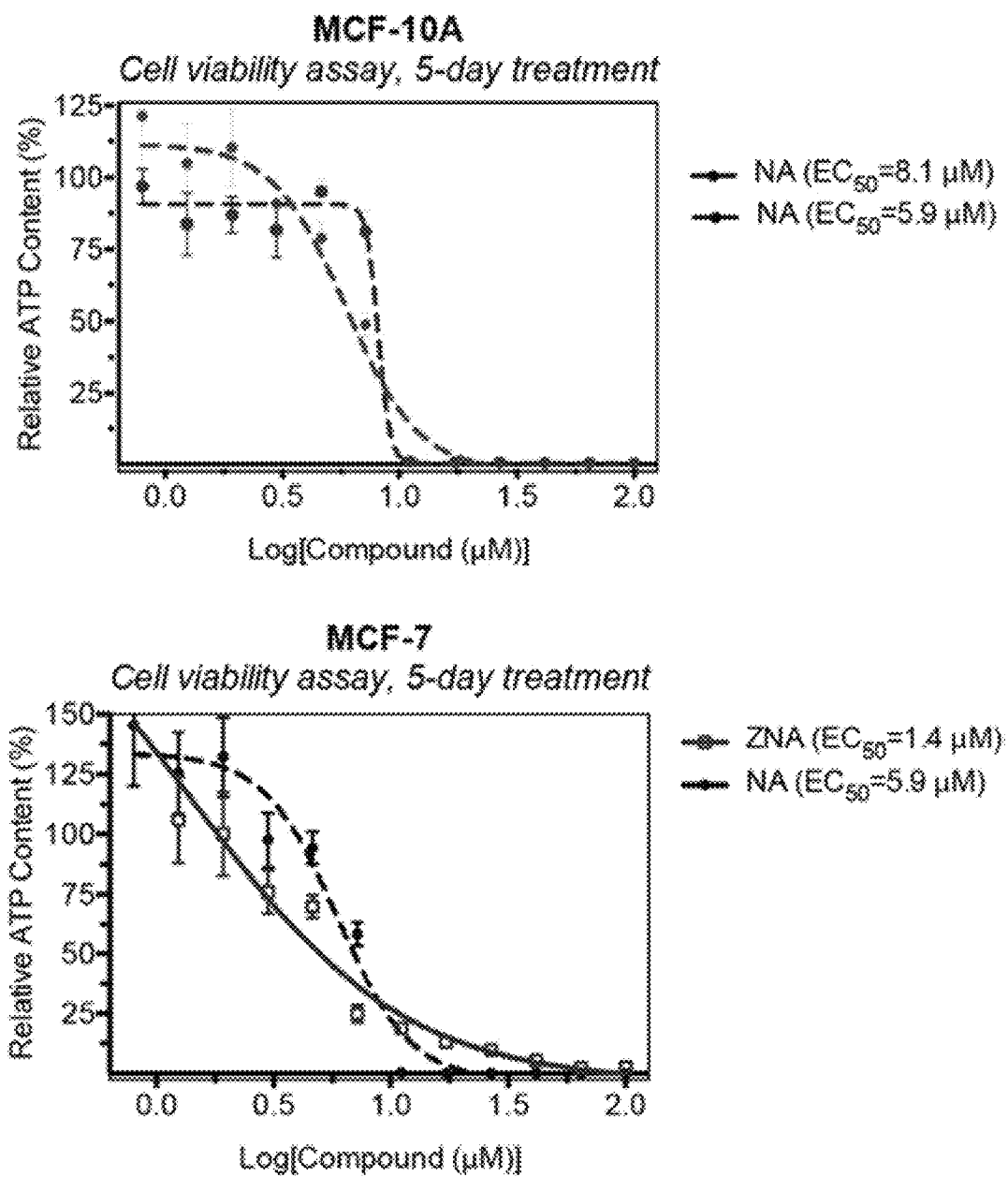
FIG. 12.
Figures 13A, 13B:
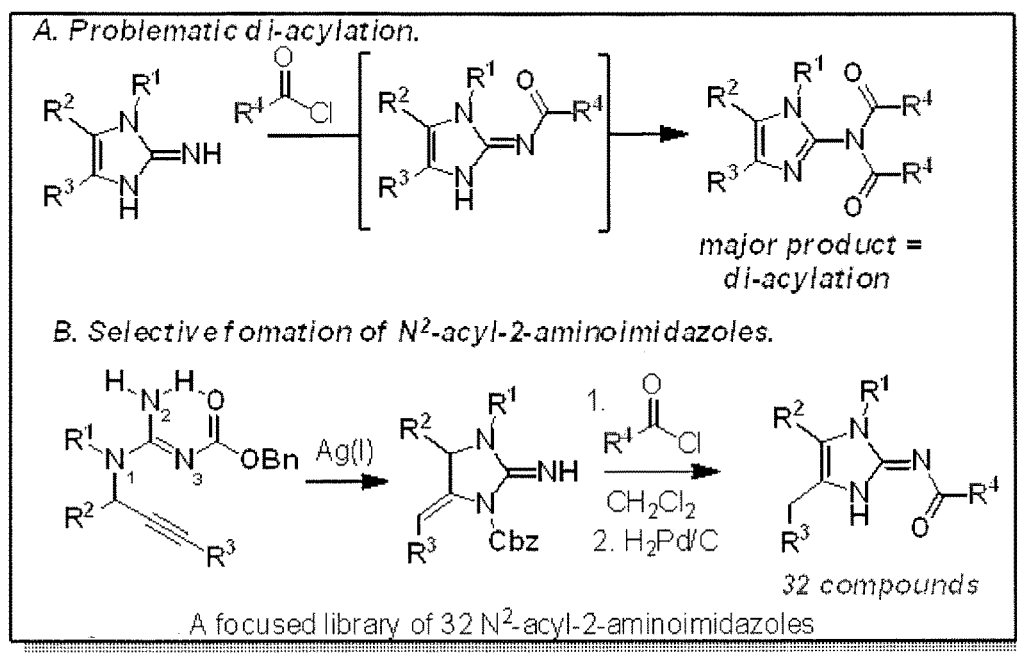
FIGS. 13A-13B.

Further probing the caspase independent cell death induced by ZNA, experiments were next conducted to characterize the extent of oxidative stress during the cell death process. Therefore, MCF-10A, MCF-7, T47D, and MDA-MB-231 cells were treated with 30 μM ZNA, 30 μM ZNA in combination with 30 μM ZnSO$_4$, or the appropriate control for up to 48 hours and the oxidation of 2',7'-dichlorodihydrofluorescein diacetate (H2DCFDA, DCF) was used as an indicator of oxidative imbalance; DCF fluorescence was measured by flow cytometry and subsequently normalized to the appropriate vehicle-treated control (FIG. 5C). The results revealed that ZNA alone stimulated a slight increase in DCF fluorescence; in contrast, combinatorial treatment of ZNA and ZnSO$_4$ resulted in a statistically significant decrease in H2DCFDA oxidation in the three cancer cell lines compared to their respective controls. The decreased levels of H2DCFDA oxidation observed with ZNA and $ZnSO_4$ combinatorial treatment are consistent with literature reports detailing a connection between increased intracellular $Zn^{2+}$ and decreased oxidative stress. E.g., Ho E, Ames B N, *Proc Natl Acad Sci USA* 2002; 99(26): 16770-75. Attempts to inhibit this increase with the antioxidant N-acetylcysteine (NAC) were successful only with T47D cells; however, a concomitant decrease in cell death was not observed (FIG. 9). Together these fail to support a significant role for oxidative stress in ZNA-mediated cell death.

In summary, ZNA-treatment resulted in rapid growth arrest and caspase independent cell death of breast cancer cells. Considering cell death pathways alternative to apoptosis, further studies were conducted to establish whether necroptosis or autophagy might play a role in ZNA-mediated cell death. While the results of these experiments suggested against necroptosis, Western blot experiments measuring the induction of the autophagy-associated protein LC3 revealed that ZNA-treatment alone stimulated cancer-cell specific increases in LC3; however, treatment with ZNA in combination with $ZnSO_4$ resulted in LC3 increases only in T47D cells. Since combinatorial treatment results in cancer cell death much more rapidly than with ZNA treatment alone, it is likely that the two treatment conditions evoke different cell death pathways. While treatment with ZNA alone appears to induce autophagy, combinatorial treatment may induce catastrophic injury before autophagic initiation can occur. In this case, the rapid loss of membrane integrity identified by propidium iodide staining is consistent with necrosis, which may occur alone or in conjunction with autophagy depending upon the cell type examined. Necrosis may be the form of cell death invoked by MCF-7 and MDA-MB-231 breast cancer cells upon ZNA-treatment even while LC3 induction is observed.

Further studies were conducted to establish whether necroptosis or autophagy might play a role in ZNA-mediated cell death. While the results of these experiments suggested against necroptosis, measurement of autophagy-associated protein LC3 revealed that ZNA-treatment stimulated cancer cell-specific increases in LC3; however, treatment with ZNA in combination with $ZnSO_4$ resulted in LC3 increases only in T47D cells. Interestingly, co-treatment of cells with ZNA and chloroquine, an inhibitor of autophagy, decreased cell death only in T47D cells, a result suggesting that autophagy mediates some component of T47D cell death. The relative ineffectiveness of chloroquine at inhibiting (or potentiating) cell death in the other three cell types tested suggests that autophagic processes do not significantly affect cell outcomes following treatment with ZNA. As such, The finding that ZNA treatment stimulated the induction of metal trafficking genes prompted evaluation of the small molecule's effect when used in combination with biologically relevant transition metals added exogenously to cells in culture. Interestingly, of the seven transition metals tested, only two affected cell viability when added simultaneously with ZNA compared to ZNA treatment alone. $Cu^{2+}$ is synergistic but non-selective, killing both MCF10As and MCF7s likely due to the general toxicity of copper. $Zn^{2+}$ however, is selectively synergistic, effective at killing MCF7s but not the untransformed 10As. Co-treatment of cells with ZNA and $ZnSO_4$ resulted in synergistic and cancer-selective cytotoxicity while co-treatment with ZNA and $CuSO_4$ killed both normal and cancer cells—a finding consistent with the hypothesis that ZNA's cancer-selective cytotoxicity is based on a mechanism involving intracellular $Zn^{2+}$ dyshomeostasis. Isothermal titration calorimetry studies designed to test direct interactions between the small molecule and either zinc or copper provided no evidence to suggest direct binding (data not shown). When considering explanations for the differential response elicited by zinc and copper when used in combination with ZNA in normal mammary epithelial cells, it is reasonable to hypothesize that ZNA can promote the uptake of $Zn^{2+}$ and $Cu^{2+}$ equally but non-transformed cells possess the ability to traffic and export $Zn^{2+}$ more efficiently than transformed cells.

Example 58: Suppression of Tumor Growth In Vivo-Mouse Mammary Tumor Model

Figure 6A:
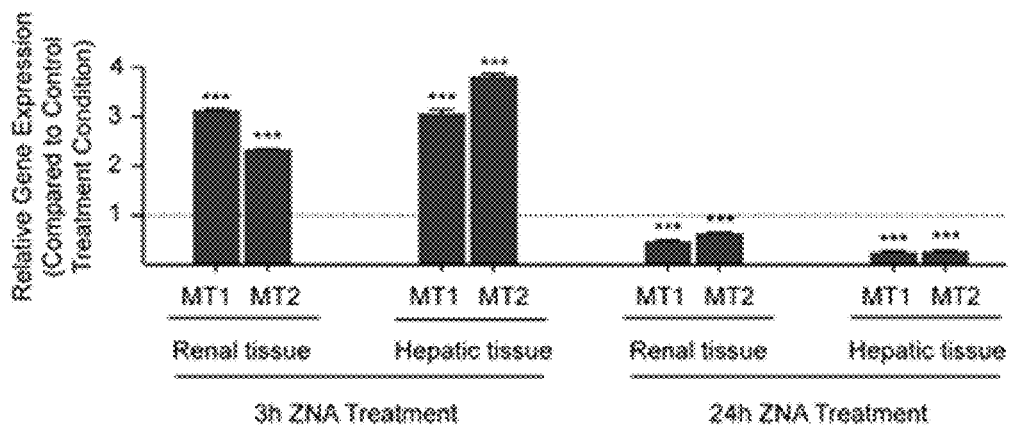
FIGS. 6A-6B.

The next experiment established the relevancy of the biological pathways targeted by ZNA in a whole organism tumor model. To establish bioactivity, the response of normal tissue to ZNA was evaluated. Non-tumor bearing FVB/NJ mice were treated with ZNA (at 100 mg/kg administered via intraperitoneal injection) or a control for either 3 or 24 hours. RT-PCR was used to assess mouse metallothionein expression (MT1 and MT2) in renal and hepatic tissue from the treated mice. The results revealed that MT1 and MT2 expression were increased following 3 hours of ZNA treatment as compared to control treated mice but were decreased following 24 hours, a trend consistent with the results of the analogous in vitro RT-PCR experiments conducted with breast cancer cell lines (FIG. 6A and FIG. 1F). These preliminary experiments suggested that ZNA modulated metal trafficking pathways similarly between in vivo and in vitro models.

Figure 6B:
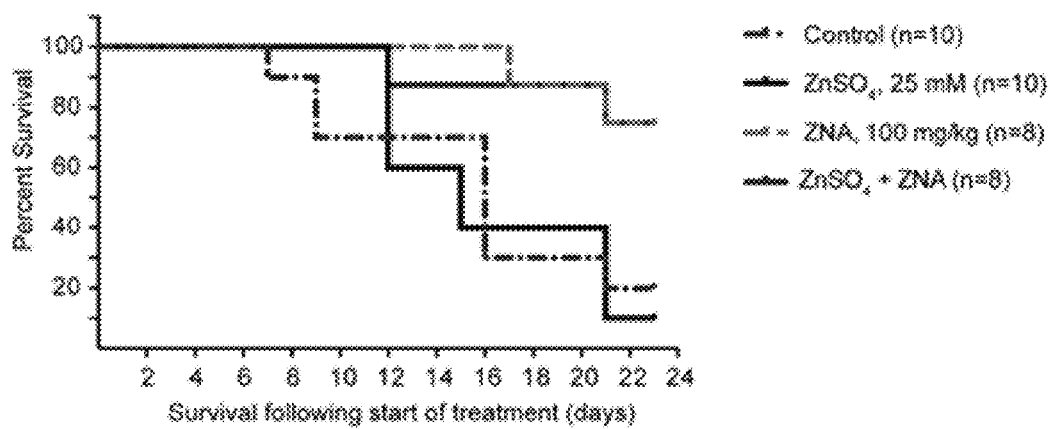

Next, the efficacy of the compound was tested in an in vivo tumor model. Mouse mammary tumors were transplanted into the fat pads of 3-week old female recipient FVB/NJ mice as per the procedure of Smith et al. Genes Cancer 2012; 3(9-10):550-63. The tumors were allowed to grow for three weeks before initiating treatment. Mice were treated once a day for 21 days, and four treatment conditions were assessed: ZNA (100 mg/kg administered via intraperitoneal), $ZnSO_4$ (25 mM administered continuously for the duration of treatment via drinking water), a combination of ZNA and $ZnSO_4$, and a control group (PBS administered via intraperitoneal injection); a tumor diameter greater than 2 cm was established as an endpoint. Following the completion of the 21-day drug treatment, treatment with either ZNA alone or ZNA administered in combination with $ZnSO_4$ resulted in a statistically significant survival advantage compared to the control-treated or $ZnSO_4$-only groups, respectively (FIG. 6B). Additionally, no general toxicity, adverse reactions, or decreases in body weight were observed in the mice treated with ZNA or with the combination of ZNA and $ZnSO_4$.

In summary, ZNA synergizes strongly with $Zn^{2+}$ to induce cancer-selective cell death via a caspase-independent mechanism. ZNA was found to be effective against primary metastatic cells derived from breast cancer patients treated with multiple frontline chemotherapeutics, and the small molecule's in vivo efficacy was established using a mouse mammary tumor model. Co-treatment of ZNA with $ZnSO_4$ induced significant increases in intracellular $Zn^{2+}$ compared to treatment with either ZNA or $ZnSO_4$ alone, a defining characteristic of ionophores, and resulted in rapid cancer cell death.

Taken together, the data presented herein suggest that destabilizing $Zn^{2+}$ trafficking pathways and inducing intracellular $Zn^{2+}$ dyshomeostasis are viable mechanisms by

Example 59: Preparation of Benzyl (E)-4-(4-(Benzyloxy)benzyl)-2-((4-methoxybenzoyl)imino)-5-((Z)-4-methoxybenzylidene)-3-methylimidazolidine-1-carboxylate (52)

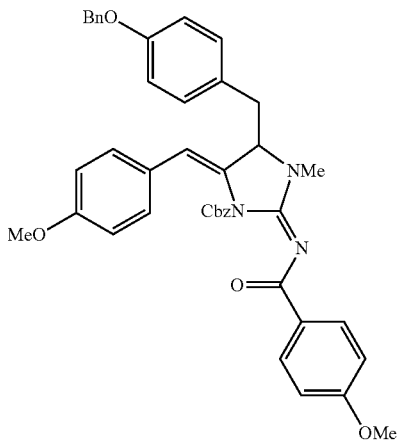

52

Example 60: Preparation of Benzyl (E)-4-(4-(Benzyloxy)benzyl)-5-((Z)-4-methoxybenzylidene)-3-methyl-2-((3-(trifluoromethyl)benzoyl)imino)imidazolidine-1-carboxylate (53)

53

To a 5-mL round-bottom flask equipped with a stir bar was added (Z)-benzyl 4-(4-(benzyloxy)benzyl)-2-imino-5-(4-methoxybenzylidene)-3-methylimidazolidine-1-carboxylate (0.05 g, 0.09 mmol), NEt$_3$ (0.025 mL, 0.18 mmol), 4-methoxybenzoyl chloride (0.023 g, 0.14 mmol) and dichloromethane (0.9 mL). The reaction was allowed to stir for 1 hour. The reaction mixture was concentrated and purified via flash chromatography using 2:1 EtOAc/hexanes to give compound 52 as a yellow oil (0.054 g, 88%). R$_f$=0.48 (2:1 EtOAc/hexanes); $^1$H NMR (CDCl$_3$, 300 MHz): δ 8.08 (d, J=8.7 Hz, 2H), 7.44-7.28 (m, 5H), 7.24-7.04 (m, 5H), 6.98 (d, J=8.4 Hz, 2H), 6.89 (d, J=9.0 Hz, 2H), 6.83-6.71 (m, 6H), 5.44 (s, 1H), 5.00 (s, 2H), 4.80 (d, J=12.0 Hz, 1H), 4.43 (d, J=12.0 Hz, 1H), 4.06 (dd, J=3.9, 6.9 Hz, 1H), 3.84 (s, 3H), 3.76 (s, 3H), 3.12 (s, 3H), 3.02 (dd, J=4.2, 13.5 Hz, 1H), 2.77 (dd, J=7.2, 13.5 Hz, 1H); $^{13}$C NMR (CDCl$_3$, 75 MHz): δ 175.3, 162.5, 158.9, 158.0, 151.6, 149.3, 137.1, 134.7, 133.7, 131.8, 131.2, 130.2, 129.8, 129.5, 128.8, 128.7, 128.3, 128.2, 128.0, 127.6, 127.4, 117.4, 114.9, 113.8, 70.1, 68.6, 64.7, 55.6, 55.4, 38.1, 31.1; IR (thin film) 3033, 2933, 2837, 1743, 1598, 1509, 1454, 1378, 1281, 1236, 1176, 1163, 1110, 1074, 1027, 907, 861, 844, 826, 726, 696 cm$^{-1}$. Calculated C$_{42}$H$_{39}$N$_3$O$_6$ m/z (M+Na) 704.2737, Obsd. 704.2742.

To a 5-mL round-bottom flask equipped with a stir bar was added (Z)-benzyl 4-(4-(benzyloxy)benzyl)-2-imino-5-(4-methoxybenzylidene)-3-methylimidazolidine-1-carboxylate (0.05 g, 0.09 mmol), NEt$_3$ (0.025 mL, 0.18 mmol), 3-(Trifluoromethyl)benzoyl chloride (0.020 mL, 0.14 mmol) and dichloromethane (0.9 mL). The reaction was allowed to stir for 1 hour. The reaction mixture was concentrated and purified via flash chromatography using 2:1 EtOAc/hexanes to give compound 53 as a yellow oil (0.060 g, 94%). R$_f$=0.66 (2:1 EtOAc/hexanes); $^1$H NMR (CDCl$_3$, 300 MHz): δ 8.41 (s, 2H), 8.35 (d, J=7.5 Hz, 1H), 8.30 (d, J=8.0 Hz, 1H), 7.96 (d, J=8.0 Hz, 1H), 7.72 (t, J=7.5 Hz, 2H), 7.50 (t, J=8.0 Hz, 1H), 7.42-7.29 (m, 4H), 7.22-7.11 (m, 4H), 7.00 (d, J=8.5 Hz, 2H), 6.80 (d, J=9.0 Hz, 2H), 6.77 (d, J=8.0 Hz, 2H), 5.53 (s, 1H), 5.00 (s, 2H), 4.79 (d, J=12.0 Hz, 1H), 4.42 (d, J=12.0 Hz, 1H), 4.13 (dd, J=4.5, 7.5 Hz, 1H), 3.77 (s, 3H), 3.18 (s, 3H), 3.04 (dd, J=4.5, 14.0 Hz, 1H), 2.84 (dd, J=7.0, 13.5 Hz, 1H); $^{13}$C NMR (CDCl$_3$, 75 MHz): δ 173.9, 160.9, 158.9, 158.0, 152.9, 149.0, 138.0, 137.0, 134.2, 133.8, 132.9, 132.0, 131.8, 131.4, 131.1, 130.4, 129.9, 129.5, 129.2, 128.5, 128.2, 127.5, 126.8, 125.4, 124.4, 123.3, 122.3, 117.7, 114.8, 113.7, 70.0, 68.9, 64.6, 55.2, 37.8, 30.9; IR (thin film) 2935. 1797, 1743, 1606, 1511, 1455, 1379, 1332, 1313, 1300, 1275, 1249, 1226, 1167, 1124, 1070, 1033, 996, 908, 858, 818, 789, 729, 693 cm$^{-1}$. Calculated C$_{42}$H$_{37}$N$_3$O$_5$F$_3$ m/z (M+Na) 720.2685, Obsd. 720.2689.

Example 61: Preparation of (E)-N-(5-(4-Hydroxybenzyl)-4-(4-methoxybenzyl)-1-methyl-1,3-dihydro-2H-imidazol-2-ylidene)benzamide (54)

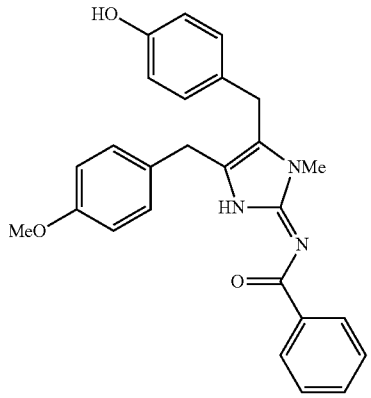

54

To a 5-mL round-bottom flask equipped with a stir bar was added (2Z,5Z)-benzyl 2-(benzoylimino)-4-(4-(benzyloxy)benzyl)-5-(4-methoxybenzylidene)-3-methylimidazolidine-1-carboxylate (0.05 g, 0.08 mmol), PdCl$_2$ (0.025 mL, 0.18 mmol) and methanol (0.9 mL). The reaction was allowed to stir until completion under an H$_2$ atmosphere balloon. The reaction mixture was gravity filtered through a Waters 0.45 μM PTFE Acrodisc syringe filter and rinsed with additional methanol and CH$_2$Cl$_2$. The solvent was removed and the product was triturated with diethyl ether. The solid was isolated to give compound 54 as an off-white solid. R$_f$=0.40 (5% MeOH in CH$_2$Cl$_2$); $^1$H NMR (DMSO-d$_6$, 500 MHz): δ 9.41 (s, 1H), 8.10 (d, J=7.3 Hz, 2H), 7.63 (t, J=7.33 Hz, 1H), 7.53 (t, J=7.8 Hz, 2H), 7.20 (d, J=8.8 Hz, 2H), 6.88 (d, J 8.3 Hz, 2H) 6.86 (d, J 8.8 Hz, 2H), 6.69 (d, J=6.4 Hz, 2H) 4.03 (s, 2H), 4.00 (s, 2H), 3.69 (s, 3H), 3.15 (s, 3H) ppm. $^{13}$C NMR (DMSO-d$_6$, 125 MHz): δ 158.5, 156.7, 133.3, 130.4, 130.0, 129.5, 129.0, 128.9, 127.0, 116.0, 114.4, 55.6, 49.0, 31.7, 28.7, 27.4 ppm. IR (thin film) 3926, 2932, 1688 1612, 1510, 1474, 1453, 1408, 1363, 1301, 1246, 1174, 1104, 1033, 908, 818, 731, 706 cm$^{-1}$. Calculated C$_{26}$H$_{26}$N$_3$O$_3$ m/z (M+H) 428.1974, Obsd. 428.1973.

Example 62: Preparation of (E)-2-Fluoro-N-(5-(4-hydroxybenzyl)-4-(4-methoxybenzyl)-1-methyl-1,3-dihydro-2H-imidazol-2-ylidene)benzamide (55)

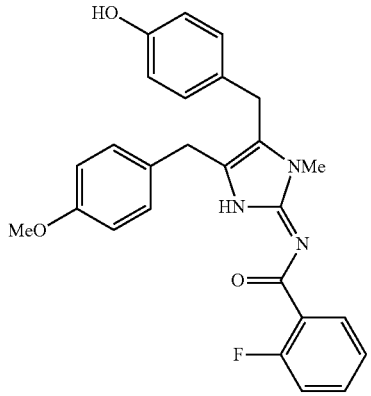

55

To a 5-mL round-bottom flask equipped with a stir bar was added (2Z,5Z)-benzyl 4-(4-(benzyloxy)benzyl)-2-((2-fluoro-benzoyl)imino)-5-(4-methoxybenzylidene)-3-methylimidazolidine-1-carboxylate (0.05 g, 0.08 mmol), PdCl$_2$ (0.025 mL, 0.18 mmol) and methanol (0.9 mL). The reaction was allowed to stir overnight under an H$_2$ atmosphere balloon. The reaction mixture was filtered through Celite and rinsed with additional methanol. One drop of (iPr)$_2$NH was added to the solution and allowed to mix. The solvent was removed and taken up in 1:1 hexanes/EtOAc. The solid was isolated via filtration and rinsed with dichloromethane to give compound 55 as an off-white solid. R$_f$=0.30 (1:1 hexanes/EtOAc); $^1$H NMR (DMSO-d$_6$, 300 MHz): δ 9.29 (s, 1H), 7.80 (s, 1H), 7.43 (s, 1H), 7.19 (d, J=8.1 Hz, 4H), 6.89 (d, J=8.1 Hz, 2H), 6.84 (d, J=8.4 Hz, 2H), 6.67 (d, J=8.1 Hz, 2H), 3.89 (s, 4H), 3.71 (s, 3H), 3.20 (s, 3H) ppm. $^{13}$C NMR (DMSO-d$_6$, 125 MHz): δ 157.8, 155.9, 131.3, 129.9, 129.7, 129.4, 128.3, 116.8, 116.6, 115.8, 114.2, 55.4, 29.5, 27.7 ppm. IR (thin film) 1686, 1581, 1512, 1478, 1441, 1305, 1247, 1173, 1156, 1105, 904 cm$^{-1}$. Calculated C$_{26}$H$_{24}$N$_3$O$_3$F m/z (M+Na) 468.1699, Obsd. 468.1700.

Example 63: Preparation of (E)-N-(5-(4-Hydroxybenzyl)-4-(4-methoxybenzyl)-1-methyl-1,3-dihydro-2H-imidazol-2-ylidene)-4-methoxybenzamide (56)

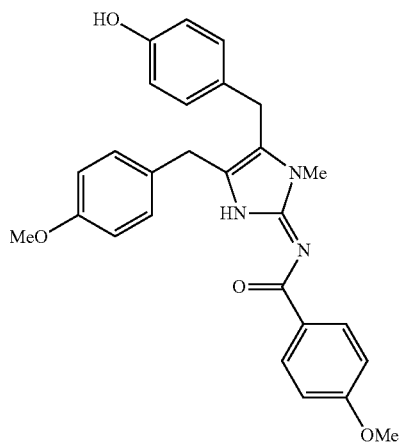

To a 5-mL round-bottom flask equipped with a stir bar was added benzyl (E)-4-(4-(benzyloxy)benzyl)-2-((4-methoxybenzoyl)imino)-5-((Z)-4-methoxybenzylidene)-3-methylimidazolidine-1-carboxylate (0.05 g, 0.08 mmol), PdCl$_2$ (0.025 mL, 0.18 mmol) and methanol (0.9 mL). The reaction was allowed to stir overnight under an H$_2$ atmosphere balloon. The reaction mixture was filtered through Celite and rinsed with additional methanol. One drop of (iPr)$_2$NH was added to the solution and allowed to mix. The solvent was removed and taken up in 1:1 hexanes/EtOAc. The solid was isolated via filtration and rinsed with dichloromethane to give compound 56 as an off-white solid. R$_f$=0.30 (1:1 hexanes/EtOAc); $^1$H NMR (DMSO-d$_6$, 300 MHz): δ 9.44 (s, 1H), 8.07 (d, J=9.3 Hz, 2H), 7.21 (d, J=8.8 Hz, 2H), 7.10 (d, J=8.8 Hz, 2H), 6.89 (d, J=8.3 Hz, 2H), 6.87 (d, J=8.3 Hz, 2H), 6.69 (d, J=8.3 Hz, 2H), 4.06 (s, 2H), 4.01 (s, 2H), 3.85 (s, 3H), 3.72 (s, 3H), 3.43 (s, 3H) ppm. $^{13}$C NMR (DMSO-d$_6$, 75 MHz): δ 162.8, 157.8, 155.9, 130.4, 129.6, 129.2, 128.8, 126.2, 115.2, 113.7, 64.6, 55.3, 54.8, 31.5, 27.8, 26.6, 14.9 ppm. IR (thin film) 2929, 1605, 1585, 1569, 1510, 1465, 1367, 1303, 1248, 1166, 1101, 1030, 906, 843, 815, 770, 728, 692, 668 cm$^{-1}$. Calculated C$_{27}$H$_{28}$N$_3$O$_4$ m/z (M+H) 458.2080, Obsd. 458.2083.

Example 64: Preparation of (E)-N-(5-(4-Hydroxybenzyl)-4-(4-methoxybenzyl)-1-methyl-1,3-dihydro-2H-imidazol-2-ylidene)-3-(trifluoromethyl)benzamide (57)

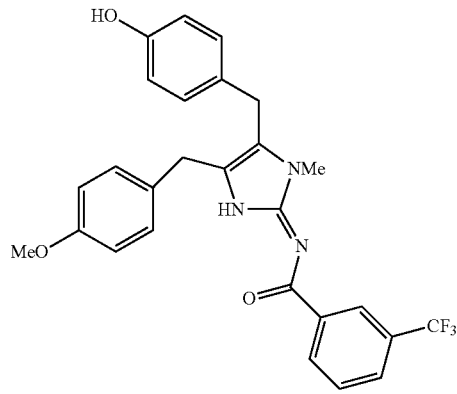

To a 5-mL round-bottom flask equipped with a stir bar was added benzyl (E)-4-(4-(benzyloxy)benzyl)-5-((Z)-4-methoxybenzylidene)-3-methyl-2-((3-(trifluoromethyl)benzoyl)imino)imidazolidine-1-carboxylate (0.05 g, 0.08 mmol), PdCl$_2$ (0.025 mL, 0.18 mmol) and methanol (0.9 mL). The reaction was allowed to stir overnight under an H$_2$ atmosphere balloon. The reaction mixture was filtered through Celite, and rinsed with additional methanol. One drop of (iPr)$_2$NH was added to the solution and allowed to mix. The solvent was removed and taken up in 1:1 hexanes/EtOAc. A solid was isolated via filtration and rinsed with dichloromethane to give compound 57 as an off-white solid. R$_f$=0.40 (2:1 EtOAc/hexanes); $^1$H NMR (DMSO-d$_6$, 300 MHz): δ 9.32 (s, 2H), 8.38 (s, 2H), 7.79 (d, J=7.8 Hz, 1H), 7.64 (t, J=7.5 Hz, 2H), 7.21 (d, J=8.7 Hz, 2H), 6.91 (d, J=8.4 Hz, 2H), 6.85 (d, J=8.7 Hz, 2H), 6.69 (d, J=8.4 Hz, 2H), 3.93 (s, 4H), 3.71 (s, 3H), 3.29 (s, 3H) ppm. $^{13}$C NMR (DMSO-d$_6$, 75 MHz): δ 157.8, 155.9, 132.2, 129.5, 129.0, 124.5, 115.4, 113.9, 55.1, 28.9, 27.1 ppm. IR (thin film) 1564, 1532, 1512, 1483, 1383, 1322, 1277, 1248, 1170, 1153, 1113, 916 cm$^{-1}$. Calculated C$_{27}$H$_{25}$N$_3$O$_3$F$_3$ m/z (M+H) 496.1848, Obsd. 496.1850.

Example 65: Preparation of N-(1-(4-Chlorophenyl)-3-phenylprop-2-yn-1-yl)-N-methylprop-2-en-1-amine (58)

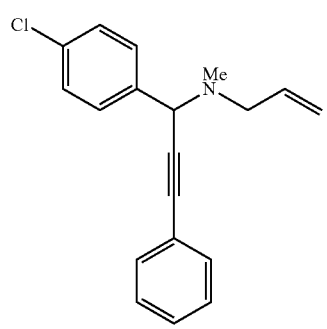 [SMILES: C=CCN(C)C(C#Cc1ccccc1)c1ccc(Cl)cc1]

In a 250-mL high-pressure flask containing a magnetic stir bar were added 4-chlorobenzaldehyde (5 g, 35.57 mmol), phenylacetylene (3.9 mL, 35.57 mmol), N-allylmethylamine (3.07 mL, 32.34 mmol), oven-dried molecular sieves (Grade 564, 3 Å, 8-12 mesh) (ca. 2 g) and acetonitrile (200 mL). The flask was sealed and placed in a preheated 80° C. oil bath for 24 h. The reaction flask was removed from the oil bath and allowed to cool to room temperature. CuBr (0.46 g, 3.23 mmol) was then added and the flask was sealed and returned to the preheated 80° C. oil bath for 48 h. The reaction tube was removed from the oil bath and allowed to cool to room temperature. The mixture was filtered through Celite and rinsed with EtOAc (50 mL). The filtrate was concentrated under reduced pressure. The crude product was purified via flash chromatography, eluting with 95:5 hexanes/EtOAc to give N-(1-(4-chlorophenyl)-3-phenylprop-2-yn-1-yl)-N-methylprop-2-en-1-amine (58) as a dark orange oil (5.84 g, 61%). $^1$H NMR (CDCl$_3$, 500 MHz): δ 7.65-7.61 (m, 2H), δ 7.59-7.56 (m, 2H), δ 7.40-7.34 (m, 5H), δ 5.90-5.91 (m, 1H), δ 5.35 (dd, J=17 Hz, 2 Hz, 1H), δ 5.23 (dd, J=10.5 Hz, 2 Hz, 1H), δ 4.98 (s, 1H), δ 3.21 (d, J=6 Hz, 2H), δ 2.26 (s, 3H). IR (thin film): 1487, 1442, 1402, 1089, 1014, 994, 962, 920, 853, 796, 689, 592, 582 cm$^{-1}$.

Example 66: Preparation of N-(3-Cyclopropyl-1-(4-methoxyphenyl)prop-2-yn-1-yl)-N-methylprop-2-en-1-amine (59)

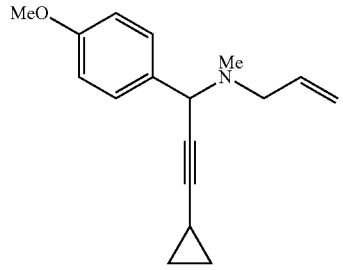 [SMILES: C=CCN(C)C(C#CC1CC1)c1ccc(OC)cc1]

59

In a 250-mL high-pressure flask containing a magnetic stir bar were added p-anisaldehyde (500 mg, 4.12 mmol), cyclopropylacetylene (0.35 mL, 4.12 mmol), N-allylmethylamine (0.36 mL, 0.38 mmol), oven-dried molecular sieves (Grade 564, 3 Å, 8-12 mesh) (ca. 2 g) and acetonitrile (100 mL). The flask was sealed and placed in a preheated 80° C. oil bath for 24 h. The reaction flask was removed from the oil bath and allowed to cool to room temperature. CuBr (0.46 g, 3.23 mmol) was then added and the flask was sealed and returned to the preheated 80° C. oil bath for 48 h. The reaction tube was removed from the oil bath and allowed to cool to room temperature. The mixture was filtered through Celite and rinsed with EtOAc (50 mL). The filtrate was concentrated under reduced pressure. The crude product was purified via flash chromatography, eluting with 95:5 hexanes/EtOAc to give N-(3-cyclopropyl-1-(4-methoxyphenyl)prop-2-yn-1-yl)-N-methylprop-2-en-1-amine (59) as a dark orange oil (226 mg, 22%). $^1$H NMR (CDCl$_3$, 500 MHz): δ 7.43 (d, J=8.5 Hz, 2H), δ 6.86 (d, J=8.5 Hz, 2H), 5.84-5.81 (m, 1H), δ 5.23 (dd, J=17 Hz, 1.5 Hz, 1H), δ 5.12 (d, J=6.5 Hz, 1H), δ 4.62 (s, 1H), δ 3.04 (t, J=7.5 Hz, 2H), δ 2.10 (s, 3H), δ 1.40-1.32 (m, 1H), δ 0.84-0.80 (m, 2H), δ 0.75-0.71 (m, 2H). $^{13}$C NMR (CDCl$_3$, 500 MHz): δ 159.1, δ 136.6, δ 131.7, δ 129.7, δ 117.5, δ 113.5, δ 91.7, δ 77.5, δ 59.0, δ 57.7, δ 55.5, δ 37.8, δ 8.8, δ 0.2 ppm. IR (thin film): 1610, 1507, 1361, 1243, 1109, 1035, 1016, 999, 918, 982, 850, 808, 777, 584 cm$^{-1}$.

Example 67: Preparation of N-Methyl-N-(1-(4-(2-morpholinoethoxy)phenyl)-3-phenylprop-2-yn-1-yl)prop-2-en-1-amine (60)

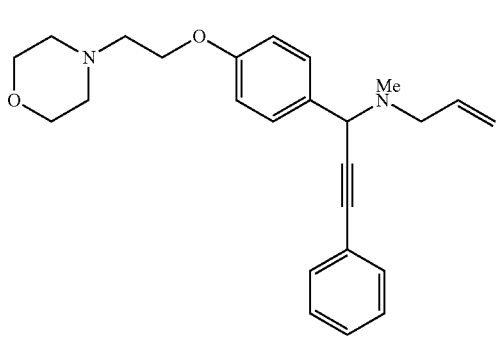 [SMILES: C=CCN(C)C(C#Cc1ccccc1)c1ccc(OCCN2CCOCC2)cc1]

60

In a 250-mL high-pressure flask containing a magnetic stir bar were added 4-(2-morpholinoethoxy)benzaldehyde (500 mg, 2.13 mmol), phenylacetylene (0.233 mL, 2.13 mmol), n-allylmethylamine (0.184 mL, 1.94 mmol), CuBr (38 mg, 0.2 mmol), oven-dried molecular sieves (Grade 564, 3 Å, 8-12 mesh) (ca. 0.5 g) and acetonitrile (50 mL). The flask was sealed and placed in a preheated 80° C. oil bath for 24 h. The reaction flask was removed from the oil bath and allowed to cool to room temperature. The mixture was filtered through Celite and rinsed with EtOAc (25 mL). The filtrate was concentrated under reduced pressure. The crude product was purified via flash chromatography, eluting with EtOAc to give N-methyl-N-(1-(4-(2-morpholinoethoxy)phenyl)-3-phenylprop-2-yn-1-yl)prop-2-en-1-amine (60) as a dark orange oil (0.394 g, 52%). $^1$H NMR (CDCl$_3$, 500 MHz): δ 7.58-7.51 (m, 4H), δ 7.35-7.32 (m, 2H), δ 6.89 (d, J 10.5 Hz), 5.90-5.85 (m, 1H), δ 5.27 (d, J=21.5 Hz, 1H), δ 5.16 (d, J=13 Hz, 1H), δ 4.92 (t, J=6.5 Hz, 2H), δ 3.73 (t, J=6 Hz, 4H), δ 3.17-3.15 (m, 2H), δ 2.80 (t, J=6.5 Hz, 2H), δ 2.58 (t, J=6 Hz, 3H), δ 2.21 (s, 3H). $^{13}$C NMR (CDCl$_3$, 500 MHz): δ 158.2, δ 136.2, δ 131.8, δ 131.2, δ 129.6, δ 128.5, δ 128.1, δ 123.2, δ 117.6, δ 114.1, δ 88.1, δ 88.0, δ 85.1, δ 66.9, δ 59.2, δ 57.6, δ 54.1, δ 37.7 ppm. IR (thin film): 2852, 2798, 1609, 1507, 1489, 1452, 1298, 1243, 1170, 1144, 1116, 1087, 1025, 1011, 960, 916, 853, 809, 756, 691 cm$^{-1}$.

Example 68: Preparation of N-Allyl-1-(4-chlorophenyl)-N-methyl-4-morpholinobut-2-yn-1-amine (61)

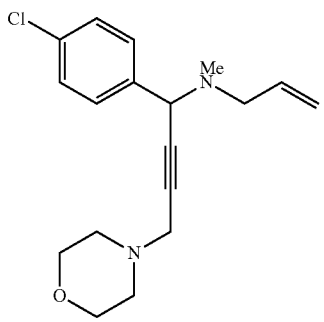 [SMILES: C=CCN(C)C(C#CCN1CCOCC1)c1ccc(Cl)cc1]

61

In a 250-mL high-pressure flask containing a magnetic stir bar were added 4-chlorobenzaldehyde (2.7 g, 19.27 mmol), 4-(prop-2-yn-1-yl)morpholine (2.63 g, 21.2 mmol), n-allylmethylamine (2.2 mL, 23.12 mmol), CuBr (272 mg, 1.9 mmol), oven-dried molecular sieves (Grade 564, 3 Å, 8-12 mesh) (ca. 1 g) and acetonitrile (100 mL). The flask was sealed and placed in a preheated 80° C. oil bath for 24 h. The reaction flask was removed from the oil bath and allowed to cool to room temperature. The mixture was filtered through Celite and rinsed with EtOAc (50 mL). The filtrate was concentrated under reduced pressure. The crude product was purified via flash chromatography, eluting with 6:4 hexanes/EtOAc to give N-allyl-1-(4-chlorophenyl)-N-methyl-4-morpholinobut-2-yn-1-amine (61) as a dark orange oil (2.217 g, 36%). $R_f$=0.12 (6:4 hexanes/EtOAc); $^1$H NMR (CDCl$_3$, 500 MHz): δ 7.44 (d, J=8 Hz, 2H), δ 7.24 (d, J 8 Hz, 2H), 5.81-5.76 (m, 1H), δ 5.17 (d, J=17 Hz, 1H), δ 5.08 (d, J=10 Hz, 1H), δ 4.69 (s, 1H), δ 3.70-3.66 (m, 4H), δ 3.43-3.31 (m, 2H), δ 3.03-3.00 (m, 2H), δ 2.57-2.55 (m, 4H), δ 2.07 (s, 3H). $^{13}$C NMR (CDCl$_3$, 500 MHz): δ 158.2, δ 136.2, δ 131.8, δ 131.2, δ 129.6, δ 128.3, δ 123.2, δ 117.6, δ 114.1, δ 88.1, δ 88.0, δ 85.1, δ 66.9, δ 65.8, δ 59.2, δ 57.6, δ 54.1, δ 37.7 ppm.

Example 69: Preparation of N-Allyl-N-(1-(4-methoxyphenyl)-3-phenylprop-2-yn-1-yl)prop-2-en-1-amine (62)

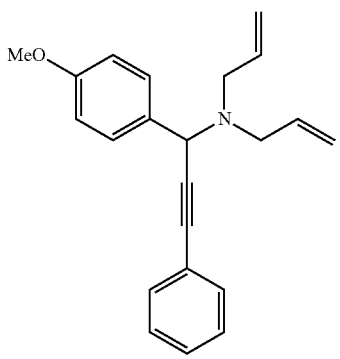 [SMILES: C=CCN(CC=C)C(C#Cc1ccccc1)c1ccc(OC)cc1]

62

In a 250-mL high-pressure flask p-anisaldehyde (4 mL, 33 mmol), phenylacetylene (3.55 mL, 33 mmol), n-diallylamine (3.7 mL, 30 mmol), CuBr (430 mg, 3 mmol), oven-dried molecular sieves (Grade 564, 3 Å, 8-12 mesh) (ca. 1 g) and acetonitrile (100 mL). The flask was sealed and placed in a preheated 80° C. oil bath for 24 h. The reaction flask was removed from the oil bath and allowed to cool to room temperature. The mixture was filtered through Celite and rinsed with EtOAc (50 mL). The filtrate was concentrated under reduced pressure. The crude product was purified via flash chromatography, eluting with 95:5 hexanes/EtOAc to give N-allyl-N-(1-(4-methoxyphenyl)-3-phenylprop-2-yn-1-yl)prop-2-en-1-amine (62) as a dark orange oil (3.55 g, 38%). $^1$H NMR (CDCl$_3$, 500 MHz): δ 7.59 (d, J=8.5 Hz, 2H), δ 7.55-7.54 (m, 2H), 7.53-7.51 (m, 3H), δ 6.89 (d, J=8.5 Hz, 2H), δ 5.90-5.83 (m, 1H), δ 5.27 (d, J=17 Hz, 1H), δ 5.14 (d, J=10 Hz, 1H), δ 5.05 (s, 1H), δ 3.82 (s, 3H), δ 3.28 (dd, J=14 Hz, 2 Hz, 2H), δ 3.04 (dd, J=14 Hz, 8 Hz, 2H). $^{13}$C NMR (CDCl$_3$, 500 MHz): δ 159.1, δ 136.8, δ 132.1, δ 132.0, δ 131.6, δ 129.6, δ 128.5, δ 128.3, δ 123.6, δ 117.5, δ 113.7, δ 88.9, δ 85.9, δ 56.2, δ 55.5, δ 53.7 ppm. IR (thin film): 1609, 1508, 1489, 1447, 1301, 1246, 1170, 1108, 1036, 995, 971, 919, 848, 811, 759, 691 cm$^{-1}$.

Example 70: Preparation of 1-(4-Chlorophenyl)-N-methyl-3-phenylprop-2-yn-1-amine (63)

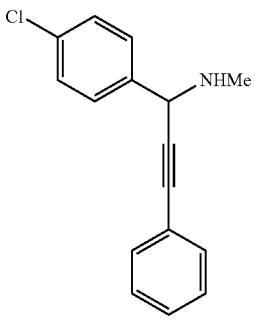 [SMILES: CNC(C#Cc1ccccc1)c1ccc(Cl)cc1]

63

In a 250-mL round-bottom flask containing a magnetic stir bar were added Pd(PPh$_3$)$_4$ (310 mg, 0.27 mmol), thiosalicylic acid (12.4 g, 80.37 mmol) and CH$_2$Cl$_2$ (100 mL). A solution of N-(1-(4-chlorophenyl)-3-phenylprop-2-yn-1-yl)-N-methylprop-2-en-1-amine (8.0 g, 26.29 mmol) in 15 mL in CH$_2$Cl$_2$ was added, and the reaction mixture was allowed to stir at room temperature under N$_2$ for 12 h. The solvent was then removed under reduced pressure and the crude product was re-dissolved in Et$_2$O (10 mL). The organic layer was washed with NaHCO$_3$ (50 mL) and brine (50 mL) and dried and filtered over Na$_2$SO$_4$. The crude product was purified via flash chromatography, eluting with 8:2 hexanes/EtOAc to give 1-(4-chlorophenyl)-N-methyl-3-phenylprop-2-yn-1-amine (63) as a dark orange oil (3.29 g, 49%). $^1$H NMR (CDCl$_3$, 500 MHz): δ 7.54-7.61 (m, 2H), δ 7.50-7.48 (m, 2H), δ 7.36-7.29 (m, 5H), δ 4.72 (s, 1H), δ 2.54 (s, 3H), δ 1.43 (s, 1H) ppm. $^{13}$C NMR (CDCl$_3$, 500 MHz): δ 139.9, δ 133.4, δ 132.0, δ 129.3, δ 128.8, δ 128.6, δ 128.5, δ 123.1, δ 88.7, δ 86.3, δ 55.8, δ 33.9 ppm.

Example 71: Preparation of 3-Cyclopropyl-1-(4-methoxyphenyl)-N-methylprop-2-yn-1-amine (64)

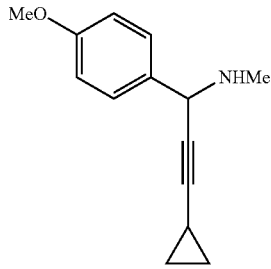 [SMILES: CNC(C#CC1CC1)c1ccc(OC)cc1]

64

In a 100-mL round-bottom flask containing a magnetic stir bar were added Pd(PPh$_3$)$_4$ (137 mg, 0.12 mmol), 1,3-dimethylbarbituric acid (5.54 g, 35.5 mmol) and CH$_2$Cl$_2$ (50 mL). A solution of (8.0 g, 26.29 mmol) in 15 mL in CH$_2$Cl$_2$ was added, and the reaction mixture was allowed to stir at room temperature under N$_2$ for 12 h. The solvent was then removed under reduced pressure and the crude product was re-dissolved in Et$_2$O (10 mL). The organic layer was washed with NaHCO$_3$ (50 mL) and brine (50 mL) and dried and filtered over Na$_2$SO$_4$. The crude product was purified via flash chromatography, eluting with 8:2 hexanes/EtOAc to give N-(3-cyclopropyl-1-(4-methoxyphenyl)prop-2-yn-1-yl)-N-methylprop-2-en-1-amine (64) as a dark orange oil (1.07 g, 42%). $^1$H NMR (CDCl$_3$, 500 MHz): δ 7.38 (d, J=8.5 Hz, 2H), δ 6.85 (d, J=8.5 Hz, 2H), δ 4.40 (s, 1H), δ 2.42 (s, 3H), δ 1.31-1.25 (m, 1H), δ 0.79-0.73 (m, 2H), δ 0.70-0.66 (m, 2H) ppm. $^{13}$C NMR (CDCl$_3$, 500 MHz): δ 159.3, δ 133.0, δ 132.3, 128.9, δ 113.9, δ 89.2, δ 75.0, δ 55.5, δ 33.7, δ 8.5, δ 0.2 ppm. IR (thin film) 1609, 1508, 1463, 1440, 1301, 1243, 1171, 1029, 892, 831, 810, 779, 722, 585, 541 cm$^{-1}$.

Example 72: Preparation of N-Methyl-1-(4-(2-morpholinoethoxy)phenyl)-3-phenylprop-2-yn-1-amine (65)

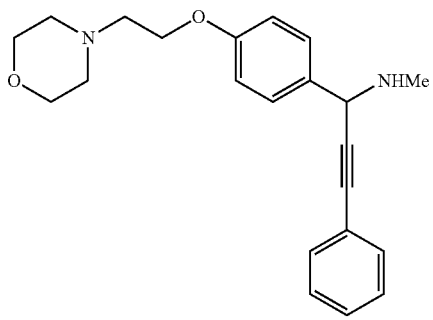 [SMILES: CNC(C#Cc1ccccc1)c1ccc(OCCN2CCOCC2)cc1]

65

In a 15-mL round-bottom flask containing a magnetic stir bar were added Pd(PPh$_3$)$_4$(11 mg, 0.01 mmol), 1,3-dimethylbarbituric acid (88 mg, 0.56 mmol) and CH$_2$Cl$_2$ (5 mL). A solution of N-methyl-N-(1-(4-(2-morpholinoethoxy)phenyl)-3-phenylprop-2-yn-1-yl)prop-2-en-1-amine (74 mg, 0.19 mmol) in 2 mL in CH$_2$Cl$_2$ was added, and the reaction mixture was allowed to stir at room temperature under N$_2$ for 12 h. The solvent was then removed under reduced pressure and the crude product was re-dissolved in Et$_2$O (10 mL). The organic layer was washed with NaHCO$_3$ (25 mL) and brine (25 mL) and dried and filtered over Na$_2$SO$_4$. The crude product was purified via flash chromatography, eluting with EtOAc to give N-methyl-1-(4-(2-morpholinoethoxy)phenyl)-3-phenylprop-2-yn-1-amine (65) as a dark orange oil (25 mg, 34%). $^1$H NMR (CDCl$_3$, 500 MHz): δ 7.51 (d, J=11.5 Hz, 2H), δ 7.48-7.44 (m, 2H), δ 7.32-7.30 (m, 3H), δ 6.90 (d, J=11.5 Hz, 2H), δ 4.75 (s, 1H), δ 4.11 (t, J=7.5 Hz, 2H), δ 3.73 (t, J=5.5 Hz, 4H), δ 3.20 (s, 1H), δ 2.80 (t, J=7.5 Hz, 2H), δ 2.57 (t, J=5.5 Hz, 4H), δ 2.54 (s, 3H) ppm. $^{13}$C NMR (CDCl$_3$, 500 MHz): δ 158.5, δ 131.7, δ 131.6, δ 128.9, δ 128.5, δ 128.2, δ 122.9, δ 114.6, δ 88.2, δ 86.0, δ 66.9, δ 65.9, δ 57.6, δ 55.4, δ 33.1 ppm.

Example 73: Preparation of 1-(4-Chlorophenyl)-N-methyl-4-morpholinobut-2-yn-1-amine (66)

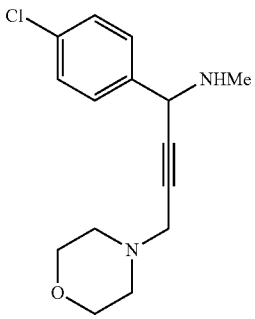 [SMILES: CNC(C#CCN1CCOCC1)c1ccc(Cl)cc1]

66

In a 100-mL round-bottom flask containing a magnetic stir bar were added Pd(PPh$_3$)$_4$ (241 mg, 0.21 mmol), 1,3-dimethylbarbituric acid (3.25 g, 20.85 mmol) and CH$_2$Cl$_2$ (25 mL). A solution of N-allyl-1-(4-chlorophenyl)-N-methyl-4-morpholinobut-2-yn-1-amine (2.22 g, 6.95 mmol) in 5 mL in CH$_2$Cl$_2$ was added, and the reaction mixture was allowed to stir at room temperature under N$_2$ for 12 h. The solvent was then removed under reduced pressure and the crude product was re-dissolved in Et$_2$O (50 mL). The organic layer was washed with NaHCO$_3$ (50 mL) and brine (25 mL) and dried and filtered over Na$_2$SO$_4$. The crude product was purified via flash chromatography, eluting with EtOAc to give 1-(4-chlorophenyl)-N-methyl-4-morpholinobut-2-yn-1-amine (66) as a dark orange oil (1.10 g, 57%). $^1$H NMR (CDCl$_3$, 500 MHz): δ 7.42 (d, J=6.5 Hz, 2H), δ 7.29 (d, J=6.5 Hz, 2H), δ 4.50 (s, 1H), δ 3.72-3.70 (m, 4H), δ 3.36 (s, 2H), δ 2.55-2.54 (m, 4H), δ 2.43 (s, 3H), δ 1.29 (s, 1H) ppm. $^{13}$C NMR (CDCl$_3$, 500 MHz): δ 138.9, δ 133.7, δ 129.1, δ 128.8, δ 84.8, δ 80.5, δ 67.0, δ 55.4, δ 52.6, δ 47.8, δ 33.9 ppm.

Example 74: Preparation of N-(1-(4-Methoxyphenyl)-3-phenylprop-2-yn-1-yl)prop-2-en-1-amine (67)

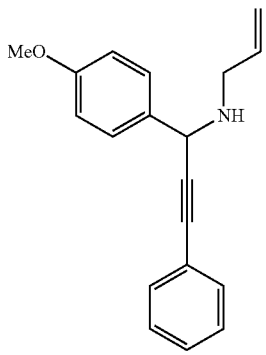 [SMILES: C=CCNC(C#Cc1ccccc1)c1ccc(OC)cc1]

In a 100-mL round-bottom flask containing a magnetic stir bar were added Pd(PPh$_3$)$_4$ (130 mg, 0.11 mmol), 1,3-dimethylbarbituric acid (3.50 g, 22.4 mmol) and CH$_2$Cl$_2$ (25 mL). A solution of N-allyl-N-(1-(4-methoxyphenyl)-3-phenylprop-2-yn-1-yl)prop-2-en-1-amine (3.55 g, 11.2 mmol) in 5 mL in CH$_2$Cl$_2$ was added, and the reaction mixture was allowed to stir at room temperature under N$_2$ for 12 h. The solvent was then removed under reduced pressure and the crude product was re-dissolved in Et$_2$O (50 mL). The organic layer was washed with NaHCO$_3$ (50 mL) and brine (25 mL) and dried and filtered over Na$_2$SO$_4$. The crude product was purified via flash chromatography, eluting with EtOAc to give N-(1-(4-methoxyphenyl)-3-phenylprop-2-yn-1-yl)prop-2-en-1-amine (67) as a dark orange oil (0.96 g, 31%). $^1$H NMR (CDCl$_3$, 500 MHz): δ 7.52 (d, J=8.5 Hz, 2H), δ 7.49-7.47 (m, 2H), δ 7.33-7.31 (m, 3H), δ 6.92 (d, J=8.5 Hz, 2H), δ 5.97 (ddt, J=7 Hz, 10.5 Hz, 6.5 Hz, 1H), δ 5.27 (dd, J 17 Hz, 1.5 Hz), δ 5.14 (dd, 10.5 Hz, 1.5 Hz), δ 4.70 (s, 1H), δ 3.82 (s, 3H), δ 3.44 (dqt, J=6 Hz, 13.5 Hz, 1.5 Hz, 2H), δ 1.67 (s, 1H) ppm. $^{13}$C NMR (CDCl$_3$, 500 MHz): δ 159.4, δ 136.6, δ 132.8, δ 131.9, δ 129.0, δ 128.5, δ 128.4, δ 116.7, δ 114.1, δ 89.7, δ 85.6, δ 55.6, δ 53.5, δ 30.1 ppm.

Example 75: Preparation of 2-Fluoro-N—(N-(1-(4-methoxyphenyl)-3-phenylprop-2-yn-1-yl)-N-methylcarbamimidoyl)benzamide (68)

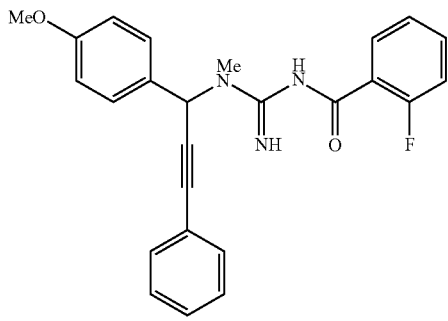

In a 50-mL round-bottom flask containing a magnetic stir bar were added potassium N-cyano-2-fluorobenzamide (89 mg, 0.48 mmol), TMSCl (0.064 mL, 0.50 mmol) and acetonitrile (10 mL). The solution was stirred at room temperature for 10 minutes. A solution of 1-(4-methoxyphenyl)-N-methyl-3-phenylprop-2-yn-1-amine in acetonitrile (10 mL) was then added, and the reaction mixture was allowed to stir at room temperature for 1 h. The solvent was then removed under reduced pressure and the crude product was re-dissolved in EtOAc (50 mL). The organic layer was washed with NaHCO$_3$ (20 mL) and brine (20 mL) and dried and filtered over Na$_2$SO$_4$. The crude product was purified via flash chromatography, eluting with 1:1 hexanes/EtOAc to give 2-fluoro-N—(N-(1-(4-methoxyphenyl)-3-phenylprop-2-yn-1-yl)-N-methylcarbamimidoyl)benzamide (68) as a white foam (134 mg, 75%). $^1$H NMR (CDCl$_3$, 500 MHz): δ 8.06 (t, J=12.5 Hz, 1H), δ 7.65 (s, 1H), δ 7.58-7.51 (m, 4H), δ 7.38-7.32 (m, 4H), δ 7.18 (t, J=13 Hz, 1H), δ 7.07 (t, J=13 Hz, 1H), δ 6.92 (d, J=14.5 Hz, 2H), δ 3.81 (s, 3H), δ 2.86 (s, 3H) ppm. $^{13}$C NMR (CDCl$_3$, 500 MHz): δ 175.6, δ 174.3, δ 163.0, δ 160.7, δ 159.7, δ 132.1, δ 129.8, δ 129.0, δ 128.6, δ 127.9, δ 123.6, δ 122.7, δ 116.9, δ 114.2, δ 87.0, δ 75.4, δ 55.6, δ 50.9, δ 29.3 ppm.

Example 76: Preparation of 4-Chloro-N—(N-(1-(4-methoxyphenyl)-3-phenylprop-2-yn-1-yl)-N-methylcarbamimidoyl)benzamide (69)

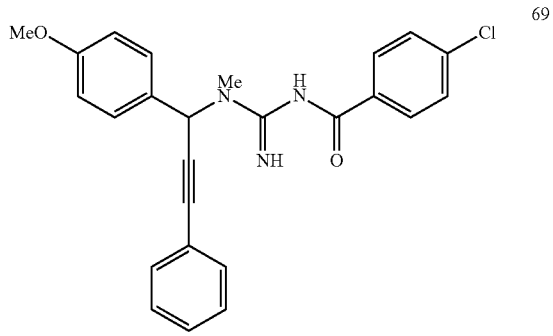

In a 50-mL round-bottom flask containing a magnetic stir bar were added potassium N-cyano-4-chlorobenzamide (105 mg, 0.48 mmol), TMSCl (0.064 mL, 0.50 mmol) and acetonitrile (10 mL). The solution was stirred at room temperature for 10 minutes. A solution of 1-(4-methoxyphenyl)-N-methyl-3-phenylprop-2-yn-1-amine in acetonitrile (10 mL) was then added, and the reaction mixture was allowed to stir at room temperature for 1 h. The solvent was then removed under reduced pressure and the crude product was re-dissolved in EtOAc (50 mL). The organic layer was washed with NaHCO$_3$ (20 mL) and brine (20 mL) and dried and filtered over Na$_2$SO$_4$. The crude product was purified via flash chromatography, eluting with 1:1 hexanes/EtOAc to give 4-chloro-N—(N-(1-(4-methoxyphenyl)-3-phenylprop-2-yn-1-yl)-N-methylcarbamimidoyl)benzamide (69) as a white foam (140 mg, 81%). $^1$H NMR (CDCl$_3$, 500 MHz): δ 8.20 (d, J=8.5 Hz, 2H), δ 7.65 (s, 1H), δ 7.57-7.51 (m, 4H), δ 7.38-7.33 (m, 5H), δ 6.92 (d, J=8.5 Hz, 2H), δ 3.82 (s, 3H), δ 2.89 (s, 3H) ppm. $^{13}$C NMR (CDCl$_3$, 500 MHz): δ 176.1, δ 160.9, δ 159.8, δ 137.5, δ 137.4, δ 132.1, δ 130.8, δ 129.4, δ 129.0, δ 128.9, δ 128.6, δ 128.3, δ 122.6, δ 114.3, δ 87.2, δ 85.2, δ 55.6, δ 50.9, δ 29.5 ppm.

Example 77: Preparation of N—(N-(1-(4-Methoxyphenyl)-3-phenylprop-2-yn-1-yl)-N-methylcarbamimidoyl)benzamide (70)

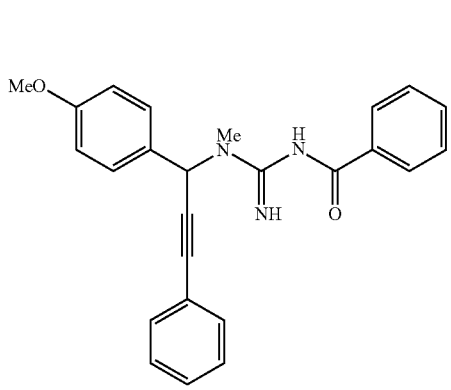 [SMILES: COc1ccc(C(C#Cc2ccccc2)N(C)C(=N)NC(=O)c2ccccc2)cc1]

N—(N-(1-(4-methoxyphenyl)-3-phenylprop-2-yn-1-yl)-N-methylcarbamimidoyl)benzamide (70) was prepared by guanylation of 1-(4-methoxyphenyl)-N-methyl-3-phenylprop-2-yn-1-amine with potassium N-cyanobenzamide as a foamy white oil (76% yield). $^1$H NMR (CDCl$_3$, 500 MHz): δ 8.28 (d, J=7 Hz, 2H), δ 7.71 (s, 1H), δ 7.58 (d, J=9 Hz, 2H), δ 7.55-7.52 (m, 2H), δ 7.47-7.33 (m, 7H), δ 6.92 (d, J=8 Hz, 2H), δ 3.82 (s, 3H), δ 2.89 (s, 3H) ppm. $^{13}$C NMR (CDCl$_3$, 500 MHz): δ 177.2, δ 160.9, δ 159.7, δ 139.0, δ 132.1, δ 131.3, δ 129.6, δ 129.4, δ 129.0, δ 128.9, δ 128.6, δ 128.1, 122.6, δ 114.2, δ 87.1, δ 85.4, δ 55.6, δ 50.9, δ 29.4 ppm.

Example 78: Preparation of 4-Methoxy-N—(N-(1-(4-methoxyphenyl)-3-phenylprop-2-yn-1-yl)-N-methylcarbamimidoyl)benzamide (71)

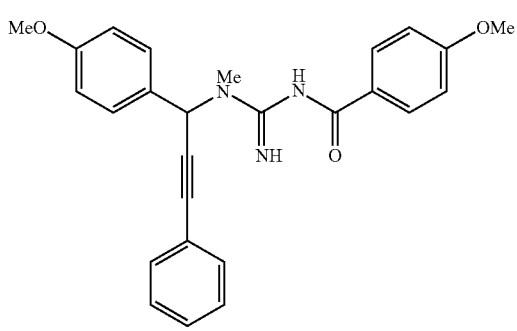

4-Methoxy-N—(N-(1-(4-methoxyphenyl)-3-phenylprop-2-yn-1-yl)-N-methylcarbamimidoyl)benzamide (71) was prepared by guanylation of 1-(4-methoxyphenyl)-N-methyl-3-phenylprop-2-yn-1-amine with potassium N-cyano-4-methoxybenzamide as a foamy white oil (70% yield). $^1$H NMR (CDCl$_3$, 500 MHz): δ 8.25 (d, J=9.5 Hz, 2H), δ 7.65 (s, 1H), δ 7.58 (d, J=9 Hz, 2H), δ 7.55-7.52 (m, 2H), δ 7.37-7.35 (m, 3H), δ 6.92-6.91 (m, 2H), δ 3.84 (s, 3H), δ 3.81 (s, 3H), δ 2.87 (s, 3H) ppm. $^{13}$C NMR (CDCl$_3$, 500 MHz): δ 176.9, δ 162.3, δ 160.7, 6 159.7, δ 132.1, δ 131.8, δ 131.3, δ 129.0, δ 128.6, δ 122.7, δ 114.3, δ 113.3, δ 87.0, δ 85.5, δ 55.6, δ 55.5, δ 50.8, δ 29.4 ppm.

Example 79: Preparation of 4-Fluoro-N—(N-(1-(4-methoxyphenyl)-3-phenylprop-2-yn-1-yl)-N-methylcarbamimidoyl)benzamide (72)

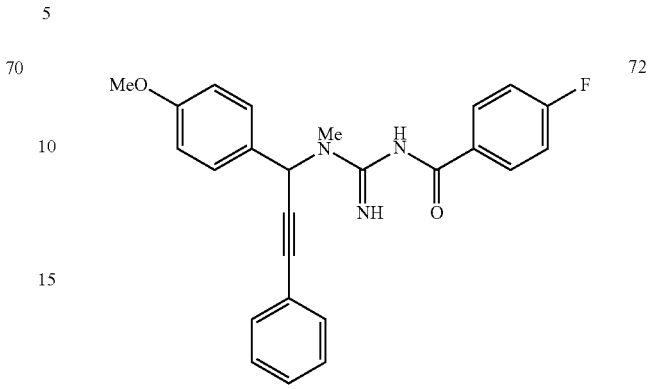

4-Fluoro-N—(N-(1-(4-methoxyphenyl)-3-phenylprop-2-yn-1-yl)-N-methylcarbamimidoyl)benzamide (72) was prepared by guanylation of 1-(4-methoxyphenyl)-N-methyl-3-phenylprop-2-yn-1-amine with potassium N-cyano-4-fluorobenzamide as a foamy white oil. $^1$H NMR (CDCl$_3$, 500 MHz): δ 8.27 (dd, J=8.5 Hz, 6 Hz, 2H), δ 7.59 (s, 1H), δ 7.58-7.52 (m, 4H), δ 7.37-7.35 (m, 4H), δ 7.06 (t, J=8.5 Hz, 2H), δ 6.91 (d, J=8.5, 2H), δ 3.81 (s, 3H), δ 2.88 (s, 3H) ppm. $^{13}$C NMR (CDCl$_3$, 500 MHz): δ 176.1, δ 166.1, δ 164.1, δ 160.9, δ 159.8, δ 135.2, δ 132.1, δ 131.7, δ 129.4, δ 128.9, δ 128.7, δ 122.6, δ 115.0, δ 114.8, δ 87.1, δ 85.3, δ 55.6, δ 29.4 ppm.

Example 80: Preparation of N—(N-(1-(4-Chlorophenyl)-3-phenylprop-2-yn-1-yl)-N-methylcarbamimidoyl)-2-fluorobenzamide (73)

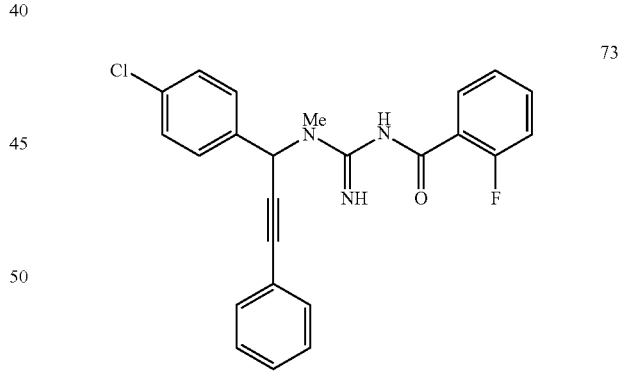

N—(N-(1-(4-Chlorophenyl)-3-phenylprop-2-yn-1-yl)-N-methylcarbamimidoyl)-2-fluorobenzamide (73) was prepared by guanylation of 1-(4-chlorophenyl)-N-methyl-3-phenylprop-2-yn-1-amine with potassium N-cyano-2-fluorobenzamide as a foamy white oil (62% yield). $^1$H NMR (CDCl$_3$, 500 MHz): δ 8.03 (t, J=7.5 Hz, 1H), δ 7.69 (s, 1H), δ 7.58 (d, J=8.5 Hz, 2H), δ 7.53-7.51 (m, 2H), δ 7.39-7.33 (m, 6H), δ 7.14 (t, J=8, 1H), δ 7.13-7.05 (m, 1H), δ 2.87 (s, 3H) ppm. $^{13}$C NMR (CDCl$_3$, 500 MHz): δ 175.7, δ 163.0, δ 161.0, δ 160.7, δ 136.1, δ 134.4, δ 132.3, δ 132.2, δ 132.1, δ 132.0, δ 129.1, δ 128.7, δ 127.7, δ 123.7, δ 122.4, δ 117.0, δ 116.8, δ 87.5, δ 84.5, δ 50.9, δ 29.4 ppm.

Example 81: Preparation of 4-Chloro-N—(N-(1-(4-chlorophenyl)-3-phenylprop-2-yn-1-yl)-N-methylcarbamimidoyl)benzamide (74)

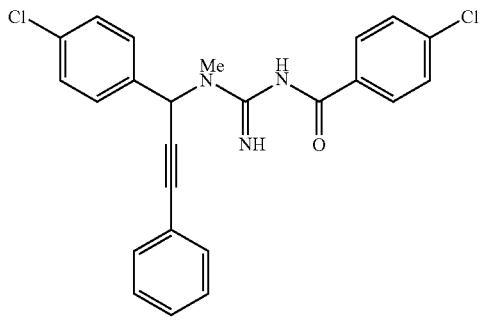 [SMILES: CN(C(=N)NC(=O)c1ccc(Cl)cc1)C(C#Cc1ccccc1)c1ccc(Cl)cc1]

4-Chloro-N—(N-(1-(4-chlorophenyl)-3-phenylprop-2-yn-1-yl)-N-methylcarbamimidoyl)benzamide (74) was prepared by guanylation of 1-(4-chlorophenyl)-N-methyl-3-phenylprop-2-yn-1-amine with potassium N-cyano-4-chlorobenzamide as a foamy white oil (47% yield). $^1$H NMR (CDCl$_3$, 500 MHz): δ 8.17 (d, J=8.5 Hz, 2H), δ 7.68 (s, 1H), δ 7.57 (d, J=8.5 Hz, 2H), δ 7.54-7.52 (m, 2H), δ 7.39-7.35 (m, 7H), δ 2.89 (s, 3H) ppm. $^{13}$C NMR (CDCl$_3$, 500 MHz): δ 176.2, δ 173.2, δ 160.9, δ 137.5, δ 137.3, δ 136.0, δ 134.5, δ 132.1, δ 130.8, δ 129.2, δ 129.1, δ 129.0, δ 128.7, δ 128.3, δ 122.3, δ 87.7, δ 84.4, δ 51.0, δ 29.6 ppm.

Example 82: Preparation of N—(N-(1-(4-Chlorophenyl)-3-phenylprop-2-yn-1-yl)-N-methylcarbamimidoyl)benzamide (75)

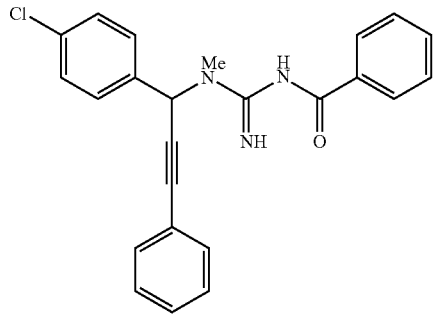 [SMILES: CN(C(=N)NC(=O)c1ccccc1)C(C#Cc1ccccc1)c1ccc(Cl)cc1]

N—(N-(1-(4-chlorophenyl)-3-phenylprop-2-yn-1-yl)-N-methylcarbamimidoyl)benzamide (75) was prepared by guanylation of 1-(4-chlorophenyl)-N-methyl-3-phenylprop-2-yn-1-amine with potassium N-cyanobenzamide as a foamy white oil (57% yield). $^1$H NMR (CDCl$_3$, 500 MHz): δ 8.26 (d, J=8 Hz, 2H), δ 7.55 (s, 1H), δ 7.60 (d, J=8.5 Hz, 2H), δ 7.58-7.52 (m, 2H), δ 7.48-7.33 (m, 8H), δ 2.88 (s, 3H) ppm. $^{13}$C NMR (CDCl$_3$, 500 MHz): δ 177.3, δ 160.9, δ 138.8, δ 136.2, δ 134.4, δ 132.1, δ 131.4, δ 129.4, δ 129.1, δ 128.7, δ 128.1, δ 122.3, δ 87.6, δ 84.6, δ 50.9, δ 29.5 ppm.

Example 83: Preparation of N—(N-(1-(4-Chlorophenyl)-3-phenylprop-2-yn-1-yl)-N-methylcarbamimidoyl)-4-methoxybenzamide (76)

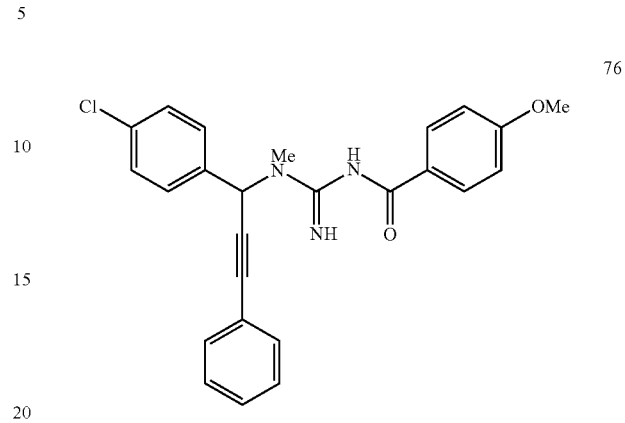

N—(N-(1-(4-chlorophenyl)-3-phenylprop-2-yn-1-yl)-N-methylcarbamimidoyl)-4-methoxybenzamide (76) was prepared by guanylation of 1-(4-chlorophenyl)-N-methyl-3-phenylprop-2-yn-1-amine with potassium N-cyano-4-methoxybenzamide as a foamy white oil (56% yield). $^1$H NMR (CDCl$_3$, 500 MHz): δ 8.21 (d, J=9 Hz, 2H), δ 7.73 (s, 1H), δ 7.59 (d, J=8.5 Hz, 2H), δ 7.53-7.51 (m, 2H), δ 7.36-7.33 (m, 5H), δ 6.89 (d, J=9 Hz, 2H), δ 3.83 (s, 3H), δ 2.86 (s, 3H) ppm. $^{13}$C NMR (CDCl$_3$, 500 MHz): δ 177.0, δ 162.4, δ 160.7, δ 136.3, δ 134.3, δ 132.1, δ 131.6, δ 131.3, δ 129.1, δ 128.7, δ 122.4, δ 113.3, δ 87.5, δ 84.7, δ 50.6, δ 50.8, 629.5 ppm.

Example 84: Preparation of N—(N-(1-Cyclopropyl-4-methylpent-1-yn-3-yl)-N-methylcarbamimidoyl)benzamide (77)

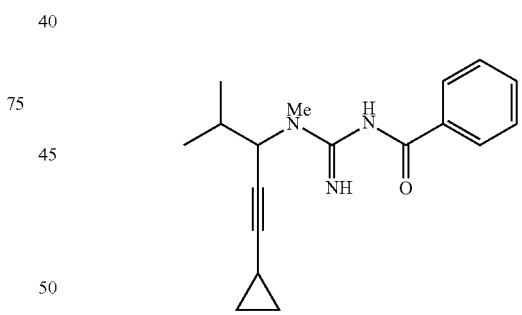

In a 50-mL round-bottom flask containing a magnetic stir bar were added potassium N-cyanobenzamide (100 mg, 0.66 mmol), TMSCl (0.08 ml, 0.66 mmol) and acetonitrile (5 mL). The solution was stirred at room temperature for 10 minutes. A solution of N-allyl-1-cyclopropyl-N,4-dimethylpent-1-yn-3-amine (111 mg, 0.66 mmol) in acetonitrile (10 mL) was then added, and the reaction mixture was allowed to stir at room temperature for 1 h. The solvent was then removed under reduced pressure and the crude product was re-dissolved in EtOAc (50 mL). The organic layer was washed with NaHCO$_3$ (20 mL) and brine (20 mL) and dried and filtered over Na$_2$SO$_4$. The crude product was purified via flash chromatography, eluting with 1:1 hexanes/EtOAc to give N—(N-(1-cyclopropyl-4-methylpent-1-yn-3-yl)-N-methylcarbamimidoyl)benzamide (77) as a white foam (78% yield). ¹H NMR (CDCl₃, 500 MHz): δ 8.18 (d, J=9 Hz, 1H), δ 7.46-7.35 (m, 2H), δ 5.51 (bs, 2H), δ 2.97 (s, 3H), δ 1.96 (sextet, J=7.3 Hz, 1H), δ 1.3-1.22 (m, 1H), δ 1.09 (d, J=7.7 Hz, 3H), δ 0.91 (d, J=6.8 Hz, 3H), δ 0.8-0.75 (m, 2H), δ 0.7-0.65 (m, 2H) ppm. ¹³C NMR (CDCl₃, 500 MHz): δ 176.7, 139.1, 131.0, 129.1, 127.8, 89.2, 77.4, 54.8, 33.0, 19.6, 19.3, 8.5, 8.4 ppm.

Example 85: Preparation of 4-Chloro-N—(N-(3-cyclopropyl-1-(4-methoxyphenyl)prop-2-yn-1-yl)-N-methylcarbamimidoyl)benzamide (78)

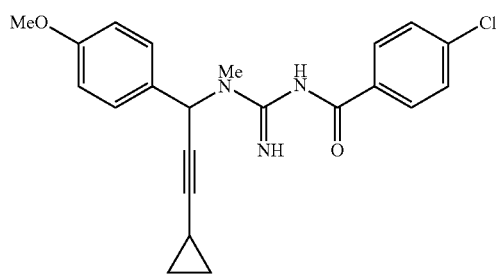

78

In a 50-mL round-bottom flask containing a magnetic stir bar were added potassium N-cyano-4-chlorobenzamide (100 mg, 0.46 mmol), TMSCl (0.07 ml, 0.46 mmol) and acetonitrile (5 mL). The solution was stirred at room temperature for 10 minutes. A solution of N-(3-cyclopropyl-1-(4-methoxyphenyl)prop-2-yn-1-yl)-N-methylprop-2-en-1-amine (100 mg, 0.46 mmol) in acetonitrile (10 mL) was then added, and the reaction mixture was allowed to stir at room temperature for 1 h. The solvent was then removed under reduced pressure and the crude product was re-dissolved in EtOAc (50 mL). The organic layer was washed with NaHCO₃ (20 mL) and brine (20 mL) and dried and filtered over Na₂SO₄. The crude product was purified via flash chromatography, eluting with 1:1 hexanes/EtOAc to give 4-chloro-N—(N-(3-cyclopropyl-1-(4-methoxyphenyl)prop-2-yn-1-yl)-N-methylcarbamimidoyl)benzamide (78) as a white foam (80% yield). ¹H NMR (CDCl₃, 500 MHz): δ 8.17 (d, J 8.4 Hz, 2H), δ 7.45 (d, J=7.9 Hz, 2H), δ 7.43 (d, J=9.1 Hz, 2H), δ 6.87 (d, J=8.4 Hz, 2H), δ 3.79 (s, 3H), δ 2.78 (s, 3H), 1.40-1.33 (m, 1H), 0.86-0.82 (m, 2H), 0.79-0.74 (m, 2H) ppm. ¹³C NMR (CDCl₃, 500 MHz): δ 175.9, 160.8, 159.5, 137.6, 137.3, 130.7, 128.7, 128.1, 114.2, 91.0, 71.1, 55.8, 50.5, 8.6, 8.5 ppm.

Example 86: Preparation of N—(N-(3-Cyclopropyl-1-(4-methoxyphenyl)prop-2-yn-1-yl)-N-methylcarbamimidoyl)benzamide (79)

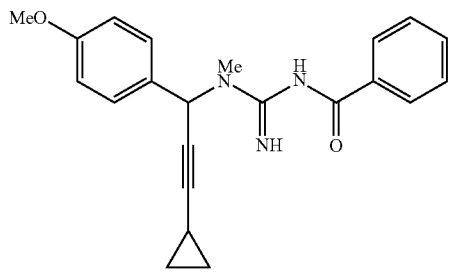

79

In a 50-mL round-bottom flask containing a magnetic stir bar were added potassium N-cyanobenzamide (85 mg, 0.46 mmol), TMSCl (0.07 ml, 0.46 mmol), and acetonitrile (5 mL). The solution was stirred at room temperature for 10 minutes. A solution of N-(3-cyclopropyl-1-(4-methoxyphenyl)prop-2-yn-1-yl)-N-methylprop-2-en-1-amine (100 mg, 0.46 mmol) in acetonitrile (10 mL) was then added, and the reaction mixture was allowed to stir at room temperature for 1 h. The solvent was then removed under reduced pressure and the crude product was re-dissolved in EtOAc (50 mL). The organic layer was washed with NaHCO₃ (20 mL) and brine (20 mL) and dried and filtered over Na₂SO₄. The crude product was purified via flash chromatography, eluting with 1:1 hexanes/EtOAc to give N—(N-(3-cyclopropyl-1-(4-methoxyphenyl)prop-2-yn-1-yl)-N-methylcarbamimidoyl)benzamide (79) as a white foam (65% yield). ¹H NMR (CDCl₃, 500 MHz): δ 8.25 (d, J=7.2 Hz, 2H), δ 7.48 (d, J=9.7 Hz, 2H), δ 7.44 (d, J 7.9 Hz, 1H), δ 7.39 (d, J=7.9 Hz, 2H), δ 6.87 (d, J=8.8 Hz, 2H), δ 3.79 (s, 3H), δ 2.78 (s, 3H), δ 1.4-1.33 (m, 1H), δ 0.86-0.81 (m, 2H), δ 0.79-0.75 (m, 2H). ¹³C NMR (CDCl₃, 500 MHz): δ 176.9, 160.8, 159.4, 139.1, 131.2, 129.3, 128.8, 127.9, 114.0, 90.7, 77.4, 71.2, 55.41, 55.4, 8.6, 8.5 ppm.

Example 87: Preparation of N—(N-(3-Cyclopropyl-1-(4-methoxyphenyl)prop-2-yn-1-yl)-N-methylcarbamimidoyl)-2-fluorobenzamide (80)

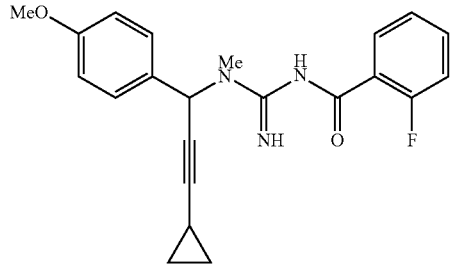

80

In a 50-mL round-bottom flask containing a magnetic stir bar were added potassium N-cyano-2-fluorobenzamide (93 mg, 0.46 mmol), TMSCl (0.07 ml, 0.46 mmol) and acetonitrile (5 mL). The solution was stirred at room temperature for 10 minutes. A solution of N-(3-cyclopropyl-1-(4-methoxyphenyl)prop-2-yn-1-yl)-N-methylprop-2-en-1-amine (100 mg, 0.46 mmol) in acetonitrile (10 mL) was then added, and the reaction mixture was allowed to stir at room temperature for 1 h. The solvent was then removed under reduced pressure and the crude product was re-dissolved in EtOAc (50 mL). The organic layer was washed with NaHCO₃ (20 mL) and brine (20 mL) and dried and filtered over Na₂SO₄. The crude product was purified via flash chromatography, eluting with 1:1 hexanes/EtOAc to give N—(N-(3-cyclopropyl-1-(4-methoxyphenyl)prop-2-yn-1-yl)-N-methylcarbamimidoyl)-2-fluorobenzamide (80) as a white foam (74% yield). ¹H NMR (CDCl₃, 500 MHz): δ 8.02 (dt, J=1.8, 7.9 Hz, 1H), δ 7.45 (d, J=8.5 Hz, 2H), δ 7.38-7.33 (m, 1H), δ 7.18 (t, J 7.8 Hz, 1H), δ 7.06 (dd, J=1.0, 8.3 Hz, 1H), δ 6.87 (d, J=7.3 Hz, 2H), δ 3.79 (s, 3H), δ 2.76 (s, 3H), δ 1.39-1.31 (m, 1H), δ 0.85-0.80 (m, 2H), δ 0.78-0.73 (m, 2H) ppm. ¹³C NMR (CDCl₃, 500 MHz): δ 175.4, 162.8, 160.9, 160.4, 159.5, 131.9, 128.8, 123.5, 116.8, 116.6, 113.9, 90.7, 71.2, 55.5, 50.4, 8.5, 8.48 ppm.

Example 88: Preparation of N—(N-(3-Cyclopropyl-1-(4-methoxyphenyl)prop-2-yn-1-yl)-N-methylcarbamimidoyl)-4-methoxybenzamide (81)

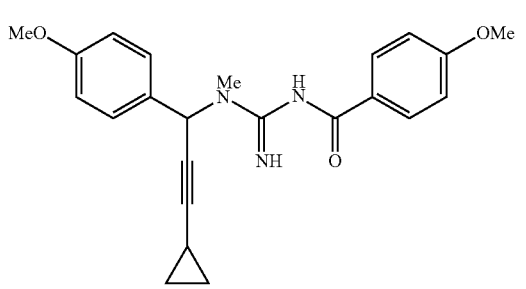

In a 50-mL round-bottom flask containing a magnetic stir bar were added potassium N-cyano-4-methoxybenzamide (100 mg, 0.46 mmol), TMSCl (0.07 ml, 0.46 mmol) and acetonitrile (5 mL). The solution was stirred at room temperature for 10 minutes. A solution of N-(3-cyclopropyl-1-(4-methoxyphenyl)prop-2-yn-1-yl)-N-methylprop-2-en-1-amine (100 mg, 0.46 mmol) in acetonitrile (10 mL) was then added, and the reaction mixture was allowed to stir at room temperature for 1 h. The solvent was then removed under reduced pressure and the crude product was re-dissolved in EtOAc (50 mL). The organic layer was washed with NaHCO$_3$ (20 mL) and brine (20 mL) and dried and filtered over Na$_2$SO$_4$. The crude product was purified via flash chromatography, eluting with 1:1 hexanes/EtOAc to give N—(N-(3-cyclopropyl-1-(4-methoxyphenyl)prop-2-yn-1-yl)-N-methylcarbamimidoyl)-4-methoxybenzamide (81) as a white foam (83% yield). $^1$H NMR (CDCl$_3$, 500 MHz): δ 8.2 (d, J=6.0 Hz, 2H), δ 7.47 (d, J=7.5 Hz, 2H), δ 6.87 (t, J 7.5 Hz, 4H), δ 3.83 (s, 3H), δ 3.78 (s, 3H), δ 2.77 (s, 3H), δ 1.40-1.32 (m, 1H), δ 0.86-0.80 (m, 2H), δ 0.79-0.73 (m, 2H) ppm. $^{13}$C NMR (CDCl$_3$, 500 MHz): δ 176.7, 162.0, 160.5, 159.5, 131.1, 128.7, 113.9, 113.0, 90.67, 71.2, 55.4, 8.6, 8.5 ppm.

Example 89: Preparation of 2-Fluoro-N—(N-methyl-N-(1-(4-(2-morpholinoethoxy)phenyl)-3-phenylprop-2-yn-1-yl)carbamimidoyl)benzamide (82)

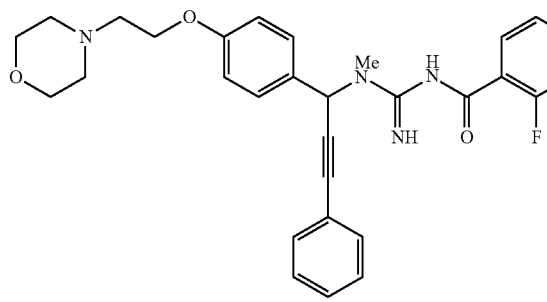

2-Fluoro-N—(N-methyl-N-(1-(4-(2-morpholinoethoxy)phenyl)-3-phenylprop-2-yn-1-yl)carbamimidoyl)benzamide (82) was prepared by guanylation of N-methyl-1-(4-(2-morpholinoethoxy)phenyl)-3-phenylprop-2-yn-1-amine with potassium N-cyano-2-fluorobenzamide as a foamy white oil (45% yield). $^1$H NMR (CDCl$_3$, 500 MHz): δ 8.05 (dt, J=7.5 Hz, 2 Hz, 2H), δ 7.57 (s, 1H), δ 7.56-7.50 (m, 4H), δ 7.38-7.33 (m, 3H), δ 7.14 (t, J=7.5 Hz, 1H), δ 7.10-7.05 (m, 1H), δ 6.91 (d, J=8.5 Hz, 2H), δ 4.12 (t, J=5.5 Hz, 2H), δ 3.73 (t, J=4.5 Hz, 4H), δ 2.86 (s, 3H), δ 3.83 (s, 3H), δ 2.86 (s, 3H) ppm. $^{13}$C NMR (CDCl$_3$, 500 MHz): δ 175.4, δ 167.8, δ 160.4, δ 158.6, δ 131.8, δ 129.5, δ 128.4, δ 127.5, δ 123.4, δ 122.4, δ 116.7, δ 114.6, δ 86.8, δ 85.1, δ 66.9, δ 65.9, δ 57.6, δ 54.0, δ 50.6 ppm.

Example 90: Preparation of N—(N-(1-(4-Chlorophenyl)-4-morpholinobut-2-yn-1-yl)-N-methylcarbamimidoyl)-2-fluorobenzamide (83)

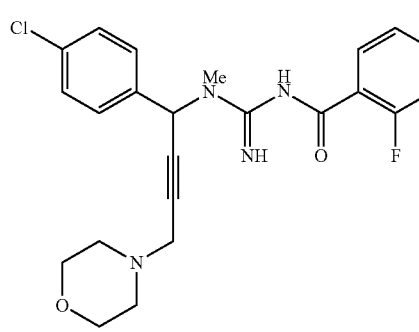

N—(N-(1-(4-chlorophenyl)-4-morpholinobut-2-yn-1-yl)-N-methylcarbamimidoyl)-2-fluorobenzamide (83) was prepared by guanylation of 1-(4-chlorophenyl)-N-methyl-4-morpholinobut-2-yn-1-amine with potassium N-cyano-2-fluorobenzamide, affording a foamy white oil (44% yield). $^1$H NMR (CDCl$_3$, 500 MHz): δ 7.96 (dt, J=8 Hz, 2 Hz, 1H), δ 7.47 (d, J=8 Hz, 2H), δ 7.36-7.28 (m, 3H), δ 7.10 (t, J=8 Hz, 1H), δ 7.03 (dd, J=11 Hz, 8 Hz, 1H), δ 3.72 (t, J=5.5 Hz, 4H), δ 3.42 (s, 2H), δ 2.77 (s, 3H), δ 2.57 (t, J=4.5 Hz, 4H) ppm. Calc. C$_{23}$H$_{24}$N4O$_2$FNaCl m/z (M+Na) 465.1470, Obsd. 465.1476 (M+Na).

Example 91: Preparation of N—(N-Allyl-N-(1-(4-methoxyphenyl)-3-phenylprop-2-yn-1-yl)carbamimidoyl)-2-fluorobenzamide (84)

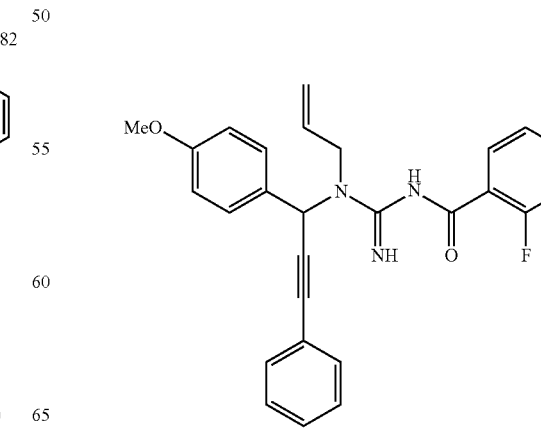

N—(N-Allyl-N-(1-(4-methoxyphenyl)-3-phenylprop-2-yn-1-yl)carbamimidoyl)-2-fluorobenzamide (84) was prepared by guanylation of N-(1-(4-methoxyphenyl)-3-phenylprop-2-yn-1-yl)prop-2-en-1-amine with potassium N-cyano-2-fluorobenzamide, affording a foamy white oil (54% yield). $^1$H NMR (CDCl$_3$, 500 MHz): δ 8.08 (dt, J=8 Hz, 2 Hz, 1H), δ 7.64 (s, 1H), δ 7.61 (d, J=9 Hz, 2H), δ 7.40-7.3 (m, 2H), δ 7.15 (t, J=7.5 Hz, 1H), δ 7.08 (dd, J=11 Hz, 8.5 Hz, 1H), δ 6.91 (d, 9 Hz, 2H), δ 5.77-5.72 (m, 1H), δ 5.32 (d, J=17 Hz, 1H), δ 5.25 (dd, J=10 Hz, 1.5 Hz, 1H), δ 3.95 (ABq, J=15 Hz, 38 Hz, 2H), δ 3.82 (s, 3H) ppm. $^{13}$C NMR (CDCl$_3$, 500 MHz): δ 175.8, δ 163.0, δ 161.1, δ 159.8, δ 134.0, δ 132.0, δ 129.7, δ 129.2, δ 128.7, δ 127.9, δ 123.7, δ 121.7, δ 118.5, δ 117.0, δ 114.2, δ 87.1, δ 85.7, δ 55.6, δ 50.8, δ 47.1 ppm.

Example 92: Preparation of Benzyl (E)-5-((Z)-benzylidene)-2-((4-methoxybenzoyl)imino)-3-methyl-4-phenylimidazolidine-1-carboxylate (85)

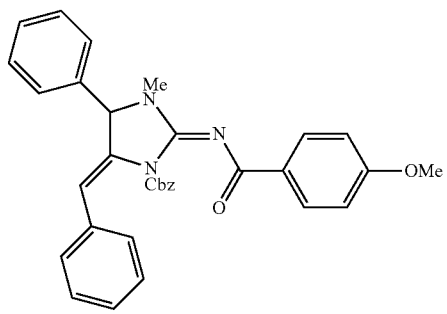

85

Benzyl (E)-5-((Z)-benzylidene)-2-((4-methoxybenzoyl)imino)-3-methyl-4-phenylimidazolidine-1-carboxylate (85) was obtained from acylation of (Z)-benzyl 5-benzylidene-2-imino-3-methyl-4-phenylimidazolidine-1-carboxylate (95.5 mg, 0.24 mmol) using 4-methoxybenzoyl chloride (0.043 mL, 0.36 mmol), triethylamine (0.067 mL, 0.48 mmol), and dichloromethane (2 mL) to give compound 85 as a light brown foam (119.8 mg, 95%). R$_f$=0.19 (3:2 hexanes/EtOAc); $^1$H NMR (CDCl$_3$, 500 MHz): δ 8.16 (d, J=9.0 Hz, 2H), 7.41-7.37 (m, 3H), 7.33-7.30 (m, 2H), 7.26-7.12 (m, 8H), 6.93 (d, J 9.0 Hz, 2H), 6.81 (d, J=7.5 Hz, 2H), 5.72 (d, J=2.0 Hz, 1H), 5.13 (s, 1H), 3.86 (s, 3H), 2.92 (s, 3H) ppm. $^{13}$C NMR (CDCl$_3$, 300 MHz): δ 175.0, 162.6, 151.5, 149.5, 137.1, 135.6, 134.8, 134.2, 131.8, 130.1, 129.5, 129.4, 1283, 127.9, 127.6, 116.9, 113.4, 68.9, 67.2, 55.6, 30.8 ppm. IR (thin film) 3058, 2951, 1745, 1652, 1597, 1507, 1456, 1427, 1249, 1227, 1177, 1162, 1022, 974, 863, 843, 731, 693 cm$^{-1}$ Calculated m/z C$_{33}$H$_{29}$N$_3$O$_4$ (M+Na) 554.2056, Obsd. 554.2061 (M+Na).

Example 93: Preparation of Benzyl (E)-5-((Z)-Benzylidene)-3-methyl-4-phenyl-2-((3-(trifluoromethyl)benzoyl)imino)imidazolidine-1-carboxylate (86)

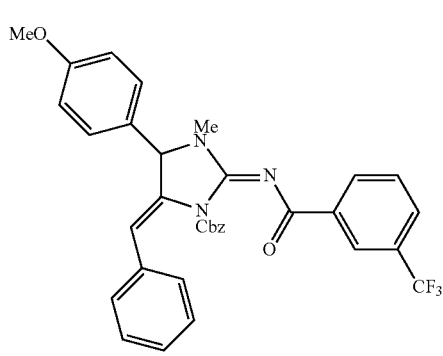

86

Benzyl (E)-5-((Z)-benzylidene)-3-methyl-4-phenyl-2-((3-(trifluoromethyl)benzoyl)imino)imidazolidine-1-carboxylate (86) was obtained from acylation of (Z)-benzyl 5-benzylidene-2-imino-3-methyl-4-phenylimidazolidine-1-carboxylate (95.5 mg, 0.24 mmol) using 3-trifluoromethylbenzoyl chloride (0.043 mL, 0.36 mmol), triethylamine (0.067 mL, 0.48 mmol), and dichloromethane (2 mL) to give compound 86 as a light brown foam (119.8 mg, 95%). R$_f$=0.31 (3:2 hexanes/EtOAc); $^1$H NMR (CDCl$_3$, 500 MHz): δ 8.47 (s, 1H), 8.37 (d, J=8.0 Hz, 1H), 7.74 (d, J=8.0 Hz, 1H), 7.55 (t, J=7.5 Hz, 1H), 7.42 (m, 4H), 7.34 (m, 2H), 7.26 (m, 3H), 7.19 (d, J=7.0 Hz, 2H), 7.15 (t, J=7.5 Hz, 2H), 6.78 (d, J=7.0 Hz, 2H), 5.80 (s, 1H), 5.20 (s, 1H), 4.66 (ABq, J=12.0, 15.5 Hz, 2H), 2.95 (s, 3H) ppm. $^{13}$C NMR (CDCl$_3$, 300 MHz): δ 173.5, 155.1, 144.3, 138.1, 136.7, 135.4, 134.4, 133.9, 133.1, 129.6, 128.8, 128.7, 128.5, 128.4, 128.3, 128.2, 128.0, 127.7, 126.8, 117.4, 69.2, 67.3, 30.8 ppm. IR (thin film) 1699, 1652, 1616, 1325, 1259, 1166, 1121, 1070, 998, 920, 855, 817, 758, 692 cm$^{-1}$. Calculated m/z C$_{33}$H$_{26}$N$_3$O$_3$F$_3$(M+Na) 592.1824, Obsd. 592.1821 (M+Na).

Example 94: Preparation of (2Z,5Z)-Benzyl 5-benzylidene-4-(4-methoxyphenyl)-3-methyl-2-((phenylcarbamoyl)imino)imidazolidine-1-carboxylate (87)

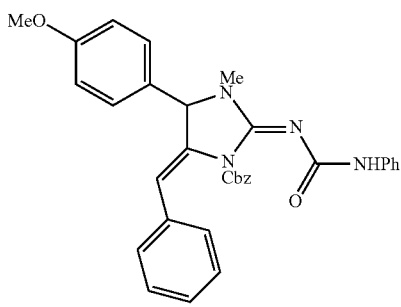

87

(2Z,5Z)-benzyl 5-benzylidene-4-(4-methoxyphenyl)-3-methyl-2-((phenylcarbamoyl)imino)imidazolidine-1-carboxylate (87) was obtained from acylation of (Z)-benzyl 5-benzylidene-2-imino-4-(4-methoxyphenyl)-3-methylimidazolidine-1-carboxylate (100 mg, 0.24 mmol) using phenyl isocyanate (0.026 mL, 0.24 mmol), and THF (2 mL) to give compound 87 as a light brown foam (26% yield). ¹H NMR (CDCl₃, 500 MHz): δ 7.52-7.48 (m, 2H), 7.34-7.13 (m, 6H), 7.11-7.09 (m, 5H), 7.09-7.01 (m, 2H), 6.90-6.87 (m, 4H), 5.77 (s, 1H), 5.02 (s, 1H), 4.69 (s, 2H), 3.89=1 (s, 3H), 2.83 (s, 3H) ppm. ¹³C NMR (CDCl₃, 500 MHz): δ 160.4, 151.6, 150.1, 139.8, 135.6, 134.9, 134.4, 129.1, 129.0, 128.7, 128.6, 128.4, 128.3, 127.6, 122.8, 119.2, 117.3, 114.9, 69.0, 66.5, 55.6, 30.3 ppm.

Example 95: Preparation of (E)-1-(4-Benzyl-5-(4-methoxyphenyl)-1-methyl-1H-imidazol-2(3H)-ylidene)-3-phenylurea (88)

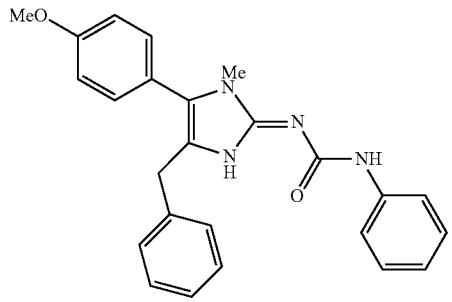

88

(E)-1-(4-Benzyl-5-(4-methoxyphenyl)-1-methyl-1H-imidazol-2(3H)-ylidene)-3-phenylurea (88) was obtained from the hydrogenation of (2Z,5Z)-benzyl 5-benzylidene-4-(4-methoxyphenyl)-3-methyl-2-((phenylcarbamoyl)imino)imidazolidine-1-carboxylate (131 mg, 0.34 mmol) using Pd/C (10% w/w, 12 mg) and distilled MeOH (2 mL) to give compound 88 as a light brown foam (39% yield). ¹H NMR (CDCl₃, 500 MHz): δ 7.48-7.43 (m, 2H), 7.33-7.20 (m, 9H), 7.03-6.98 (m, 3H), 3.88 (s, 3H), 3.81 (s, 2H), 3.36 (s, 3H) ppm. Calc. C₂₅H₂₄N₄O₂Na m/z (M+Na) 435.1797, Obsd. 435.1797 (M+Na).

Example 96: Preparation of (E)-N-(4-Benzyl-1-methyl-5-phenyl-1,3-dihydro-2H-imidazol-2-ylidene)-4-methoxybenzamide (89)

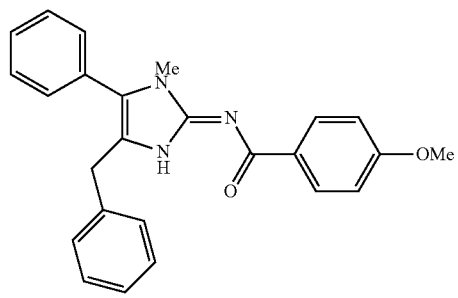

89

(E)-N-(4-Benzyl-1-methyl-5-phenyl-1,3-dihydro-2H-imidazol-2-ylidene)-4-methoxybenzamide (89) was obtained from the hydrogenation of benzyl (E)-5-((Z)-benzylidene)-2-((4-methoxybenzoyl)imino)-3-methyl-4-phenylimidazolidine-1-carboxylate (45.1 mg, 0.096 mmol) using Pd/C (10% w/w, 5 mg) and distilled MeOH (2 mL) to give compound 89 as a light brown foam (23.8 mg, 74%).

R_f=0.29 (3:2 hexanes/EtOAc); ¹H NMR (CDCl₃, 500 MHz): δ 8.30 (d, J=9.0 Hz, 2H), 7.48-7.44 (m, 3H), 7.31-7.27 (m, 2H), 7.10-7.02 (m, 3H), 7.00-6.95 (m, 4H), 3.85 (s, 3H), 3.60 (s, 2H), 3.48 (s, 3H) ppm. ¹³C NMR (CDCl₃, 500 MHz): δ 163.3 137.8, 131.4, 130.5, 129.7, 129.3, 128.9, 128.4, 127.3, 126.9, 113.9, 55.7, 32.9, 30.8 ppm. IR (thin film) 2858, 1678, 1603, 1573, 1514, 1494, 1453, 1401, 1348, 1311, 1176, 1027, 846, 766 cm⁻¹. Calculated m/z C₂₅H₂₃N₃O₂ (M+Na) 420.1688, Obsd. 420.1688 (M+Na).

Example 97: Preparation of (E)-N-(4-benzyl-1-methyl-5-phenyl-1,3-dihydro-2H-imidazol-2-ylidene)-3-(trifluoromethyl)benzamide (90)

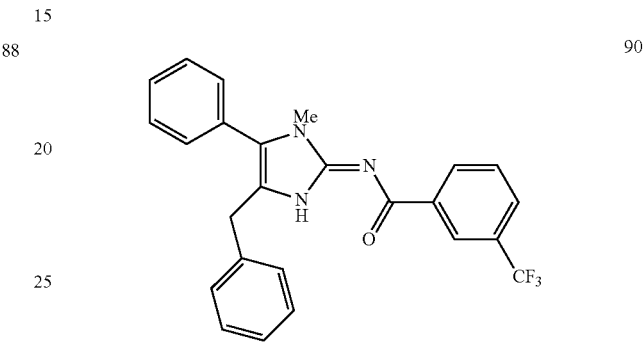

90

(E)-N-(4-Benzyl-1-methyl-5-phenyl-1,3-dihydro-2H-imidazol-2-ylidene)-3-(trifluoromethyl)benzamide (90) was obtained from the hydrogenation of benzyl (E)-5-((Z)-benzylidene)-3-methyl-4-phenyl-2-((3-(trifluoromethyl)benzoyl)imino)imidazolidine-1-carboxylate (45.1 mg, 0.096 mmol) using Pd/C (10% w/w, 5 mg) and distilled MeOH (2 mL) to give compound 90 as a light brown foam (23.8 mg, 74%). R_f=0.76 (3:2 hexanes/EtOAc); ¹H NMR (CDCl₃, 500 MHz): δ 8.55 (s, 1H), 8.43 (d, J=7.5 Hz, 1H), 7.68 (d, J=7.5 Hz, 1H), 7.53-7.48 (m, 4H), 7.40-7.37 (m, 2H), 7.32-7.29 (m, 2H), 7.26-7.24 (m, 1H), 7.15 (d, J=8.0 Hz, 2H), 3.87 (s, 2H), 3.54 (s, 3H) ppm. ¹³C NMR (CDCl₃, 500 MHz): δ 173.3, 150.8, 139.5, 137.3, 132.1, 120.5, 129.5, 129.3, 129.2, 128.5, 128.4, 127.7, 127.3, 127.2, 125.9, 124.8, 120.6, 95.0, 30.8, 30.3 ppm. IR (thin film) 3062, 1598, 1568, 1471, 1362, 1315, 1276, 1216, 1162, 1117, 1084, 1067, 907, 795, 763, 726 cm⁻¹. Calculated m/z C₂₅H₂₁N₃O₂F₃(M+H) 436.1637, Obsd. 436.1639 (M+H).

Example 98: Preparation of (E)-N-(4-Benzyl-5-(4-methoxyphenyl)-1-methyl-1H-imidazol-2(3H)-ylidene)-3-(trifluoromethyl)benzamide (91)

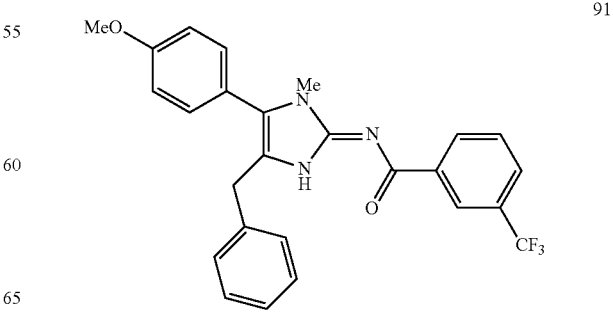

91

(E)-N-(4-Benzyl-5-(4-methoxyphenyl)-1-methyl-1H-imidazol-2(3H)-ylidene)-3-(trifluoromethyl)benzamide (91) was obtained from the hydrogenation of (2Z,5Z)-benzyl 5-benzylidene-4-(4-methoxyphenyl)-3-methyl-2-((3-(trifluoromethyl)benzoyl)imino)imidazolidine-1-carboxylate (240 mg, 0.4 mmol) using Pd/C (10% w/w, 25 mg) and distilled MeOH (2 mL) to give compound 91 as a light brown foam (53% yield). $^1$H NMR (CDCl$_3$, 300 MHz): δ 8.54 (s, 1H), 8.42 (d, J=7.8 Hz, 1H), 7.67 (d, J=7.2 Hz, 1H), 7.50 (t, J=8.4 Hz, 1H), 7.32-7.23 (m, 5H), 7.15 (d, J=6.9 Hz, 2H), 7.03 (d, J=9.0 Hz, 2H), 3.87 (s, 3H), 3.84 (s, 2H), 3.50 (s, 3H) ppm. $^{13}$C NMR (CDCl$_3$, 500 MHz): δ 173.0, 160.4, 150.5, 139.5, 137.3, 132.0, 131.6, 130.3, 130.0, 128.9, 128.7, 128.3, 128.1, 127.0, 126.9, 125.6, 125.4, 124.3, 120.1, 119.5, 114.6, 55.4, 30.5, 29.9 ppm.

Example 99: Preparation of (E)-N-(4-Benzyl-5-(4-methoxyphenyl)-1-methyl-1H-imidazol-2(3H)-ylidene)-4-fluorobenzamide (92)

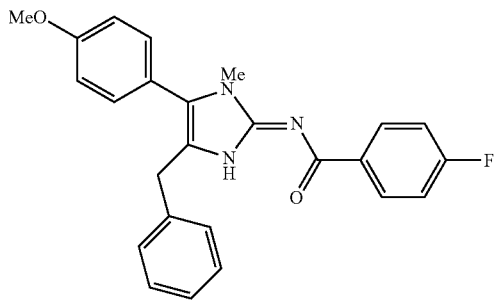

(E)-N-(4-Benzyl-5-(4-methoxyphenyl)-1-methyl-1H-imidazol-2(3H)-ylidene)-4-fluorobenzamide (92) was obtained via NaH-mediated cyclization of 4-fluoro-N—(N-(1-(4-methoxyphenyl)-3-phenylprop-2-yn-1-yl)-N-methylcarbamimidoyl)benzamide in THF in 84.1% yield as a brown solid. $^1$H NMR (CDCl$_3$, 500 MHz): δ 8.28-8.25 (m, 2H), δ 7.32-7.25 (m, 4H), δ 7.23-7.20 (m, 1H), δ 7.17-7.14 (m, 2H), δ 7.06-7.00 (m, 4H), δ 3.86 (s, 3H), δ 3.82 (s, 2H), δ 3.46 (s, 3H) ppm. $^{13}$C NMR (CDCl$_3$, 500 MHz): δ 173.8, 165.8, 163.8, 160.5, 150.7, 137.6, 134.9, 131.8, 131.2, 131.1, 129.2, 128.4, 127.2, 124.5, 119.8, 114.9, 114.7, 55.6, 30.8, 30.1 ppm.

Example 100: Preparation of (E)-Benzyl (4-benzyl-5-(4-methoxyphenyl)-1-methyl-1H-imidazol-2(3H)-ylidene)carbamate (93)

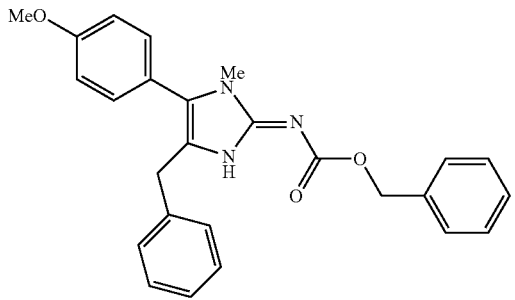

(E)-Benzyl (4-benzyl-5-(4-methoxyphenyl)-1-methyl-1H-imidazol-2(3H)-ylidene)carbamate (93) was obtained via NaH-mediated cyclization in THF in 84.1% yield as a brown solid. $^{13}$C NMR (CDCl$_3$, 500 MHz): δ 160.4, 138.0, 137.8, 131.8, 129.1, 128.5, 128.4, 128.1, 127.8, 127.1, 124.7, 120.1, 114.7, 66.9, 55.6, 30.9, 30.2 ppm.

Example 101: Preparation of N-(4-Benzyl-5-(4-methoxyphenyl)-1-methyl-1H-imidazol-2-yl)-2-fluoro-N-methylbenzamide (94)

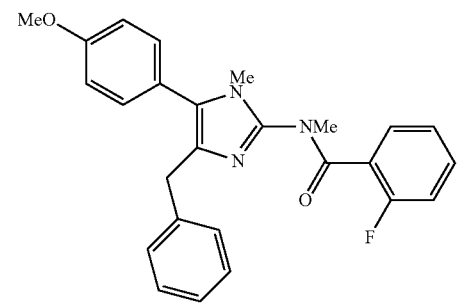

In a 25-mL flask containing a magnetic stir bar were added (E)-N-(4-benzyl-5-(4-methoxyphenyl)-1-methyl-1H-imidazol-2(3H)-ylidene)-2-fluorobenzamide (100 mg, 0.24 mmol), NaH (12 mg, 0.48 mmol), MeI (0.015 mL, 0.24 mmol), and distilled DMF (5 mL) under a stream of N$_2$, and the reaction was stirred at room temperature for 24 hours. The resulting solution was taken up in EtOAc (30 mL), washed with brine (3×20 mL), dried over Na$_2$SO$_4$, and concentrated under reduced pressure. The crude mixture was then purified by flash chromatography with EtOAc as an eluent to yield a colorless oil (34% yield). $^1$H NMR (CDCl$_3$, 500 MHz): δ 7.37 (t, J=7.0 Hz, 1H), 7.32-7.28 (m, 1H), 7.26-7.22 (m, 1H), 7.16-7.11 (m, 3H), 7.00-6.88 (m, 5H), 6.83 (d, J=7.0 Hz, 2H), 3.82 (s, 3H), 3.70 (s, 2H), 3.47 (s, 3H), 3.26 (s, 3H) ppm. $^{13}$C NMR (CDCl$_3$, 500 MHz): δ 167.3, 159.8, 157.7, 141.9, 140.9, 135.6, 131.6, 131.5, 131.3, 130.2, 129.2, 128.3, 125.5, 124.4, 124.2, 124.1, 121.8, 115.7, 115.6, 114.4, 55.5, 25.9, 33.2, 31.1 ppm.

Example 102: Preparation of Zn-Bound Dimer of (E)-N-(4-Benzyl-5-(4-methoxyphenyl)-1-methyl-1H-imidazol-2(3H)-ylidene)-2-fluorobenzamide (95)

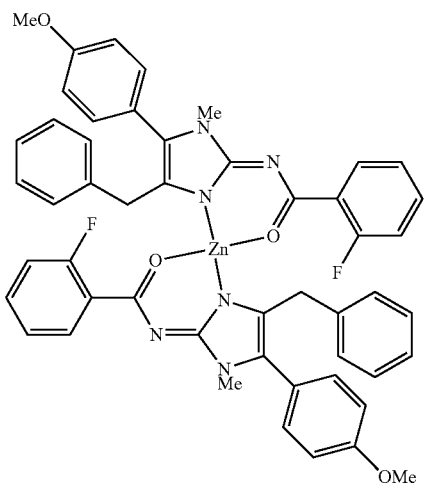

In a 25-mL flask containing a magnetic stir bar were added (E)-N-(4-benzyl-5-(4-methoxyphenyl)-1-methyl-1H-imidazol-2(3H)-ylidene)-2-fluorobenzamide (100 mg, 0.24 mmol), $ZnSO_4$ (345.9 mg, 1.2 mmol), and distilled MeOH (5 mL) under a stream of $N_2$, and the reaction was stirred at room temperature for 24 hours. The resulting white precipitate was collected as the Zn-bound dimer 95. $^1$H NMR ($CDCl_3$, 500 MHz): δ 7.85 (t, J=7.0 Hz, 2H), δ 7.34-7.30 (m, 2H), δ 7.22 (d, J=9 Hz, 4H), δ 7.12-7.03 (m, 4H), δ 6.96-6.91 (m, 8H), 6.90-6.84 (m, 6H), 3.85 (s, 6H), 3.59 (ABq, J=16 Hz, 9.5 Hz, 4H), δ 3.51 (s, 3H) ppm. $^{13}$C NMR ($CDCl_3$, 500 MHz): δ 174.5, 166.0, 160.3, 159.8, 150.4, 139.3, 132.0, 131.6, 131.0, 130.0, 128.5, 128.2, 128.1, 126.1, 125.8, 123.5, 121.9, 116.6, 116.5, 114.4, 55.6, 32.7, 30.5 ppm.

Example 103: Proposed Mechanism of Action for Zinaamidole (ZNA)

Naamidine A (NA) was the first small molecule to show the ability to induce ERKs kinase, presenting a new class of chemotherapeutic agents. But an aspect of NA's activity that initially went unappreciated was its ability to bind $Zn^{2+}$. Several natural products have been isolated from their marine sponge as the $Zn^{2+}$ dimer (FIG. 6B). Mancini et al. *Helv. Chim. Acta* 1995, 78, 1178-1184. These sponges might have evolved these natural products as $Zn^{2+}$ siderophores to ensure that they acquired enough zinc, normally limited in the marine environment, for survival.

With ample natural product in hand we conducted ITC experiments and found that the binding of NA to $ZnCl_2$ does occur in a ~2:1 stoichiometry with a $K_d$~0.35 µM (FIG. 6C). While this is believed to be a reasonable approximation of this binding, these ITC experiments were convoluted by solubility issues of the different species, requiring significant amounts of MeOH which can affect the accuracy of ITC experiments. Fisicaro et al. *Thermochim. Acta* 2014, 586 (0), 40-44. With a $Zn^{2+}$ binding affinity in the high nanomolar range, NA's phenotypic activity is likely a result of both kinase modulation and zinc binding.

ZNA binds $Zn^{2+}$ in a pH dependent fashion. ZNA binds $Zn^{2+}$ akin to naamidine A. Upon mixing a solution of ZNA in MeOH with $ZnSO_4$ in MeOH, the $(ZNA)_2Zn$ dimer quickly precipitates (FIG. 14A). The structure of the solid product was confirmed by X-ray crystallography (FIG. 14B). $(ZNA)_2Zn$ is freely soluble in DMSO-$d_6$, but the addition of 2 equiv. HCl in $D_2O$ protonates the ligand off the metal center, as evidenced by the disappearance of the diastereotopic benzyllic AB quartet in the dimer and its appearance as a singlet in the monomer.

ZNA analogues suggest responses to tuning of electronic properties. Considering the activities of these compounds likely result from a complex interplay of factors that govern $pK_a$ and $Zn^{2+}$ binding affinity, initial results suggest that meaningful potency increases are attainable (FIG. 9C). The $N^2$-methylated derivative is incapable of binding $Zn^{2+}$ and not active. Of the analogues evaluated, those with more electron-donating groups at C5 or on the $N^2$-carbonyl seem to improve activity. When compared to ZNA (IC50=8.8 µM, 24 h treatment), single point data suggests a 4-10 fold increase in potency against MCF-7s.

ZNA has promising pkpd parameters. An initial pharmacokinetic (PK) analysis on ZNA was performed at 1 mg/kg IV, 5 mg/kg PO. ZNA was dosed to female Sprague-Dawley rats at either 1 mg/kg intravenously or at 5 mg/kg orally. Plasma was collected with K2EDTA and stored at −80° C. until analysis. Quantification of ZNA was performed by protein precipitation followed by ultra-high performance liquid chromatography (UHPLC) interfaced to an electrospray ionization quadrapole time-of-flight mass spectrometer (ESI-QTOF). Plasma concentrations were determined from a calibration curve using ZNA as an internal standard. The values determined were fit with Phoenix WinNonlin and pharmacokinetic values reported.

TABLE 3

Pharmacokinetic Parameters for Individual Rats Dosed at 1 mg/kg IV

| Animal ID | C0 ng/mL | HL h | AUCall h * ng/mL | AUCINF_obs h * ng/mL | AUC_% Extrap_obs % | Vz_obs mL/kg | Cl_obs mL/h/kg | MRTINF_obs h |
|---|---|---|---|---|---|---|---|---|
| M1 | 168 | 1.5 | 133.7 | 147.8 | 9.5 | 14962 | 6768 | 2.1 |
| M2 | 134 | 1.9 | 118.6 | 128.9 | 8.0 | 20816 | 7758 | 2.0 |
| M3 | 72 | 1.8 | 89.4 | 101.2 | 11.7 | 26055 | 9879 | 2.3 |
| Median | 134 | 1.8 | 118.6 | 128.9 | 9.5 | 20816 | 7758 | 2.1 |

TABLE 4

Pharmacokinetic Parameters for Individual Rats Dosed at 5 mg/kg PO

| Animal_ID | Cmax ng/mL | Tmax h | HL_Lambda_z h | AUCall h * ng/mL | AUCINF_obs h * ng/mL | AUC_% Extrap_obs % | F % |
|---|---|---|---|---|---|---|---|
| M1 | 10.0 | 2 | 3.5 | 43.8 | 66.7 | 34.3 | 10.3 |
| M2 | 12.1 | 0.5 | 2.4 | 28.2 | 37.9 | 36.0 | 5.9 |
| M3 | 11.5 | 0.5 | 1.5 | 13.0 | 28.0 | 70.0 | 4.4 |
| Median | 11.5 | 0.5 | 2.4 | 28.2 | 37.9 | 36.0 | 5.9 |

The plasma concentrations for ZNA were very low, and most samples fell below the lower limit of quantification for the assay (10.0 ng/mL). This limited the data available for fitting in WinNonlin. To increase the amount of data for fitting, values from below the curve were extrapolated to approximately 40% of the LLOQ and were used for PK fitting. The percent of the area extrapolated in the PO PK animals ranged from 34-70% which was considered quite high. A more reasonable value is 15-20% of the AUC. The oral bioavailability determined was approximately 6%. This value is considered a rough estimate based upon the area extrapolated and the unusually high clearance determined. The intravenous data enabled a reasonable fit in WinNonlin and suggested that ZNA has a very high volume of distribution and a clearance that exceeds hepatic blood flow (235%). Possible explanations for the high clearance are binding of compound to red blood cells, extremely rapid clearance that requires collection of earlier time points to establish a more accurate C0, and extrahepatic elimination.

The results show that ZNA seems to have a high clearance rate and relatively short half-life ($T_{1/2}$=1.9 h). (FIG. 14C) (These results are complicated by the appearance of a major circulating metabolite in a 1:1 ratio with ZNA, which is the demethylated derivative and is also active.) Because ZNA could be dosed at 100 mg/kg in the previously described mouse tumorograft study without detrimental effects on mouse weight and health, it likely will be a well-tolerated compound.

Figure 15:
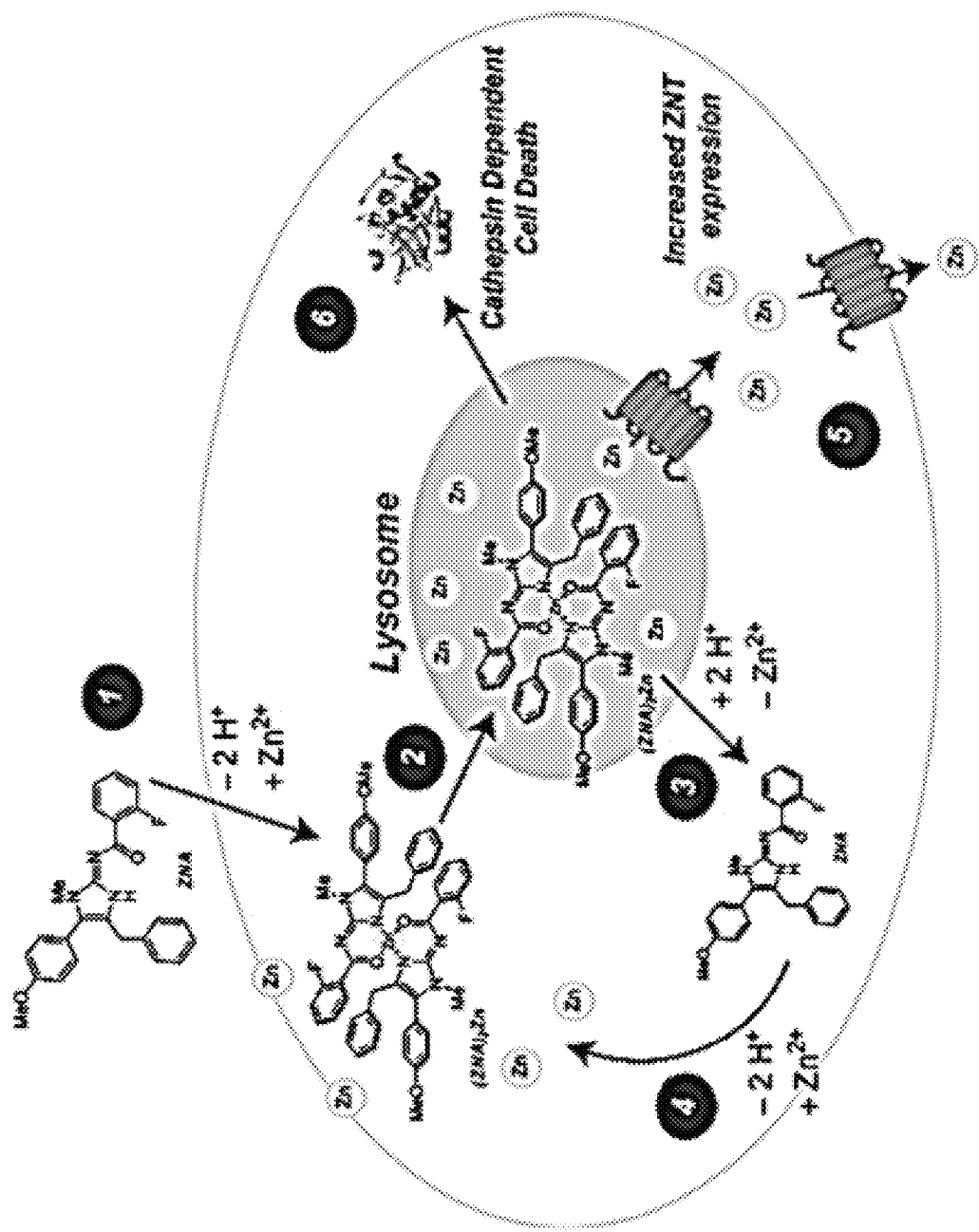
FIG. 15.
Figure 16:
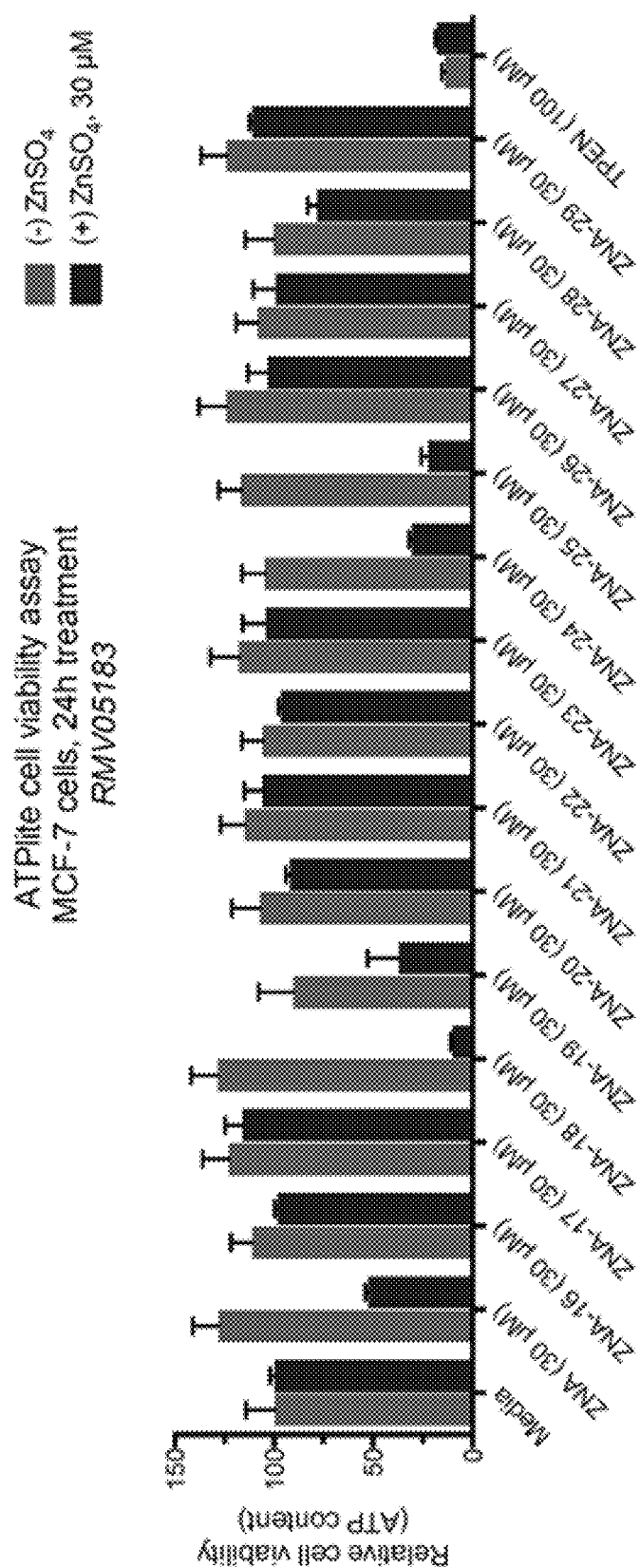
FIG. 16.

The data presented above and in the previous Examples is consistent with the following mechanism of action for ZNA (FIG. 15):

1) ZNA enters the cell in its monomeric form. Concomitant with the loss of a proton in the neutral cytoplasm (pH=7.2), a ZNA-$Zn^{2+}$ complex is formed. Given the results of a Job's analysis, it is likely that the 2:1 complex (ZNA)$_2$Zn is formed preferentially in solution. Job, P., Formation and stability of inorganic complexes in solution. *Ann. Chim. Appl.* 1928, 9, 113-203.

2) The (ZNA)$_2$Zn complex enters the lysosome and encounters the increased pH of the lysosome (pH ~4.8). The acidic environment causes protonation of the ZNA ligand and releases $Zn^{2+}$ in the interior of the lysosome.

3) ZNA is then free to leave the lysosome and repeat the $Zn^{2+}$ uptake cycle after 4) complexation and deprotonation to re-form the (ZNA)$_2$Zn complex.

5) Cells increase the expression of metal housekeeping genes, such as the metallothioneins (MT1F, MT1X and MT2A) and attempt to stop the $Zn^{2+}$ influx by increasing the expression of the zinc transport proteins (SLC30A1 and SLC30A2).

6) Ultimately this attempt to fails. An osmotic imbalance initiates lysosome membrane permeabilization (LMP), leading to the release of cathepsins and other hydrolases contained in the organelle, ultimately leading to cell death.

As noted in the literature, chloroquine and cliquinol, which are also thought to act as zinc ionophores, cause $Zn^{2+}$ accumulation in lysosomes and ultimately lead to caspase-dependent cell death. In contrast, ZNA induces caspase-independent cell death (in this case, necrosis). This seems to be related to the kinetics of LMP, for when treated with ZNA, cell death is extremely rapid. LMP may be catastrophic in this case and generates a significant increase in cytosolic cathepsin activity that bypasses the traditional apoptoic machinery.

Example 104: Preparation of Potassium N-Cyanobenzamide (96)

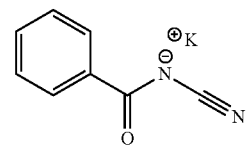

A one-necked 500-mL round-bottom flask open to the atmosphere, equipped with a magnetic stirring bar was charged with cyanamide (6.3 g, 0.15 mol) and distilled water (200 mL). Sodium hydroxide pellets (12.3 g, 0.308 mol) were then added in portions (~3×4 g) over a 15 minute period. The mixture was stirred for 30 min at room temperature and then cooled to 0° C. The flask was fitted with a 1000 mL addition funnel, and the addition funnel was charged with benzoyl chloride (21.1 g, 17.4 mL, 0.15 mol). The benzoyl chloride solution was then added dropwise over 20 min. After addition of the benzoyl chloride, the reaction was stirred for an additional 3 hours at room temperature. The mixture was then transferred to a 500-mL separatory funnel and washed with diethyl ether (1×50 ML). The aqueous layer was transferred to a 1-L Erlenmeyer flask equipped with a magnetic stirring bar and was acidified to pH 2 with concentrated aqueous HCl (approx. 15 mL). Dichloromethane (200 mL) was then added to dissolve the solids, and the mixture transferred to a 500-mL separatory funnel. After separation of the layers, the aqueous fraction was extracted with dichlormethane (2×100 mL), and the combined organics were dried over anhydrous $Na_2SO_4$. The organics were filtered through a sintered glass funnel and the resultant sodium sulfate was washed with dichloromethane (2×50 mL). The solvent was removed on a rotary evaporator, and then the flask was transferred to a high-vacuum line for 3 hours. The resulting white solid was then dissolved in MeOH (50 mL), and the solution was added dropwise to a 500-mL round-bottom flask equipped with a stir bar containing potassium hydroxide (8.0 g, 0.143 mol) dissolved in MeOH (200 mL) at 0° C. The flask was stoppered and allowed to stand in a −20° C. freezer overnight. The crude solid was collected on a Buchner funnel and washed with cold MeOH (2×50 mL) to give potassium N-cyanobenzamide as a fine white powder (17.9 g, 65%) after sufficient drying under vacuum. $^1$H NMR (CH$_3$OD, 400 MHz): δ 7.95 (t, J=7.2 Hz, 2H), δ 7.44 (d, J=7.2 Hz, 1H), δ 7.35 (t, J=7.2 Hz, 2H) ppm. Calc. C$_8$H5N$_2$O m/z (M−H) 145.0402, Obsd. 145.0398 (M−H).

Example 105: Preparation of Potassium N-Cyano-4-methoxybenzamide (97)

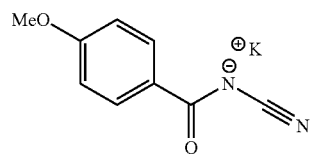

97

Potassium N-cyano-4-methoxybenzamide was prepared in a similar fashion to Example 104 to yield a white solid. $^1$H NMR (CH$_3$OD, 500 MHz): δ 7.91 (d, J=7.3 Hz, 2H), δ 6.88 (d, J=9.3 Hz, 2H), δ 3.81 (s, 3H) ppm. Calc. C$_9$H7N$_2$O$_2$ m/z (M−H) 175.0508, Obsd. 175.0513 (M−H).

Example 106: Preparation of Potassium N-Cyano-2-fluorobenzamide (98)

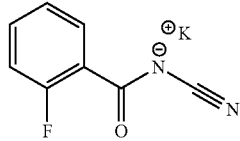

98

Potassium N-cyano-2-fluorobenzamide was prepared in a similar fashion to Example 104 to yield a white solid. $^1$H NMR (CH$_3$OD, 500 MHz): δ 7.68 (t, J=7.3 Hz, 1H), δ 7.43-7.37 (m, 1H), δ 7.14 (t, J=8.4 Hz, 1H), δ 7.08 (dd, J=2, 8.4 Hz, 1H) ppm. Calc. C8H$_4$N$_2$OF m/z (M−H) 163.0308, Obsd. 163.0308 (M−H).

Example 107: Preparation of Potassium N-Cyano-4-chlorobenzamide (99)

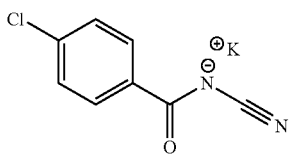

99

Potassium N-cyano-4-fluorobenzamide was prepared in a similar fashion to Example 104 to yield a white solid. $^1$H NMR (CH$_3$OD, 500 MHz): δ 8.00 (dd, J=3.4, 6.1 Hz, 2H), δ 7.06 (t, J=9.1 Hz, 2H) ppm. Calc. C$_8$H4N$_2$OF m/z (M−H) 163.0308, Obsd. 163.0317 (M−H).

Example 108: Preparation of Potassium N-Cyano-4-fluorobenzamide (100)

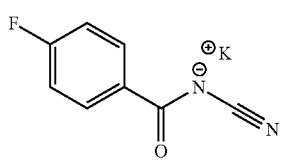

100

Potassium N-cyano-4-fluorobenzamide was prepared in a similar fashion to Example 104 to yield a white solid. $^1$H NMR (CH$_3$OD, 500 MHz): δ 8.00 (dd, J=3.4, 6.1 Hz, 2H), δ 7.06 (t, J=9.1 Hz, 2H) ppm. Calc. C$_8$H4N$_2$OF m/z (M−H) 163.0308, Obsd. 163.0317 (M−H).

Example 109: Preparation of (E)-N-(4-Benzyl-5-(4-hydroxyphenyl)-1-methyl-1H-imidazol-2(3H)-ylidene)-2-fluorobenzamide (101)

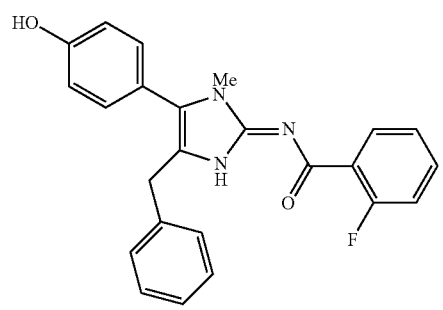

101

In a 25 mL flask containing a magnetic stir bar were added (E)-N-(4-benzyl-5-(4-methoxyphenyl)-1-methyl-1H-imidazol-2(3H)-ylidene)-2-fluorobenzamide (50 mg, 0.12 mmol), BBr$_3$ (0.012 mL, 0.12 mmol), and distilled DCM (5 mL) under a stream of N$_2$, and the reaction was stirred at room temperature for 24 hours. The resulting solution was taken up in EtOAc (30 mL), washed with saturated NaHCO$_3$ (10 mL) and brine (10 mL), dried over Na$_2$SO$_4$, and concentrated under reduced pressure. The crude mixture was then purified by trituration with Et$_2$O to yield compound 101 as a white solid (58% yield). $^1$H NMR (CDCl$_3$, 500 MHz): δ 8.04 (t, J=8.5 Hz, 1H), 7.38-7.35 (m, 1H), 7.35-7.05 (m, 9H), 6.92-6.89 (m, 2H), 3.80 (s, 2H), 3.42 (s, 3H), 3.26 (s, 3H) ppm. Calc. C$_{24}$H$_{20}$N3O$_2$FNa m/z (M+Na) 424.1437, Obsd. 424.1439 (M+Na).

Example 110: Preparation of (E)-N-(4-Benzyl-5-(4-hydroxyphenyl)-1-methyl-1H-imidazol-2(3H)-ylidene)-2-fluorobenzamide (102)

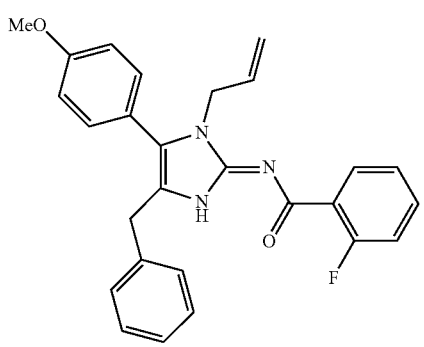

(E)-N-(1-Allyl-4-benzyl-5-(4-methoxyphenyl)-1,3-dihydro-2H-imidazol-2-ylidene)-2-fluorobenzamide (102) was obtained via NaH-mediated cyclization cyclization of compound 84 in THF. $^1$H NMR (CDCl$_3$, 500 MHz): δ 8.06 (dt, J=1.5, 8.0 Hz, 1H), δ 7.56-7.53 (m, 1H), δ 7.29-7.26 (m, 4H), δ 7.23-7.20 (m, 1H), δ 7.15-7.12 (m, 2H), δ 7.09-7.05 (m, 1H), δ 6.98 (d, J=9 Hz, 2H), δ 5.91-5.83 (m, 1H), δ 5.12 (dd, J=1 Hz, 10 Hz, 1H), δ 4.96 (dd, J=1 Hz, 17.5 Hz, 1H), δ 3.86 (s, 3H), δ 3.80 (s, 2H) ppm. $^{13}$C NMR (CDCl$_3$, 500 MHz): δ 162.9, 160.9, 160.5, 137.9, 132.9, 132.2, 132.8, 132.0, 129.1, 128.4, 127.1, 123.7, 120.0, 117.8, 116.8, 116.6, 114.5, 55.6, 45.5, 31.1 ppm.

Example 111: Antibacterial Activity of Naamidine A, Kealiinine B, and Kealiinine C In addition to the anti-cancer activity of the analogues described herein, naamidine A was also shown to have anti-proliferative activity against both *Mycobacterium tuberculosis* (IC$_{50}$=0.94 μM or 0.41 g/mL), *Candida albicans* (MIC$_{100}$=0.78 μM and *A. baumanii* MIC$_{100}$=79 μM) as measured by an MTT assay (details below; FIG. 17). The related natural products kealiinines B and C also displays anti-tubercular activity (IC$_{50}$=8.9 μM and 42 μM respectively).

Library screening and MIC determination for the compounds were performed in 96-well plates as described previously in Koch et al. Planta Med 2009; 75(12): 1326-1330. Different media were used for respective test organisms. Mueller-Hinton II media (Difco B D, Franklin Lakes, N.J.) was used for *Escherichia coli* (ATCC 25922). *Acinetobacter baumannii* (ATCC 19606), *Bacillus subtilis* (ATCC 6633), *Candida albicans* (ATCC 90028) were all grown in MOPS buffered RPMI-1640 (NCCLS 2007). *Mycobacterium tuberculosis* H37Ra (ATCC 25177) was grown in 7H9 medium with ADC supplement (Remel, Lenexa, Kans.). Final well volume was 200 μL. Each plate had 4 wells of uninoculated no-growth control, 4 wells of growth control (DMSO) and 8 wells of an appropriate antibiotic [Sigma Aldrich, St. Louis, Mo.) as positive control (Gentamycin for *B. subtilis*, Kanamycin for *E. coli* and *A. baumannii*, itraconazole for *C. albicans* and rifampicin for *M. tuberculosis*). The remaining wells received 1 μL of test compound in DMSO, in triplicates for MIC determination. Incubation was overnight at 37° C. for other organisms except for *M. tuberculosis* which was incubated for 5 days. *B. subtilis* and *M. tuberculosis* received 11 μL of sterile 5 mg/mL 3-(4,5-dimethylthiazol-2-yl)-2,5-diphenyltetrazolium bromide (MTT) in PBS on day 1 or 4, respectively. Formazan precipitate was dissolved with 50 μL solubilization reagent (50% DMF, 5% SDS, 45% water). Plates were evaluated on a Muliskan FC plate reader (Fisher Scientific, Waltham, Mass.). Percent inhibition was calculated using an Excel™ spreadsheet as previously described in Noro et al. *J. Nat. Prod.* 2008, 71, 1623-1624.

All publications, including patents and patent applications, in this application are incorporated herein by reference in their entirety, except insofar as they expressly contradict the present application (e.g., two contradictory definitions of the same term).

REFERENCES

1. Gligorich K, Vaden R, Shelton D, Wang G, Matsen C, Looper R, et al. Development of a screen to identify selective small molecules active against patient-derived metastatic and chemoresistant breast cancer cells. Breast Cancer Res 2013; 15(4):R58.
2. Anders S, Huber W. Differential expression analysis for sequence count data. Genome Biol 2010; 11(10):R106.
3. Mididoddi S, McGuirt J P, Sens M A, Todd J H, Sens D A. Isoform-specific expression of metallothionein mRNA in the developing and adult human kidney. Toxicol Lett 1996; 85(1):17-27.
4. Schmittgen T D, Livak K J. Analyzing real-time PCR data by the comparative C T method. Nat Protocols 2008; 3(6): 1101-08.
5. Martin T D, Brockhoff C A, Creed J T. Method 200.7 Determination of Metals and Trace Elements in Water and Wastes by Inductively Coupled Plasma-Atomic Emission Spectrometry. Environmental Monitoring Systems Laboratory, US Environmental Protection Agency 1994.
6. Smith B A, Shelton D N, Kieffer C, Milash B, Usary J, Perou C M, et al. Targeting the PyMT Oncogene to Diverse Mammary Cell Populations Enhances Tumor Heterogeneity and Generates Rare Breast Cancer Subtypes. Genes Cancer 2012; 3(9-10):550-63.
7. Thirumoorthy N, Shyam Sunder A, Manisenthil Kumar K T, Senthil kumar M, Ganesh GNK, Chatterjee M. A Review of Metallothionein Isoforms and their Role in Pathophysiology. World J Surg Oncol 2011; 9(1):54.
8. Thornalley P J, Vašák M. Possible role for metallothionein in protection against radiation-induced oxidative stress. Kinetics and mechanism of its reaction with superoxide and hydroxyl radicals. Biochim Biophys Acta—Protein Structure and Molecular Enzymology 1985; 827(1):36-44.
9. Chiaverini N, De Ley M. Protective effect of metallothionein on oxidative stress-induced DNA damage. Free Radical Research 2010; 44(6):605-13.
10. Degterev A, Huang Z, Boyce M, Li Y, Jagtap P, Mizushima N, et al. Chemical inhibitor of nonapoptotic cell death with therapeutic potential for ischemic brain injury. Nat Chem Biol 2005; 1(2):112-19.
11. Kabeya Y, Mizushima N, Ueno T, Yamamoto A, Kirisako T, Noda T, et al. LC3, a mammalian homologue of yeast Apg8p, is localized in autophagosome membranes after processing. EMBO J 2000; 19(21):5720-28.
12. Ho E, Ames B N. Low intracellular zinc induces oxidative DNA damage, disrupts p53, NFκB, and AP1 DNA binding, and affects DNA repair in a rat glioma cell line. Proc Natl Acad Sci USA 2002; 99(26):16770-75.

13. Zhou Z, Wang L, Song Z, Saari J T, McClain C J, Kang Y J. Zinc Supplementation Prevents Alcoholic Liver Injury in Mice through Attenuation of Oxidative Stress. Am J Path 2005; 166(6):1681-90.
14. Kilari S, Pullakhandam R, Nair K M. Zinc inhibits oxidative stress-induced iron signaling and apoptosis in Caco-2 cells. Free Radic Biol Med 2010; 48(7):961-68.
15. Andreini C, Banci L, Bertini I, Rosato A. Counting the Zinc-Proteins Encoded in the Human Genome. J Proteome Res 2005; 5(1):196-201.
16. Religa D, Strozyk D, Cherny R A, Volitakis I, Haroutunian V, Winblad B, et al. Elevated cortical zinc in Alzheimer disease. Neurol 2006; 67(1):69-75.
17. Margalioth E J, Schenker J G, Chevion M. Copper and Zinc levels in normal and malignant tissues. Cancer 1983; 52(5):868-72.
18. Geraki K, Farquharson M J, Bradley D A. X-ray fluorescence and energy dispersive x-ray diffraction for the quantification of elemental concentrations in breast tissue. Phys Med Biol 2004; 49(1):99.
19. Palmiter R D, Cole T B, Dindley S D. ZnT-2, a mammalian protein that confers resistance to zinc by facilitating vesicular sequestration. EMBO J 1996; 15(8):1784-91.
20. Qin Y, Thomas D, Fontaine C P, Colvin R A. Silencing of ZnT1 reduces Zn2+ efflux in cultured cortical neurons. Neurosci Lett 2009; 450(2):206-10.
21. Dairkee S, Ji Y, Ben Y, Moore D, Meng Z, Jeffrey S. A molecular 'signature' of primary breast cancer cultures; patterns resembling tumor tissue. BMC Genomics 2004; 5(1):47.
22. Franken NAP, Rodermond H M, Stap J, Haveman J, van Bree C. Clonogenic assay of cells in vitro. Nat Protocols 2006; 1(5):2315-19.
23. Jänicke R U, Sprengart M L, Wati M R, Porter A G. Caspase-3 Is Required for DNA Fragmentation and Morphological Changes Associated with Apoptosis. J Biol Chem 1998; 273(16):9357-60.
24. Han W, Li L, Qiu S, Lu Q, Pan Q, Gu Y, et al. Shikonin circumvents cancer drug resistance by induction of a necroptotic death. Mol Cancer Ther 2007; 6(5):1641-49.
25. Dalby K, Tekedereli I, Lopez-Berestein G, Ozpolat B. Targeting the pro-death and pro-survival functions of autophagy as novel therapeutic strategies in cancer. Autophagy 2010; 6(3):322-29.
26. Kimura T, Takabatake Y, Takahashi A, Isaka Y. Chloroquine in Cancer Therapy: A Double-Edged Sword of Autophagy. Cancer Res 2013; 73(1):3-7.
27. Liu, Y.; Gray, N. S. Rational design of inhibitors that bind to inactive kinase conformations. Nature Chem. Bio. 2006, 2(7), 358-364
28. Bain, J.; Plater, L.; Elliott, M.; Shpiro, N.; Hastie, C. J.; McLauchlan, H.; Klevernic, I.; Arthur, J. S.; Alessi, D. R.; Cohen, P. The selectivity of protein kinase inhibitors: a further update. Biochem. J. 2007, 408, 297-315.
29. Deacon, S. W.; Beeser, A.; Fukui, J. A.; Rennefahrt, U. E. E.; Meyers, C.; Chernoff, J.; Peterson, J. R. An isoform selective, small molecule inhibitor targets the autoregulatory mechanism of p21-Activated Kinase. Chem. Biol. 2008, 14, 322-331.
30. May, L. T.; Leach, K.; Sexton, P. M.; Christopoulos, A. Allosteric Modulation of G Protein-Coupled Receptors. Annu Rev Pharmacol Toxicol 2007, 47, 1-51.
31. Sewing, A., Wiseman, B., Lloyd, A. C., Land, H. High-intensity Raf signal causes a cell cycle arrest mediated by p21cipl. Mol. Cell. Biol. 1997, 17, 5588-5597.
32. Pumiglia, K. M., and Decker, S. J. Cell cycle arrest mediated by the MEK/mitogen-activated protein kinase pathway. Proc. Natl. Acad. Sci. USA, 1997, 94, 448-452.
33. Ermolat'ev, D. S.; Bariwal, J. B.; Steenackers, H. P. L.; De Keersmaecker, S. C. J.; Van der Eycken, E. V. Angew. Chem. Int. Ed. 2010, 49, 9465.
34. Huang, C. J.; Harootunian, A.; Maher, M. P.; Quan, C.; Raj, C. D.; McCormack, K.; Numann, R.; Negulescu, P. A.; Gonzalez, J. E. Nat. Biotech. 2006, 24, 439.
35. Zhang, M. M., Gruszczynski, P., Walewska, A., Bulaj, G., Olivera, B. M., and Yoshikami, D. J Neurophysiol 2010, 104, 88-97.
36. Zhang, M. M., Fiedler, B., Green, B. R., Catlin, P., Watkins, M., Garrett, J. E., Smith, B. J., Yoshikami, D., Olivera, B. M., and Bulaj, G. Biochemistry 2006, 45, 3723-3732.

What is claimed is:

1. A composition for therapeutic use, the composition comprising: a pharmaceutically acceptable excipient and a 2-(acylamino)imidazole compound selected from the group consisting of

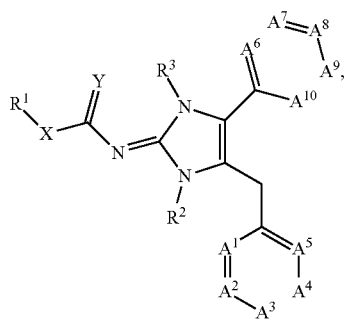

(Ia)

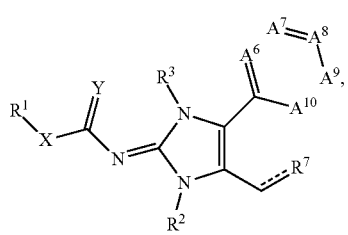

(Ib)

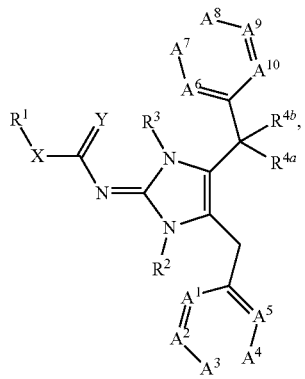

(Ic)

and salts thereof wherein:

$R^1$ is a member selected from the group consisting of alkyl, alkenyl, alkynyl, aryl, arylalkyl, heteroaryl, and heteroarylalkyl;

X is a member selected from the group consisting of a bond, O, and $NR^{5a}$;

Y is a member selected from the group consisting of O, S, or $NR^{5b}$; wherein when X is O or a bond, Y is O;

$R^2$ is a member independently selected from the group consisting of hydrogen, alkyl, fluoroalkyl, alkenyl, arylalkyl, acyl, and carbamoyl;

R³ is alkyl;

R⁴ᵃ and R⁴ᵇ are each a member independently selected from the group consisting of hydrogen, alkyl, fluoro, fluoroalkyl, alkenyl, aryl, and heteroaryl; or, alternatively, the two R⁴ join to form a spirocycloalkyl ring;

R⁵ᵃ and R⁵ᵇ are each a member independently selected from the group consisting of hydrogen, alkyl, fluoroalkyl, alkenyl, alkynyl, cycloalkyl, cycloalkylalkyl, arylalkyl, and heteroarylalkyl;

A¹, A², A³, A⁴, A⁵, A⁶, A⁷, A⁸, A⁹, and A¹⁰ are each independently selected from the group consisting of N and CR⁶ⁿ;

each of the R⁶ⁿ members is independently selected from the group consisting of hydrogen, alkyl, hydroxy, alkoxy, aminoalkoxy, alkylamino, alkylaminoalkoxy, alkenyl, alkynyl, aryl, aryloxy, arylamino, cycloalkyl, cycloalkylalkyl, cycloalkoxy, cycloalkylalkoxy, cycloalkylamino, cycloalkylalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, and heteroarylalkylamino; or, alternatively, a pair of adjacent R⁶ⁿ members join to form an additional fused ring that is selected from the group consisting of cycloalkyl, aryl, heterocyclyl, and heterocycloaryl; and R⁷ is a member independently selected from the group consisting of alkyl, aminoalkyl, alkenyl, arylalkyl, and heteroarylalkyl;

wherein the 2-(acylamino)imidazole has <2% (w/w) of N²,N²-diacylation; and wherein the 2-(acylamino)imidazole has <2% (w/w) of acyl regioisomers.

2. The composition of claim 1, wherein the 2-(acylamino)imidazole compound is

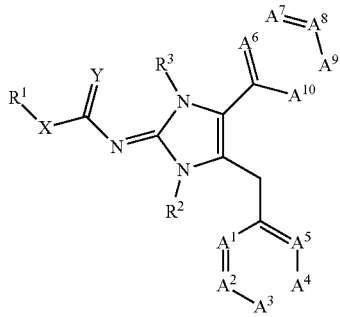

or a salt thereof.

3. The composition of claim 2, wherein the 2-(acylamino)imidazole compound is substantially free from a regioisomeric compound

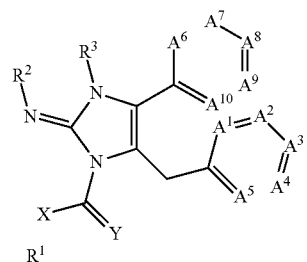

(IIa)

or a salt thereof.

4. The composition of claim 1, wherein the 2-(acylamino)imidazole compound is

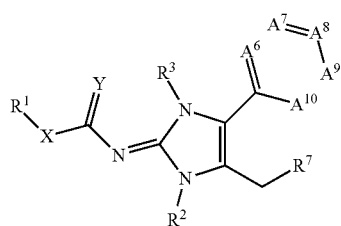

(Ib-1)

or a salt thereof.

5. The composition of claim 1, wherein the 2-(acylamino)imidazole compound is

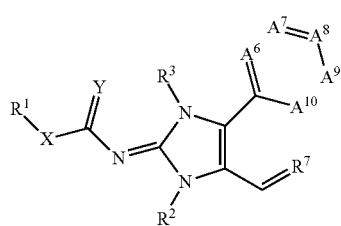

(Ib-2)

or a salt thereof.

6. The composition of claim 4, wherein the 2-(acylamino)imidazole compound is substantially free from a regioisomeric compound

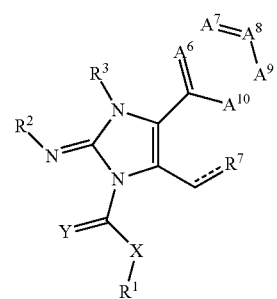

(IIb)

or a salt thereof.

7. The composition of claim 1, wherein the 2-(acylamino)imidazole compound is

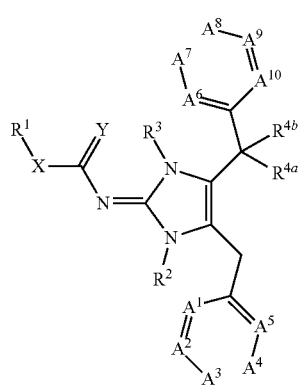

(Ic)

or a salt thereof.

8. The composition of claim 7, wherein the 2-(acylamino) imidazole compound is substantially free from a regioisomeric compound

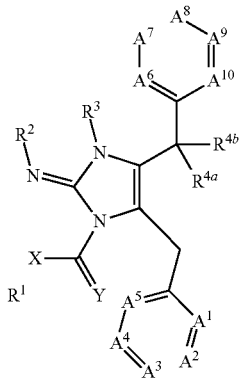

(IIc)

or a salt thereof.

9. The composition of claim 1, wherein $R^1$ is a member selected from the group consisting of alkyl, aryl, arylalkyl, and heteroaryl.

10. The composition of claim 9, wherein $R^1$ is a member selected from the group consisting of isopropyl, sec-butyl, phenyl, 2-fluorophenyl, 2,4-dichlorophenyl, and 2-thiazolyl.

11. The composition of claim 1, wherein X is a bond.

12. The composition of claim 1, wherein Y is O.

13. The composition of claim 1, wherein X is $NR^{5a}$; and wherein Y is $NR^{5b}$.

14. The composition of claim 1, wherein X is O; and wherein Y is O.

15. The composition of claim 1, wherein $R^2$ is a member independently selected from the group consisting of hydrogen, alkyl, acyl, and carbamoyl.

16. The composition of claim 15, wherein $R^2$ is a member independently selected from the group consisting of hydrogen and carbamoyl.

17. The composition of claim 16, wherein $R^2$ is a member independently selected from the group consisting of hydrogen, tert-butyloxycarbonyl (Boc), and benzyloxycarbonyl (Cbz).

18. The composition of claim 1, wherein $R^3$ is methyl.

19. The composition of claim 1, wherein $R^{4a}$ and $R^{4b}$ are each a member independently selected from the group consisting of hydrogen, alkyl, fluoro, and fluoroalkyl.

20. The composition of claim 19, wherein $R^{4a}$ and $R^{4b}$ are hydrogen.

21. The composition of claim 1, wherein $R^{5a}$ and $R^{5b}$ are each a member independently selected from the group consisting of hydrogen, alkyl, fluoroalkyl, alkenyl, alkynyl, cycloalkyl, cycloalkylalkyl, arylalkyl, and heteroarylalkyl.

22. The composition of claim 1, wherein $A^1$, $A^2$, $A^3$, $A^4$, $A^5$, $A^6$, $A^7$, $A^8$, $A^9$, and $A^{10}$ is each an independently selected $CR^{6n}$.

23. The composition of claim 1, wherein only one of $A^1$, $A^2$, $A^3$, $A^4$, $A^5$, $A^6$, $A^7$, $A^8$, $A^9$, and $A^{10}$ is N.

24. The composition of claim 1, wherein each of the $R^{6n}$ members is independently selected from the group consisting of hydrogen, alkyl, hydroxy, alkoxy, aryl, aryloxy, cycloalkyl, cycloalkoxy, cycloalkylalkoxy, heterocyclyl, heterocycyloxy, halo, fluoroalkyl, fluoroalkyloxy, heteroaryl, heteroaryloxy, arylalkyl, arylalkyloxy, arylalkylamino, and heteroarylalkyloxy.

25. The composition of claim 1, wherein each of the $R^{6n}$ members is independently selected from the group consisting of hydrogen, alkyl, hydroxy, alkoxy, cycloalkylalkoxy, halo, fluoroalkyl, fluoroalkyloxy, and arylalkyloxy.

26. The composition of claim 1, wherein each of the $R^{6n}$ members is independently selected from the group consisting of hydrogen, alkyl, hydroxy, and alkoxy.

27. The composition of claim 1, wherein $A^8$ is C(OH) or C(OMe).

28. The composition of claim 1, wherein at least six of the $R^{6n}$ members are hydrogen.

29. The composition of claim 1, wherein

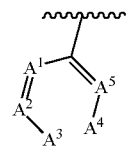

has from one to three hydroxyl substituents.

30. The composition of claim 1, wherein $A^3$ is C(OH) or C(OMe).

31. The pharmaceutical formulation of claim 1, wherein

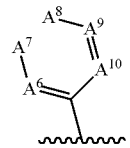

has from one to three hydroxyl substituents.

32. The composition of claim 1, wherein $A^8$ is C(OH) or C(OMe).

33. The composition of claim 1, wherein $R^7$ is alkyl or heteroarylalkyl.

34. The composition of claim 1, the composition comprising a 2-(acylamino)imidazole compound

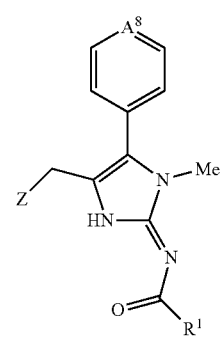

(IIIa)

and a salt thereof;
wherein $R^1$ and Z are each selected from the group consisting of phenyl, 2-fluorophenyl, 2,4-dichlorophenyl, 2-thiazolyl, isopropyl, and sec-butyl; and
wherein $A^8$ is selected from the group consisting of CH and C(OMe).

35. The composition of claim 1, the composition comprising a 2-(acylamino)imidazole compound

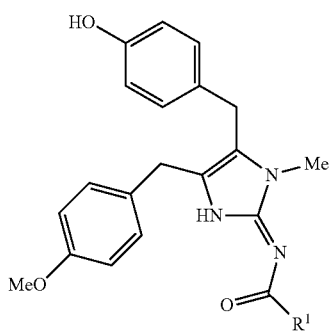

(IIIb)

and a salt thereof;

wherein $R^1$ is selected from the group consisting of phenyl, 2-fluorophenyl, 2,4-dichlorophenyl, 2-thiazolyl, isopropyl, and sec-butyl.

36. The composition of claim 1, the composition comprising a 2-(acylamino)imidazole compound

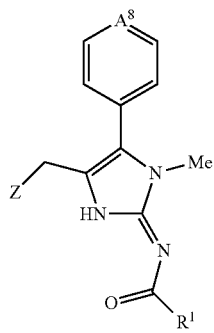

(IIIa)

and a salt thereof;

wherein $R^1$ and Z are each selected from the group including phenyl, 2-fluorophenyl, 3-trifluoromethylphenyl, 4-chlorophenyl, 4-methoxyphenyl, and cyclopropyl; and wherein $A^8$ is CCl.

37. The composition of claim 1, the composition comprising a 2-(acylamino)imidazole compound selected from the group consisting of

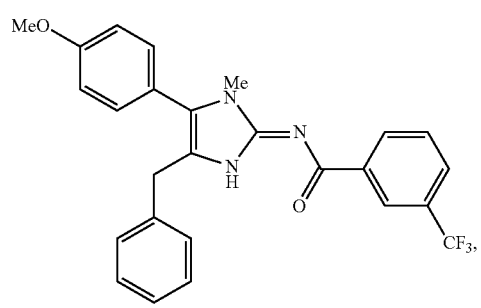

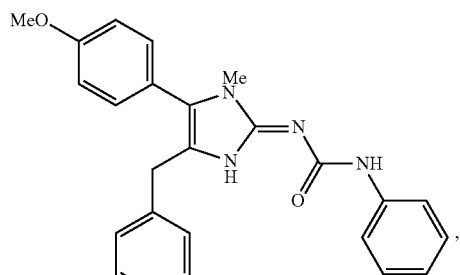

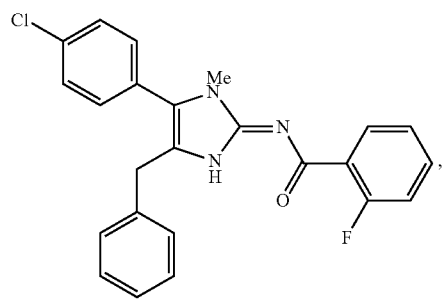

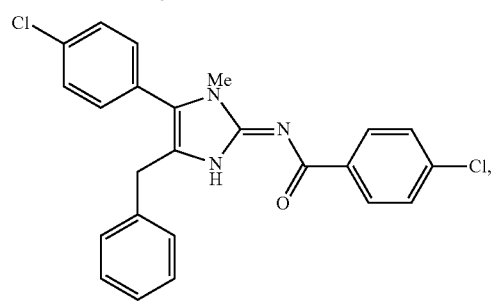

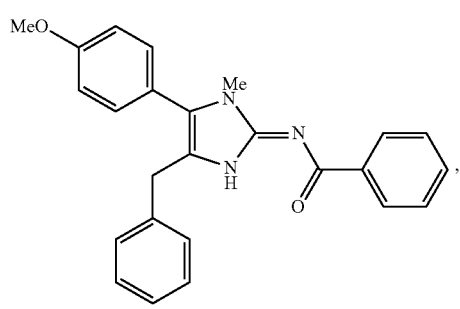

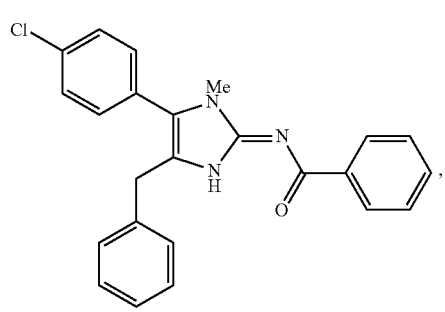

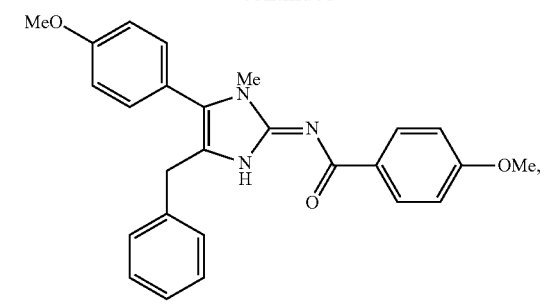
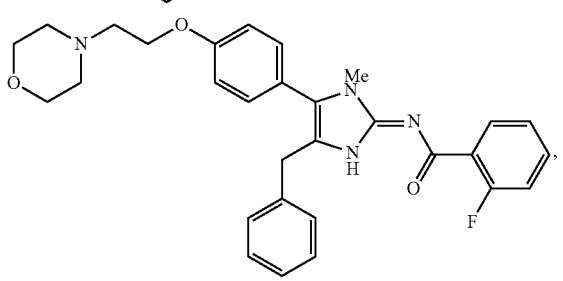
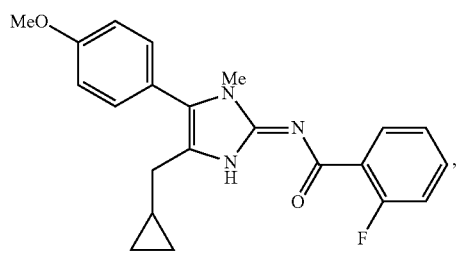
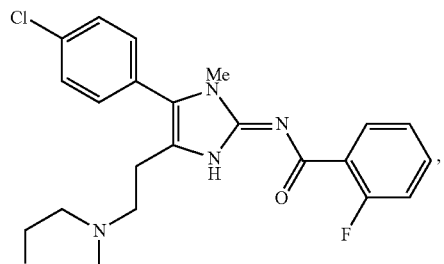
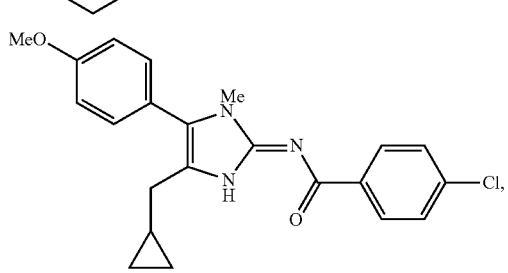
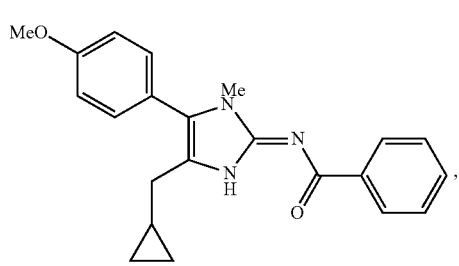
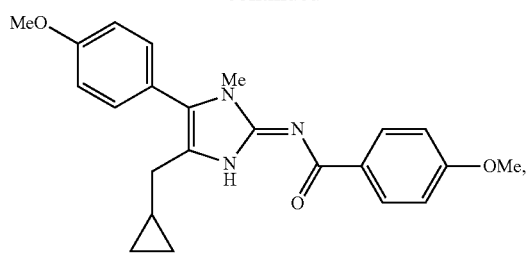
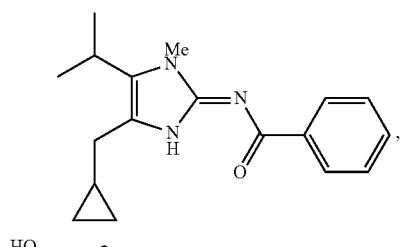
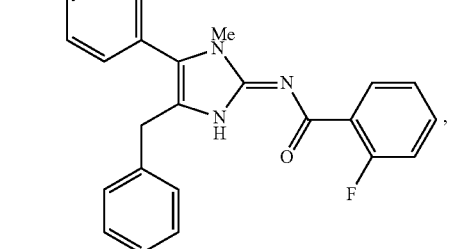
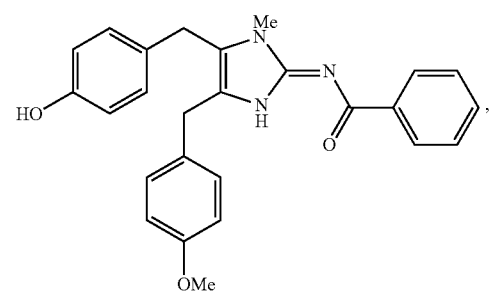
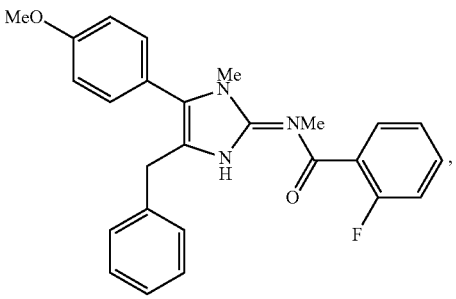
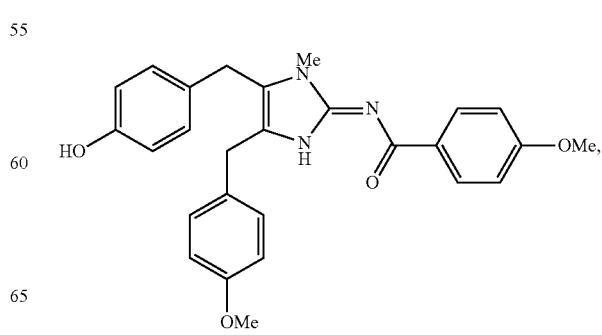

147
-continued
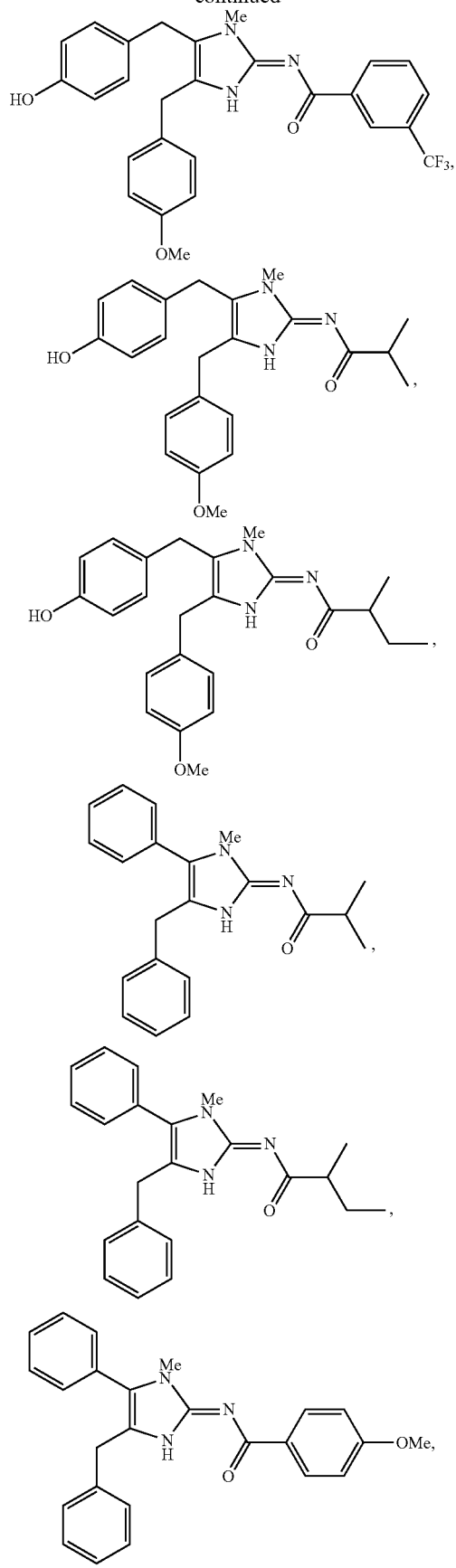
148
-continued
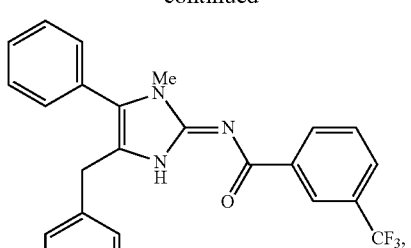
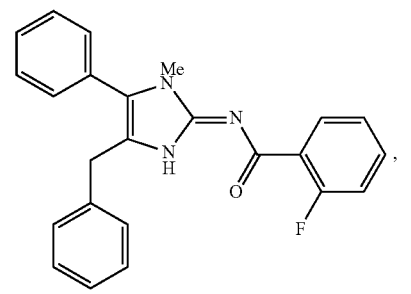
and salts thereof.
38. The composition of claim 1, the composition comprising a 2-(acylamino)imidazole compound selected from the group consisting of
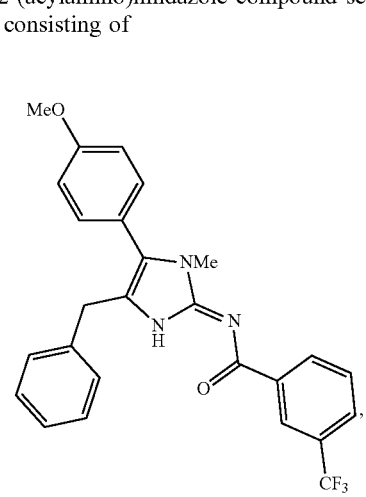
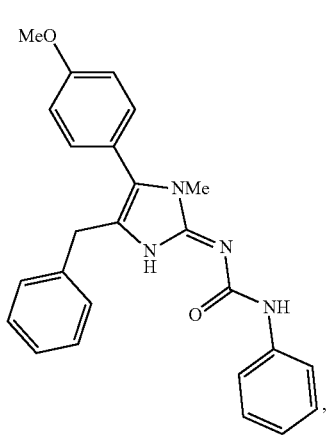

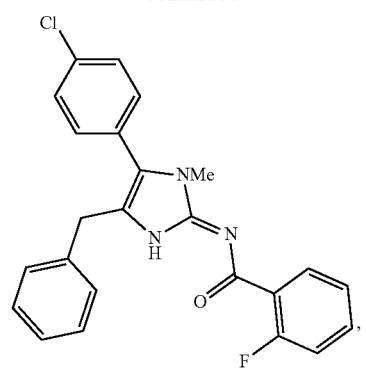
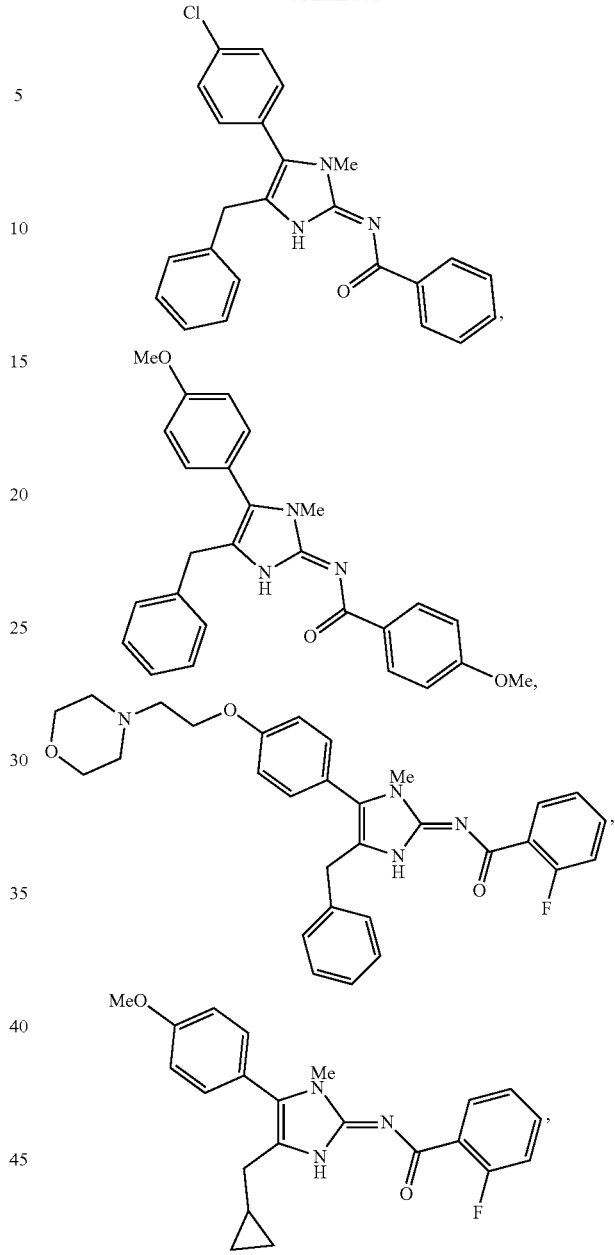
and salts thereof.
39. The composition of claim 38, wherein the 2-(acylamino)imidazole compound is
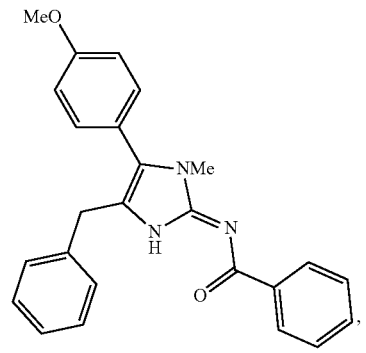
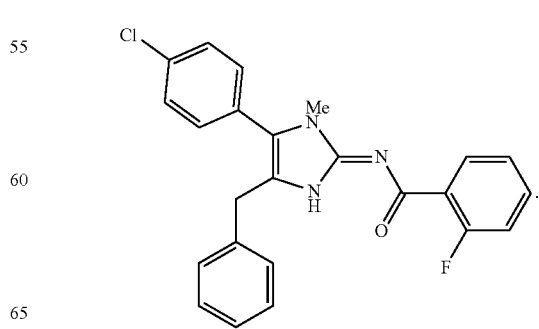

40. A method of treating cancer, the method comprising administering the composition of claim 1 to a patient with cancer, thereby treating the patient.

41. A method of selectively preparing a 2-acylamino imidazole, the method comprising the steps:
cyclizing an N-monoprotected α-guanidinyl alkyne reactant to form an 3-N-protected imidazolidin-2-imine product with a 4-exocyclic olefin; and
selectively acylating at the 2-amino position to form a 2-acylamino product;
wherein the 2-acylamino product is substantially free from 1-acyl and 3-acyl regioisomers.

42. The method of claim 41, the method further comprising the step of deprotecting the 3-N-protected 2-acyl imidazolidin-2-imine to produce a 2-acyl imidazolidin-2-imine.

43. The method of claim 42, the method further comprising the step of isomerizing the 2-acyl imidazolidin-2-imine to produce a 2-acylamino imidazole.

44. The method of claim 41, the method further comprising the step of isomerizing the 3-N-protected imidazolidin-2-imine to produce a 3-N-protected 2-aminoimidazole.

45. The method of claim 44, the method further comprising the step of deprotecting the 3-N-protected 2-acylamino imidazole to produce a 2-acylamino imidazole.

46. The method of claim 41, wherein the 3-N-protecting group is a carbamate protecting group.

47. The method of claim 46, wherein the 3-N-protecting group is a Cbz group.

48. The method of claim 41, wherein the 2-acylamino imidazole is a compound of claim 1.

* * * * *

UNITED STATES PATENT AND TRADEMARK OFFICE
CERTIFICATE OF CORRECTION

PATENT NO. : 10,493,061 B2  
APPLICATION NO. : 15/268410  
DATED : December 3, 2019  
INVENTOR(S) : Ryan E. Looper et al.

Page 1 of 1

It is certified that error appears in the above-identified patent and that said Letters Patent is hereby corrected as shown below:

On the Title Page

Item (73):
Delete "University of Utag Research Foundation" and enter --University of Utah Research Foundation--.

Signed and Sealed this
Twenty-eighth Day of January, 2020

Andrei Iancu
*Director of the United States Patent and Trademark Office*